US012478696B2

(12) United States Patent
Berger et al.

(10) Patent No.: US 12,478,696 B2
(45) **Date of Patent: *Nov. 25, 2025**

(54) GADOLINIUM CHELATE COMPOUNDS FOR USE IN MAGNETIC RESONANCE IMAGING

(71) Applicant: Bayer Pharma Aktiengesellschaft, Berlin (DE)

(72) Inventors: Markus Berger, Berlin (DE); Jessica Lohrke, Berlin (DE); Christoph-Stephan Hilger, Berlin (DE); Gregor Jost, Berlin (DE); Thomas Frenzel, Berlin (DE); Detlev Suelzle, Berlin (DE); Johannes Platzek, Berlin (DE); Olaf Panknin, Berlin (DE); Hubertus Pietsch, Kleinmachnow (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/983,625

(22) Filed: Dec. 17, 2024

(65) Prior Publication Data

US 2025/0114485 A1 Apr. 10, 2025

Related U.S. Application Data

(63) Continuation of application No. 17/979,367, filed on Nov. 2, 2022, which is a continuation of application No. 16/947,272, filed on Jul. 27, 2020, now Pat. No. 11,491,245, which is a continuation of application No. 16/192,185, filed on Nov. 15, 2018, now Pat. No. 10,722,601, which is a continuation of application No. 15/578,687, filed as application No. PCT/EP2016/062105 on May 30, 2016, now Pat. No. 10,137,209.

(30) Foreign Application Priority Data

Jun. 4, 2015 (EP) .................................... 15170658

(51) Int. Cl.
*C07D 257/02* (2006.01)
*A61K 49/10* (2006.01)

(52) U.S. Cl.
CPC .......... *A61K 49/106* (2013.01); *C07D 257/02* (2013.01)

(58) Field of Classification Search
CPC ............................. A61K 49/00; C07D 257/01
See application file for complete search history.

(56) References Cited

U.S. PATENT DOCUMENTS

| | | | |
|---|---|---|---|
| 4,485,237 | A | 11/1984 | Willer |
| 4,647,447 | A | 3/1987 | Gries et al. |
| 5,011,925 | A | 4/1991 | Rajagopalan et al. |
| 5,039,512 | A | 8/1991 | Kraft et al. |
| 5,141,740 | A | 8/1992 | Rajagopalan et al. |
| 5,281,704 | A | 1/1994 | Love et al. |
| 5,284,647 | A | 2/1994 | Niedballa et al. |
| 5,403,572 | A | 4/1995 | Gries et al. |
| 5,560,903 | A | 10/1996 | Gries et al. |
| 5,650,133 | A | 7/1997 | Carvalho et al. |
| 5,679,810 | A | 10/1997 | Love et al. |
| 5,863,518 | A | 1/1999 | Hashiguchi et al. |
| 5,866,562 | A | 2/1999 | Schohe-Loop et al. |
| 5,876,695 | A | 3/1999 | Gries et al. |
| 5,919,433 | A | 7/1999 | Platzek et al. |
| 6,019,959 | A | 2/2000 | Platzek et al. |
| 6,045,776 | A | 4/2000 | Platzek et al. |
| 6,056,939 | A | 5/2000 | Desreux et al. |
| 6,248,306 | B1 | 6/2001 | Schmitt-Willich et al. |
| 6,440,956 | B1 | 8/2002 | Port |
| 6,447,749 | B1 | 9/2002 | Licha et al. |
| 6,511,649 | B1 | 1/2003 | Harris et al. |
| 6,537,520 | B1 | 3/2003 | Rajopadhye et al. |
| 6,693,190 | B1 | 2/2004 | Ranganathan et al. |
| 7,294,615 | B1 | 11/2007 | Bovin et al. |
| 8,545,813 | B2 | 10/2013 | Song et al. |

(Continued)

FOREIGN PATENT DOCUMENTS

| | | | |
|---|---|---|---|
| CA | 2274132 | A1 | 6/1998 |
| CN | 102442996 | A | 5/2012 |

(Continued)

OTHER PUBLICATIONS

Van Alphen J., et al., "On Aliphatic Polyamines VII," 1938, vol. 57 (3), pp. 265-276.

(Continued)

*Primary Examiner* — Michael G. Hartley
*Assistant Examiner* — Jagadishwar R Samala
(74) *Attorney, Agent, or Firm* — Joseph L. Kent; James R. Stevenson

(57) ABSTRACT

An aqueous pharmaceutical composition including compound having the formula of tetragadolinium [4,10-bis(carboxylatomethyl)-7-{-3,6,12,15-tetraoxo-16-[4,7,10-tris(carboxylatomethyl)-1,4,7,10-tetraazacyclododecan-1-yl]-9,9-bis({[({2-[4,7,10-tris(carboxylatomethyl)-1,4,7,10-tetraazacyclododecan-1-yl]propanoyl}amino)acetyl]amino}methyl)-4,7,11,14-tetraazaheptadecan-2-yl}-1,4,7,10-tetraazacyclododecan-1-yl]acetate wherein the stereochemistry at the chiral carbon of the four alanine substituents is selected from the group consisting of RRRR, SSSS, RSSS, RRSS, and RRRS stereoisomers, and racemic and diastereomeric mixtures of any thereof, or a tautomer, a hydrate, a solvate, or a salt thereof, or a mixture of same is described. The compounds may be used as an MRI contrast imaging agent.

14 Claims, 11 Drawing Sheets

(56) References Cited

U.S. PATENT DOCUMENTS

| | | | | |
|---|---|---|---|---|
| 10,137,209 | B2 * | 11/2018 | Berger | A61K 49/106 |
| 10,722,601 | B2 * | 7/2020 | Berger | A61K 49/106 |
| 11,021,451 | B2 | 6/2021 | Lattuada et al. | |
| 11,110,185 | B2 | 9/2021 | Meijer et al. | |
| 11,491,245 | B2 * | 11/2022 | Berger | C07D 257/02 |
| 2002/0052354 | A1 | 5/2002 | Platzek et al. | |
| 2002/0077456 | A1 | 6/2002 | Takano et al. | |
| 2003/0004236 | A1 | 1/2003 | Meade | |
| 2003/0171561 | A1 | 9/2003 | Pillai et al. | |
| 2004/0170566 | A1 | 9/2004 | Chang et al. | |
| 2006/0093554 | A1 | 5/2006 | Platzek et al. | |
| 2006/0104908 | A1 | 5/2006 | Grimmond et al. | |
| 2007/0202047 | A1 | 8/2007 | Wolf et al. | |
| 2009/0143355 | A1 | 6/2009 | Yuan et al. | |
| 2009/0196829 | A1 | 8/2009 | Song et al. | |
| 2011/0081428 | A1 | 4/2011 | Lithgow et al. | |
| 2011/0108767 | A1 | 5/2011 | Akino | |
| 2012/0244070 | A1 | 9/2012 | Lu et al. | |
| 2013/0302258 | A1 | 11/2013 | Meade et al. | |
| 2014/0363376 | A1 | 12/2014 | Sun et al. | |
| 2016/0101196 | A1 | 4/2016 | Medina et al. | |
| 2017/0293009 | A1 | 10/2017 | Meade et al. | |
| 2020/0017453 | A1 | 1/2020 | Boi et al. | |

FOREIGN PATENT DOCUMENTS

| | | | |
|---|---|---|---|
| CN | 102614531 | A | 8/2012 |
| CN | 102973955 | A | 3/2013 |
| CN | 103554185 | A | 2/2014 |
| CN | 103611171 | A | 3/2014 |
| DE | 19525924 | A1 | 1/1997 |
| DE | 19652386 | A1 | 6/1998 |
| DE | 19652387 | A1 | 6/1998 |
| DE | 102007058220 | A1 | 6/2009 |
| DE | 102009053171 | A1 | 5/2011 |
| EP | 0255471 | A1 | 2/1988 |
| EP | 0305320 | A2 | 3/1989 |
| EP | 0438206 | A1 | 7/1991 |
| EP | 0454078 | A2 | 10/1991 |
| EP | 0946525 | A1 | 10/1999 |
| EP | 0946526 | A1 | 10/1999 |
| EP | 1931673 | A1 | 6/2008 |
| EP | 2042491 | A1 | 4/2009 |
| EP | 2457594 | A1 | 5/2012 |
| EP | 2457914 | A1 | 5/2012 |
| EP | 3101012 | A1 | 12/2016 |
| EP | 3551614 | B1 | 8/2021 |
| JP | 2008012596 | A | 1/2008 |
| KR | 20130080245 | A | 7/2013 |
| KR | 20140021742 | A | 2/2014 |
| KR | 20140021743 | A | 2/2014 |
| WO | 9002652 | A1 | 3/1990 |
| WO | 9103200 | A1 | 3/1991 |
| WO | 9105762 | A1 | 5/1991 |
| WO | 9209527 | A1 | 6/1992 |
| WO | 9209884 | A1 | 6/1992 |
| WO | 9218536 | A2 | 10/1992 |
| WO | 9221017 | A1 | 11/1992 |
| WO | 9311120 | A1 | 6/1993 |
| WO | 9311800 | A1 | 6/1993 |
| WO | 9316375 | A1 | 8/1993 |
| WO | 9407894 | A1 | 4/1994 |
| WO | 9427644 | A1 | 12/1994 |
| WO | 9501966 | A1 | 1/1995 |
| WO | 9509848 | A2 | 4/1995 |
| WO | 9520353 | A1 | 8/1995 |
| WO | 9531444 | A1 | 11/1995 |
| WO | 9601655 | A1 | 1/1996 |
| WO | 9616677 | A2 | 6/1996 |
| WO | 9638184 | A2 | 12/1996 |
| WO | 9702051 | A2 | 1/1997 |
| WO | 9718231 | A1 | 5/1997 |
| WO | 9723245 | A1 | 7/1997 |
| WO | 9726017 | A2 | 7/1997 |
| WO | 9730969 | A1 | 8/1997 |
| WO | 9732862 | A1 | 9/1997 |
| WO | WO 9732862 | * | 9/1997 |
| WO | 9824775 | A1 | 6/1998 |
| WO | 9901161 | A1 | 1/1999 |
| WO | 9916757 | A1 | 4/1999 |
| WO | 9921592 | A1 | 5/1999 |
| WO | 0001698 | A1 | 1/2000 |
| WO | 0009169 | A1 | 2/2000 |
| WO | 0076616 | A1 | 12/2000 |
| WO | 0076760 | A1 | 12/2000 |
| WO | 0151095 | A2 | 7/2001 |
| WO | 0152906 | A2 | 7/2001 |
| WO | 0164708 | A1 | 9/2001 |
| WO | 0197848 | A2 | 12/2001 |
| WO | 0197860 | A2 | 12/2001 |
| WO | 0213874 | A2 | 2/2002 |
| WO | 0213875 | A2 | 2/2002 |
| WO | 0214309 | A1 | 2/2002 |
| WO | 02051854 | A1 | 7/2002 |
| WO | 03009874 | A1 | 2/2003 |
| WO | 03011115 | A2 | 2/2003 |
| WO | 03013617 | A2 | 2/2003 |
| WO | 03014157 | A2 | 2/2003 |
| WO | 03074523 | A2 | 9/2003 |
| WO | 03088823 | A2 | 10/2003 |
| WO | 2004006965 | A2 | 1/2004 |
| WO | 2004006979 | A2 | 1/2004 |
| WO | 2004065407 | A2 | 8/2004 |
| WO | 2004074267 | A1 | 9/2004 |
| WO | 2005001415 | A2 | 1/2005 |
| WO | 2005007200 | A1 | 1/2005 |
| WO | 2005108379 | A1 | 11/2005 |
| WO | 2005115997 | A1 | 12/2005 |
| WO | 2006002873 | A2 | 1/2006 |
| WO | 2006002874 | A1 | 1/2006 |
| WO | 2006014530 | A2 | 2/2006 |
| WO | 2006029560 | A1 | 3/2006 |
| WO | 2006080022 | A2 | 8/2006 |
| WO | 2006136460 | A2 | 12/2006 |
| WO | 2007042506 | A1 | 4/2007 |
| WO | 2007064226 | A2 | 6/2007 |
| WO | 2007064227 | A1 | 6/2007 |
| WO | 2007069909 | A2 | 6/2007 |
| WO | 2007084264 | A2 | 7/2007 |
| WO | 2007088129 | A2 | 8/2007 |
| WO | 2007100563 | A2 | 9/2007 |
| WO | 2007111514 | A1 | 10/2007 |
| WO | 2007111515 | A2 | 10/2007 |
| WO | 2007112100 | A2 | 10/2007 |
| WO | 2007128567 | A1 | 11/2007 |
| WO | 2007128873 | A1 | 11/2007 |
| WO | 2007141009 | A1 | 12/2007 |
| WO | 2008017122 | A1 | 2/2008 |
| WO | 2008022263 | A2 | 2/2008 |
| WO | 2008087017 | A2 | 7/2008 |
| WO | 2008125594 | A1 | 10/2008 |
| WO | 2009013350 | A2 | 1/2009 |
| WO | 2009018332 | A1 | 2/2009 |
| WO | 2009027388 | A2 | 3/2009 |
| WO | 2009030735 | A1 | 3/2009 |
| WO | 2009047245 | A1 | 4/2009 |
| WO | 2009077575 | A1 | 6/2009 |
| WO | 2009080739 | A1 | 7/2009 |
| WO | 2009093082 | A1 | 7/2009 |
| WO | 2009098191 | A2 | 8/2009 |
| WO | 2009098192 | A1 | 8/2009 |
| WO | 2009103744 | A2 | 8/2009 |
| WO | 2009127715 | A1 | 10/2009 |
| WO | 2009143101 | A2 | 11/2009 |
| WO | 2010006755 | A2 | 1/2010 |
| WO | 2010039609 | A2 | 4/2010 |
| WO | 2010056590 | A2 | 5/2010 |
| WO | 2010066815 | A2 | 6/2010 |
| WO | 2010108125 | A2 | 9/2010 |
| WO | 2010147666 | A1 | 12/2010 |
| WO | 2011031740 | A1 | 3/2011 |
| WO | 2011073371 | A1 | 6/2011 |
| WO | 2011088193 | A2 | 7/2011 |
| WO | 2011117254 | A1 | 9/2011 |

(56) References Cited

FOREIGN PATENT DOCUMENTS

| | | | |
|---|---|---|---|
| WO | 2011124672 | A1 | 10/2011 |
| WO | 2011158189 | A1 | 12/2011 |
| WO | 2012059576 | A1 | 5/2012 |
| WO | 2012142702 | A1 | 10/2012 |
| WO | 2012143355 | A1 | 10/2012 |
| WO | 2013022797 | A1 | 2/2013 |
| WO | 2013087965 | A1 | 6/2013 |
| WO | 2013189801 | A1 | 12/2013 |
| WO | 2014052471 | A1 | 4/2014 |
| WO | 2014075079 | A1 | 5/2014 |
| WO | 2014110372 | A1 | 7/2014 |
| WO | 2014124943 | A1 | 8/2014 |
| WO | 2014197763 | A1 | 12/2014 |
| WO | 2015071856 | A1 | 5/2015 |
| WO | 2015071857 | A1 | 5/2015 |
| WO | 2015171792 | A1 | 11/2015 |
| WO | 2016050210 | A1 | 4/2016 |
| WO | 2016149363 | A1 | 9/2016 |
| WO | 2016193190 | A1 | 12/2016 |
| WO | 2017004220 | A1 | 1/2017 |
| WO | 2017030728 | A1 | 2/2017 |
| WO | 2017098038 | A1 | 6/2017 |
| WO | 2017098044 | A1 | 6/2017 |
| WO | 2017178301 | A1 | 10/2017 |
| WO | 2018096082 | A1 | 5/2018 |
| WO | 2018108780 | A1 | 6/2018 |

OTHER PUBLICATIONS

Verwilst P., et al., "A Tripodal Ruthenium-Gadolinium Metallostar as a Potential alphavBeta3 Integrin Specific Bimodal Imaging Contrast Agent," Inorganic Chemistry, May 2012, vol. 51 (11), pp. 6405-6411.

Verwilst P., et al., "Recent Advances in Gd-chelate Based Bimodal Optical/MRI Contrast Agents," Chemical Society Reviews, Jan. 2015, vol. 44 (7), pp. 1791-1806.

Vetterlein K., et al., "Capillary Electrophoresis for the Characterization of the Complex Dendrimeric Contrast Agent Gadomer," Electrophoresis, Jun. 2006, vol. 27 (12), pp. 2400-2412.

Vetterlein K., et al., "Comprehensive Profiling of the Complex Dendrimeric Contrast Agent Gadomer Using a Combined Approach of CE, MS, and CE-MS," Electrophoresis, Aug. 2007, vol. 28 (17), pp. 3088-3099.

Wang J., et al., "Anion Separation and Preconcentration with Cyclen and Cyclen-Resorcinarene Derivatives," Journal of Chromatographic Science, Aug. 2009, vol. 47 (7), pp. 510-515.

Wang J., et al., "Multiple Anion Binding by a Zinc-containing Tetratopic Cyclen-resorcinarene," Journal of Inclusion Phenomena and Macrocyclic Chemistry, Jun. 2010, vol. 67 (1), pp. 55-61.

Wang J., et al., "Synthesis, Characterization, and Activity of Cyclotriphosphazene-Cyclene Conjugates," Phosphorus, Sulfur, and Silicon and the Related Elements, 2013, vol. 188 (1-3), pp. 54-58.

Wang L., et al., "A Multiple Gadolinium Complex Decorated Fullerene as a Highly Sensitive T(1) Contrast Agent," Chemical Communications, Mar. 2015, vol. 51 (21), pp. 4390-4393.

Wang L., et al., "Catalytic Cooperativity, Nuclearity, and O02/H2O2 Specificity of Multi-Copper(II) Complexes of Cyclen-Tethered Cyclotriphosphazene Ligands in Aqueous Media," European Journal of Inorganic Chemistry, Nov. 2017, vol. 2017 (42), pp. 4899-4908.

Wang Y., et al., "Incidence of Nephrogenic Systemic Fibrosis After Adoption of Restrictive Gadolinium-based Contrast Agent Guidelines," Radiology, Jul. 2011, vol. 260 (1), pp. 105-111.

Wangler C., et al., "Antibody-dendrimer Conjugates: the Number, Not the Size of the Dendrimers, Determines the Immunoreactivity," Bioconjugate Chemistry, Apr. 2008, vol. 19 (4), pp. 813-820.

Wangler C., et al., "Improved Syntheses and Applicability of Different DOTA Building Blocks for Multiply Derivatized Scaffolds," Bioorganic Medicinal Chemistry, Mar. 2008, vol. 16 (5), pp. 2606-2616.

Werner E.J., et al., "High-Relaxivity MRI Contrast Agents: Where Coordination Chemistry Meets Medical Imaging," Angewandte Chemie, 2008, vol. 47 (45), pp. 8568-8580.

Wischnjow A., et al., "Renal Targeting: Peptide-Based Drug Delivery to Proximal Tubule Cells," Bioconjugate Chemistry, Apr. 2016, vol. 27 (4), pp. 1050-1057.

Wu X., et al., "Synthesis and Evaluation of a Peptide Targeted Small Molecular Gd-DOTA Monoamide Conjugate for MR Molecular Imaging of Prostate Cancer," Bioconjugate Chemistry, Aug. 2012, vol. 23 (8), pp. 1548-1556.

Xiao Yu-dong et al., MRI contrast agents: Classification and application (Review), International Journal of Molecular Medicine, 2016, 38, 1319-1326.

Xu H., et al., "Tetraphenylethene Based Zinc Complexes as Fluorescent Chemosensors for Pyrophosphate Sensing," Chinese Chemical Letters, Jul. 2015, vol. 26 (7), pp. 877-880.

Yang L., et al., "Nephrogenic Systemic Fibrosis and Class Labeling of Gadolinium-based Contrast Agents by the Food and Drug Administration," Radiology, Oct. 2012, vol. 265 (1), pp. 248-253.

Yang X., et al., "Synthesis and Characterization of Side Group-Modified Tetradentate Cyclotriphosphazene Derivatives," Phosphorus, Sulfur, and Silicon and the Related Elements, 2012, vol. 187 (6), pp. 722-727.

Yoo C.E., et al., "Degradation of Myoglobin by Polymeric Artificial Metalloproteases Containing Catalytic Modules with Various Catalytic Group Densities: Site Selectivity in Peptide Bond Cleavage," Journal of the American Chemical Society, Nov. 2003, vol. 125 (47), pp. 14580-14589.

Zhang W., et al., "A Tetranuclear Gadolinium(III) Macrocyclic Complex: Towards High Relaxivity with the Rigid Linkers for Magnetic Resonance Imaging Contrast Agent," Zeitschrift Fur Anorganische Und Allgemeine Chemie, Mar. 2015, vol. 641 (3-4), pp. 578-585.

Zhang Y., et al., "Small Cyclenylmidazolium-Containing Molecules and Their Interactions with DNA," Chemistry Biodiversity, 2014, vol. 11, pp. 233-244.

Zhao G., et al., "Two Multinuclear Gdlll Macrocyclic Complexes as Contrast Agents with High Relaxivity and Stability Using Rigid Linkers," Inorganica Chimica Acta, Sep. 2013, vol. 406, pp. 146-152.

Zhou Z., et al., "Peptide Targeted Tripod Macrocyclic Gd(III) Chelates for Cancer Molecular MRI," Biomaterials, Oct. 2013, vol. 34 (31), pp. 7683-7693.

Zompa L.J., et al., "Equilibrium Studies of Polynucleating Ligands. I. The Interaction of Tetrakis(aminomethyl)methane with Copper(II) and Hydrogen Ions," Journal of the American Chemical Society, Nov. 1966, vol. 88 (22), pp. 5186-5191.

Zulkefeli M., et al., "Design and Synthesis of a Stable Supramolecular Trigonal Prism Formed by the Self-assembly of a Linear Tetrakis(Zn2+-cyclen) Complex and Trianionic Trithiocyanuric Acid in Aqueous Solution and its Complexation with DNA (Cyclen = 1,4,7, 10-tetraazacyclododecane)," Inorganic Chemistry, Oct. 2009, vol. 48 (19), pp. 9567-9578.

Notni J., et al., "Convenient Synthesis of 68Ga-Labeled Gadolinium(III) Complexes: Towards Bimodal Responsive Probes for Functional Imaging with PET/MRI," Chemistry a European Journal, Sep. 2013, vol. 19 (38), pp. 12602-12606.

Olga Capasso "Letter accompanying Notice of OppositionAgainst EP 3303307B1" and "Notice of Opposition Against EP 3303307B1", submitted to European Patent Office, Jun. 4, 2020.

Oltmanns D., et al., "Zn(II)-bis(cyclen) Complexes and the Imaging of Apoptosis/Necrosis," Bioconjugate Chemistry, Oct. 2011, vol. 22 (12), pp. 2611-2624.

Overoye-Chan K., et al., "EP-2104R: A Fibrin-Specific Gadolinium-Based MRI Contrast Agent for Detection of Thrombus," Journal of the American Chemical Society, May 2008, vol. 130 (18), pp. 6025-6039.

Pang X., et al., "Bimetallic Schiff-base Aluminum Complexes Based on Pentaerythrityl Tetramine and their Stereoselective Polymerization of Racemic Lactide," RSC Advances, May 2014, vol. 4, pp. 22561-22566.

Paris J., et al., "Auto-assembling of Ditopic Macrocyclic Lanthanide Chelates with Transition-metal Ions. Rigid Multimetallic High

(56) References Cited

OTHER PUBLICATIONS

Relaxivity Contrast Agents for Magnetic Resonance Imaging," Inorganic Chemistry, Jun. 2006, vol. 45 (13), pp. 5092-5102.
Pikkemaat J.A., et al., "Dendritic PARACEST Contrast Agents for Magnetic Resonance Imaging," Contrast Media Molecular Imaging, Sep.-Oct. 2007, vol. 2 (5), pp. 229-239.
Pittman C.U., et al., "Columns: Polymer Supports in Synthesis," Polymer News, 2005, vol. 30 (1), pp. 14-15.
Polyanichko K.V., et al., "Synthesis of Dendronized Polymeric Chelating Agents using Hydrazone Ligation Strategy," European Polymer Journal, Jul. 2017, vol. 92, pp. 117-125.
Preslar A.T., et al., "Correction to Gd(III)-Labeled Peptide Nanofibers for Reporting on Biomaterial Localization in Vivo," ACS Nano, Nov. 2015, vol. 9 (11), p. 11502.
Preslar A.T., et al., "Gd(III)-Labeled Peptide Nanofibers for Reporting on Biomaterial Localization in Vivo," ACS Nano, Jun. 2014, vol. 8 (7), pp. 7325-7332.
Ranganathan R.S., et al., "New Multimeric Magnetic Resonance Imaging Agents," Investigative Radiology, Nov. 1998, vol. 33 (11), pp. 779-797.
Raymond Kenneth n., et al., Next Generation, Hight Relaxivity Gadolinium MRI Agents, Bioconjugate Chem., 2005, vol. 16, Issue 1, 3-8.
Regueiro-Figueroa M., et al., "Structure and Dynamics of Lanthanide(III) Complexes with an N-Alkylated do3a Ligand (H3do3a = 1,4,7, 10-Tetraazacyclododecane-1,4,7-triacetic Acid): A Combined Experimental and DFT Study," European Journal of Inorganic Chemistry, Aug. 2010, vol. 2010 (23), pp. 3586-3595.
Reichert D.E., et al., "Molecular Mechanics Investigation of Gadolinium(III) Complexes," Inorganic Chemistry, Nov. 1996, vol. 35 (24), pp. 7013-7020.
Revesz L., et al., "Synthesis of Novel Piperazine Based Building Blocks: 3,7,9-triazabicyclo[3.3.1]nonane, 3,6,8-triazabicyclo[3.2.2]nonane, 3-oxa-7,9-diazabicyclo[3.3.1]nonane and 3-oxa-6, 8-diazabicyclo[3.2.2]nonane," Tetrahedron Letters, Aug. 2005, vol. 46 (33), pp. 5577-5580.
Riechers A., et al., "Binding of Phosphorylated Peptides and Inhibition of their Interaction with Disease-relevant Human Proteins by Synthetic Metal-chelate Receptors," Journal of Molecular Recognition, May-Jun. 2010, vol. 23 (3), pp. 329-334.
Rinck et al, Field strength and dose dependence of contrast enhancement by gadolinium-based MR contrast agents, European Radiology, 1999, vol. 9, 998-1004.
Rodriguez-Rodriguez A., et al., "Stable Mn2+, Cu2+ and Ln3+ Complexes with Cyclen-based Ligands Functionalized with Picolinate Pendant Arms," Dalton Transactions, 2015, vol. 44, pp. 5017-5031.
Rohrer M., et al., "Comparison of Magnetic Properties of MRI Contrast Media Solutions at Different Magnetic Field Strengths," Investigative Radiology, Nov. 2005, vol. 40 (11), pp. 715-724.
Rompp Kompakt., Basislexikon Chemie, 1998, 1213-1214.
Rompp Kompakt., Basislexikon Chemie, 1999, 2436.
Roy O., et al., The tert-Butyl Side Chain: A Powerful Means to Lock Peptoid Amide Bonds in the Cis Conformation, Organic Letters, 2013, vol. 15, No. 9, 2246-2249.
Scarso A., et al., "Tripodal, Cooperative, and Allosteric Transphosphorylation Metallocatalysts," The Journal of Organic Chemistry, Jan. 2007, vol. 72 (2), pp. 376-385.
Schmidek H.H., et al., "Morphological Studies of Rat Brain Tumors Induced by N-nitrosomethylurea," Mar. 1971, vol. 34 (3), pp. 335-340.
Schuhle D.T., et al., "Calix[4]arenes as Molecular Platforms for Magnetic Resonance Imaging (MRI) Contrast Agents," Chemistry a European Journal, 2009, vol. 15 (13), pp. 3290-3296.
Schuhle D.T., et al., "Densely Packed Gd(III)-chelates with Fast Water Exchange on a Calix[4]arene Scaffold: a Potential MRI Contrast Agent," Dalton Transactions, Jan. 2010, vol. 39, pp. 185-191.
Schuhle D.T., et al., "Liposomes with Conjugates of a Calix[4]arene and a Gd-DOTA Derivative on the Outside Surface; an Efficient Potential Contrast Agent for MRI," Chemical Communications, 2010, vol. 46, pp. 4399-4401.
Schurink H.B., "Pentaerythrityl Bromide and lodide," Organic Syntheses, 1937, vol. 17, p. 73.
Sherry A. dean, et al., Chemical Exchange Saturation Transfer Contrast Agents For Magnetic Resonance Imaging, Annu Rev. Biomed Eng., 2008, 10, 391-411.
Siegfried L., et al., "Homo- and Heteropolynuclear Ni2+ and Cu2+ Complexes of Polytopic Ligands, Consisting of a Tren Unit Substituted with Three 12-membered Tetraazamacrocycles," Dalton Transactions, Nov. 2007, pp. 4797-4810.
Song Y., et al., "Synthesis of Multimeric MR Contrast Agents for Cellular Imaging," Journal of the American Chemical Society, May 2008, vol. 130 (21), pp. 6662-6663.
Sorensen T.J., et al., "Preparation and Study of an f,f,f',f'' Covalently Linked Tetranuclear Hetero-trimetallic Complex—a Europium, Terbium, Dysprosium Triad," Chemical Communications, 2013, vol. 49 (8), pp. 783-785.
Sorensen T.J., et al., "Triheterometallic Lanthanide Complexes Prepared from Kinetically Inert Lanthanide Building Blocks," European Journal of Inorganic Chemistry, Apr. 2017, vol. 2017 (15), pp. 2165-2172.
Suchy et al., A paramagnetic chemical exchange-based MRI probe metabolized by cathepsin D: design, synthesis and cellular uptake studies, Organic Biomolecular Chemistry, Mar. 26, 2010, vol. 8, 2560-2566.
Suh John t., et al., Angiotensin-Convertin Enzyme Inhibitors. New Orally Active Antihypertensive (Mercaptoalkanoyl)- and [(Acylthio)alkanoyl]glycine Derivatives, Journal of Medicinal Chemistry, 1985, vol. 28, No. 1, 57-66.
Sung S., et al., "Multimetallic Complexes and Functionalized Gold Nanoparticles Based on a Combination of d- and f-Elements," Inorganic Chemistry, Feb. 2014, vol. 53 (4), pp. 1989-2005.
Sy M., et al., "Spectroscopic Properties of a Family of Mono- to Trinuclear Lanthanide Complexes," European Journal of Inorganic Chemistry, Apr. 2017, vol. 2017 (14), pp. 2122-2129.
Takemura H., et al., "Synthesis and Inclusion Properties of Pyridinophane-linked Macrocycles," Journal of the Chemical Society, Perkin Transactions 1, Jan. 1996, pp. 277-280.
Tamain C., et al., "Coordination of Tetravalent Actinides (An=ThIV, UIV, NpIV, PuIV) with DOTA: from Dimers to Hexamers," Chemistry a European Journal, May 2017, vol. 23 (28), pp. 6864-6875.
Tamain C., et al., "First Evidence of a Water-Soluble Plutonium(IV) Hexanuclear Cluster," European Journal of Inorganic Chemistry, Aug. 2016, vol. 2016 (22), pp. 3536-3540.
Tanaka T., et al., "11B Nmr Probes of Copper(II): Finding and Implications of the Cu2+-Promoted Decomposition of ortho-Carborane Derivatives," European Journal of Inorganic Chemistry, Apr. 2016, vol. 2016 (12), pp. 1819-1834.
Tei L., et al., "Target Visualization by MRI Using the Avidin/Biotin Amplification Route: Synthesis and Testing of a Biotin-Gd-DOTA Monoamide Trimer," Chemistry a European Journal, Jul. 2010, vol. 16 (27), pp. 8080-8087.
Terreno E., et al., "Highly Shifted Lipocest Agents Based on the Encapsulation of Neutral Polynuclear Paramagnetic Shift Reagents," Chemical Communications, 2008, pp. 600-602.
Thompson M.K., et al., "Cooperative Processes Governing Formation of Small Pentanuclear Lanthanide(III) Nanoclusters and Energy Transport within and between Them," Inorganic Chemistry, Aug. 2001, vol. 40 (17), pp. 4332-4341.
Thompson M.K., et al., "Formation of Two Diverse Classes of Poly(amino-alkoxide) Chelates and their Mononuclear and Polynuclear Lanthanide(III) Complexes," Inorganic Chemistry, Jul. 2003, vol. 42 (16), pp. 4828-4841.
Tombach B., et al., "Value of 1.0- M Gadolinium Chelates: Review of Preclinical and Clinical Data on Gadobutrol," European Radiology, Jun. 2002, vol. 12 (6), pp. 1550-1556.
Toth E., et al., Chapter 2: Relaxivity of Gadolinium(III) Complexes: Theory and Mechanism, The Chemistry of Contrast Agents in Medical Magnetic Resonance Imaging, John Wiley Sons, Ltd., 2013, Second Edition, 25-81.

(56) References Cited

OTHER PUBLICATIONS

Tremblay M.S., et al., "Synthesis of Luminescent Heterometallic Bis-lanthanide Complexes via Selective, Sequential Metallation," Chemical Communications, Sep. 2006, pp. 4116-4118.
Tropiano M., et al., "Using Remote Substituents to Control Solution Structure and Anion Binding in Lanthanide Complexes," Chemistry a European Journal, Dec. 2013, vol. 19 (49), pp. 16566-16571.
Aime S., et al., "Biodistribution of Gadolinium-Based Contrast Agents, Including Gadolinium Deposition," Journal of Magnetic Resonance Imaging, Dec. 2009, vol. 30 (6), pp. 1259-1267.
Averin A.D., et al., "Synthesis of a New Family of bi- and Polycyclic Compounds via Pd-catalyzed Amination of 1,7-di (3-bromobenzyl)cyclen," Tetrahedron Letters, Jun. 2008, vol. 49 (24), pp. 3950-3954.
Banerjee S.R., et al., "Synthesis and Evaluation of Gd(III) -Based Magnetic Resonance Contrast Agents for Molecular Imaging of Prostate-Specific Membrane Antigen," Angewandte Chemie, Sep. 2015, vol. 54 (37), pp. 10778-10782.
Bazzicalupi C., et al., "Tren-based Tris-macrocycles as Anion Hosts. Encapsulation of Benzenetricarboxylate Anions within Bowl-shaped Polyammonium Receptors," The Journal of Organic Chemistry, May 2005, vol. 70 (11), pp. 4257-4266.
Bazzicalupi C., et al., "Synthesis of New Tren-based Tris-macrocycles. Anion Cluster Assembling Inside the Cavity Generated by a Bowl-shaped Receptor," The Journal of Organic Chemistry, Dec. 2002, vol. 67 (25), pp. 9107-9110.
Bazzicalupi C., et al., "Zn(II) Coordination to Tren-based Tris-macrocycles. Activity of their Trinuclear Zn(II) Complexes in Carboxy- and Phosphate-ester Hydrolysis," Dalton Transactions, Aug. 2003, pp. 3574-3580.
Becker S., et al., "Application of Gadolinium-Based Contrast Agents and Prevalence of Nephrogenic Systemic Fibrosis in a Cohort of End-Stage Renal Disease Patients on Hemodialysis," Nephron Clinical Practice, Nov. 2012, vol. 121 (1-2), pp. C91-C94.
Bencini A., et al., "A Tris-Macrocycle with Proton Sponge Characteristics as Efficient Receptor for Inorganic Phosphate and Nucleotide Anions," European Journal of Organic Chemistry, Nov. 2009, vol. 2009 (32), pp. 5610-5621.
Bencini A., et al., "Proton and Cu(II) Binding to Tren-based Tris-macrocycles. Affinity Towards Nucleic Acids and Nuclease Activity," Dalton Transactions, Feb. 2003, pp. 793-800.
Berge S.M., et al., "Pharmaceutical Salts," Journal of Pharmaceutical Sciences, Jan. 1977, vol. 66 (1), pp. 1-19.
Besenius P., et al., "Controlling the Growth and Shape of Chiral Supramolecular Polymers in Water," Proceedings of the National Academy of Sciences of the United States of America, Oct. 2010, vol. 107 (42), pp. 17888-17893.
Besenius P., et al., "Peptide Functionalised Discotic Amphiphiles and their Self-assembly into Supramolecular Nanofibres," Soft Matter, 2011, vol. 7, pp. 7980-7983.
Bhuniya S., et al., "Uridine-based Paramagnetic Supramolecular Nanoaggregate with High Relaxivity Capable of Detecting Primitive Liver Tumor Lesions," Biomaterials, Sep. 2011, vol. 32 (27), pp. 6533-6540.
Bhuyan M., et al., "BiomaterialsRigid Luminescent Bis-Zinc(II)-Bis-Cyclen Complexes for the Detection of Phosphate Anions and Non-Covalent Protein Labeling in Aqueous Solution," European Journal of Organic Chemistry, May 2011, vol. 2011(15), pp. 2807-2817.
Boldrini V., et al., "Expeditious N-monoalkylation of 1,4,7,10-tetraazacyclododecane (Cyclen) via Formamido Protection," Tetrahedron Letters, Aug. 2000, vol. 41 (33), pp. 6527-6530.
Boros E., et al., "Gd(DOTAla): A Single Amino Acid Gd-complex as a Modular Tool for High Relaxivity MR Contrast Agent Development," Journal of the American Chemical Society, Dec. 2012, vol. 134 (48), pp. 19858-19868.
Bruckner K., et al., "Solid Phase Synthesis of Short Peptide-Based Multimetal Tags for Biomolecule Labeling," Bioconjugate Chemistry, May 2014, vol. 25 (6), pp. 1069-1077.
Bumb et al.,, Macromolecular and Dendrimer Based Magnetic Resonance Contrast Agents, Acta Radiol., Sep. 2010, vol. 51/Issue 7, 751-767.
Caravan P., "Strategies for Increasing the Sensitivity of Gadolinium Based Mri Contrast Agents," Chemical Society Reviews, Jun. 2006, vol. 35 (6), pp. 512-523.
Carney C.E., et al., "Cell Labeling via Membrane-Anchored Lipophilic MR Contrast Agents," Bioconjugate Chemistry, May 2014, vol. 25 (5), pp. 945-954.
Carney C.E., et al., "Nanodiscs as a Modular Platform for Multimodal MR-Optical Imaginga," Bioconjugate Chemistry, May 2015, vol. 26 (5), pp. 899-905.
Chang C.A., et al., "Synthesis, Characterization, and Crystal Structures of M(D03A) (M=Fe, Gd) and Na[M(DOTA)] (M=Fe, Y, Gd)," Inorganic Chemistry, Aug. 1993, vol. 32 (16), pp. 3501-3508.
Chen Liu qi, et al., Evaluating pH in the Extracellular Tumor Microenvironment Using CEST MRI and Other Imaging Methods, Adv. Radiol., 2015, 1-39.
Chen Z., et al., "Fullerenes Cn 36 (n = 0, 2+, 2-) and their B- and N-doped Analogues," Chemical Physics Letters, Oct. 2000, vol. 329 (2000), pp. 47-51.
Coderre J.A., et al., "Selective Delivery of Boron by the Melanin Precursor Analogue p. Boronophenylalanine to Tumors Other Than Melanoma," Cancer Research, Jan. 1990, vol. 50, pp. 138-141.
Cross L.C., et al., "IUPAC Commission on Nomenclature of Organic Chemistry, Rules for Nomenclature of Organic Chemistry Section E: Stereochemistry, ," Pure and Applied Chemistry, 1976, vol. 45, pp. 11-30.
Cui P., et al., "An lon Pair Scandium Hydride Supported by a Dianionic (NNNN)-type Macrocycle Ligand," Chemical Communications, 2014, vol. 50, pp. 424-426.
Cui P., et al., "Dehydrogenation of Amine-borane Me2NH. BH3 Catalyzed by a Lanthanum-hydride Complex," Chemistry a European Journal, Sep. 2013, vol. 19 (40), pp. 13437-13444.
Cui P., et al., "Heterometallic Potassium Rare-Earth-Metal Allyl and Hydrido Complexes Stabilized by a Dianionic (NNNN)-Type Macrocyclic Ancillary Ligand," Organometallics, 2013, vol. 32 (5), pp. 1176-1182.
Cvrtila I., et al., "Redox Control over Acyl Hydrazone Photoswitches," Journal of the American Chemical Society, Jul. 2017, vol. 139 (36), pp. 12459-12465.
Decision of the Opposition Division on EP3303307B1, Dec. 20, 2021.
Declaration by Dr. Markus Berger, Senior Scientist and Dr. Thomas Frenzel, Senior Scientist, Bayer AG, Jul. 2, 2021.
Delepine A., et al., "Selective Mono-n-alkylation of Triethylenetetraamine. A New Versatile Route to Polylinear Aza-ligands," Tetrahedron Letters, May 2009, vol. 50 (21), pp. 2521-2524.
Delepine A., et al., "From Flexible to Constrained Tris(tetraamine) Ligands: Synthesis, Acid-Base Properties, and Structural Effect on the Coordination Process with Nucleotides," European Journal of Organic Chemistry, Oct. 2010, vol. 2010 (28), pp. 5380-5390.
Di Gregorio E., et al., "Gd Loading by Hypotonic Swelling: an Efficient and Safe Route for Cellular Labeling," Contrast Media Molecular Imaging, Nov.-Dec. 2013, vol. 8 (6), pp. 475-486.
Eggenspiller A., et al., "Design of Porphyrin-dota-Like Scaffolds as All-in-One Multimodal Heterometallic Complexes for Medical Imaging," European Journal of Organic Chemistry, Oct. 2013, vol. 2013 (29), pp. 6629-6643.
European Search Report for Application No. EP15170658.7, mailed on Dec. 4, 2015, 6 pages.
Faulkner S., et al., "Lanthanide-Sensitized Lanthanide Luminescence: Terbium-Sensitized Ytterbium Luminescence in a Trinuclear Complex," Journal of the American Chemical Society, Aug. 2003, vol. 125 (35), pp. 10526-10527.
Fischer Gunter, Chemical aspects of peptide bond isomerisation, The Royal Society of Chemistry, Chem Soc Rev, 2000, 29, 119-127.
Fisher M.J., et al., "Trivalent Gd-DOTA Reagents for Modification of Proteins," RSC Advances, Dec. 2015, vol. 5 (116), pp. 96194-96200.

(56) References Cited

OTHER PUBLICATIONS

Fleischer E.B., et al., "Conversion of Aliphatic and Alicyclic Polyalcohols to the Corresponding Primary Polyamines," The Journal of Organic Chemistry, Oct. 1971, vol. 36 (20), pp. 3042-3044.
Frenzel T., et al., "Stability of Gadolinium-Based Magnetic Resonance Imaging Contrast Agents in Human Serum at 37°C," Investigative Radiology, Dec. 2008, vol. 43 (12), pp. 817-828.
Fries Peter, md, et al., P03277 - A New Approach to Achieve High-Contrast Enhancement, Investigative Radiology, Dec. 2015, vol. 50 No. 12, 835-842.
Galibert M., et al., "RGD-cyclam Conjugate: Synthesis and Potential Application for Positron Emission Tomography," Bioorganic Medicinal Chemistry Letters, Sep. 2010, vol. 20 (18), pp. 5422-5425.
Ganb A., et al., "Synthesis and Structural Characterization of a Cyclen-Derived Molecular Cage," Organic Letters, Nov. 2015, vol. 17 (23), pp. 5850-5853.
Giesel F.L., et al., "High-relaxivity Contrast-enhanced Magnetic Resonance Neuroimaging: a Review," European Radiology, Oct. 2010, vol. 20 (10), pp. 2461-2474.
Grauer A., et al., "Synthetic Receptors for the Differentiation of Phosphorylated Peptides with Nanomolar Affinities," Chemistry a European Journal, Oct. 2008, vol. 14 (29), pp. 8922-8927.
Greene and Wuts., Chapter 7: Protection For The Amino Group, Protective Groups in Organic Synthesis, John Wiley Sons, Inc., 1999, Third Edition, 494-653.
Grunberg J., et al., "DOTA-Functionalized Polylysine: A High Number of DOTA Chelates Positively Influences the Biodistribution of Enzymatic Conjugated Anti-Tumor Antibody chCE7agl," PLoS One, 2013, vol. 8 (4), pp. 1-11.
Harrison V.S.R., et al., "A Multimeric MR-optical Contrast Agent for Multimodal Imaging," Chemical Communications, Aug. 2014, vol. 50, pp. 11469-11471.
Harrison V.S.R., et al., "Multimeric Near IR-MR Contrast Agent for Multimodal In Vivo Imaging," Journal of the American Chemical Society, Jul. 2015, vol. 137 (28), pp. 9108-9116.
Hayes W., et al., "One-pot Synthesis of Multivalent Arrays of Mannose Monoand Disaccharides," Tetrahedron, Sep. 2003, vol. 59 (40), pp. 7983-7996.
Helm L., "Optimization of Gadolinium-based MRI Contrast Agents for High Magnetic-field Applications," Future Medicinal Chemistry, Mar. 2010, vol. 2 (3), pp. 385-396.
Hermann P., et al., "Gadolinium(III) Complexes as MRI Contrast Agents: Ligand Design and Properties of the Complexes," Dalton Transactions, Jun. 2008, pp. 3027-3047.
Hill L.R., et al., "Ternary Self-assemblies in Water: Forming a Pentanuclear ReLn4 Assembly by Association of Binuclear Lanthanide Binding Pockets With Fac-Re(CO)3(Dinicotinate)2cl," Dalton Transactions, Aug. 2013, vol. 42, pp. 16255-16258.
Huang Z., et al., "A Fluorinated Dendrimer-Based Nanotechnology Platform: New Contrast Agents for High Field Imaging," Investigative Radiology, Oct. 2010, vol. 45 (10), pp. 641-654.
International Preliminary Report on Patentability from PCT Application No. PCT/EP2019/082117, May 25, 2021.
International Search Report and Written Opinion for Application No. PCT/EP2016/062105, mailed on Jul. 13, 2016, 10 pages.
International Search Report and Written Opinion from PCT Application No. PCT/EP2017/080306, Mar. 6, 2018.
Iwaki S., et al., "A Design Strategy for Small Molecule-based Targeted MRI Contrast Agents: Their Application for Detection of Atherosclerotic Plaques," Organic Biomolecular Chemistry, Nov. 2014, vol. 12 (43), pp. 8611-8618.
Jacques V., et al., "High-relaxivity Magnetic Resonance Imaging Contrast Agents. Part 2. Optimization of Inner- and Second-sphere Relaxivity," Investigative Radiology, Oct. 2010, vol. 45 (10), pp. 613-624.
Jacques V., et al., Synthesis of MRI Contrast Agents II. Macrocyclic Ligands, Table of Contents.
Jagadish B., et al., On the synthesis of 1,4,7-tris(tert-butoxycarbonylmethyl)-1,4,7, 10-tetraazacyclododecane, Tetrahedron Letters, 2011, 52, 2058-2061.
Jebasingh B., et al., "Synthesis and Relaxivity Studies of a Tetranuclear Gadolinium(III) Complex of DO3A as a Contrast-Enhancing Agent for MRI," Inorganic Chemistry, Nov. 2005, vol. 44 (25), pp. 9434-9443.
Kimura E., et al., "A Tris(Znll-1,4,7, 10-tetraazacyclododecane) Complex as a New Receptor for Phosphate Dianions in Aqueous Solution," Journal of the American Chemical Society, Apr. 1997, vol. 119 (13), pp. 3068-3076.
Kimura E., et al., "Selective and Efficient Recognition of Thymidylylthymidine (TpT) by Bis(Znll-cyclen) and Thymidylylthymidylylthymidine (TpTpT) by Tris(Znll-cyclen) at Neutral pH in Aqueous Solution," Chemistry a European Journal, Nov. 1999, vol. 5 (11), pp. 3113-3123.
Kobelev S.M., et al., "Macrobicycles Based on Cyclen and Cyclam Containing 1,3-disubstituted Adamantane Moieties," Archive for Organic Chemistry, Sep. 2012, vol. 2012 (7), pp. 196-209.
Kobelev S.M., et al., "Synthesis of Macrobi- and Macrotricyclic Compounds Comprising Pyrimidyl Substituted Cyclen and Cyclam," Heterocycles, 2011, vol. 82 (2), pp. 1447-1476.
Kompp Kompakt., Basislexikon Chemie, 1999, 2586.
Konig B., et al., "Synthesis of Functionalized Aza-macrocycles and the Application of their Metal Complexes in Binding Processes," Journal of Inclusion Phenomena and Macrocyclic Chemistry, May 2000, vol. 37 (1-4), pp. 39-57.
Kriemen E., et al., "Synthesis and Structural Analysis of 1,4,7, 10-Tetraazacyclododecane-1,4,7,10-tetraazidoethylacetic Acid (DOTAZA) Complexes," European Journal of Inorganic Chemistry, Nov. 2015, vol. 2015 (32), pp. 5368-5378.
Kriemen E., et al., "Synthesis of 1,4,7,10-Tetra-azacyclododecan-1,4,7,10-tetra-azidoethylacetic Acid (DOTAZA) and Related "Clickable" DOTA Derivatives," Chemistry an Asian Journal, Aug. 2014, vol. 9 (8), pp. 2197-2204.
Krishan Kumar., et al., "Synthesis, Stability, and Crystal Structure Studies of Some Ca2+, Cu2+, and Zn2+ Complexes of Macrocyclic Polyamino Carboxylates," Inorganic Chemistry, Dec. 1995, vol. 34 (26), pp. 6472-6480.
Kumar A., et al., "Molecular Platform for Design and Synthesis of Targeted Dual-Modality Imaging Probes," Bioconjugate Chemistry, Jan. 2015, vol. 26 (3), pp. 549-558.
Laurent S., et al., "Stability of MRI Paramagnetic Contrast Media: a Proton Relaxometric Protocol for Transmetallation Assessment," Investigative Radiology, Feb. 2001, vol. 36 (2), pp. 115-122.
Leich V., et al., "Formation of a Cationic Calcium Hydride Cluster with a "Naked" Triphenylsilyl Anion by Hydrogenolysis of Bis(triphenylsilyl) calcium," Inorganic Chemistry, May 2015, vol. 54 (10), pp. 4927-4933.
Li C., et al., "Multimodal Image-Guided Enzyme/Prodrug Cancer Therapy," Journal of the American Chemical Society, Nov. 2006, vol. 128 (47), pp. 15072-15073.
Li N., et al., "Cation Separation and Preconcentration Using cols. Containing Cyclen and Cyclen-resorcinarene Derivatives," Journal of Chromatography, Jul. 2012, vol. 1245 (2012), pp. 83-89.
Li W.S., et al., "A Gd3Al Tetranuclear Complex as a Potential Bimodal MRI/optical Imaging Agent," Dalton Transactions, Aug. 2012, vol. 41 (31), pp. 9405-9410.
Liu J., et al., "Molecular Engineering of Aqueous Soluble Triarylboron-Compound-Based Two-Photon Fluorescent Probe for Mitochondria H2S with Analyte-Induced Finite Aggregation and Excellent Membrane Permeability," Analytical Chemistry, 2016, vol. 88 (1), pp. 1052-1057.
Livramento et al., A benzene-core trinuclear Gdlll complex: towards the optimization of relaxivity for MRI contrast agent applications at hight magnetic field, The Royal Society of Chemistry 2008, 2008, 1195-1202.
Lopez-Martinez L.M., et al., "Synthesis, Characterization, and Cu2+ Coordination Studies of a 3-Hydroxy-4-pyridinone Aza Scorpiand Derivative," Inorganic Chemistry, Jul. 2016, vol. 55 (15), pp. 7564-7575.
Maindron N., et al., "Near-Infrared-Emitting BODIPY-trisDOTA(111) in as a Monomolecular Multifunctional Imaging

(56) References Cited

OTHER PUBLICATIONS

Probe: from Synthesis to In Vivo Investigations," Chemistry a European Journal, Aug. 2016, vol. 22 (36), pp. 12670-12674.
Mamedov I., et al., "Structure-related Variable Responses of Calcium Sensitive MRI Probes," Organic Biomolecular Chemistry, Aug. 2011, vol. 9 (16), pp. 5816-5824.
Martin D., et al., "Discrete Magnesium Hydride Aggregates: A Cationic Mg13H18 Cluster Stabilized by NNNN-Type Macrocycles," Angewandte Chemie, Mar. 2015, vol. 54 (13), pp. 4115-4118.
Martin D., et al., "Hydrido and Allyl/Hydrido Complexes of Early Lanthanides Supported by an NNNN-Type Macrocyclic Ligand," European Journal of Inorganic Chemistry, Aug. 2013, vol. 2013 (22-23), pp. 3987-3992.
Martinez G.V., et al., "Demonstration of a Sucrose-derived Contrast Agent for Magnetic Resonance Imaging of the GI Tract," Bioorganic Medicinal Chemistry Letters, Apr. 2013, vol. 23 (7), pp. 2061-2064.
Mastarone D.J., et al., "A Modular System for the Synthesis of Multiplexed Magnetic Resonance Probes," Journal of the American Chemical Society, Mar. 2011, vol. 133 (14), pp. 5329-5337.
Merbach A.E., et al., "Chapter II: Relaxivity of Gadolinium(III) Complexes: Theory and Mechanism" in: The Chemistry of Contrast Agents in Medical Magnetic Resonance Imaging, 2nd Edition, 2013, Table of Contents.
Merbach Andre et al., The Chemistry of Contrast Agents in Medical Magnetic Resonance Imaging, 2nd Edition, John Wiley Sons Ltd., 2013, 31-32, 194.
Mier W., et al., "Synthesis of Peptide Conjugated Chelator Oligomers for Endoradiotherapy and MRT Imaging," Tetrahedron Letters, Jul. 2004, vol. 45 (28), pp. 5453-5455.
Mieville P., et al., "Synthesis, Complexation and NMR Relaxation Properties of Gd3+ Complexes of Mes(DO3A)3," Dalton Transactions, Mar. 2011, vol. 40, pp. 4260-4267.
Mishra A., et al., "Facile Synthesis and Relaxation Properties of Novel Bispolyazamacrocyclic Gd3+ Complexes: an Attempt Towards Calcium-sensitive MRI Contrast Agents," Inorganic Chemistry, Feb. 2008, vol. 47 (8), p. 3460.
Montalbetti C.A., et al., "Amide Bond Formation and Peptide Coupling," Tetrahedron, 2005, vol. 61, pp. 10827-10852.
Morcos S.k., Extracellular gadolinium contrast agents: Differences in stability, European Journal of Radiology, May 2008, vol. 66/Issue 2, 175-179.
Muller A., et al., "Preparation of Luminescent Chemosensors by Post-functionalization of Vesicle Surfaces," Organic Biomolecular Chemistry, 2015, vol. 13 (6), pp. 1690-1699.
Napolitano R., et al., "Synthesis and Relaxometric Characterization of a MRI Gd-Based Probe Responsive to Glutamic Acid Decarboxylase Enzymatic Activity," Journal of Medical Chemistry, Mar. 2013, vol. 56 (6), pp. 2466-2477.
Niedbalski P., et al., "13C Dynamic Nuclear Polarization Using a Trimeric Gd3+ Complex as an Additive," The Journal of Physical Chemistry, Jul. 2017, vol. 121 (27), pp. 5127-5135.
Nithyakumar A., et al., "Tri- and Tetranuclear RuII-GdIII2 and RuII-GdIII3 d-f Heterometallic Complexes as Potential Bimodal Imaging Probes for MRI and Optical Imaging," New Journal of Chemistry, Mar. 2016, vol. 40, pp. 4606-4616.
NMRD measurements—final report and Sample characteristics of the samples used in the experimental report, Dec. 19, 2014.

* cited by examiner

FIG. 5A
Example 3
baseline
0.5 min
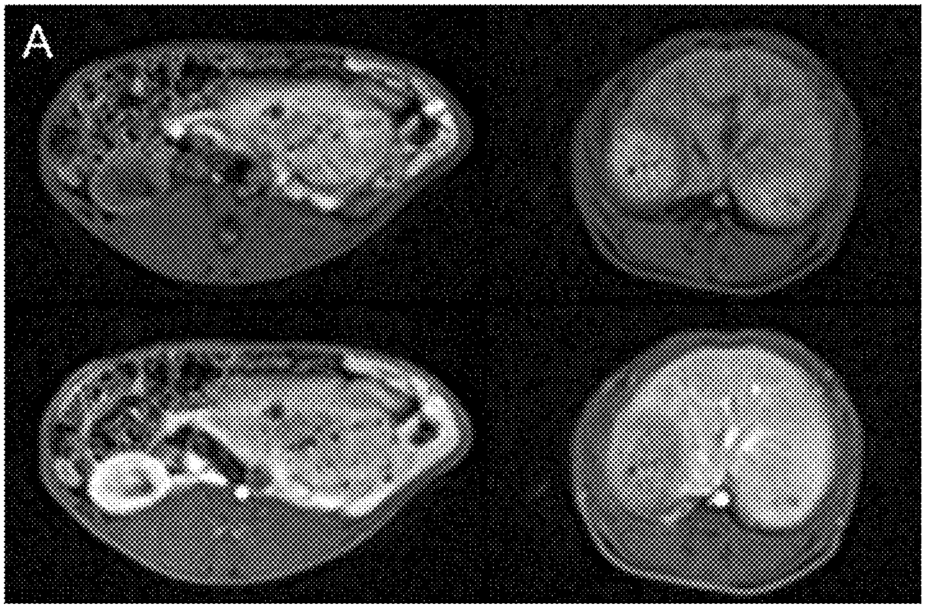
Gadovist®
baseline
0.5 min
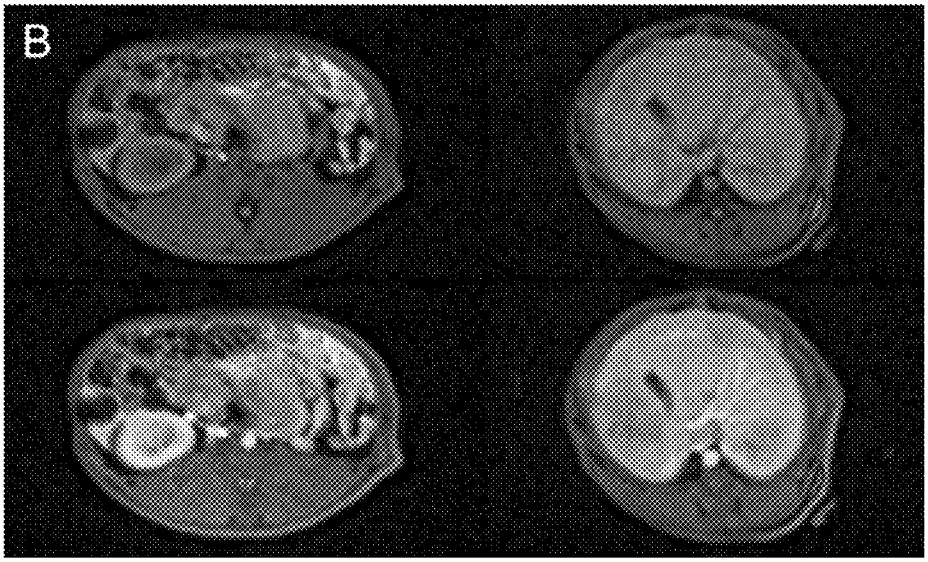
FIG. 5B FIG. 9A
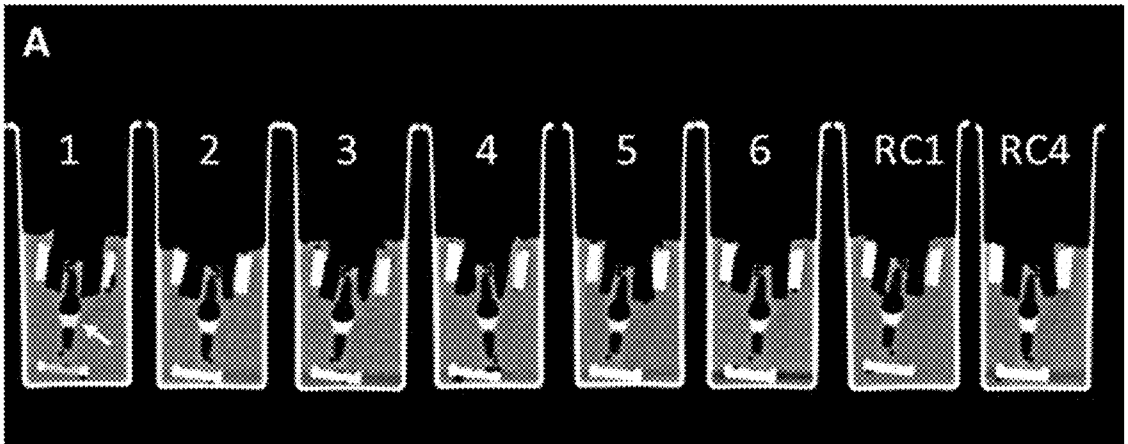
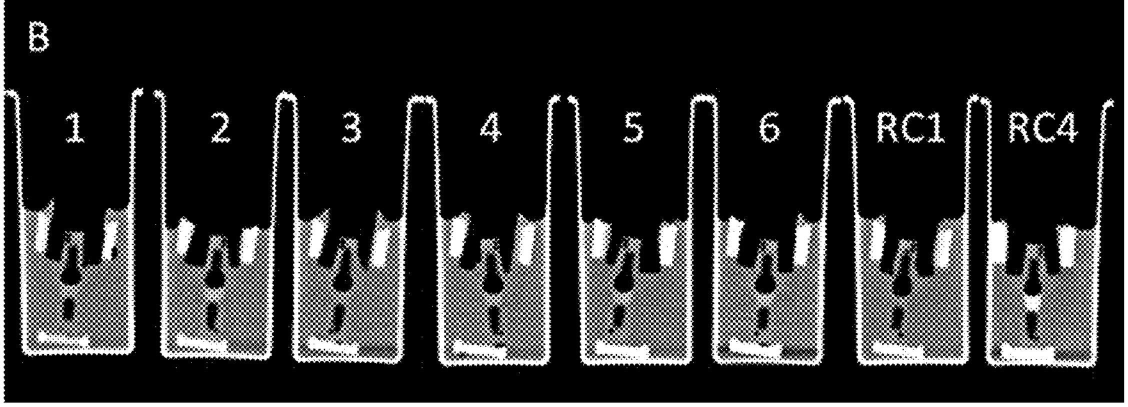
FIG. 9B

GADOLINIUM CHELATE COMPOUNDS FOR USE IN MAGNETIC RESONANCE IMAGING

CROSS REFERENCE TO RELATED APPLICATIONS

The present application is a Continuation application of U.S. Ser. No. 17/979,367, filed Nov. 2, 2022; which is a Continuation application of U.S. Ser. No. 16/947,272, filed Jul. 27, 2020, now U.S. Pat. No. 11,491,245, issued Nov. 8, 2022; which is a Continuation application of U.S. Ser. No. 16/192,185, filed Nov. 15, 2018, now U.S. Pat. No. 10,722,601, issued Jul. 28, 2020; which is a Continuation application of U.S. Ser. No. 15/578,687, filed Nov. 30, 2017, now U.S. Pat. No. 10,137,209, issued Nov. 27, 2018; which is a U.S. national stage filing under 35 U.S.C. § 371 of International Application No. PCT/EP2016/062105, filed May 30, 2016; which claims priority to European Patent Application No. EP 15170658.7, filed Jun. 4, 2015, the disclosures of each of which are incorporated in their entirety herein by this reference.

FIELD OF THE INVENTION

The present invention relates to the items characterized in the patent claims, namely to new high relaxivity extracellular gadolinium chelates based on low molecular weight core polyamines, to methods of preparing said compounds, to the use of said compounds as MRI contrast agents and to their use in a mammalian body.

BACKGROUND

1. Introduction

Nine gadolinium-based contrast agents (GBCAs) have been approved for clinical use: gadopentetate dimeglumine (Magnevist®), gadoterate meglumine (Dotarem®), gadoteridol (ProHance®), gadodiamide (Omniscan®), gadobutrol (Gadovist®), gadoversetamide (OptiMARK®), gadoxetic acid (Primovist®), gadobenate dimeglumine (MultiHance®) and gadofosveset trisodium (Vasovist®/Ablavar®). With the exception of gadoxetic acid, gadobenate dimeglumine and gadofosveset trisodium, the GBCAs exhibit a strictly extracellular passive distribution in the body and are excreted exclusively via the kidney.

Gadoxetic acid and gadobenate dimeglumine exhibit a different pharmacokinetic profile than the other agents. In addition to the extracellular distribution, they are taken up and are also excreted partially via the liver. This allows, besides the classical imaging possibilities (e.g. central nervous system, angiography, extremities, heart, head/face/neck, abdomen and breast imaging), also liver imaging due to the enhancement of liver parenchyma caused by the GBCAs uptake in hepatocytes.

In contrast to the other GBCAs gadofosveset trisodium shows no passive diffusion in the body and remains in the vascular space. The prolonged period in the blood vessels caused by the reversible binding to HSA (human serum albumin) allows high resolution MR angiographies.

The various GBCAs differ in their efficacy which is given by their longitudinal (r1) and transversal (r2) relaxivity and is dependent on magnetic field strengths, temperature and different intrinsic factors of the metal chelates. The intrinsic relaxivity influencing parameters are mainly the number of water molecules directly bound to the gadolinium (so-called inner-sphere water, q), the mean residence time of the inner sphere water molecules (τm), the number and residence times of water molecules in the second hydration sphere (so-called second sphere water) and the rotational diffusion (τr) (Helm L. et al., *Future Med. Chem.* 2010; 2: 385-396). In terms of their relaxivity all the commercially available GBCAs are very similar to each other and derived from a range of 4 to 7 L $mmol^{-1}s^{-1}$.

Strategies for increasing the sensitivity of GBCAs are frequently described in the literature (Caravan P. et al. *Chem. Soc. Rev.,* 2006, 35, 512-523, Helm et. al. *Future Med. Chem.* 2010; 2:385-396, Jacques V. Invest. *Radiol.* 2010; 45:613-624). One of the strategies is the increase of the inner sphere water molecules (q) that are water molecules which are directly coordinated to the gadolinium ion in the chelate. As the examples of AAZTA and HOPO-based ligands show, the increase of the inner sphere water molecules from one to two leads to a significant increase in relaxivity. Another strategy to increase the relaxivity is the slowing of the rotational diffusion of the molecule. The so-called tumbling rate (τr, see introduction) describes the tumbling of the molecule in solution and is mainly affected by the molecular size and protein binding of the GBCA (Merbach A. S. et al., The Chemistry of Contrast Agents in Medical Magnetic Resonance Imaging, 2013, ISBN: 978-1-119-99176-2).

A further important characteristic of the GBCAs is their complex stability. The potential of the GBCAs to release free toxic $Gd^{3+}$ ions is a major safety issue and of utmost importance in particular for patients with end-stage renal disease. Nephrogenic systemic fibrosis (NSF) is a rare and serious syndrome that is associated with the exposure to GBCAs in patients with severe kidney failure. NSF involves fibrotic changes in the skin and many organs. In 2010, the Food and Drug Administration (FDA) published revised labeling recommendations for four GBCAs which have been principally implicated in NSF, including gadodiamide (Omniscan®), gadobenate dimeglumine (MultiHance®), gadopentetate dimeglumine (Magnevist®) and gadoversetamide (OptiMARK®) (Yang L et al. *Radiology.* 2012; 265:248-253). At first glance the stability of all GBCAs is very high, but significant differences exist between the linear and macrocyclic agents and between the ionic and nonionic representatives of the linear agents. The macrocyclic GBCAs possess the highest complex stabilities (Frenzel T. et al. *Invest. Radiol.* 2008; 43:817-828). Due to the better awareness of risk patients, the use of lower doses and more widespread use of the macrocyclic GBCAs the incidence of NSF has decreased in the last years (Wang Y. et. al. *Radiology.* 2011; 260:105-111 and Becker S. et. al. *Nephron. Clin. Pract.* 2012; 121:091-094).

The crucial issue for clinical applications is in vivo stability. The kinetic inertness combined with the thermodynamic stability is particularly with regard to the risk of nephrogenic systemic fibrosis (NSF) the best predictor of the in vivo toxicity of q=2 chelates (Merbach A. S. et al., The Chemistry of Contrast Agents in Medical Magnetic Resonance Imaging, 2013, ISBN: 978-1-119-99176-2, page 157-208). The complexes with q=2 show two-fold enhancement of relaxivity but, unfortunately, they have a lower stability than q=1 compounds (Hermann P. et. al. *Dalton Trans.,* 2008, 3027-3047).

2. Description of the Prior Art, Problem to be Solved and its Solution

Several macrocyclic compounds are described in the prior art.

EP1931673 B1 and EP2457914 B1 relate to pyDO3A (q=2), DO3A and DOTA compounds comprising short aminoalcohol chains and metal complexes for medical imaging.

Macrocyclic lanthanide DO3A- and DOTA-like GBCAs with high relaxivities are described in the prior art.

Ranganathan R. S. et. al. (Investigative Radiology 1998; 33:779-797) investigated the effect of multimerization on the relaxivity of macrocyclic gadolinium chelates. WO199531444 relates to monomeric and multimeric compounds having enhanced relaxivities.

U.S. Pat. No. 5,679,810 relates to linear oligomer polychelant compounds and chelates formed therewith, having alternating chelant and linker moieties bound together by amide or ester moieties, and to their use in diagnostic imaging.

U.S. Pat. No. 5,650,133 relates to dichelants, in particular compounds having two macrocyclic chelant groups linked by a bridge containing an ester or amide bond, and to metal chelates thereof, and to their use in diagnostic imaging.

WO 97/32862 A1 describes gadolinium polychelants as magnetic resonance imaging agents which are linking at least two units of chelant to the amino groups of a target carrier structure (like e.g. a protein, aminoacid or peptide).

US 2007/202047 relates to gadolinium chelate compounds for use in magnetic resonance imaging, which are derived from a chelating molecule selected from 1,4,7,10-tetraazacyclo-dodecane-1,4,7,10-tetraacetic acid (DOTA) and diethylentriaminepentaacetic acid (DTPA), wherein at least one of the carboxylic groups of the chelating molecule is reacted with an amine.

GBCAs with higher relaxivity offer on the one hand the opportunity of a significant dose reduction and on the other an increased sensitivity in the MRI examination of many diseases using the standard dose (Giesel F. L. et. al. *Eur. Radiol.* 2010, 20:2461-2474).

However, there is an unmet medical need to provide GBCAs for general use in magnetic resonance imaging, which:

- exhibit high relaxivity,
- show a favorable pharmacokinetic profile,
- are completely excreted,
- are chemically stable,
- exhibit high water solubility,
- offer the potential for a significant dose reduction,
- are suitable for imaging of different body regions, and
- are very well-tolerated.

The state of the art described above does not describe the specific high relaxivity extracellular gadolinium chelate compounds of general formula (I) of the present invention as defined herein, or a stereoisomer, a tautomer, an N-oxide, a hydrate, a solvate, or a salt thereof, or a mixture of same, as described and defined herein, and as hereinafter referred to as "compounds of the present invention".

It has now been found, and this constitutes the basis of the present invention, that said compounds of the present invention have surprisingly and advantageous properties.

In particular, said compounds of the present invention have been found to exhibit a balanced profile of a high relaxivity, a favorable pharmacokinetic profile, a complete excretion, a high stability, a high solubility, the potential for a significant dose reduction and the potential for whole body imaging, and they may therefore be used as contrast agents for magnetic resonance imaging (MRI).

DESCRIPTION OF THE FIGURES

(FIG. 3A) 30 μmol Gd/kg bw Reference compound 1 (Gadovist®); (FIG. 3B) 30 μmol Gd/kg bw Example 3 and (FIG. 3C) 100 μmol Gd/kg bw Reference compound 1. The contrast enhancement of the low dose protocol with Example 3 (FIG. 3B) is comparable to that of the standard dose of Reference compound 1 (FIG. 3C). Furthermore, the image quality of the low dose protocol of Example 3 (FIG. 3B) is significantly better than the low dose protocol of Reference compound 1 (FIG. 3A). The angiography study demonstrates the potential for Example 3 for a significant dose reduction.

FIGS. 5A and 5B: MR images before and after administration of contrast agent. Representative images of the abdominal region before and 0.5 min after administration of Example 3 (FIG. 5A) and reference compound 1 (FIG. 5B). The strong signal enhancement is visible for example in the aorta, kidney, liver and spleen.

FIGS. 9A and 9B: Diffusion of different contrast agents through semipermeable membranes (20 kDa). Dynamic CT measurements were performed to show the ability of different contrast agents to diffuse through a semipermeable membrane. (FIG. 9A and FIG. 9B) CT images of Example 1, 2, 3, 4, 5 and 6 in comparison to that of Reference compound 1 (Gadovist®) and 4 (Gadomer). A representative measurement region for the signal evaluation over time is indicated in the image A1.

(FIG. 11A) Intraindividual comparison of Reference compound 1 (Gadovist®) and Example 3 at the same dose of 0.1 mmol Gd/kg body weight (bw). Example 3 showed higher lesion-to-brain contrast and an excellent demarcation of the tumor rim. (FIG. 11B) Comparison of the Reference compound 1 (Gadovist®) at 0.3 mmol Gd/kg bw and Example 3 at 0.1 mmol Gd/kg bw. Example 3 showed similar lesion-to-brain contrast at one third of the dose of Reference compound 1.

SUMMARY

Figure 1:
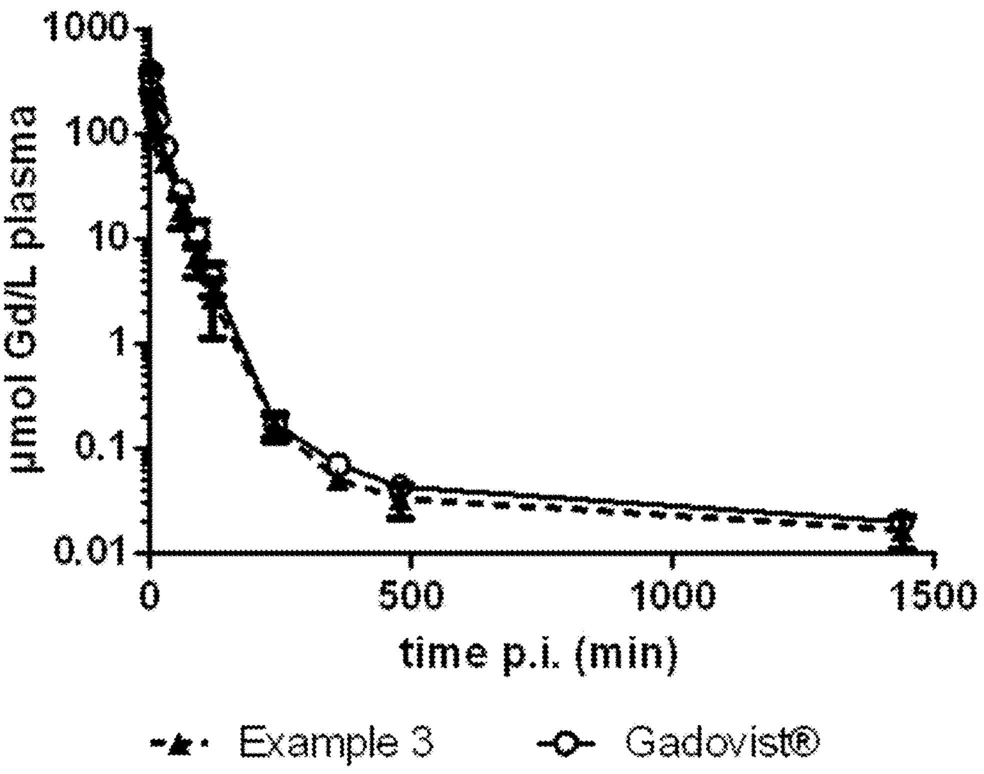
FIG. 1: shows the blood plasma kinetic of Example 3 versus Gadovist® in rats. The pharmacokinetic profile of Example 3 is comparable to that of Gadovist®.

The present invention describes a new class of high relaxivity extracellular gadolinium chelate complexes, methods for their preparation and their use as MRI contrast agents.

DESCRIPTION OF THE INVENTION

In accordance with a first aspect, the present invention covers compounds of general formula (I), comprising 4, 5, 6, 7 or 8 gadolinium[4,7,10-tris(carboxylatomethyl)-1,4,7,10-tetraazacyclododecan-1-yl]groups,

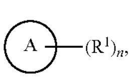

(I)

in which:

represents a group selected from:

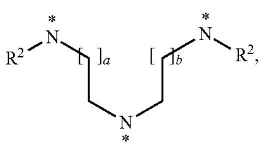

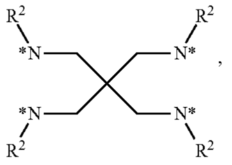

-continued

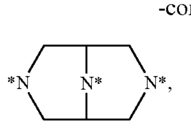

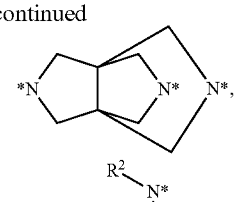

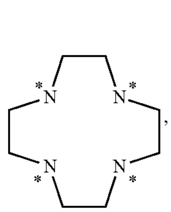

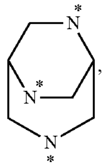

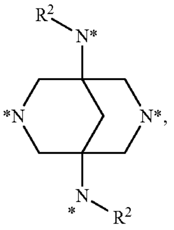

and

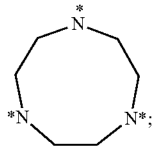

in which groups a and b represent, independently from each other, an integer of 1 or 2; and, in which groups * indicates the point of attachment of said group with $R^1$;

$R^1$ represents, independently from each other, a hydrogen atom or a group selected $R^3$,

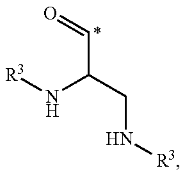

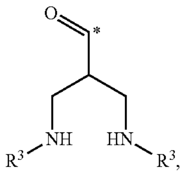

and

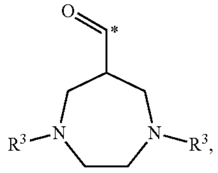

in which groups * indicates the point of attachment of said group with A, with the proviso that only one of the substituents $R^1$ may represent a hydrogen atom;

n represents an integer of 3 or 4;

$R^2$ represents, independently from each other, a hydrogen atom or a methyl group;

$R^3$ represents a group selected from:

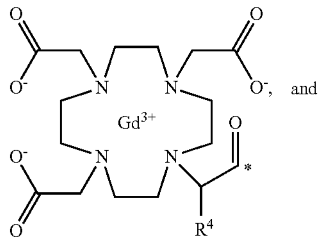

and

-continued

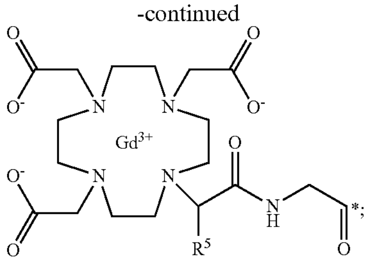

in which groups * indicates the point of attachment of said group with the rest of the molecule;

$R^4$ represents, independently from each other, a hydrogen atom or a methyl group;

$R^5$ represents, independently from each other, a hydrogen atom or a methyl group; or a stereoisomer, a tautomer, an N-oxide, a hydrate, a solvate, or a salt thereof, or a mixture of same.

The compounds of this invention may contain one or more asymmetric center, depending upon the location and nature of the various substituents desired. Asymmetric carbon atoms may be present in the (R) or (S) configuration, which can result in racemic mixtures in the case of a single asymmetric center, and in diastereomeric mixtures in the case of multiple asymmetric centers. In certain instances, asymmetry may also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivatization, optimally chosen to maximize the separation of the enantiomers. Suitable chiral HPLC columns are manufactured by Daicel, e.g., Chiracel OD and Chiracel OJ among many others, all routinely selectable. Enzymatic separations, with or without derivatization, are also useful. The optically active compounds of this invention can likewise be obtained by chiral syntheses utilizing optically active starting materials.

In order to limit different types of isomers from each other reference is made to IUPAC Rules Section E (Pure Appl. Chem. 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention can exist as N-oxides, which are defined in that at least one nitrogen of the compounds of the present invention is oxidized. The present invention includes all such possible N-oxides.

The present invention also relates to useful forms of the compounds as disclosed herein, such as metabolites, hydrates, solvates, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in the form of a salt. Said salt may be either an inorganic or organic addition salt, particularly any pharmaceutically acceptable inorganic or organic addition salt, customarily used in pharmacy.

The term "pharmaceutically acceptable salt" refers to a relatively non-toxic, inorganic or organic acid addition salt of a compound of the present invention. For example, see S. M.

Berge, et al. "Pharmaceutical Salts," *J. Pharm. Sci.* 1977, 66, 1-19. The production of especially neutral salts is described in U.S. Pat. No. 5,560,903.

Pharmaceutically acceptable salts of the compounds according to the invention include salts of mineral acids and carboxylic acids, for example, without being limited thereto, salts of hydrochloric acid, sulfuric acid, phosphoric acid, acetic acid, propionic acid, lactic acid, tartaric acid, malic acid, citric acid, fumaric acid, maleic acid, aspartic acid and glutamic acid.

Those skilled in the art will further recognize that acid addition salts of the claimed compounds may be prepared by reaction of the compounds with the appropriate inorganic or organic acid via any of a number of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

This applies analogously to cases in which synthesis intermediates or example compounds or salts thereof have been obtained, by the preparation and/or purification processes described, as solvates, such as hydrates with (if defined) unknown stoichiometric composition.

In accordance with a second embodiment of the first aspect, the present invention covers compounds of general formula (I), supra, comprising 4, 5 or 6, gadolinium[4,7,10-tris-(carboxylatomethyl)-1,4,7,10-tetraazacyclododecan-1-yl]groups, wherein:

represents a group selected from:

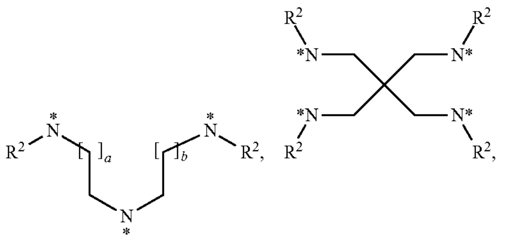

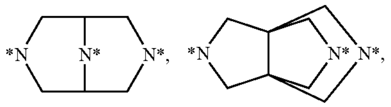

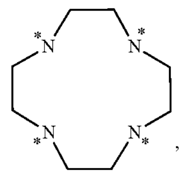

, and

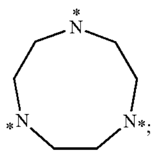

in which groups a and b represent, independently from each other, an integer of 1 or 2; and, in which groups * indicates the point of attachment of said group with $R^1$;

$R^1$ represents, independently from each other, a hydrogen atom or a group selected from:

$R^3$,

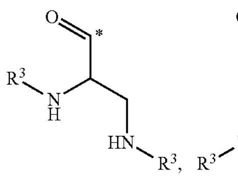

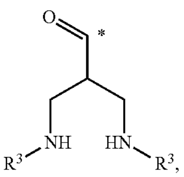

and

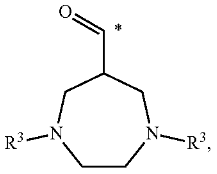

in which groups * indicates the point of attachment of said group with A, with the proviso that only one of the substituents $R^1$ may represent a hydrogen atom;

n represents an integer of 3 or 4;

$R^2$ represents, independently from each other, a hydrogen atom or a methyl group;

$R^3$ represents a group selected from:

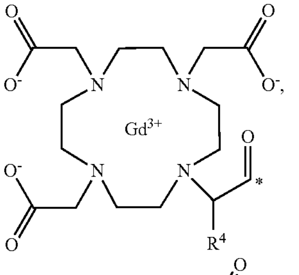

and

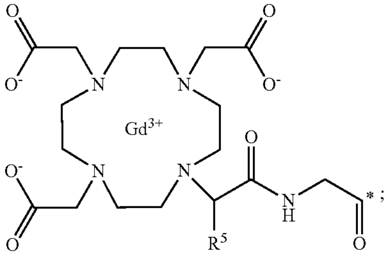

in which groups * indicates the point of attachment of said group with the rest of the molecule;

$R^4$ represents, independently from each other, a hydrogen atom or a methyl group;

$R^5$ represents, independently from each other, a hydrogen atom or a methyl group; or a stereoisomer, a tautomer, an N-oxide, a hydrate, a solvate, or a salt thereof, or a mixture of same.

In accordance with a third embodiment of the first aspect, the present invention covers compounds of general formula (I), supra, comprising 4, 5 or 6, gadolinium[4,7,10-tris-(carboxylatomethyl)-1,4,7,10-tetraazacyclododecan-1-yl] groups, wherein:

represents a group selected from:

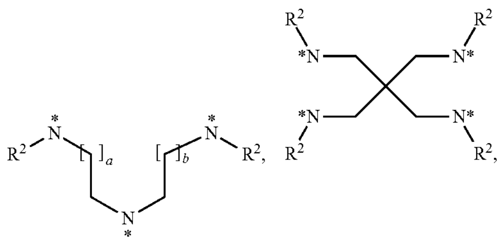

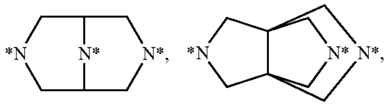

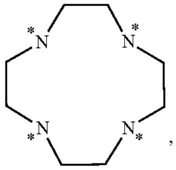

, and

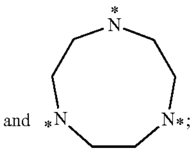

in which groups a and b represent an integer of 1; and, in which groups * indicates the point of attachment of said group with $R^1$ $R^1$ represents, independently from each other, a hydrogen atom or a group selected from: $R^3$,

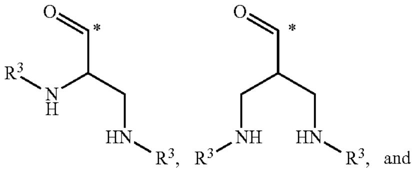

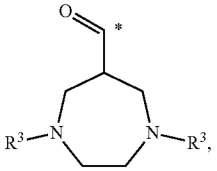

in which groups * indicates the point of attachment of said group with A, with the proviso that only one of the substituents $R^1$ may represent a hydrogen atom, n represents an integer of 3 or 4, $R^2$ represents a hydrogen atom;

$R^3$ represents a group selected from:

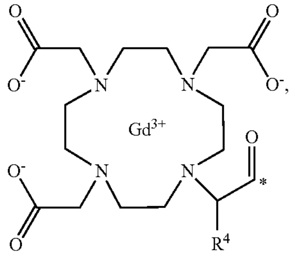

and

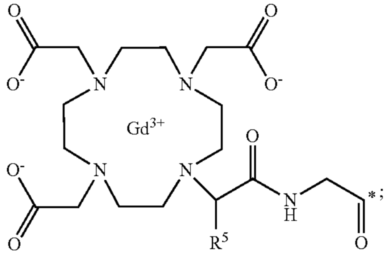

in which groups * indicates the point of attachment of said group with the rest of the molecule;

$R^4$ represents a hydrogen atom;

$R^5$ represents a hydrogen atom or a methyl group;

or a stereoisomer, a tautomer, an N-oxide, a hydrate, a solvate, or a salt thereof, or a mixture of same.

In accordance with a fourth embodiment of the first aspect, the present invention covers compounds of general formula (I), supra, comprising 4, 5 or 6, gadolinium[4,7,10-tris-(carboxylatomethyl)-1,4,7,10-tetraazacyclododecan-1-yl]groups, wherein:

represents a group selected from:

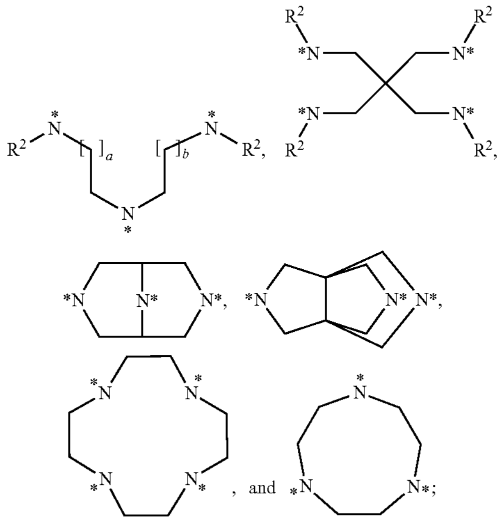

in which groups a and b represent an integer of 1; and, in which groups * indicates the point of attachment of said group with $R^1$;

$R^1$ represents, independently from each other, a hydrogen atom or a group selected from:

$R^3$,

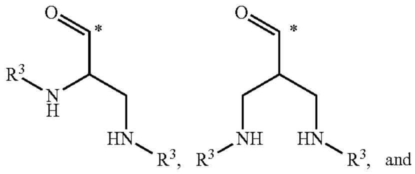

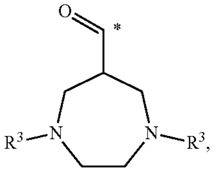

in which groups * indicates the point of attachment of said group with A, with the proviso that only one of the substituents $R^1$ may represent a hydrogen atom;

n represents an integer of 3 or 4;

$R^2$ represents a hydrogen atom;

$R^3$ represents a group selected from:

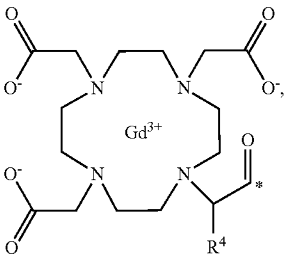

and

-continued

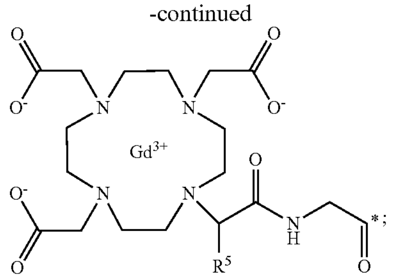

in which groups * indicates the point of attachment of said group with the rest of the molecule;

$R^4$ represents a hydrogen atom;

$R^5$ represents a methyl group;

or a stereoisomer, a tautomer, an N-oxide, a hydrate, a solvate, or a salt thereof, or a mixture of same.

In accordance with another aspect, the present invention covers compounds of general formula (I), (I)

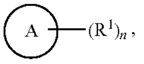

in which:

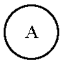

represents a

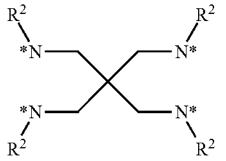

group, in which group * indicates the point of attachment of said group with $R^1$;

$R^1$ represents a group $R^3$;

n represents an integer of 4;

$R^2$ represents a hydrogen atom;

$R^3$ represents a group selected from:

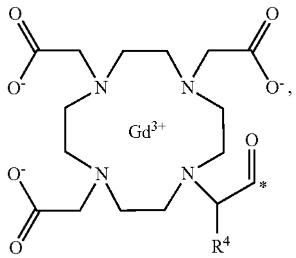

, and

-continued

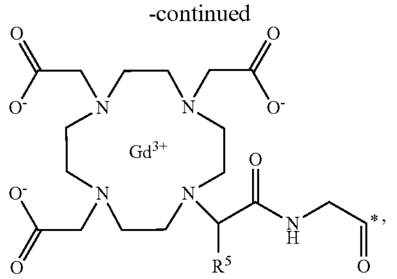

in which groups * indicates the point of attachment of said group with the rest of the molecule;

$R^4$ represents a hydrogen atom;

$R^5$ represents a hydrogen atom or a methyl group;

or a stereoisomer, a tautomer, an N-oxide, a hydrate, a solvate, or a salt thereof, or a mixture of same.

In a further embodiment of the above-mentioned aspect, the invention relates to compounds of formula (I), comprising 4, 5, 6, 7 or 8 gadolinium[4,7,10-tris(carboxylatomethyl)-1,4,7,10-tetraazacyclododecan-1-yl]groups.

In a further embodiment of the above-mentioned aspect, the invention relates to compounds of formula (I), comprising 4, 5 or 6 gadolinium[4,7,10-tris(carboxylatomethyl)-1,4,7,10-tetraazacyclododecan-1-yl]groups.

In a further embodiment of the above-mentioned aspect, the invention relates to compounds of formula (I), comprising 4 gadolinium[4,7,10-tris(carboxylatomethyl)-1,4,7,10-tetraazacyclododecan-1-yl]groups.

In a further embodiment of the above-mentioned aspect, the invention relates to compounds of formula (I), comprising 5 gadolinium[4,7,10-tris(carboxylatomethyl)-1,4,7,10-tetraazacyclododecan-1-yl]groups.

In a further embodiment of the above-mentioned aspect, the invention relates to compounds of formula (I), comprising 6 gadolinium[4,7,10-tris(carboxylatomethyl)-1,4,7,10-tetraazacyclododecan-1-yl]groups.

In a further embodiment of the above-mentioned aspect, the invention relates to compounds of formula (I), comprising 7 gadolinium[4,7,10-tris(carboxylatomethyl)-1,4,7,10-tetraazacyclododecan-1-yl]groups.

In a further embodiment of the above-mentioned aspect, the invention relates to compounds of formula (I), comprising 8 gadolinium[4,7,10-tris(carboxylatomethyl)-1,4,7,10-tetraazacyclododecan-1-yl]groups.

In a further embodiment of the above-mentioned aspect, the invention relates to compounds of formula (I), wherein:

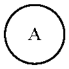

represents a group selected from:

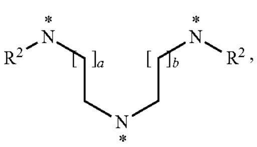

,

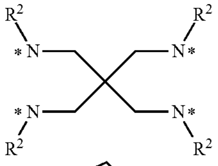

,

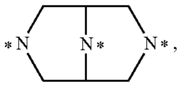

,

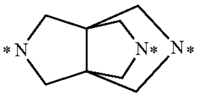

,

-continued

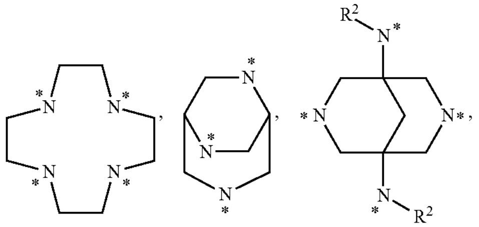

and

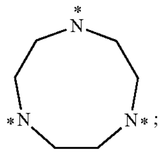

in which groups a and b represent, independently from each other, an integer of 1 or 2; and in which groups * indicates the point of attachment of said group with $R^1$.

In a further embodiment of the above-mentioned aspect, the invention relates to compounds of formula (I), wherein:

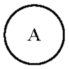

represents a group selected from:

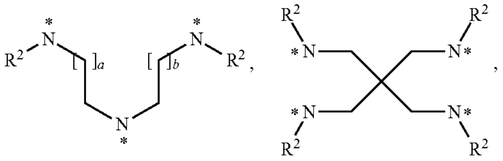

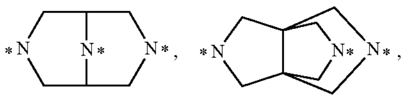

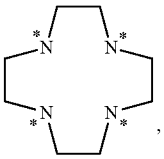

, and

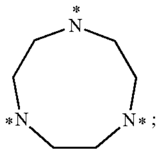

in which groups a and b represent, independently from each other, an integer of 1 or 2; and in which groups * indicates the point of attachment of said group with $R^1$.

In a further embodiment of the above-mentioned aspect, the invention relates to compounds of formula (I), wherein:

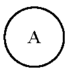

represents a group selected from:

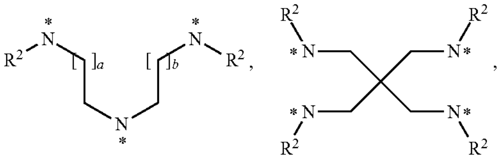

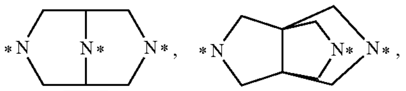

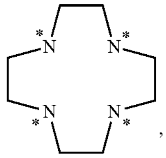

, and

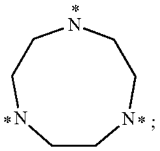

in which groups a and b represent an integer of 1; and in which groups * indicates the point of attachment of said group with $R^1$.

In a further embodiment of the above-mentioned aspect, the invention relates to compounds of formula (I), wherein:

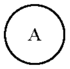

represents a

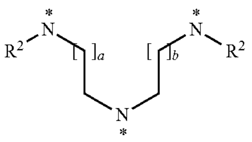

group, in which groups a and b represent, independently from each other, an integer of 1 or 2; and in which group * indicates the point of attachment of said group with $R^1$.

In a further embodiment of the above-mentioned aspect, the invention relates to compounds of formula (I), wherein:

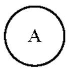

represents a

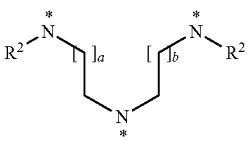

group, in which groups a and b represent an integer of 1; and in which group * indicates the point of attachment of said group with $R^1$.

In a further embodiment of the above-mentioned aspect, the invention relates to compounds of formula (I), wherein:

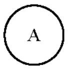

represents a

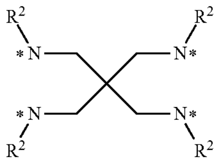

group, in which group * indicates the point of attachment of said group with $R^1$.

In a further embodiment of the above-mentioned aspect, the invention relates to compounds of formula (I), wherein:

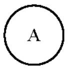

represents a

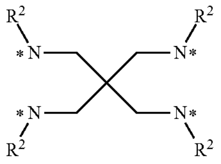

group, in which group * indicates the point of attachment of said group with $R^1$, and $R^2$ represents a hydrogen atom.

In a further embodiment of the above-mentioned aspect, the invention relates to compounds of formula (I), wherein:

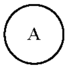

represents a

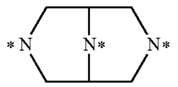

group, in which group * indicates the point of attachment of said group with $R^1$.

In a further embodiment of the above-mentioned aspect, the invention relates to compounds of formula (I), wherein:

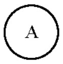

represents a

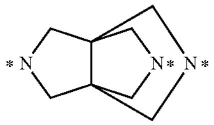

group, in which group * indicates the point of attachment of said group with $R^1$.

In a further embodiment of the above-mentioned aspect, the invention relates to compounds of formula (I), wherein:

represents a

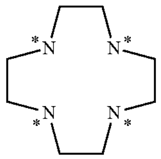

group, in which group * indicates the point of attachment of said group with $R^1$.

In a further embodiment of the above-mentioned aspect, the invention relates to compounds of formula (I), wherein:

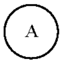

represents a

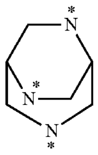

group, in which group * indicates the point of attachment of said group with $R^1$.

In a further embodiment of the above-mentioned aspect, the invention relates to compounds of formula (I), wherein:

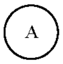

represents a

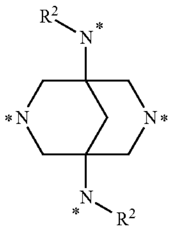

group, in which group * indicates the point of attachment of said group with $R^1$.

In a further embodiment of the above-mentioned aspect, the invention relates to compounds of formula (I), wherein:

represents a

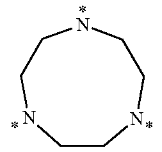

group, in which group * indicates the point of attachment of said group with $R^1$.

In a further embodiment of the above-mentioned aspect, the invention relates to compounds of formula (I), wherein: $R^1$ represents, independently from each other, a hydrogen atom or a group selected from:

$R^3$,

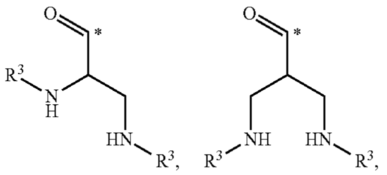

and

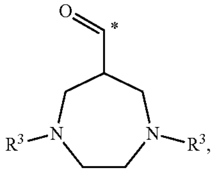

in which groups * indicates the point of attachment of said group with A, with the proviso that only one of the substituents $R^1$ may represent a hydrogen atom.

In a further embodiment of the above-mentioned aspect, the invention relates to compounds of formula (I), wherein: $R^1$ represents, independently from each other a group selected from:

$R^3$,

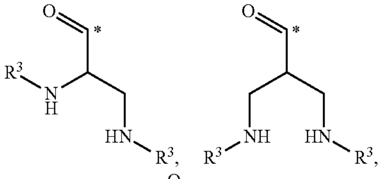

and

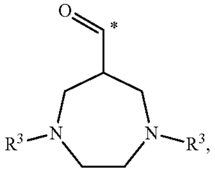

in which groups * indicates the point of attachment of said group with A.

In a further embodiment of the above-mentioned aspect, the invention relates to compounds of formula (I), wherein: $R^1$ represents, independently from each other a group selected from:

$R^3$, and

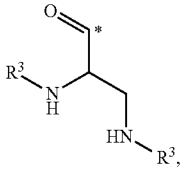

in which groups * indicates the point of attachment of said group with A.

In a further embodiment of the above-mentioned aspect, the invention relates to compounds of formula (I), wherein: $R^1$ represents, independently from each other a group selected from:

$R^3$, and

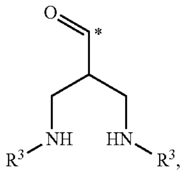

in which group * indicates the point of attachment of said group with A.

In a further embodiment of the above-mentioned aspect, the invention relates to compounds of formula (I), wherein: $R^1$ represents, independently from each other a group selected from:

$R^3$, and

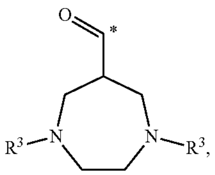

in which group * indicates the point of attachment of said group with A.

In a further embodiment of the above-mentioned aspect, the invention relates to compounds of formula (I), wherein: $R^1$ represents a group $R^3$.

In a further embodiment of the above-mentioned aspect, the invention relates to compounds of formula (I), wherein:

$R^1$ represents a

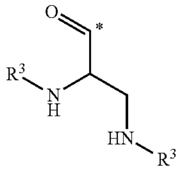

group, in which group * indicates the point of attachment of said group with A.

In a further embodiment of the above-mentioned aspect, the invention relates to compounds of formula (I), wherein:

$R^1$ represents a

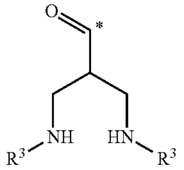

group, in which group * indicates the point of attachment of said group with A.

In a further embodiment of the above-mentioned aspect, the invention relates to compounds of formula (I), wherein:

$R^1$ represents a

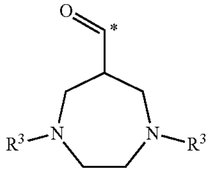

group, in which group * indicates the point of attachment of said group with A.

In a further embodiment of the above-mentioned aspect, the invention relates to compounds of formula (I), wherein: $R^1$ represents, independently from each other, a hydrogen atom or a $R^3$ group, with the proviso that only one of the substituents $R^1$ may represent a hydrogen atom.

In a further embodiment of the above-mentioned aspect, the invention relates to compounds of formula (I), wherein:

$R^1$ represents, independently from each other, a hydrogen atom or a

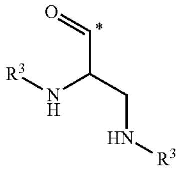

group, in which group * indicates the point of attachment of said group with A, with the proviso that only one of the substituents $R^1$ may represent a hydrogen atom.

In a further embodiment of the above-mentioned aspect, the invention relates to compounds of formula (I), wherein:

$R^1$ represents, independently from each other, a hydrogen atom or a

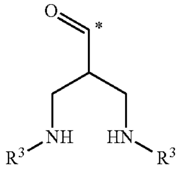

group, in which group * indicates the point of attachment of said group with A, with the proviso that only one of the substituents $R^1$ may represent a hydrogen atom.

In a further embodiment of the above-mentioned aspect, the invention relates to compounds of formula (I), wherein: $R^1$ represents, independently from each other, a hydrogen atom or a

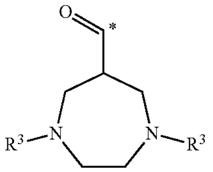

group, in which group * indicates the point of attachment of said group with A, with the proviso that only one of the substituents $R^1$ may represent a hydrogen atom.

In a further embodiment of the above-mentioned aspect, the invention relates to compounds of formula (I), wherein: n represents an integer of 3 or 4.

In a further embodiment of the above-mentioned aspect, the invention relates to compounds of formula (I), wherein: n represents an integer of 3.

In a further embodiment of the above-mentioned aspect, the invention relates to compounds of formula (I), wherein: n represents an integer of 4.

In a further embodiment of the above-mentioned aspect, the invention relates to compounds of formula (I), wherein: $R^2$ represents, independently from each other, a hydrogen atom or a methyl group.

In a further embodiment of the above-mentioned aspect, the invention relates to compounds of formula (I), wherein: $R^2$ represents a hydrogen atom.

In a further embodiment of the above-mentioned aspect, the invention relates to compounds of formula (I), wherein: $R^2$ represents a methyl group.

In a further embodiment of the above-mentioned aspect, the invention relates to compounds of formula (I), wherein: $R^3$ represents a group selected from:

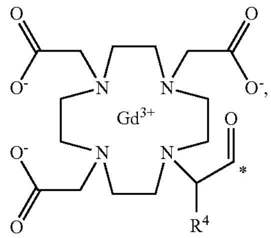

and

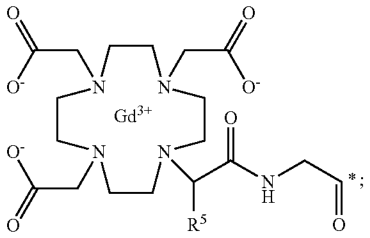

in which groups * indicates the point of attachment of said group with the rest of the molecule.

In a further embodiment of the above-mentioned aspect, the invention relates to compounds of formula (I), wherein:

$R^3$ represents a

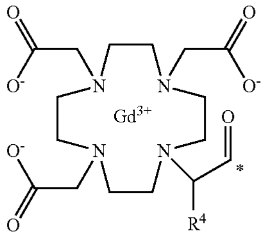

group, in which group * indicates the point of attachment of said group with the rest of the molecule.

In a further embodiment of the above-mentioned aspect, the invention relates to compounds of formula (I), wherein:

$R^3$ represents a

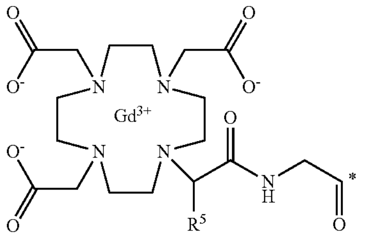

group;

in which group * indicates the point of attachment of said group with the rest of the molecule.

In a further embodiment of the above-mentioned aspect, the invention relates to compounds of formula (I), wherein:

$R^3$ represents a

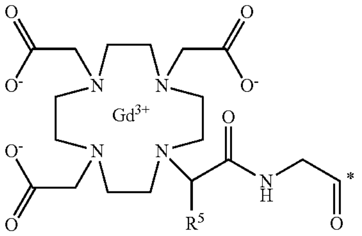

group;

in which group * indicates the point of attachment of said group with the rest of the molecule; and $R^5$ represents a hydrogen atom or a methyl group.

In a further embodiment of the above-mentioned aspect, the invention relates to compounds of formula (I), wherein:

$R^3$ represents a

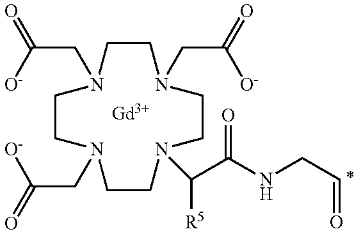

group;

in which group * indicates the point of attachment of said group with the rest of the molecule; and $R^5$ represents a hydrogen atom.

In a further embodiment of the above-mentioned aspect, the invention relates to compounds of formula (I), wherein:

$R^3$ represents a

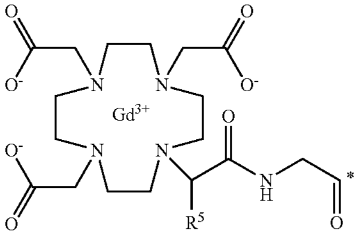

group;

in which group * indicates the point of attachment of said group with the rest of the molecule; and $R^5$ represents a methyl group.

In a further embodiment of the above-mentioned aspect, the invention relates to compounds of formula (I), wherein: $R^4$ represents, independently from each other, a hydrogen atom or a methyl group.

In a further embodiment of the above-mentioned aspect, the invention relates to compounds of formula (I), wherein: $R^4$ represents hydrogen atom.

In a further embodiment of the above-mentioned aspect, the invention relates to compounds of formula (I), wherein: $R^4$ represents a methyl group.

In a further embodiment of the above-mentioned aspect, the invention relates to compounds of formula (I), wherein: $R^5$ represents, independently from each other, a hydrogen atom or a methyl group.

In a further embodiment of the above-mentioned aspect, the invention relates to compounds of formula (I), wherein: $R^5$ represents hydrogen atom.

In a further embodiment of the above-mentioned aspect, the invention relates to compounds of formula (I), wherein: $R^5$ represents a methyl group.

It is to be understood that the present invention relates also to any combination of the embodiments described above.

Another embodiment of the first aspect are compounds of formula (I) selected from the group consisting of:

Pentagadolinium[4,10-bis(carboxylatomethyl)-7-{3,6,10,18,22,25-hexaoxo-26-[4,7,10-tris(carboxylatomethyl)-1,4,7,10-tetraazacyclododecan-1-yl]-14-[({2-[4,7,10-tris(carboxylatomethyl)-1,4,7,10-tetraazacyclododecan-1-yl]propanoyl}amino)acetyl]-9,19-bis({[({2-[4,7,10-tris(carboxylatomethyl)-1,4,7,10-tetraazacyclododecan-1-yl]-propanoyl}amino)acetyl]amino}methyl)-4,7,11,14,17,21,24-heptaazaheptacosan-2-yl}-1,4,7,10-tetraazacyclododecan-1-yl]acetate, Hexagadolinium[4,10-bis(carboxylatomethyl)-7-{3,6,10,15,19,22-hexaoxo-23-[4,7,10-tris(carboxylatomethyl)-1,4,7,10-tetraazacyclododecan-1-yl]-9,16-bis({[({2-[4,7,10-tris-(carboxylatomethyl)-1,4,7,10-tetraazacyclododecan-1-yl]propanoyl}amino)acetyl]amino}-methyl)-11-(2-{[3-{[({2-[4,7,10-tris(carboxylatomethyl)-1,4,7,10-tetraazacyclododecan-1-yl]-propanoyl}amino)acetyl]amino}-2-({[({2-[4,7,10-tris(carboxylatomethyl)-1,4,7,10-tetraaza-cyclododecan-1-yl]propanoyl}amino)acetyl]amino}methyl)propanoyl]amino}ethyl)-4,7,11,14,18,21-hexaazatetracosan-2-yl}-1,4,7,10-tetraazacyclododecan-1-yl]acetate, Tetragadolinium [4,10-bis(carboxylatomethyl)-7-{3,6,12,15-tetraoxo-16-[4,7,10-tris-(carboxylatomethyl)-1,4,7,10-tetraazacyclododecan-1-yl]-9,9-bis({[({2-[4,7,10-tris-(carboxylatomethyl)-1,4,7,10-tetraazacyclododecan-1-yl]propanoyl}amino)acetyl]amino}-methyl)-4,7,11,14-tetraazaheptadecan-2-yl}-1,4,7,10-tetraazacyclododecan-1-yl]acetate, Tetragadolinium {4,10-bis(carboxylatomethyl)-7-[(2R,16R)-3,6,12,15-tetraoxo-16-[4,7,10-tris(carboxylatomethyl)-1,4,7,10-tetraazacyclododecan-1-yl]-9,9-bis({[({(2R)-2-[4,7,10-tris(carboxylatomethyl)-1,4,7,10-tetraazacyclododecan-1-yl]propanoyl}amino)acetyl]amino}-methyl)-4,7,11,14-tetraazaheptadecan-2-yl]-1,4,7,10-tetraazacyclododecan-1-yl}acetate, Tetragadolinium {4,10-bis(carboxylatomethyl)-7-[(2S,16S)-3,6,12,15-tetraoxo-16-[4,7,10-tris(carboxylatomethyl)-1,4,7,10-tetraazacyclododecan-1-yl]-9,9-bis({[({(2S)-2-[4,7,10-tris(carboxylatomethyl)-1,4,7,10-tetraazacyclododecan-1-yl]propanoyl}amino)acetyl]amino}-methyl)-4,7,11,14-tetraazaheptadecan-2-yl]-1,4,7,10-tetraazacyclododecan-1-yl}acetate, Pentagadolinium[4-(1-{[2-(bis{2-[({1,4-bis[({2-[4,7,10-tris(carboxylatomethyl)-1,4,7,10-tetraazacyclododecan-1-yl]propanoyl}amino)acetyl]-1,4-diazepan-6-yl}carbonyl)amino]ethyl}-amino)-2-oxoethyl]amino}-1-oxopropan-2-yl)-7,10-bis(carboxylatomethyl)-1,4,7,10-tetraazacyclododecan-1-yl]acetate, Hexagadolinium 2,2',2",2''',2'''',2''''',2'''''', 2''''''',2'''''''',2''''''''', 2'''''''''',2''''''''''',2'''''''''''',2''''''''''''', 2'''''''''''''',2''''''''''''''', 2'''''''''''''''',2'''''''''''''''''-{ethane-1,2-diylcarbamoyl-1,4-diazepane-6,1,4-triyltris[(2-oxoethane-2,1-diyl)imino(I-oxopropane-1,2-diyl)-1,4,7,10-tetraazacyclododecane-10,1,4,7-tetrayl]}octadecaacetate, Hexagadolinium 2,2',2",2''',2'''',2''''',2'''''',2''''''',2'''''''',2''''''''', 2'''''''''',2''''''''''',2'''''''''''',2''''''''''''', 2'''''''''''''',2''''''''''''''', 2'''''''''''''''',2'''''''''''''''''-(1,4,7-triazonane-1,4,7-triyltris{carbonyl-1,4-diazepane-6,1,4-triylbis[(2-oxoethane-2,1-diyl)imino(I-oxopropane-1,2-diyl)-1,4,7,10-tetraaza cyclododecane-10,1,4,7-tetrayl]}) octadecaacetate, Tetragadolinium 2,2',2",2''', 2'''', 2''''',2'''''',2''''''',2'''''''',2''''''''', 2'''''''''',2'''''''''''-{1,4,7,10-tetraazacyclododecane-1,4,7,10-tetrayltetrakis[(2-oxoethane-2,1-diyl)imino(I-oxopropane-1,2-diyl)-1,4,7,10-tetraazacyclododecane-10,1,4,7-tetrayl]}dodecaacetate, Hexagadolinium 2,2',2",2''', 2'''', 2''''',2'''''', 2''''''', 2'''''''', 2''''''''', 2'''''''''', 2''''''''''',2'''''''''''',2''''''''''''', 2'''''''''''''',2''''''''''''''', 2'''''''''''''''',2'''''''''''''''''-{3,7,10-triazatricyclo[3.3.3.$0^{1,5}$]undecane-3,7,10-triyltris[carbonyl(3,6,11,14-tetraoxo-4,7,10,13-tetraazahexadecane-8,2,15-triyl)di-1,4,7,10-tetraazacyclododecane-10,1,4,7-tetrayl]}octadecaacetate, Tetragadolinium 2,2',2",2''', 2'''', 2''''',2'''''',2''''''',2'''''''',2''''''''', 2''''''''''-(3,7,9-triazabicyclo[3.3.1]nonane-3,7-diylbis{carbonyl-1,4-diazepane-6,1,4-triylbis[(2-oxoethane-2,1-diyl)-1,4,7,10-tetraazacyclododecane-10,1,4,7-tetrayl]})dodecaacetate, Tetragadolinium {4,10-bis(carboxylatomethyl)-7-[2-oxo-2-({3-({[4,7,10-tris(carboxylatomethyl)-1,4,7,10-tetraaza-cyclododecan-1-yl]acetyl}amino)-2,2-bis[({[4,7,10-tris(carboxylatomethyl)-1,4,7,10-tetraazacyclododecan-1-yl]acetyl}amino)methyl]propyl}amino)ethyl]-1,4,7,10-tetraazacyclododecan-1-yl}acetate, and Tetragadolinium [4,10-bis(carboxylatomethyl)-7-{2,5,11,14-tetraoxo-15-[4,7,10-tris-(carboxylatomethyl)-1,4,7,10-tetraazacyclododecan-1-yl]-8,8-bis({[({[4,7,10-tris(carboxylato-methyl)-1,4,7,10-tetraazacyclododecan-1-yl]acetyl}amino)acetyl]amino}methyl)-3,6,10,13-tetraazapentadec-1-yl}-1,4,7,10-tetraazacyclododecan-1-yl]acetate, or a stereoisomer, a tautomer, an N-oxide, a hydrate, a solvate, or a salt thereof, or a mixture of same.

In accordance with another aspect, the present invention covers methods of preparing compounds of the present invention, said methods comprising the steps as described in the Experimental Section herein.

In accordance with a further aspect, the present invention covers intermediate compounds which are useful for the preparation of the compounds of general formula (I), supra.

Particularly, the invention covers compounds of general formula (II-a):

(II-a)

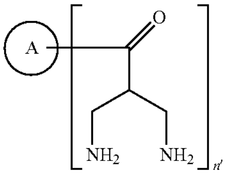

in which

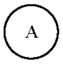

is as defined for the compounds of general formula (I), supra, and n' represents an integer of 2, 3 and 4, and salts thereof; and compounds of general formula (II-b):

(II-b)

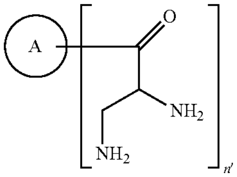

in which

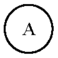

is as defined for the compounds of general formula (I), supra, and n' represents an integer of 2, 3 and 4, and salts thereof; and compounds of general formula (II-c):

(II-c)

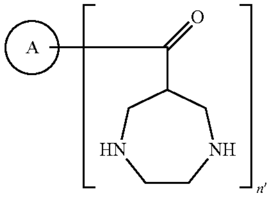

in which

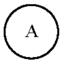

is as defined for the compounds of general formula (I), supra, and n' represents an integer of 2, 3 and 4, and salts thereof.

More particularly still, the present invention covers the intermediate compounds which are disclosed in the example section of this text, infra.

In accordance with a further aspect, the present invention covers the use of the compounds of general formula (II-a):

(II-a)

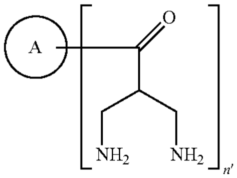

in which

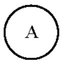

is as defined for the compounds of general formula (I), supra, and n' represents an integer of 2, 3 and 4, and salts thereof, for the preparation of a compound of general formula (I) as defined supra.

In accordance with a further aspect, the present invention covers the use of the compounds of general formula (II-b):

(II-b)

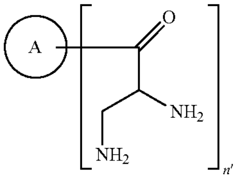

in which

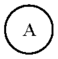

is as defined for the compounds of general formula (I), supra, and n' represents an integer of 2, 3 and 4, and salts thereof, for the preparation of a compound of general formula (I) as defined supra.

In accordance with a further aspect, the present invention covers the use of the compounds of general formula (II-c):

(II-c)

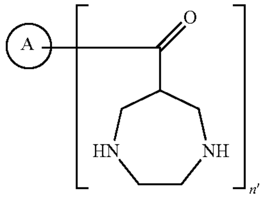

in which

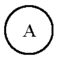

is as defined for the compounds of general formula (I), supra, and n' represents an integer of 2, 3 and 4, and salts thereof, for the preparation of a compound of general formula (I) as defined supra.

In accordance with a further aspect, the present invention covers the use of the compounds of general formula (III):

(III)

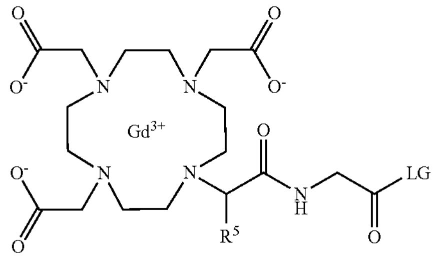

in which $R^5$ is as defined for the compounds of general formula (I), supra, and LG represents an activating leaving group, such as for example 4-nitrophenol, or a group as defined for the synthesis of the compounds of the general formula (I-a) infra, for the preparation of a compound of general formula (I) as defined supra.

In accordance with a further aspect, the present invention covers the use of the compounds of general formula (IV):

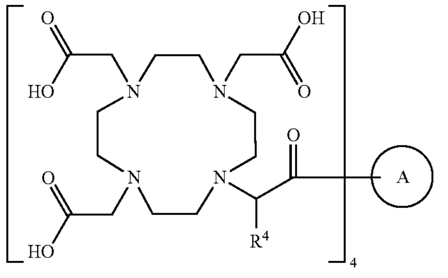

in which $R^4$ is as defined for the compounds of general formula (I), supra, and

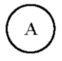

represents a tetraamine as defined for the compounds of general formula (I), supra, for the preparation of a compound of general formula (I) as defined supra.

Another aspect of the invention is the use of a compound of general formula (I) for diagnostic imaging.

Preferably, the use of a compound of the invention in the diagnosis is performed using magnetic resonance imaging (MRI).

Other aspects of the invention are compounds of general formula (I) for use in diagnostic imaging.

Other aspects of the invention are compounds of general formula (I) for use in magnetic resonance imaging (MRI).

The invention also contains compounds of general formula (I) for the manufacture of diagnostic agents.

Another aspect of the invention is the use of the compounds of general formula (I) or mixtures thereof for the manufacture of diagnostic agents.

Another aspect of the invention is the use of the compounds of general formula (I) or mixtures thereof for the manufacture of diagnostic agents for magnetic resonance imaging (MRI).

Another aspect of the invention is a method of imaging body tissue in a patient, comprising the steps of administering to the patient an effective amount of one or more compounds of general formula (I) in a pharmaceutically acceptable carrier, and subjecting the patient to NMR tomography. Such a method is described in U.S. Pat. No. 5,560,903.

For the manufacture of diagnostic agents, for example the administration to human or animal subjects, the compounds of general formula (I) or mixtures will conveniently be formulated together with pharmaceutical carriers or excipient. The contrast media of the invention may conveniently contain pharmaceutical formulation aids, for example stabilizers, antioxidants, pH adjusting agents, flavors, and the like. Production of the diagnostic media according to the invention is also performed in away known in the art, see U.S. Pat. No. 5,560,903. They may be formulated for parenteral or enteral administration or for direct administration into body cavities. For example, parenteral formulations contain a sterile solution or suspension in a dose of 0.0001-5 mmol gadolinium/kg body weight, especially 0.005-0.5 mmol gadolinium/kg body weight of the compound of formula (I) according to this invention. Thus, the media of the invention may be in conventional pharmaceutical formulations such as solutions, suspensions, dispersions, syrups, etc. in physiologically acceptable carrier media, preferably in water for injections. When the contrast medium is formulated for parenteral administration, it will be preferably isotonic or hypertonic and close to pH 7.4.

In a further aspect, the invention is directed to a method of diagnosing and health monitoring of patients. This method comprises a) administering to a human in need of such diagnosis a compound of the invention for detecting the compound in the human as described above and herein, and b) measuring the signal arising from the administration of the compound to the human, preferably by magnetic resonance imaging (MRI).

General Synthesis

The compounds according to the invention can be prepared according to the following schemes 1 through 12.

The schemes and procedures described below illustrate synthetic routes to the compounds of general formula (I) of the invention and are not intended to be limiting. It is obvious to the person skilled in the art that the order of transformations as exemplified in the schemes can be modified in various ways. The order of transformations exemplified in the schemes is therefore not intended to be limiting. Appropriate protecting groups and their introduction and cleavage are well-known to the person skilled in the art (see for example T. W. Greene and P. G. M. Wuts in *Protective Groups in Organic Synthesis,* $3^{rd}$ edition, Wiley 1999). Specific examples are described in the subsequent paragraphs.

The term "amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N-P protecting groups, N-sulfenyl, N-sulfonyl and N-silyl, and which is chosen from but not limited to those described in the textbook Greene and Wuts, Protective Groups in Organic Synthesis, third edition, pages 494-653, included herewith by reference. The "amine-protecting group" is preferably carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT) or the protected amino group is a 1,3-dioxo-1,3-dihydro-2H-isoindol-2-yl (phthalimido) or an azido group.

The term "carboxyl-protecting group" as employed herein by itself or as part of another group is known or obvious to someone skilled in the art, which is chosen from but not limited to a class of protecting groups namely esters, amides and hydrazides, and which is chosen from but not limited to those described in the textbook Greene and Wuts, Protective Groups in Organic Synthesis, third edition, pages 369-453, included herewith by reference. The "carboxyl-protecting group" is preferably methyl, ethyl, propyl, butyl, tert-butyl, allyl, benzyl, 4-methoxybenzyl or 4-methoxyphenyl.

The contents of the documents which are cited herein are hereby incorporated by reference.

A route for the preparation of compounds of general formula (I-a) is described in Scheme 1.

Scheme 1

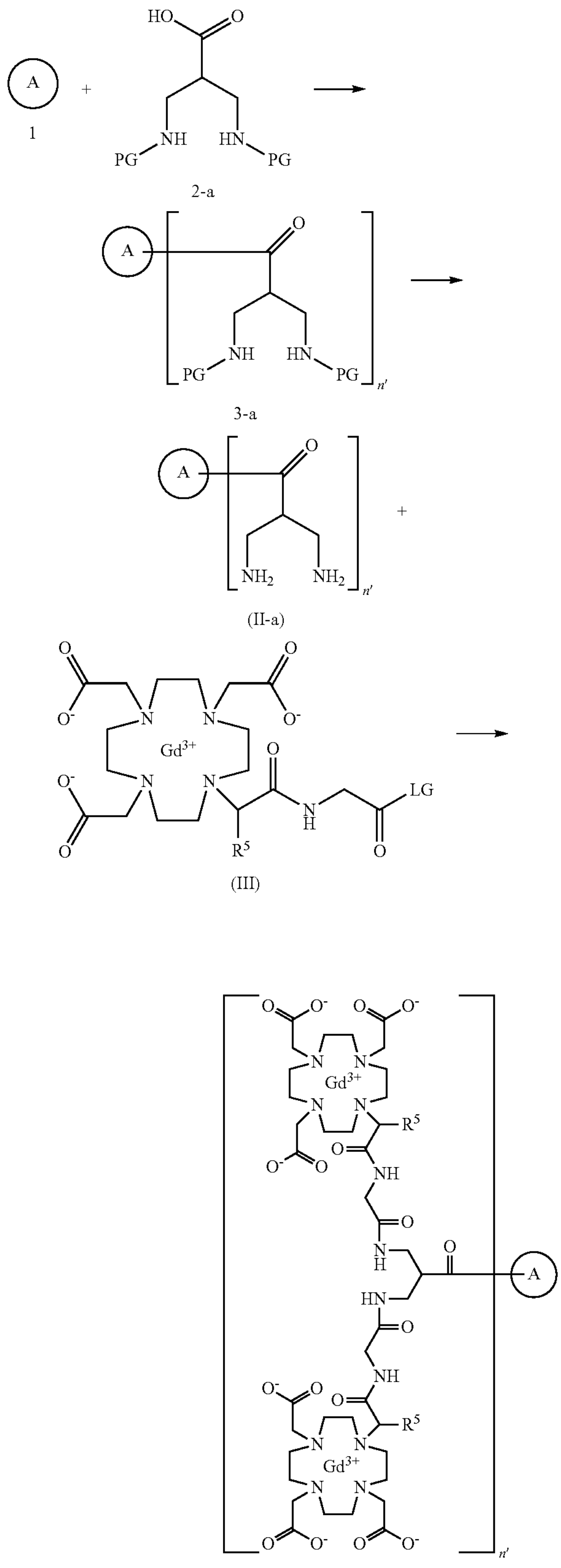

1 2-a 3-a (II-a) (III) (I-a)

Scheme 1: Route for the preparation of compounds of general formula (I-a), wherein

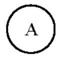

and $R^5$ have the meaning as given for general formula (I), supra, n' represents an integer of 2, 3 and 4, and PG represents an amine-protecting group, such as for example a tert-butyloxycarbonyl group (BOC) or a group as defined below.

The starting materials 1 are either commercially available polyamines or salts thereof [for example CAS 111-40-0, CAS 28634-67-5, CAS 4730-54-5, CAS 4742-00-1, CAS 294-90-6] or polyamines or salts thereof which are known from the literature, or which can be prepared in analogy to compounds which are described in the literature or in the experimental part, infra [for example CAS 41077-50-3].

A triamine or tetraamine 1 or a salt thereof is reacted with a protected 3-amino-2-(aminomethyl)propionic acid 2-a, [for example CAS 496974-25-5] or a salt thereof, leading to an intermediate 3-a. Suitable amine-protecting groups for 3-amino-2-(aminomethyl)propionic acid are for example carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT) or the protected amino group is a 1,3-dioxo-1,3-dihydro-2H-isoindol-2-yl (phthalimido) or an azido group. The coupling reaction of polyamines 1 with propionic acid derivatives 2-a is carried out employing standard peptide coupling conditions, such as for example coupling in the presence of HATU and N,N-diisopropylethylamine, in a suitable solvent such as for example N,N-dimethylformamide, in a temperature range from room temperature up to 80° C., to furnish the intermediates of general formula 3-a.

Deprotection of intermediates of general formula 3-a leading to intermediates of general formula (II-a) or salts thereof is performed in analogy to methods described in the textbook Greene and Wuts, Protective Groups in Organic Synthesis, second edition, pages 309-405, included herewith by reference. The amine-protecting group tert-butyloxycarbonyl (BOC) is removed by dissolving a BOC-protected intermediate of general formula 3-a in a suitable solvent, such as for example an alcohol, tetrahydrofuran, dioxane or N,N-dimethylformamide, or a mixture thereof, by adding suitable acids, such as for example aqueous hydrochloric or hydrobromic acid or trifluoroacetic acid in organic solvents like dichloromethane. The deprotection reaction is carried out at temperatures ranging from room temperature to the boiling point of the respective solvent or solvent mixture, preferably the reaction is carried out at temperatures ranging from room temperature to 80° C.

Intermediates of general formula (II-a) or salts thereof are reacted with Gd-complexes of the general formula (III), which are activated by a leaving group (LG), such as for example pentafluorophenol, 4-nitrophenol, 1-hydroxypyrrolidine-2,5-dione, hydroxybenzotriazole or 3H-[1,2,3]triazolo[4,5-b]pyridin-3-ol, leading to compounds of the general formula (I-a). The preparation of activated esters is well known to the person skilled in the art and is described in detail for example by C. A. Montalbetti and V. Falque in Tetrahedron 61 (2005), 10827-10852. For example, the preparation of gadolinium 2,2',2''-[10-(1-{[2-(4-nitrophenoxy)-2-oxoethyl]amino}-1-oxopropan-2-yl)-1,4,7,10-tetraazacyclododecane-1,4,7-triyl]triacetate is described in detail in WO 2001/051095 A2. The reaction of intermediates of general formula (II-a) with the activated Gd-complexes of general formula (III) is carried out in a suitable solvent, such as for example dimethyl sulfoxide, N,N-dimethylformamide, pyridine or a mixture thereof, optionally the reaction is carried out in the presence of a base. Suitable bases are for example trialkylamines, such as for example triethylamine or N,N-diisopropylethylamine. The reaction is carried out at temperatures ranging from room temperature to 100° C., preferably the reaction is carried out at temperatures ranging from 50° C. to 70° C.

A route for the preparation of compounds of general formula (I-b) is described in Scheme 2.

Scheme 2

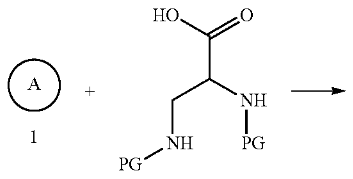

1

2-b

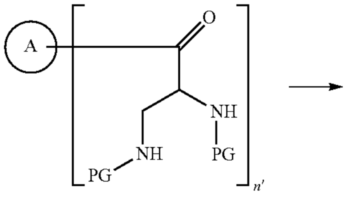

3-b

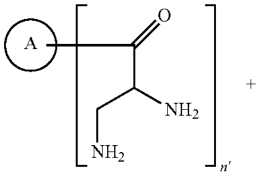

(II-b)

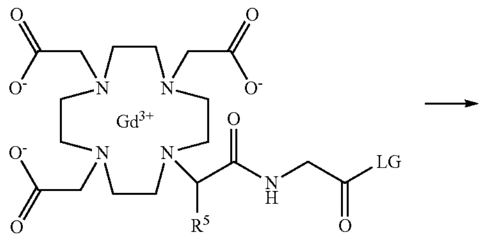

(III)

-continued

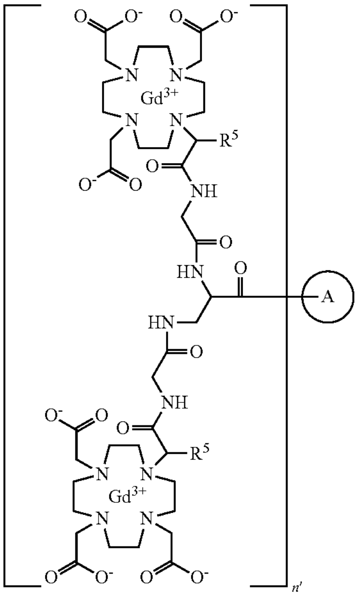

(I-b)

Scheme 2: Route for the preparation of compounds of general formula (I-b), wherein

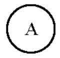

and $R^5$ have the meaning as given for general formula (I), supra, n' represents an integer of 2, 3 and 4, and PG represents an amine-protecting group, such as for example a tert-butyloxycarbonyl group (BOC) or a group as defined for the synthesis of the compounds of the general formula (I-a) supra.

The compounds of general formula (I-b) are synthesized in analogy to the compounds of general formula (I-a), as described above.

The starting materials 1 are either commercially available polyamines or salts thereof [for example CAS 111-40-0, CAS 28634-67-5, CAS 4730-54-5, CAS 4742-00-1, CAS 294-90-6] or polyamines or salts thereof which are known from the literature, or which can be prepared in analogy to compounds which are described in the literature or in the experimental part, infra [for example CAS 41077-50-3].

A triamine or tetraamine 1 or a salt thereof is reacted with a protected 2,3-diaminopropionic acid 2-b [for example CAS 201472-68-6] or a salt thereof, to furnish an intermediate of general formula 3-b, which after deprotection furnishes an intermediate of general formula (II-b) or a salt thereof. In the final step an intermediate of general formula (II-b) or a salt thereof is reacted with a Gd-complex of the general formula (III), leading to a compound of the general formula (I-b).

A route for the preparation of compounds of general formula (I-c) is described in Scheme 3.

Scheme 3

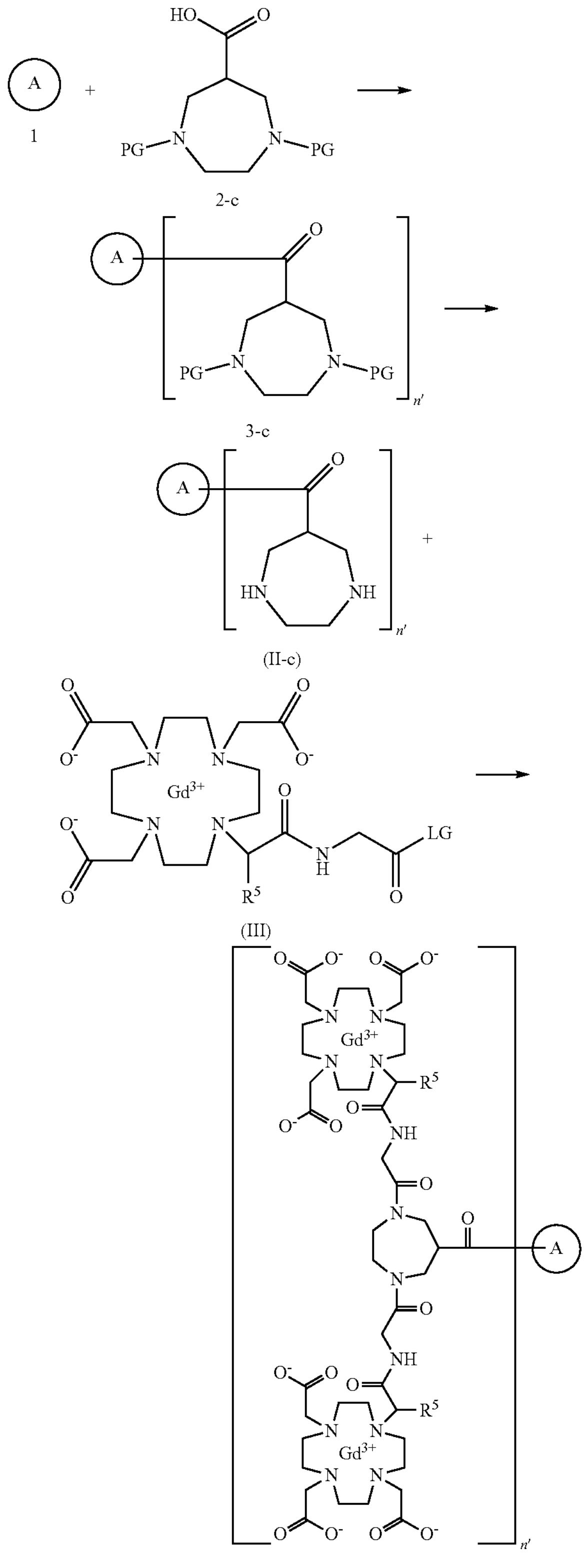

1

2-c 3-c (II-c)

(III)

(I-c)

Scheme 3: Route for the preparation of compounds of general formula (I-c), wherein

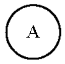

and $R^5$ have the meaning as given for general formula (I), supra, n' represents an integer of 2, 3 and 4, and PG represents an amine-protecting group, such as for example a tert-butyloxycarbonyl group (BOC) or a group as defined for the synthesis of the compounds of the general formula (I-a) supra.

The compounds of general formula (I-c) are synthesized in analogy to the compounds of general formula (I-a), as described above.

The starting materials 1 are either commercially available polyamines or salts thereof [for example CAS 111-40-0, CAS 28634-67-5, CAS 4730-54-5, CAS 4742-00-1, CAS 294-90-6] or polyamines or salts thereof which are known from the literature, or which can be prepared in analogy to compounds which are described in the literature or in the experimental part, infra [for example CAS 41077-50-3].

A triamine or tetraamine 1 or a salt thereof is reacted with a protected 1,4-diazepane-6-carboxylic acid 2-c, which can be synthesized as described in the experimental part infra, starting from methyl 1,4-dibenzyl-1,4-diazepane-6-carboxylate [see U.S. Pat. No. 5,866,562], to furnish an intermediate of general formula 3-c, which after deprotection furnishes an intermediate of general formula (II-c) or a salt thereof. In the final step an intermediate of general formula (II-c) or a salt thereof is reacted with a Gd-complex of the general formula (III), leading to a compound of the general formula (I-c).

A route for the preparation of compounds of general formula (I-d) is described in Scheme 4.

Scheme 4

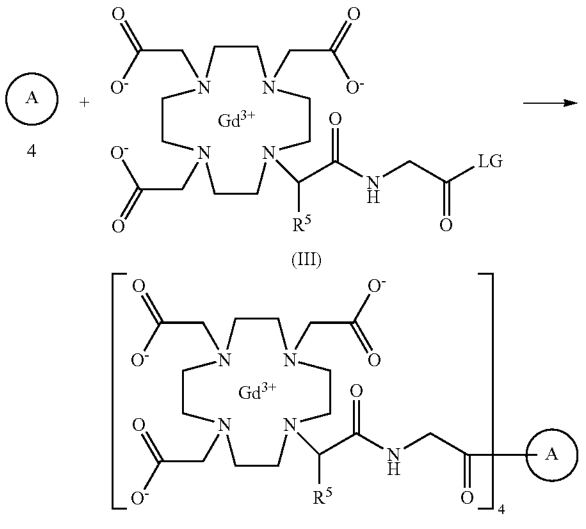

4

(III)

(I-d)

Scheme 4: Route for the preparation of compounds of general formula (I-d), wherein $R^5$ has the meaning as given for general formula (I), supra,

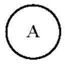

represents a tetraamine as given for general formula (I), supra, and LG represents an activating leaving group, such as for example 4-nitrophenol, or a group as defined for the synthesis of the compounds of the general formula (I-a) supra.

The starting materials 4 are either commercially available tetraamines or salts thereof [for example CAS 4742-00-1, CAS 294-90-6] or tetraamines or salts thereof which are known from the literature, or which can be prepared in analogy to compounds which are described in the literature.

A tetraamine 4 or a salt thereof is reacted with a Gd-complex of the general formula (III), which is activated by a leaving group (LG), such as for example pentafluorophenol, 4-nitrophenol, 1-hydroxypyrrolidine-2,5-dione, hydroxybenzotriazole or 3H-[1,2,3]triazolo[4,5-b]pyridin-3-ol, leading to a compound of the general formula (I-d). The preparation of activated esters is well known to the person skilled in the art and is described in detail for example by C. A. Montalbetti and V. Falque in Tetrahedron 61 (2005), page 10827-10852. For example, the preparation of gadolinium 2,2',2''-[10-(1-{[2-(4-nitrophenoxy)-2-oxoethyl]amino}-1-oxopropan-2-yl)-1,4,7,10-tetraazacyclodode-cane-1,4,7-triyl]triacetate is described in detail in WO 2001/051095 A2. The reaction of polyamine 4 or a salt thereof with the activated Gd-complexes of general formula (III) is carried out in a suitable solvent, such as for example dimethyl sulfoxide, N,N-dimethylformamide, pyridine or a mixture thereof, optionally the reaction is carried out in the presence of a base. Suitable bases are for example trialkylamines, such as for example triethylamine or N,N-diisopropylethylamine. The reaction is carried out at temperatures ranging from room temperature to 100° C., preferably the reaction is carried out at temperatures ranging from 50° C. to 70° C.

A route for the preparation of compounds of general formula (I-e) is described in Scheme 5.

Scheme 5

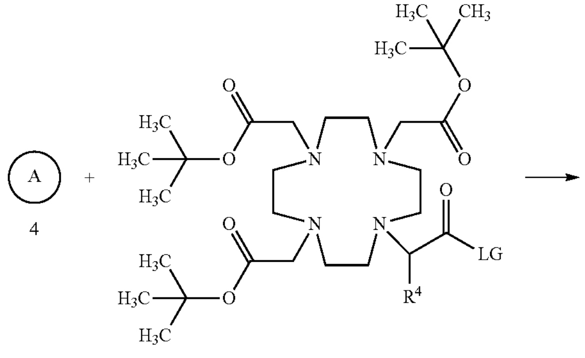

4

5

-continued

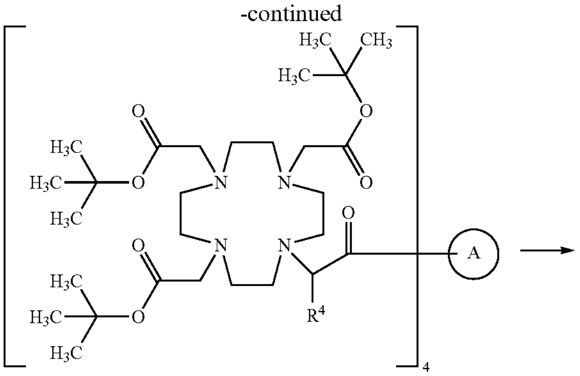

6

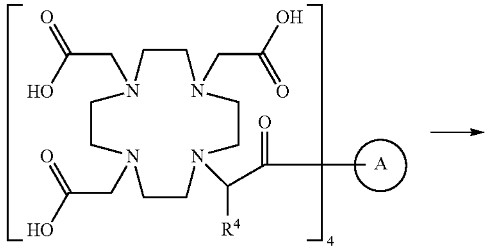

(IV)

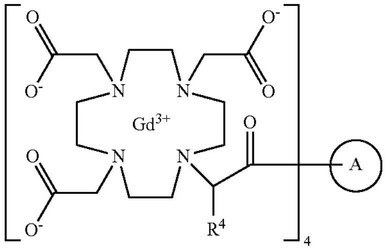

(I-e)

Scheme 5: Route for the preparation of compounds of general formula (I-e), wherein $R^4$ has the meaning as given for general formula (I), supra,

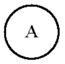

represents a tetraamine as given for general formula (I), supra, and LG represents an activating leaving group, such as for example 4-nitrophenol, or a group as defined for the synthesis of the compounds of the general formula (I-a) supra.

The starting materials 4 are either commercially available tetraamines or salts thereof [for example CAS 4742-00-1, CAS 294-90-6] or tetraamines or salts thereof which are known from the literature, or which can be prepared in analogy to compounds which are described in the literature.

A tetraamine 4 or a salt thereof is reacted with a [4,7,10-tris(2-tert-butoxy-2-oxoethyl)-1,4,7,10-tetraazacyclododecan-1-yl]acetic acid derivative 5, which is activated by a leaving group (LG), such as for example pentafluorophenol, 4-nitrophenol, 1-hydroxypyrrolidine-2,5-dione [for example, the synthesis of tri-tert-butyl 2,2',2''-(10-{2-[(2,5-dioxopyrrolidin-1-yl)oxy]-2-oxoethyl}-1,4,7,10-tetraazacyclododecane-1,4,7-triyl)triacetate is described in detail by Cong Li et al., *J. Am. Chem. Soc.* 2006, 128, p. 15072-

15073; S3-5 and Galibert et al., *Biorg. and Med. Chem. Letters* 20 (2010), 5422-5425] or hydroxybenzotriazole, leading to an intermediate 6. The preparation of activated esters is well known to the person skilled in the art and is described in detail for example by C. A. Montalbetti and V. Falque in *Tetrahedron* 61 (2005), 10827-10852. The coupling reaction of polyamines 4 with [4,7,10-tris(2-tert-butoxy-2-oxoethyl)-1,4,7,10-tetraazacyclododecan-1-yl]acetic acid derivatives 5 is carried out in a suitable solvent, such as for example N,N-dimethylformamide or dimethyl sulfoxide, or a mixture thereof, in a temperature range from room temperature up to 80° C., to furnish the intermediates 6. Cleavage of the carboxyl-protecting groups of intermediates 6 to yield the intermediates of general formula (IV) can be achieved as described in the textbook Greene and Wuts, Protective Groups in Organic Synthesis, second edition, pages 245-247. The deprotection is, for example, performed by dissolving and stirring of intermediates 6 in trifluoroacetic acid at room temperature for several hours. The complexation of intermediates of general formula (IV) with suitable gadolinium (Ill) compounds or salts, such as for example gadolinium trioxide, gadolinium triacetate or hydrates of gadolinium triacetate, gadolinium trichloride or gadolinium trinitrate, is well known to a person skilled in the art. The intermediates of general formula (IV) are dissolved in water and after adding of suitable gadolinium (Ill) compounds the resulting mixtures are stirred in a temperature range from room temperature up to 100° C. at pH=1-7 for several hours, to furnish the compounds of general formula (I-e). Intermediates of general formula (IV) are, for example, dissolved in water, gadolinium triacetate tetrahydrate is added, the pH is adjusted to 3.5-5.5 by addition of a suitable base, such as for example aqueous sodium hydroxide solution. The reaction is carried out at temperatures ranging from 50° C. to 80° C., leading to compounds of general formula (I-e).

A route for the preparation of compounds of general formula (I-f) is described in Scheme 6.

Scheme 6

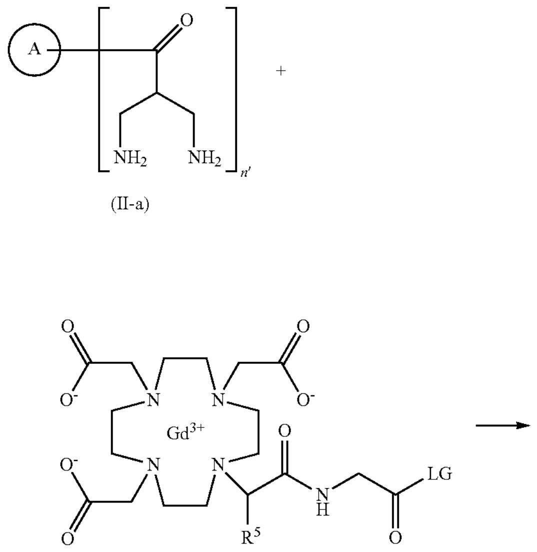

(II-a)

(III)

-continued

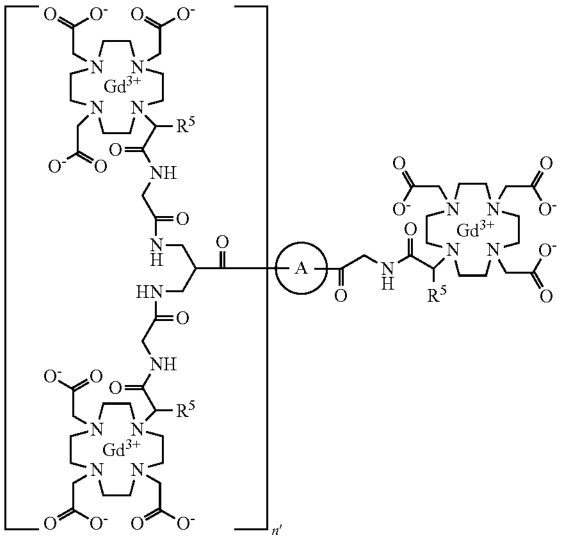

(I-f)

Scheme 6: Route for the preparation of compounds of general formula (I-f), wherein n' represents an integer of 2, if

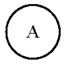

represents a triamine as defined supra, or n' represents an integer of 3, if

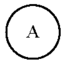

represents tetraamine as defined supra, and $R^5$ has the meaning as given for general formula (I), supra, and LG represents activating leaving groups, such as for example 4-nitrophenol or a group as defined below.

Intermediates of general formula (II-a) or salts thereof, as described in Scheme 1 and in the experimental part infra, wherein n' represents an integer of 2 and

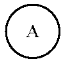

represents a triamine core as defined supra, or intermediates of general formula (II-a) or salts thereof, wherein n' represents an integer of 3 and

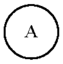

represents a tetraamine core as defined supra, are reacted with Gd-complexes of the general formula (III), which are activated by a leaving group (LG), such as for example pentafluorophenol, 4-nitrophenol, 1-hydroxypyrrolidine-2,5-dione, hdyroxybenzotriazole or 3H-[1,2,3]triazolo[4,5-b]pyridin-3-ol, leading to compounds of the general formula (I-f). The preparation of activated esters is well known to the person skilled in the art and is described in detail for example by C. A. Montalbetti and V. Falque in Tetrahedron 61 (2005), 10827-10852. For example, the preparation of gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl]triacetate is described in detail in WO 2001/051095 A2. The reaction of intermediates of general formula (II-a) or salts thereof with the activated Gd-complexes of general formula (III) is carried out in a suitable solvent, such as for example dimethyl sulfoxide, N,N-dimethylformamide, pyridine or a mixture thereof, optionally the reaction is carried out in the presence of a base. Suitable bases are for example trialkylamines, such as for example triethylamine or N,N-diisopropylethylamine. The reaction is carried out at temperatures ranging from room temperature to 100° C., preferably the reaction is carried out at temperatures ranging from 50° C. to 70° C.

A route for the preparation of compounds of general formula (I-g) is described in Scheme 7.

Scheme 7

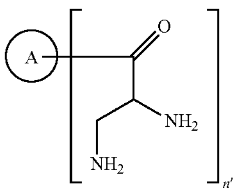

(II-b)

+

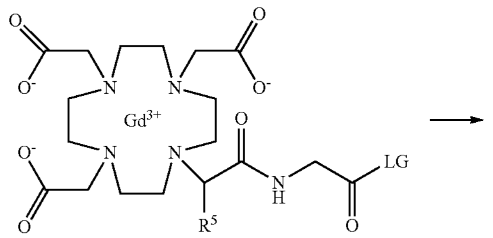

(III)

-continued

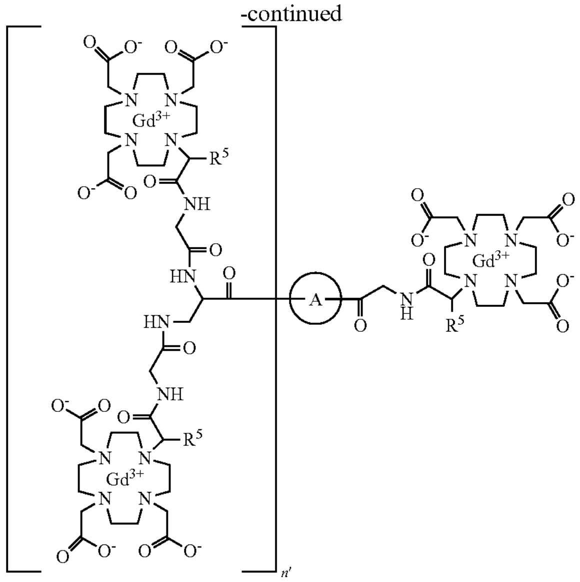

(I-g)

Scheme 7: Route for the preparation of compounds of general formula (I-g), wherein n' represents an integer of 2, if

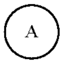

represents a triamine as defined supra, or n' represents an integer of 3 if

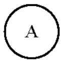

represents a tetraamine as defined supra, and $R^5$ has the meaning as given for general formula (I), supra, and LG represents activating leaving groups, such as for example 4-nitrophenol or a group as defined below.

The compounds of general formula (I-g) are synthesized in analogy to the compounds of general formula (I-f), as described above.

Intermediates of general formula (II-b) or salts thereof, as described in Scheme 2, wherein n' represents an integer of 2 and

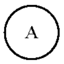

represents a triamine core as defined supra, or intermediates of general formula (II-b) or salts thereof, wherein n' represents an integer of 3 and

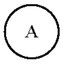

represents a tetraamine core as defined supra, are reacted with Gd-complexes of the general formula (III), which are activated by a leaving group (LG), such as for example pentafluorophenol, 4-nitrophenol, 1-hydroxypyrrolidine-2,5-dione, hydroxybenzotriazole or 3H-[1,2,3]triazolo[4,5-b]pyridin-3-ol, leading to compounds of the general formula (I-g).

A route for the preparation of compounds of general formula (I-h) is described in Scheme 8.

Scheme 8

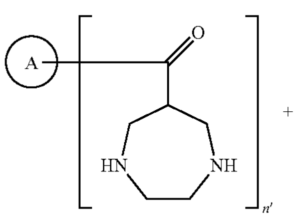

(II-c)

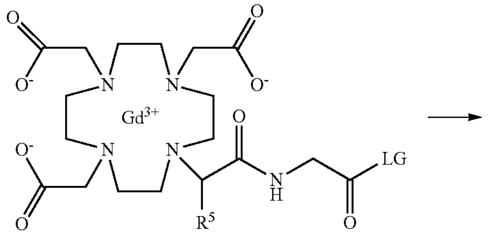

(III)

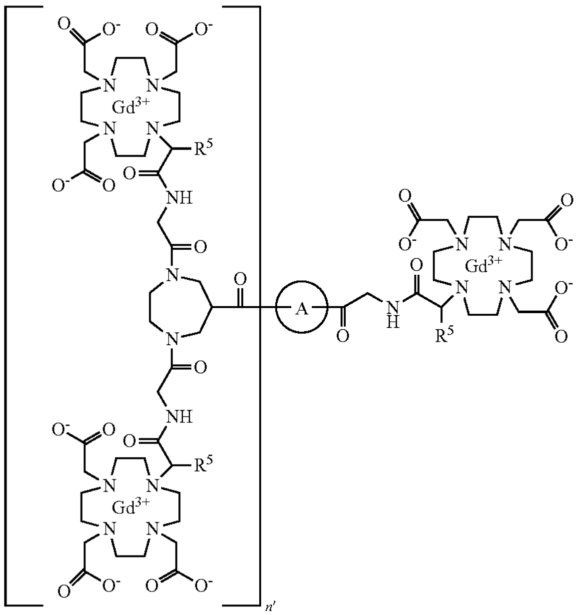

(I-h)

Scheme 8: Route for the preparation of compounds of general formula (I-h), wherein n' represents an integer of 2, if

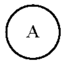

represents a triamine as defined supra, or n' represents an integer of 3, if

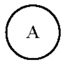

represents a tetraamine as defined supra, and $R^5$ has the meaning as given for general formula (I), supra, and LG represents activating leaving groups, such as for example 4-nitrophenol or a group as defined below.

The compounds of general formula (I-h) are synthesized in analogy to the compounds of general formula (I-f), as described above.

Intermediates of general formula (II-c) or salts thereof, as described in Scheme 3, wherein n' represents an integer of 2 and

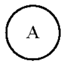

represents a triamine core as defined supra, or intermediates of general formula (II-c) or salts thereof, wherein n' represents an integer of 3 and

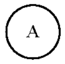

represents a tetraamine core as defined supra, are reacted with Gd-complexes of the general formula (III), which are activated by a leaving group (LG), such as for example pentafluorophenol, 4-nitrophenol, 1-hydroxypyrrolidine-2,5-dione, hydroxybenzotriazole or 3H-[1,2,3]triazolo[4,5-b]pyridin-3-ol, leading to compounds of the general formula (I-h).

A route for the preparation of compounds of general formula (I-k) is described in Scheme 9.

Scheme 9
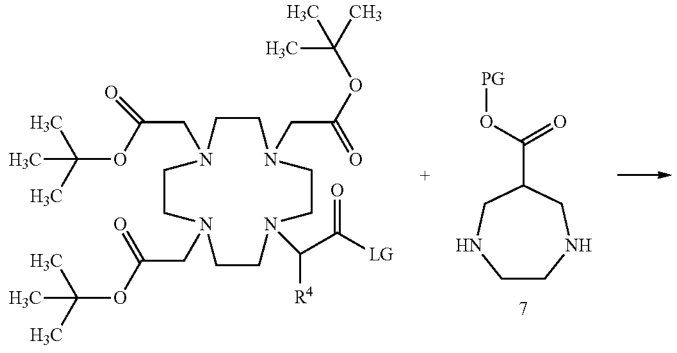
5
7
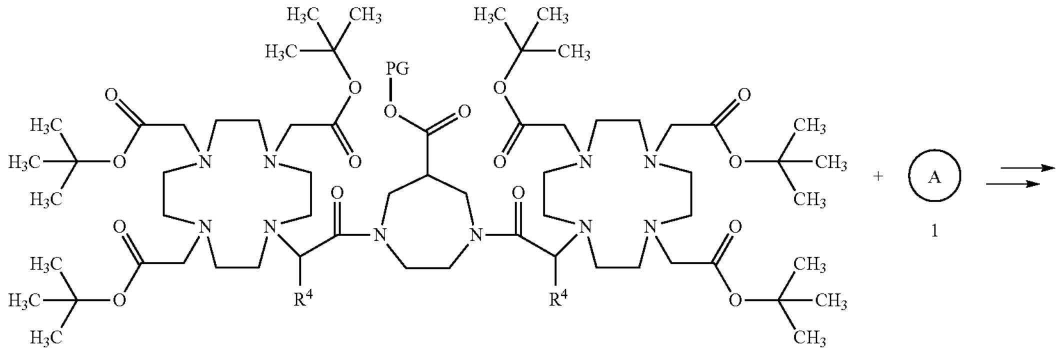
8
1
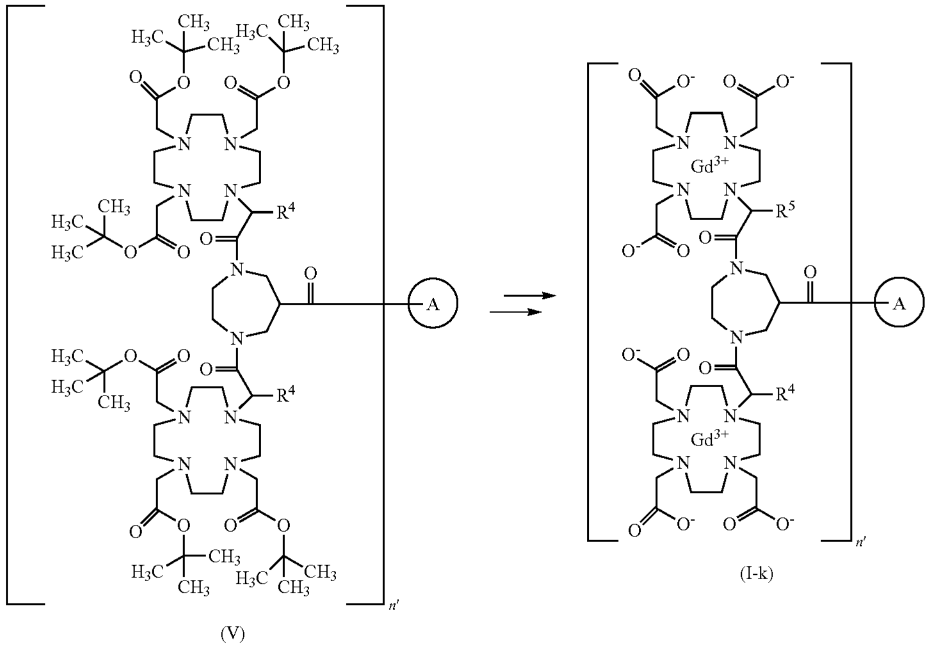
(V)
(I-k)

Scheme 9: Route for the preparation of compounds of general formula (I-k), wherein

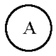

and $R^4$ have the meaning as given for general formula (I), supra, n' represents an integer of 2, 3 and 4, LG represents activating leaving groups, such as for example 1-hydroxy-pyrrolidine-2,5-dione, or a group as defined for the synthesis of the compounds of the general formula (I-a) supra, and PG represents a carboxyl-protecting group, such as for example a methyl or ethyl group.

The starting materials 1 are either commercially available polyamines or salts thereof [for example CAS 111-40-0, CAS 28634-67-5, CAS 4730-54-5, CAS 4742-00-1, CAS 294-90-6] or polyamines or salts thereof which are known from the literature, or which can be prepared in analogy to compounds which are described in the literature or in the experimental part, infra [for example CAS 41077-50-3].

Diamines 7 or salts thereof are commercially available [for example CAS 1417898-94-2] or can be synthesized by methods which are well known to a person skilled in the art.

Diamines 7 or salts thereof can be reacted with a [4,7,10-tris(2-tert-butoxy-2-oxoethyl)-1,4,7,10-tetraazacyclododecan-1-yl]acetic acid derivative 5, which is activated by a leaving group (LG), such as for example pentafluorophenol, 4-nitrophenol, 1-hydroxypyrrolidine-2,5-dione [for example, the synthesis of tri-tert-butyl 2,2',2"-(10-{2-[(2,5-dioxopyrrolidin-1-yl)oxy]-2-oxoethyl}-1,4,7,10-tetraazacyclododecane-1,4,7-triyl)triacetate is described in detail by Cong Li et al., *J. Am. Chem. Soc.* 2006, 128, p. 15072-15073; S3-5 and. Galibert et al., *Biorg. and Med. Chem. Letters* 2010, 20, p. 5422-5425] or hydroxybenzotriazole, leading to intermediates 8. The preparation of activated esters is well known to the person skilled in the art and is described in detail for example by C. A. Montalbetti and V. Falque in *Tetrahedron* 2005, 61, 10827-10852. The protection group PG of intermediates 8 can be cleaved under basic conditions, such as for example by treatment with alkali metal hydroxides, such as for example lithium hydroxide, in water or a mixture of water and tetrahydrofuran, to yield the corresponding salt of the carboxylic acid. This salt can be coupled with polyamines 1 employing standard peptide coupling conditions, such as for example coupling in the presence of HATU and 3H-[1,2,3]triazolo[4,5-b]pyridin-3-ol in the presence of N,N-diisopropylethylamine, in a suitable solvent, such as for example dichloromethane, at room temperature, to furnish the intermediates of general formula (V). Cleavage of the carboxyl-protecting groups of intermediates of general formula (V) can be achieved employing standard conditions, such as for example, by dissolving and stirring of intermediates (V) in aqueous hydrochloric acid at room temperature. The subsequent complexation with suitable gadolinium (Ill) compounds or salts, such as for example gadolinium trioxide, gadolinium triacetate or hydrates of gadolinium triacetate, gadolinium trichloride or gadolinium trinitrate, is well known to a person skilled in the art, and can, for example, be achieved by the reaction with suitable gadolinium (Ill) compounds in a temperature range from room temperature up to 100° C. at pH=1-7 for several hours, to furnish the compounds of general formula (I-k). The raw carboxylic acids derived from the compounds of general formula (V) are, for example, reacted with gadolinium trioxide at 80° C., leading to compounds of general formula (I-k).

A route for the preparation of compounds of general formulae (I-m) and (I-n) is described in Scheme 10.

Scheme 10

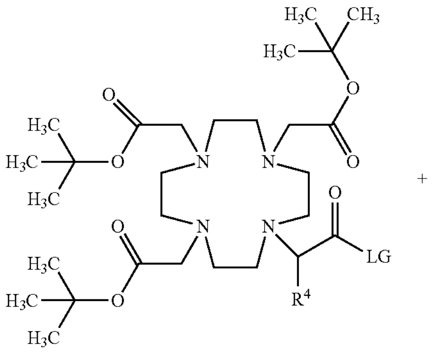

5

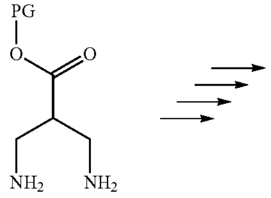

9

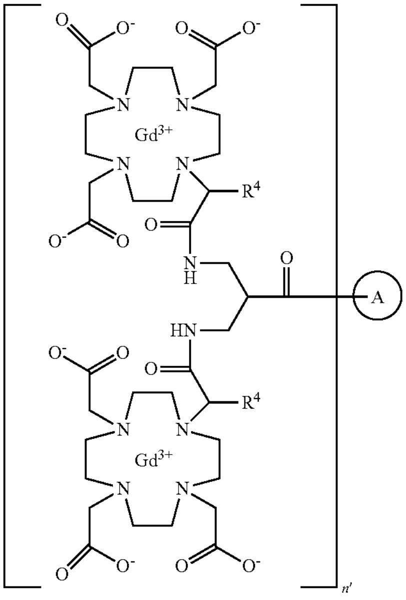

(I-m)

-continued

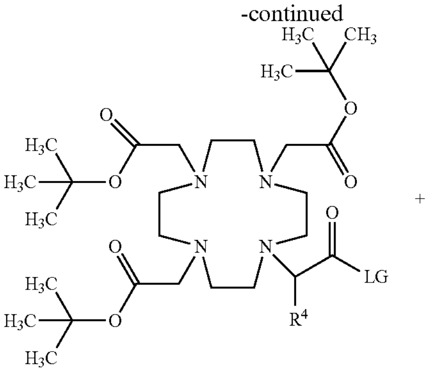

5

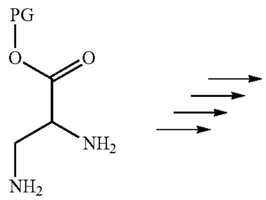

10

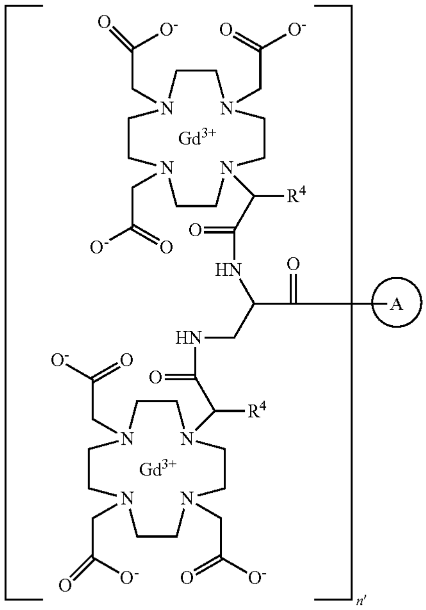

(I-n)

Scheme 10: Route for the preparation of compounds of general formulae (I-m) and (I-n), wherein

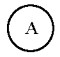

and $R^4$ have the meaning as given for general formula (I), supra, n' represents an integer of 2, 3 and 4, LG represents activating leaving groups, such as for example 1-hydroxy-pyrrolidine-2,5-dione, or a group as defined for the synthesis of the compounds of the general formula (I-a) supra, and PG represents a carboxyl-protecting group, such as for example a methyl or ethyl group.

When instead of the diamines of formula 7, as described in Scheme 9, diamines of formulae 9 and 10 or salts thereof are used in the analogous synthesis as described in Scheme 9, the compounds of general formulae (I-m) and (I-n) can be obtained.

Diamines 9 or salts thereof are commercially available [for example CAS 159029-33-1, CAS 440644-06-4] or can be synthesized by methods which are well known to a person skilled in the art.

Diamines 10 or salts thereof are commercially available [for example CAS 20610-20-2, CAS 6059-44-5] or can be synthesized by methods which are well known to a person skilled in the art.

An alternative route to the one described in Scheme 4 for the preparation of compounds of general formula (I-d) is described in Scheme 11.

Scheme 11

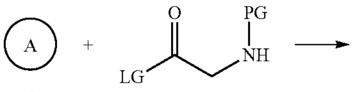

4 11

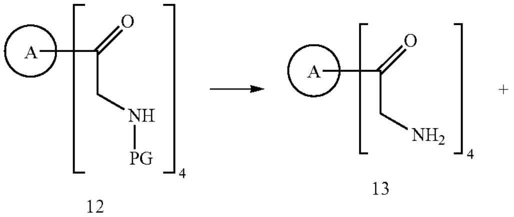

12 13

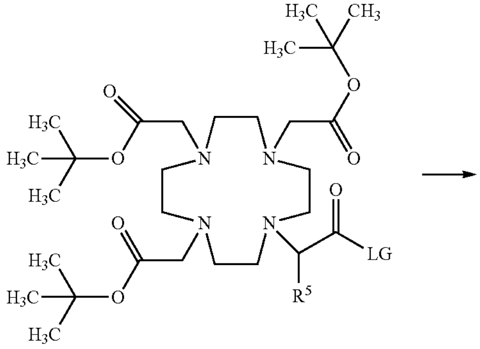

14

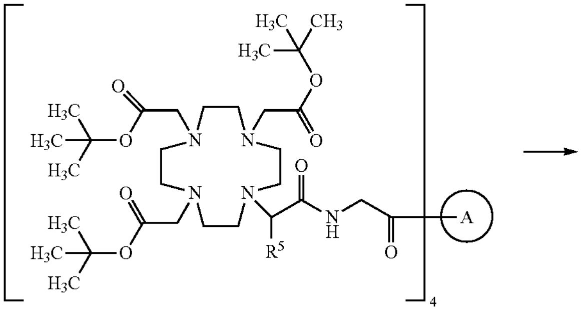

15

-continued

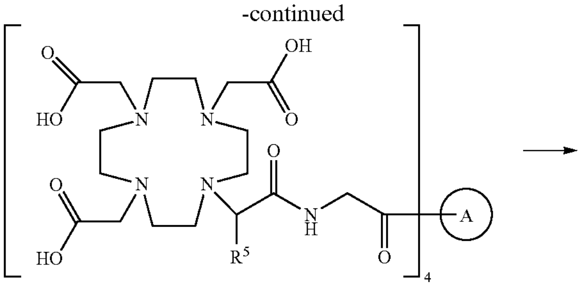

(VI)

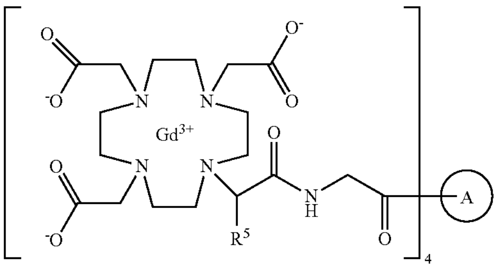

(I-d)

Scheme 11: Alternative route for the preparation of compounds of general formula (I-d), wherein $R^5$ has the meaning as given for general formula (I), supra,

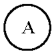

represents a tetraamine as given for general formula (I), supra, and LG represents an activating leaving group, such as for example 3H-[1,2,3]triazolo[4,5-b]pyridin-3-ol, or a group as defined for the synthesis of the compounds of the general formula (I-a) supra.

The starting materials 4 are either commercially available tetraamines or salts thereof [for example CAS 4742-00-1, CAS 294-90-6] or tetraamines or salts thereof which are known from the literature, or which can be prepared in analogy to compounds which are described in the literature. The starting materials 14 are either commercially available or known from the literature or can be synthesized in analogy to compounds which are described in the literature, e.g. by step-wise alkylation of the cyclen core.

A tetraamine 4 or a salt thereof is reacted with an amino acid derivative 11, which is activated by a leaving group (LG), such as for example 1-hydroxypyrrolidine-2,5-dione, pentafluorophenol, 4-nitrophenol or 3H-[1,2,3]triazolo[4,5-b]pyridin-3-ol, leading to an intermediate 12. The preparation of activated esters is well known to the person skilled in the art and is described in detail for example by C. A. Montalbetti and V. Falque in Tetrahedron 61 (2005), 10827-10852. The coupling reactions of polyamines 4 with amino acid derivatives 11 are carried out in a suitable solvent, such as for example dichloromethane or N,N-dimethylformamide, in a temperature range from room temperature up to 50° C., to furnish the intermediates 12. Cleavage of the amino protecting groups (PG) of intermediates 12 to yield the intermediates 13 can be achieved as described in the textbook Greene and Wuts, Protective Groups in Organic Synthesis, second edition. In case of tert-butoxycarbonyl protecting groups the deprotection is, for example, performed by reacting intermediates 12 with HCl in CPME in a suitable solvent, such as for example CPME or 1,4-dioxane or a mixture thereof in a temperature range from 0° C. to room temperature for several hours.

A tetraamine 13 or a salt thereof is reacted with a [4,7,10-tris(2-tert-butoxy-2-oxoethyl)-1,4,7,10-tetraazacyclododecan-1-yl]acetic acid derivative 14, which is activated by a leaving group (LG), such as for example 3H-[1,2,3]triazolo[4,5-b]pyridin-3-ol, 4-nitrophenol or 1-hydroxypyrrolidine-2,5-dione leading to an intermediate 15. The coupling reaction of tetraamines 13 with [4,7,10-tris(2-tert-butoxy-2-oxoethyl)-1,4,7,10-tetraazacyclododecan-1-yl] acetic acid derivatives 14 is carried out in a suitable solvent, such as for example N,N-dimethylacetamide or dimethyl sulfoxide, or a mixture thereof, in a temperature range from room temperature to 80° C., to furnish the intermediates 15.

Cleavage of the carboxyl-protecting groups of intermediates 15 to yield the intermediates of general formula (VI) can be achieved as described in the textbook Greene and Wuts, Protective Groups in Organic Synthesis, second edition, pages 245-247. The deprotection is, for example, performed by dissolving and stirring of intermediates 15 in trifluoroacetic acid at room temperature for several hours.

The complexation of intermediates of general formula (VI) with suitable gadolinium (III) compounds or salts, such as for example gadolinium trioxide, gadolinium triacetate or hydrates of gadolinium triacetate, gadolinium trichloride or gadolinium trinitrate, is well known to a person skilled in the art. The intermediates of general formula (VI) are dissolved in water and after adding of suitable gadolinium (III) compounds the resulting mixtures are stirred in a temperature range from room temperature up to 100° C. at pH=1-7 for several hours, to furnish the compounds of general formula (I-d). Intermediates of general formula (VI) are, for example, dissolved in water, gadolinium triacetate tetrahydrate is added and the pH is adjusted to 3.5-5.5 by addition of a suitable base, such as for example aqueous sodium hydroxide solution. The reaction is carried out at temperatures ranging from 50° C. to 80° C., leading to compounds of general formula (I-d).

An alternative route to the one described in Scheme 4 for the preparation of compounds of general formula (I-d) is described in Scheme 12.

Scheme 12

+

4

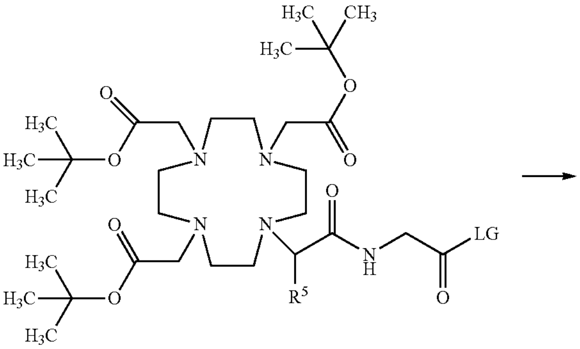

16

-continued

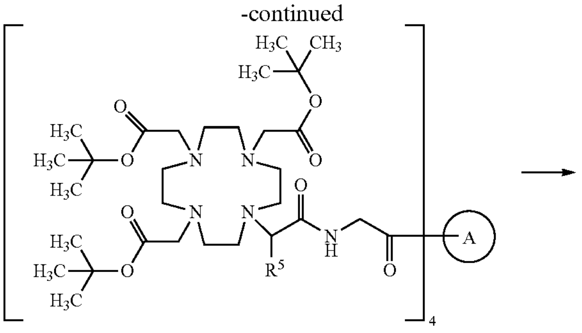

15

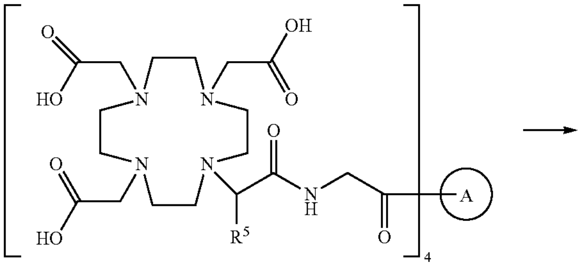

(VI)

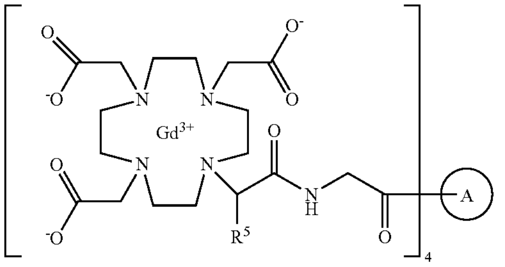

(I-d)

Scheme 12: Alternative route for the preparation of compounds of general formula (I-d), wherein $R^5$ has the meaning as given for general formula (I), supra,

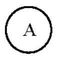

represents a tetraamine as given for general formula (I), supra, and LG represents an activating leaving group, such as for example 3H-[1,2,3]triazolo[4,5-b]pyridine-3-ol, or a group as defined for the synthesis of the compounds of the general formula (I-a) supra.

The starting materials 4 are either commercially available tetraamines or salts thereof [for example CAS 4742-00-1, CAS 294-90-6] or tetraamines or salts thereof which are known from the literature, or which can be prepared in analogy to compounds which are described in the literature. The starting materials 16 are either known from the literature or can be synthesized in analogy to compounds which are described in the literature, e.g. by step-wise alkylation of the cyclen core.

A tetraamine 4 or a salt thereof is reacted with a [4,7,10-tris(2-tert-butoxy-2-oxoethyl)-1,4,7,10-tetraazacyclododecan-1-yl]acetic acid derivative 16, which is activated by a leaving group (LG), such as for example 3H-[1,2,3]triazolo [4,5-b]pyridin-3-ol, 4-nitrophenol or 1-hydroxypyrrolidine-2,5-dione leading to an intermediate 15. The coupling reaction of tetraamines 4 with [4,7,10-tris(2-tert-butoxy-2-oxoethyl)-1,4,7,10-tetraazacyclododecan-1-yl]acetic acid derivatives 16 is carried out in a suitable solvent, such as for example N,N-dimethylformamide, to furnish the intermediates 16.

The complexation of intermediates of general formula (VI) with suitable gadolinium (III) compounds or salts, such as for example gadolinium trioxide, gadolinium triacetate or hydrates of gadolinium triacetate, gadolinium trichloride or gadolinium trinitrate, is well known to a person skilled in the art. The intermediates of general formula (VI) are dissolved in water and after adding of suitable gadolinium (III) compounds the resulting mixtures are stirred in a temperature range from room temperature up to 100° C. at pH=1-7 for several hours, to furnish the compounds of general formula (I-d). Intermediates of general formula (VI) are, for example, dissolved in water, gadolinium triacetate tetrahydrate is added and the pH is adjusted to 3.5-5.5 by addition of a suitable base, such as for example aqueous sodium hydroxide solution.

The reaction is carried out at temperatures ranging from 50° C. to 80° C., leading to compounds of general formula (I-d).

In accordance with an embodiment, the present invention also relates to a method of preparing a compound of general formula (I-a) as defined supra, said method comprising the step of allowing an intermediate compound of general formula (II-a):

(II-a)

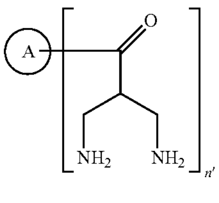

in which

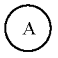

is as defined for the compound of general formula (I), supra, and n' represents an integer of 2, 3 and 4, or a salt thereof, to react with a compound of general formula (III):

(III)

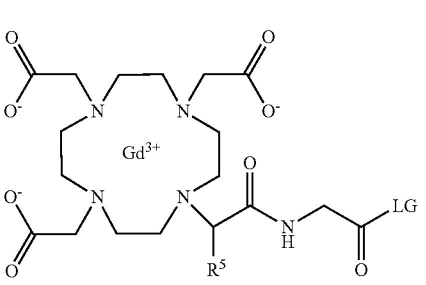

in which $R^5$ is as defined for the compound of general formula (I), supra, and LG represents an activating leaving group, such as for example 4-nitrophenol, or a group as defined for the synthesis of the compounds of the general formula (I-a) supra, thereby giving a compound of general formula (I-a):

(I-a)

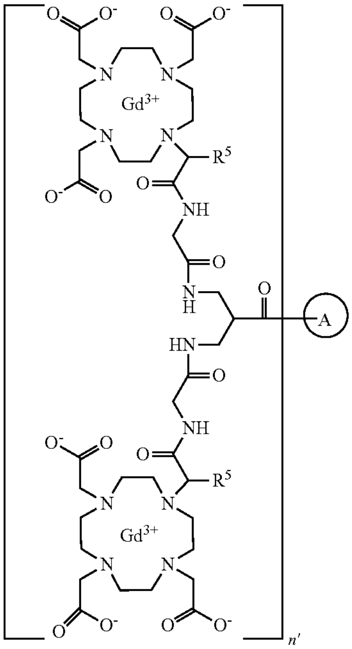

in which

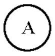

and $R^5$ are as defined for the compound of general formula (I) supra, and n' represents an integer of 2, 3 and 4.

In accordance with another embodiment, the present invention also relates to a method of preparing a compound of general formula (I-b) as defined supra, said method comprising the step of allowing an intermediate compound of general formula (II-b):

(II-b)

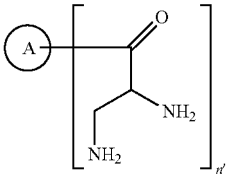

in which

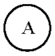

is as defined for the compound of general formula (I), supra, and n' represents an integer of 2, 3 and 4, or a salt thereof, to react with a compound of general formula (III):

(III)

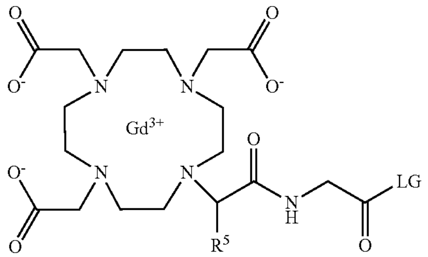

in which $R^5$ is as defined for the compound of general formula (I), supra, and LG represents an activating leaving group, such as for example 4-nitrophenol, or a group as defined for the synthesis of the compounds of the general formula (I-a) supra, thereby giving a compound of general formula (I-b):

(I-b)

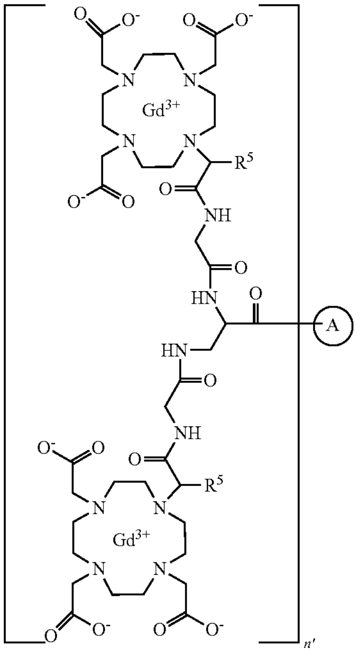

in which

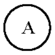

and $R^5$ are as defined for the compound of general formula (I) supra, and n' represents an integer of 2, 3 and 4.

In accordance with another embodiment, the present invention also relates to a method of preparing a compound of general formula (I-c) as defined supra, said method comprising the step of allowing an intermediate compound of general formula (II-c):

(II-c)

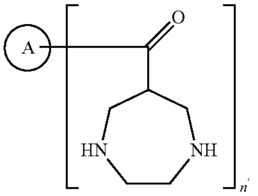

in which

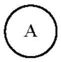

is as defined for the compound of general formula (I), supra, and n' represents an integer of 2, 3 and 4, or a salt thereof, to react with a compound of general formula (III):

(III)

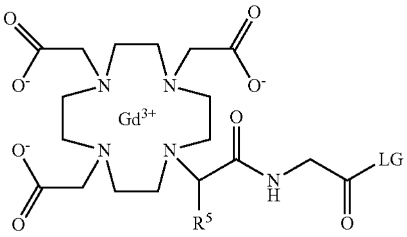

in which $R^5$ is as defined for the compound of general formula (I), supra, and LG represents an activating leaving group, such as for example 4-nitrophenol, or a group as defined for the synthesis of the compounds of the general formula (I-a) supra, thereby giving a compound of general formula (I-c):

(I-c)

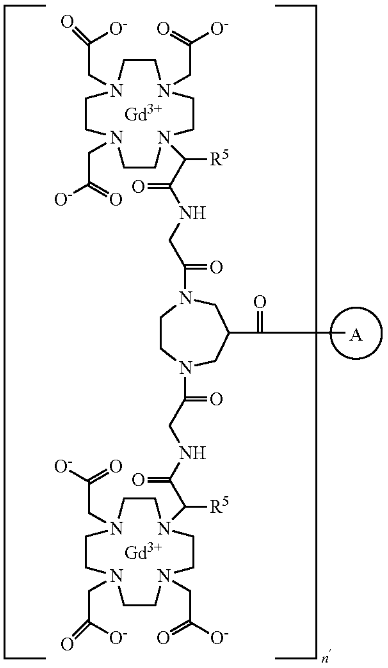

in which

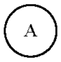

and $R^5$ are as defined for the compound of general formula (I) supra, and n' represents an integer of 2, 3 and 4.

In accordance with another embodiment, the present invention also relates to a method of preparing a compound of general formula (I-d) as defined supra, said method comprising the step of allowing a compound of formula 4,

4

in which

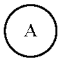

is a tetraamine as defined for the compound of general formula (I), supra, or a salt thereof, to react with a compound of general formula (III):

(III)

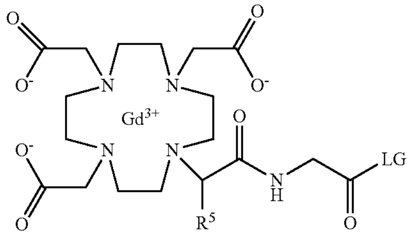

in which $R^5$ is as defined for the compound of general formula (I), supra, and LG represents an activating leaving group, such as for example 4-nitrophenol, or a group as defined for the synthesis of the compounds of the general formula (I-a) supra, thereby giving a compound of general formula (I-d):

(I-d)

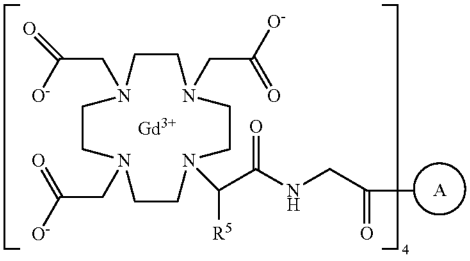

in which $R^5$ is as defined for the compound of general formula (I) supra, and

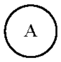

is a tetraamine as defined for the compound of general formula (I), supra.

In accordance with another embodiment, the present invention also relates to a method of preparing a compound of general formula (I-e) as defined supra, said method comprising the step of allowing an intermediate compound of general formula (IV):

(IV)

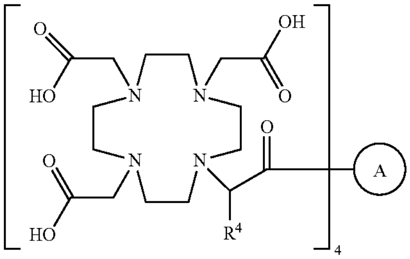

in which $R^4$ is as defined for the compound of general formula (I), supra, and

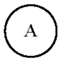

is a tetraamine as defined for the compound of general formula (I), supra, to react with a gadolinium (Ill) compound, such as for example gadolinium trioxide, gadolinium triacetate or hydrates of gadolinium triacetate, gadolinium trichloride or gadolinium trinitrate, or with a salt thereof, thereby giving a compound of general formula (I-e):

(I-e)

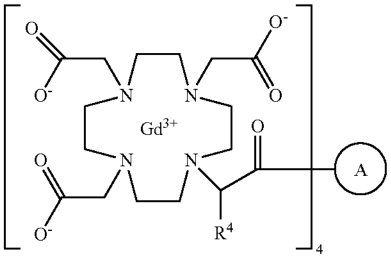

in which $R^4$ is as defined for the compound of general formula (I), supra, and

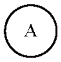

is a tetraamine as defined for the compound of general formula (I), supra.

In accordance with another embodiment, the present invention also relates to a method of preparing a compound of general formula (I-f) as defined supra, said method comprising the step of allowing an intermediate compound of general formula (II-a):

(II-a)

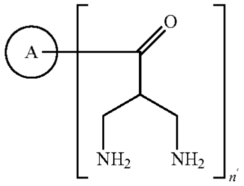

in which

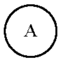

is a triamine as defined for the compound of general formula (I), supra, and n' represents an integer of 2, or a salt thereof, or in which

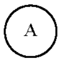

is a tetraamine as defined for the compound of general formula (I), supra, and n' represents an integer of 3, or a salt thereof, to react with a compound of general formula (III):

(III)

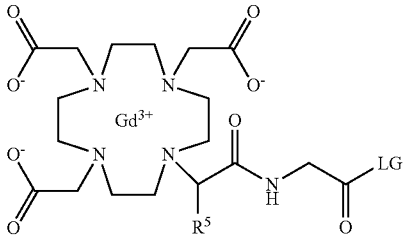

in which $R^5$ is as defined for the compound of general formula (I), supra, and LG represents an activating leaving group, such as for example 4-nitrophenol, or a group as defined for the synthesis of the compounds of the general formula (I-a) supra, thereby giving a compound of general formula (I-f):

(I-f)

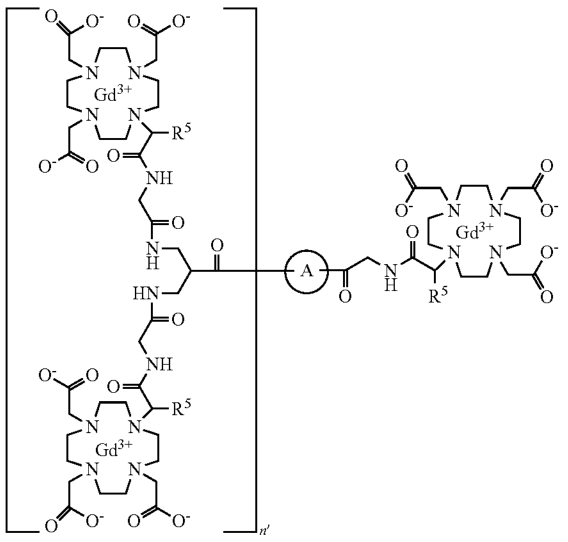

in which $R^5$ is as defined for the compound of general formula (I), supra, and in which

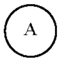

is a triamine as defined for the compound of general formula (I), supra, and n' represents an integer of 2, or in which

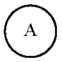

is a tetraamine as defined for the compound of general formula (I), supra, and n' represents an integer of 3.

In accordance with another embodiment, the present invention also relates to a method of preparing a compound of general formula (I-h) as defined supra, said method comprising the step of allowing an intermediate compound of general formula (II-c):

(II-c)

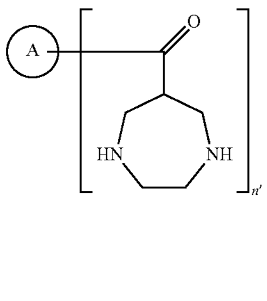

in which

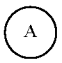

is a triamine as defined for the compound of general formula (I), supra, and n' represents an integer of 2, or a salt thereof, or in which

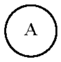

is a tetraamine as defined for the compound of general formula (I), supra, and n' represents an integer of 3, or a salt thereof, to react with a compound of general formula (III):

(III)

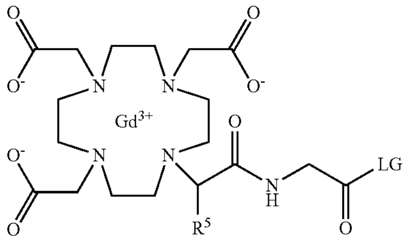

in which $R^5$ is as defined for the compound of general formula (I), supra, and LG represents an activating leaving group, such as for example 4-nitrophenol, or a group as defined for the synthesis of the compounds of the general formula (I-a) supra, thereby giving a compound of general formula (I-h):

(I-h)

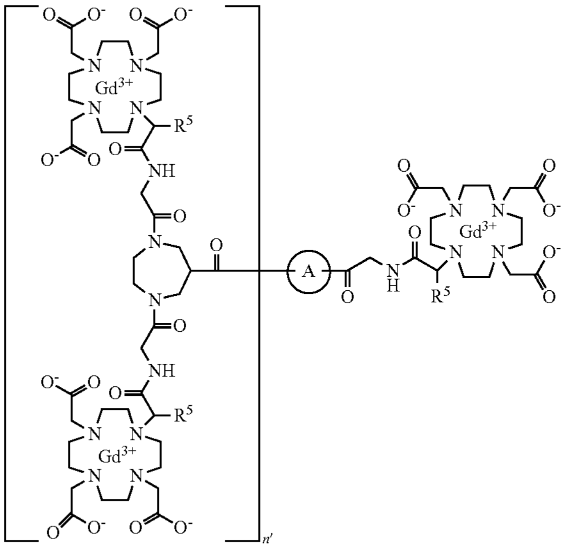

in which $R^5$ is as defined for the compound of general formula (I), supra, and in which

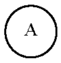

is a triamine as defined for the compound of general formula (I), supra, and n' represents an integer of 2, or in which

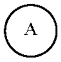

is a tetraamine as defined for the compound of general formula (I), supra, and n' represents an integer of 3.

In accordance with another embodiment, the present invention also relates to a method of preparing a compound of general formula (I-k) as defined supra, said method comprising the step of allowing an intermediate compound of general formula (V):

(V)

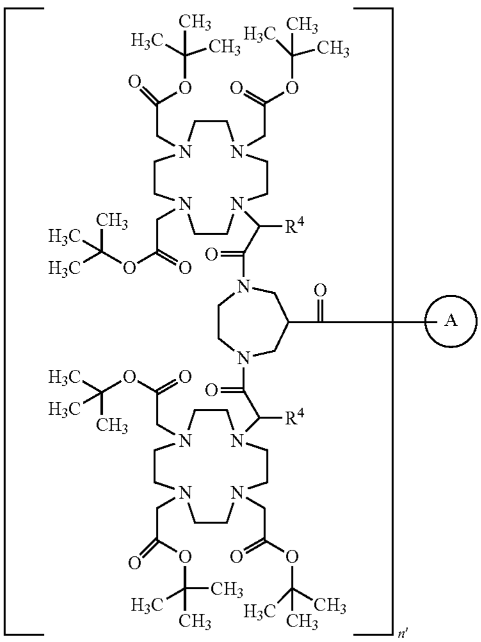

in which

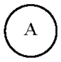

and $R^4$ are as defined for the compound of general formula (I), supra, and n' represents an integer of 2, 3 and 4, in a first step to react with an acid, such as for example aqueous hydrochloric acid, and in a second step to react with a gadolinium (III) compound, such as for example gadolinium trioxide, gadolinium triacetate or hydrates of gadolinium triacetate, gadolinium trichloride or gadolinium trinitrate, or with a salt thereof, thereby giving a compound of general formula (I-k):

(I-k)

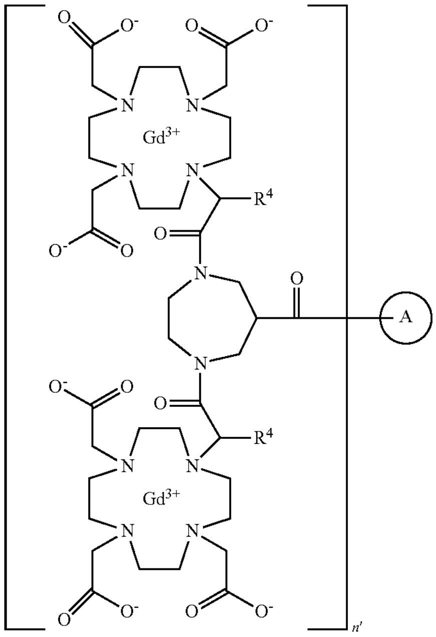

in which

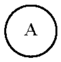

and $R^4$ are as defined for the compound of general formula (I), supra, and n' represents an integer of 2, 3 and 4.

EXPERIMENTAL SECTION

| | |
|---|---|
| ACN | acetonitrile |
| AUC | area under the curve |
| br | broad signal (in NMR data) |
| bw | body weight |
| CPME | cyclopentyl methyl ether |
| CPMG | Carr-Purcell-Meiboom-Gill (MRI sequence) |
| $C_{Gd}$ | concentration of the compound normalized to the Gadolinium |
| CI | chemical ionization |
| $Cl_{tot}$ | total clearance |
| d | day(s) |
| DAD | diode array detector |
| DCM | dichloromethane |
| DMF | N,N-dimethylformamide |
| DMSO | dimethylsulfoxide |
| DMSO-$d_6$ | deuterated dimethylsulfoxide |
| ECCM | extracellular contrast media |
| EI | electron ionization |
| ELSD | evaporative light scattering detector |
| ESI | electrospray ionization |
| FBS | fetal bovine serum |
| h | hour |

-continued

| | |
|---|---|
| HATU | N-[(dimethylamino)(3H-[1,2,3]triazolo[4,5-b]pyridin-3-yloxy)-methylidene]-N-methylmethanaminium hexafluorophosphate |
| HCOOH | formic acid |
| HPLC | high performance liquid chromatography |
| HU | Hounsfield units |
| IR | inversion recovery |
| kDa | kilo Dalton |
| LCMS | liquid chromatography-mass spectroscopy |
| ICP-MS | Inductively coupled plasma mass spectrometry |
| MRI | magnetic resonance imaging |
| MRT | mean residence time |
| MS | mass spectrometry |
| m | multiplet |
| min | minute(s) |
| NMR | nuclear magnetic resonance spectroscopy: chemical shifts (δ) are given in ppm. |
| $r_i$ | (where i = 1, 2) relaxivities in L $mmol^{-1}$ $s^{-1}$ |
| Rt. | retention time |
| s | singlet |
| RC | reference compound |
| $R_i$ | (where i = 1, 2) relaxation rates ($1/T_{1,2}$) |
| $R_{i(0)}$ | relaxation rate of the respective solvent |
| $T_{1,2}$ | relaxation time |
| T | Tesla |
| t | triplet |
| t½ α | plasma half-life, compartment V1 |
| t½ β | plasma half-life, compartment V2 |
| t½ γ | plasma half-life, compartment V3 |
| TFA | trifluoroacetic acid |
| THF | tetrahydrofuran |
| TI | inversion time |
| UPLC | ultra performance liquid chromatography |
| V1 + V2 | volume, compartments V1 + V2 |
| $V_c$ (V1) | volume, central compartment V1 |
| $V_{d,ss}$ | volume of distribution at steady state |

Materials and Instrumentation

The chemicals used for the synthetic work were of reagent grade quality and were used as obtained.

All reagents, for which the synthesis is not described in the experimental section, are either commercially available, or are known compounds or may be formed from known compounds by known methods by a person skilled in the art.

$^1$H-NMR spectra were measured in $CDCl_3$, $D_2O$ or DMSO-$d_6$, respectively (room temperature, Bruker Avance 400 spectrometer, resonance frequency: 400.20 MHz for $^1$H or Bruker Avance 300 spectrometer, resonance frequency: 300.13 MHz for $^1$H. Chemical shifts are given in ppm relative to sodium (trimethylsilyl)propionate-$d_4$ ($D_2O$) or tetramethylsilane (DMSO-$d_6$) as external standards (5=0 ppm).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

Examples were analysed and characterized by the following HPLC based analytical methods to determine characteristic retention time and mass spectrum:

Method 1: UPLC (ACN-HCOOH)

Instrument: Waters Acquity UPLC-MS SQD 3001; column: Acquity UPLC BEH C18 1.7 μm, 50×2.1 mm; eluent A: water+0.1% formic acid, eluent B: acetonitrile; gradient: 0-1.6 min 1-99% B, 1.6-2.0 min 99% B; flow 0.8 mL/min; temperature: 60° C.; injection: 2 μl; DAD scan: 210-400 nm; ELSD.

Method 2: UPLC (ACN-HCOOH Polar)

Instrument: Waters Acquity UPLC-MS SQD 3001; column: Acquity UPLC BEH C18 1.7 μm, 50×2.1 mm; eluent A: water+0.1% formic acid, eluent B: acetonitrile; gradient: 0-1.7 min 1-45% B, 1.7-2.0 min 45-99% B; flow 0.8 mL/min; temperature: 60° C.; injection: 2 μl; DAD scan: 210-400 nm; ELSD.

Method 3: UPLC (ACN-HCOOH Long Run)

Instrument: Waters Acquity UPLC-MS SQD 3001; column: Acquity UPLC BEH C18 1.7 μm, 50×2.1 mm; eluent A: water+0.1% formic acid, eluent B: acetonitrile; gradient: 0-4.5 min 0-10% B; flow 0.8 mL/min; temperature: 60° C.; injection: 2 μl; DAD scan: 210-400 nm; ELSD.

Method 4: UPLC (ACN-$NH_3$)

Instrument: Waters Acquity UPLC-MS ZQ2000; column: Acquity UPLC BEH C18 1.7 μm, 50×2.1 mm; Eluent A: water+0.2% ammonia, eluent B: acetonitrile; gradient: 0-1.6 min 1-99% B, 1.6-2.0 min 99% B; flow rate 0.8 mL/min; temperature: 60° C.; injection: 1 μL; DAD scan: 210-400 nm; ELSD.

Method 5: LC-MS

Instrument: Agilent 1290 UHPLCMS Tof; column: BEH C18 (Waters) 1.7 μm, 50×2.1 mm; eluent A: water+0.05 vol-% formic acid (99%), eluent B: acetonitrile+0.05% formic acid; gradient: 0-1.7 min 98-10% A, 1.7-2.0 min 10% A, 2.0-2.5 min 10-98% A, flow 1.2 mL/min; temperature: 60° C.; DAD scan: 210-400 nm.

EXAMPLE COMPOUNDS
Example 1
Pentagadolinium[4,10-bis(carboxylatomethyl)-7-{3,6,10,18,22,25-hexaoxo-26-[4,7,10-tris(carboxylatomethyl)-1,4,7,10-tetraazacyclododecan-1-yl]-14-[({2-[4,7,10-tris-(carboxylatomethyl)-1,4,7,10-tetraazacyclododecan-1-yl]propanoyl}amino)acetyl]-9,19-bis({[({2-[4,7,10-tris(carboxylatomethyl)-1,4,7,10-tetraazacyclododecan-1-yl]-propanoyl}amino)acetyl]amino}methyl)-4,7,11,14,17,21,24-heptaazaheptacosan-2-yl}-1,4,7,10-tetraazacyclododecan-1-yl]acetate
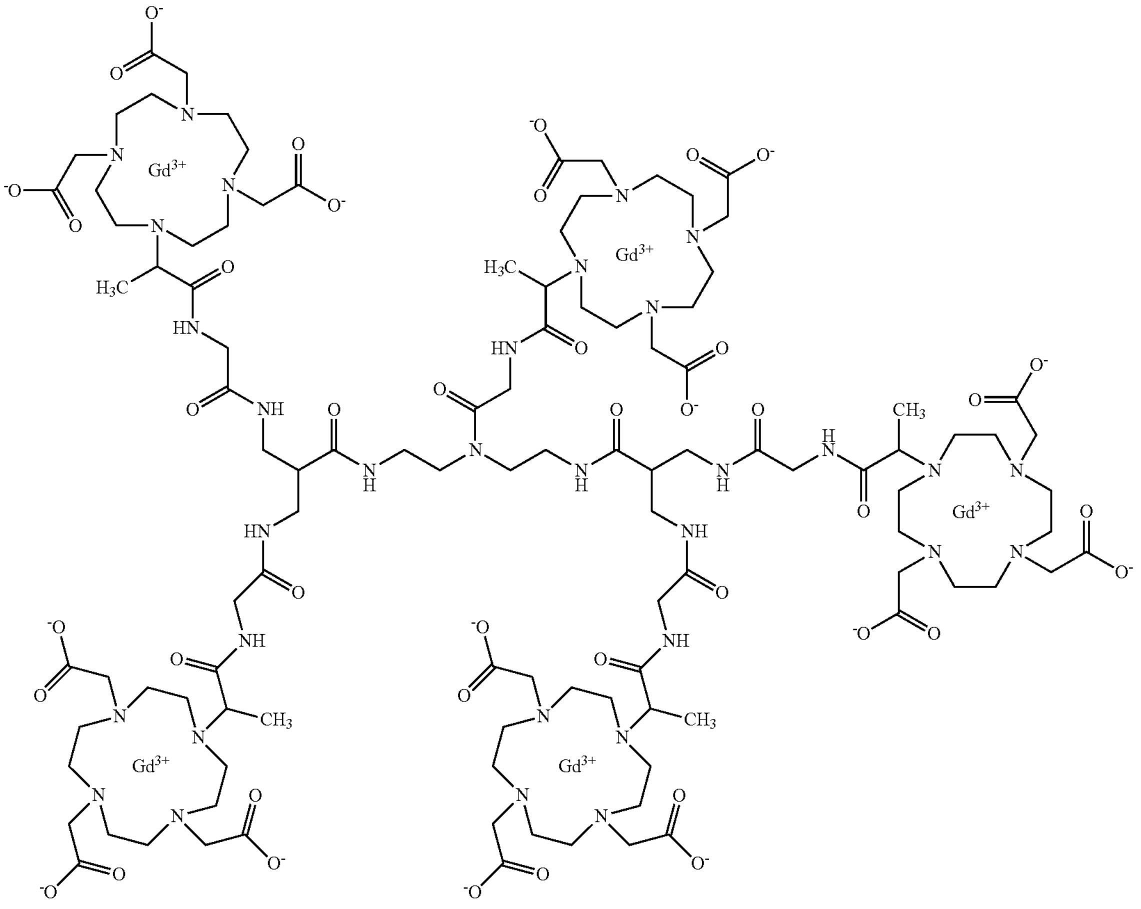

Example 1a

Di-tert-butyl (2-{[(2,5-dioxopyrrolidin-1-yl)oxy]carbonyl}propane-1,3-diyl)biscarbamate

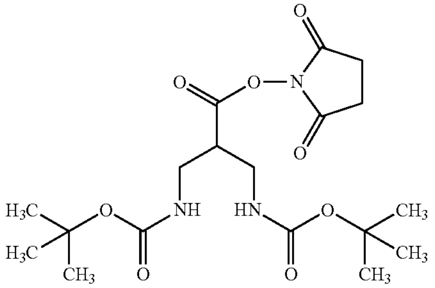 [SMILES: CC(C)(C)OC(=O)NCC(CNC(=O)OC(C)(C)C)C(=O)ON1C(=O)CCC1=O]

3.60 g (11.3 mmol, 1 eq.) 3-[(tert-butoxycarbonyl)amino]-2-{[(tert-butoxycarbonyl)amino]methyl}propanoic acid (see WO 2006/136460 A2) and 1.43 g (12.4 mmol, 1.1 eq.) 1-hydroxypyrrolidine-2,5-dione were dissolved in 120 mL THF. To the reaction mixture was added dropwise a solution of 2.57 g (12.4 mmol, 1.1 eq.) N,N-dicyclohexylcarbodiimide in 60 mL THF. After stirring for 3 hours at room temperature, the resulting suspension was cooled to 0° C. and the precipitated urea was filtered off. The clear solution was evaporated to dryness yielding 5.50 g (13.24 mmol, 117%) of the title compound.

UPLC (ACN-HCOOH): Rt.=1.15 min.

MS ($ES^+$): m/z=416.3 $(M+H)^+$.

Example 1 b

Tert-butyl (7,17-bis{[(tert-butoxycarbonyl)amino]methyl}-2,2-dimethyl-4,8,16-trioxo-3-oxa-5,9,12,15-tetraazaoctadecan-18-yl)carbamate

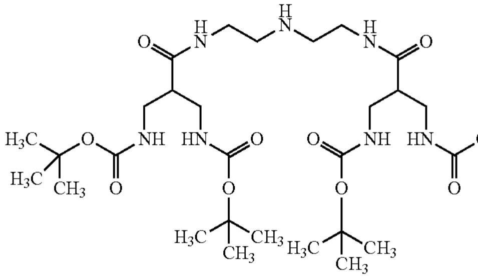

4.70 g (11.3 mmol, 2.22 eq.) Di-tert-butyl (2-{[(2,5-dioxopyrrolidin-1-yl)oxy]carbonyl}propane-1,3-diyl)biscarbamate (example 1a) were dissolved in 120 mL THF. To the reaction mixture was added dropwise a solution of 0.53 g (5.10 mmol, 1 eq.) N-(2-aminoethyl)ethane-1,2-diamine and 1.14 g (11.3 mmol, 2.22 eq.) triethylamine in 40 mL THF. After stirring for 3 hours at room temperature, the resulting suspension was diluted with dichloromethane. The organic solution was washed with aqueous sodium hydroxide (0.1 M), with water, and was dried over sodium sulfate. The crude product was isolated by evaporation under reduced pressure and was purified by silica gel chromatography yielding 2.81 g (3.99 mmol, 78%) of the title compound.

$^1$H-NMR (400 MHz, DMSO-$d_6$): δ=1.36 (s, 36H), 2.39-2.47 (m, 3H), 2.52-2.58 (m, 4H), 2.95-3.20 (m, 12H), 6.64 (t, 4H), 7.72 (t, 2H) ppm.

UPLC (ACN-HCOOH): Rt.=1.06 min.

MS ($ES^+$): m/z=704.6 ($M^+$+H).

Example 1c

N,N'-(Iminodiethane-2,1-diyl)bis[3-amino-2-(aminomethyl)propanamide]pentahydrochloride

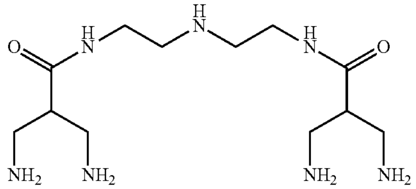

x5HCl 600 mg (0.85 mmol) Tert-butyl (7,17-bis{[(tert-butoxycarbonyl)amino]methyl}-2,2-dimethyl-4,8,16-trioxo-3-oxa-5,9,12,15-tetraazaoctadecan-18-yl)carbamate (example 1b) were dissolved in 9.6 mL methanol and 2.85 mL aqueous hydrochloric acid (37%). The reaction mixture was heated under stirring for 2 hours at 50° C. For isolation, the suspension was evaporated to dryness yielding 423 mg (0.87 mmol, 102%) of the title compound.

$^1$H-NMR (400 MHz, $D_2O$): δ=3.04-3.15 (m, 2H), 3.17-3.27 (m, 8H), 3.29-3.38 (m, 4H), 3.55 (t, 4H) ppm.

UPLC (ACN-HCOOH): Rt.=0.19 min.

MS ($ES^+$): m/z=304.2 $(M+H)^+$, free base.

Example 1

Pentagadolinium[4,10-bis(carboxylatomethyl)-7-{3,6,10,18,22,25-hexaoxo-26-[4,7,10-tris(carboxylatomethyl)-1,4,7,10-tetraazacyclododecan-1-yl]-14-[({2-[4,7,10-tris-(carboxylatomethyl)-1,4,7,10-tetraazacyclododecan-1-yl]propanoyl}amino)acetyl]-9,19-bis({[({2-[4,7,10-tris(carboxylatomethyl)-1,4,7,10-tetraazacyclododecan-1-yl]-propanoyl}amino)acetyl]amino}methyl)-4,7,11,14,17,21,24-heptaazaheptacosan-2-yl}-1,4,7,10-tetraazacyclododecan-1-yl]acetate 150 mg (309 μmol, 1 eq.) N,N'-(Iminodiethane-2,1-diyl)bis[3-amino-2-(aminomethyl)-propanamide]pentahydrochloride (example 1c) were dissolved in 60 mL DMSO. After adding of 499 mg (3.86 mmol, 12.5 eq.) N,N-diisopropylethylamine and 4.06 g (5.40 mmol, 17.5 eq.) gadolinium 2,2',2''-[10-(1-{[2-(4-nitrophenoxy)-2-oxoethyl]amino}-1-oxopropan-2-yl)-1,4,7,10-tetraazacyclododecane-1,4,7-triyl]triacetate (see WO 2001051095 A2), the resulting reaction mixture was stirred and heated for 8 hours at 50° C. The cooled solution was concentrated under reduced pressure to a final volume of 15-20 mL. The concentrate was poured in 400 mL ethyl acetate under stirring, the formed precipitate was filtered off and was dried in vacuo. The solid was dissolved in water, the resulting solution was ultrafiltered with water using a 1 kDa membrane, and the final retentate was lyophilized. The crude product was purified by RP-chromatography yielding 668 mg (64%, 199 μmol) of the title compound.

UPLC (ACN-HCOOH): Rt.=0.46 min.

MS ($ES^-$): m/z (z=2)=1680.5 $(M-2H)^{2-}$; ($ES^+$): m/z (z=3)=1121.3 $(M+H)^{3+}$, m/z (z=4)=841.4 $[(M+H)^{4+}$.

Example 2

Hexagadolinium[4,10-bis(carboxylatomethyl)-7-{3,6,10,15,19,22-hexaoxo-23-[4,7,10-tris(carboxylatomethyl)-1,4,7,10-tetraazacyclododecan-1-yl]-9,16-bis({[({2-[4,7,10-tris(carboxylatomethyl)-1,4,7,10-tetraazacyclododecan-1-yl]propanoyl}amino)acetyl]-amino}methyl)-11-(2-{[3-{[({2-[4,7,10-tris(carboxylatomethyl)-1,4,7,10-tetraazacyclododecan-1-yl]propanoyl}amino)acetyl]amino}-2-({[({2-[4,7,10-tris(carboxylatomethyl)-1,4,7,10-tetraazacyclododecan-1-yl]propanoyl}amino)acetyl]amino}methyl)propanoyl]-amino}ethyl)-4,7,11,14,18,21-hexaazatetracosan-2-yl}-1,4,7,10-tetraazacyclododecan-1-yl]acetate

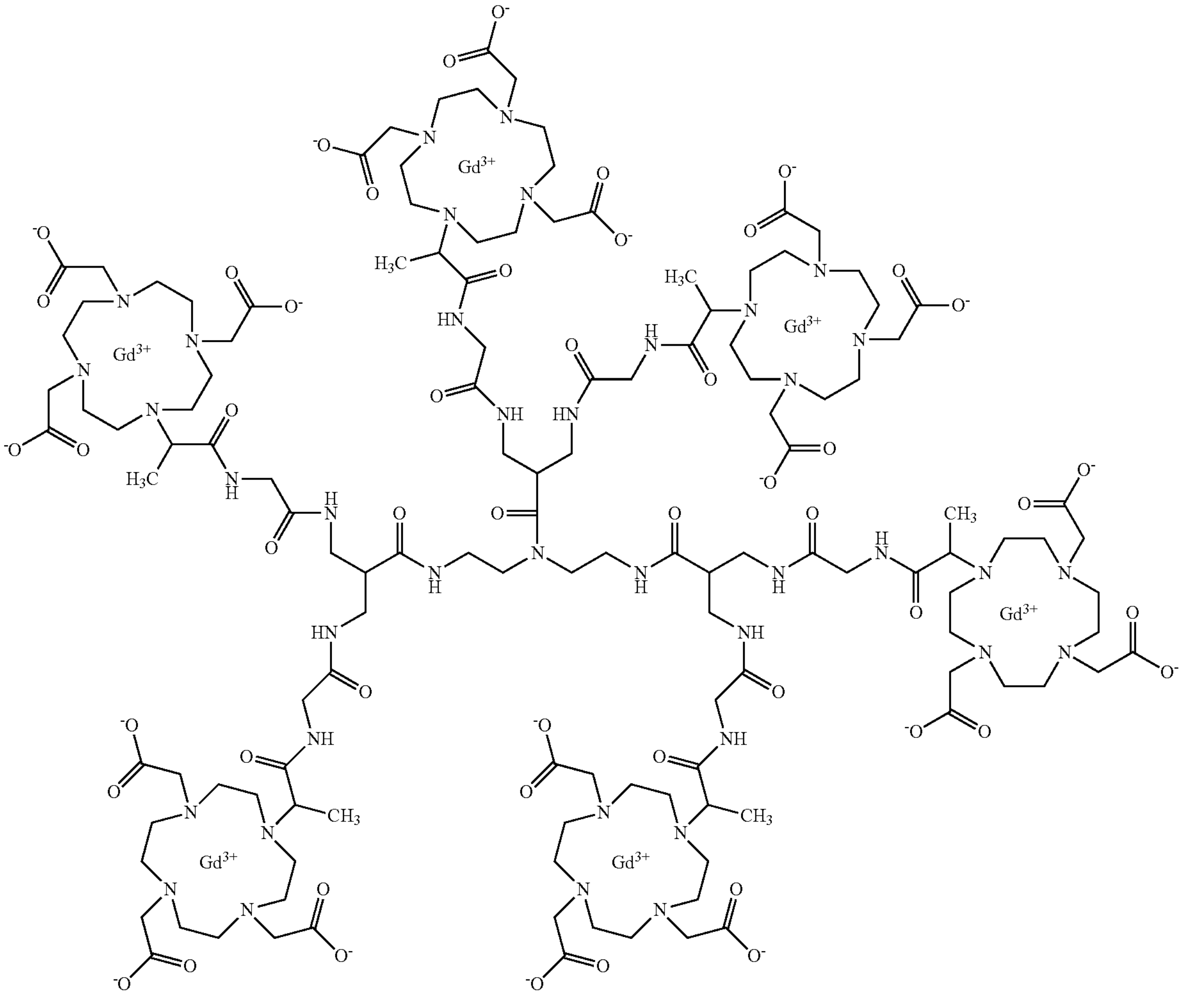

Example 2a

Tert-butyl (12-{2-[(3-[(tert-butoxycarbonyl)amino]-2-{[(tert-butoxycarbonyl)amino]-methyl}propanoyl) amino]ethyl}-7,14-bis{[(tert-butoxycarbonyl)amino] methyl}-2,2-dimethyl-4,8,13-trioxo-3-oxa-5,9,12-triazapentadecan-15-yl)carbamate

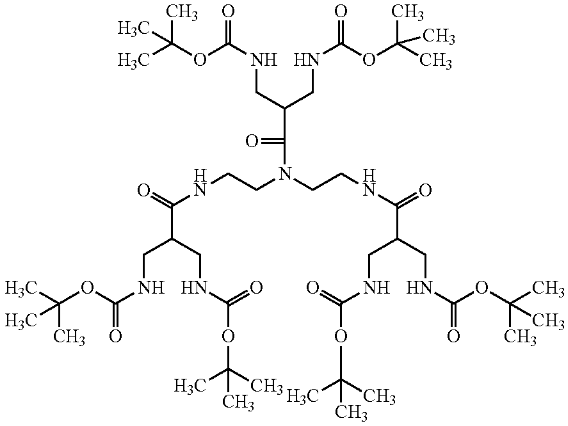 [SMILES: CC(C)(C)OC(=O)NCC(CNC(=O)OC(C)(C)C)C(=O)NCCN(CCNC(=O)C(CNC(=O)OC(C)(C)C)CNC(=O)OC(C)(C)C)C(=O)C(CNC(=O)OC(C)(C)C)CNC(=O)OC(C)(C)C]

890 mg (2.80 mmol, 3 eq.) 3-[(Tert-butoxycarbonyl) amino]-2-{[(tert-butoxycarbonyl)amino]-methyl}propanoic acid (see WO 2006/136460 A2) were dissolved in 22 mL DMF. To the solution were added 434 mg (3.36 mmol, 3.6 eq.) N,N-diisopropylethylamine and 1.28 g (3.36 mmol, 3.6 eq.) HATU. The resulting reaction mixture was stirred for 2 hours at room temperature. After dropwise adding of a solution of 96.1 mg (0.93 mmol, 1 eq.) N-(2-amino-ethyl) ethane-1,2-diamine and of 434 mg (3.36 mmol, 3.6 eq.) N,N-diisopropylethylamine in 9 mL DMF, the resulting reaction mixture was heated under stirring for 3 hours at 70° C. After cooling and diluting with dichloromethane, the solution was washed with aqueous sodium hydroxide (0.1 M), aqueous citric acid (1%), and water and was dried over sodium sulfate. The crude product was isolated by evaporation under reduced pressure and was purified by silica gel chromatography yielding 451 mg (0.45 mmol, 48%) of the title compound.

$^1$H-NMR (400 MHz, DMSO-$d_6$): δ=1.37 (s, 54H), 2.36-2.49 (m, 3H), 2.81-3.30 (m, 17H), 3.36-3.70 (m, 3H), 6.16-6.92 (m, 6H), 7.77-8.35 (m, 2H) ppm.

UPLC (ACN-HCOOH): Rt.=1.49 min.

MS (ES$^+$): m/z=1004.6 (M+H)$^+$.

Example 2b

3-Amino-N,N-bis(2-{[3-amino-2-(aminomethyl) propanoyl]amino}ethyl)-2-(aminomethyl)-propanamide hexahydrochloride

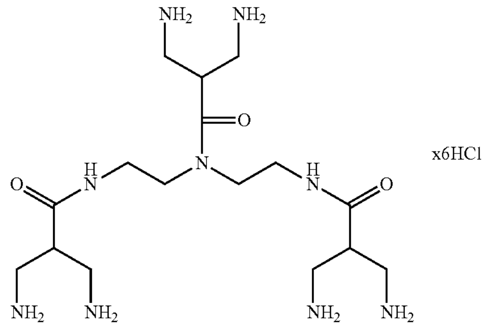 [SMILES: NCC(CN)C(=O)NCCN(CCNC(=O)C(CN)CN)C(=O)C(CN)CN]

581 mg (0.58 mmol) Tert-butyl (12-{2-[(3-[(tert-butoxy-carbonyl)amino]-2-{[(tert-butoxy-carbonyl)amino] methyl}propanoyl)amino]ethyl}-7,14-bis{[(tert-butoxycarbonyl)amino]methyl}-2,2-dimethyl-4,8,13-trioxo-3-oxa-5,9,12-triazapentadecan-15-yl)carbamate (example 2a) were dissolved in 9.3 mL methanol and 2.9 mL aqueous hydrochloric acid (37%). The reaction mixture was heated under stirring for 2 hours at 50° C. For isolation, the suspension was evaporated to dryness yielding 376 mg (0.60 mmol, 103%) of the title compound.

$^1$H-NMR (400 MHz, $D_2O$): δ=3.13-3.27 (m, 2H), 3.28-3.85 (m, 21H) ppm.

UPLC (ACN-HCOOH): Rt.=0.19 min.

MS (ES$^+$): m/z=404.3 (M+H)$^+$, free base.

Example 2

Hexagadolinium[4,10-bis(carboxylatomethyl)-7-{3,6,10,15,19,22-hexaoxo-23-[4,7,10-tris(carboxylatomethyl)-1,4,7,10-tetraazacyclododecan-1-yl]-9,16-bis({[({2-[4,7,10-tris(carboxylatomethyl)-1,4,7,10-tetraazacyclododecan-1-yl]propanoyl}amino) acetyl]-amino}methyl)-11-(2-{[3-{[({2-[4,7,10-tris (carboxylatomethyl)-1,4,7,10-tetraazacyclo-dodecan-1-yl]propanoyl}amino)acetyl]amino}-2-({[({2-[4,7,10-tris(carboxylatomethyl)-1,4,7,10-tetraazacyclododecan-1-yl]propanoyl}amino)acetyl] amino}methyl)propanoyl]-amino}ethyl)-4,7,11,14,18,21-hexaazatetracosan-2-yl}-1,4,7,10-tetraazacyclododecan-1-yl]acetate 150 mg (241 μmol, 1 eq.) 3-Amino-N,N-bis(2-{[3-amino-2-(aminomethyl)propanoyl]amino}-ethyl)-2-(aminomethyl) propanamide hexahydrochloride (example 2b) were dissolved in 60 mL DMSO. After adding of 467 mg (3.62 mmol, 15 eq.) N,N-diisopropylethylamine and 3.80 g (5.06 mmol, 21 eq.) gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl]triacetate (see WO 2001/051095 A2), the resulting reaction mixture was stirred and heated for 8 hours at 50° C. The cooled solution was concentrated under reduced pressure to a final volume of 15-20 mL. The concentrate was poured under stirring in 400 mL ethyl acetate, the formed precipitate was filtered off and was dried in vacuo. The solid was dissolved in water, the resulting solution was ultrafiltered with water using a 1 kDa membrane and the final retentate was lyophilized. The crude product was purified by RP-chromatography yielding 677 mg (166 μmol, 69%) of the title compound.

UPLC (ACN-HCOOH): Rt.=0.44 min.

MS ($ES^+$): m/z (z=3)=1357.4 $(M+3H)^{3+}$, m/z (z=4)=1018.8 $(M+4H)^{4+}$], m/z (z=5)=815.7 $(M+5H)^{5+}$.

Example 3

Tetragadolinium [4,10-bis(carboxylatomethyl)-7-{3,6,12,15-tetraoxo-16-[4,7,10-tris-(carboxylatomethyl)-1,4,7,10-tetraazacyclododecan-1-yl]-9,9-bis({[({2-[4,7,10-tris-(carboxylatomethyl)-1,4,7,10-tetraazacyclododecan-1-yl]propanoyl}amino)acetyl]-amino}methyl)-4,7,11,14-tetraazaheptadecan-2-yl}-1,4,7,10-tetraazacyclododecan-1-yl]acetate

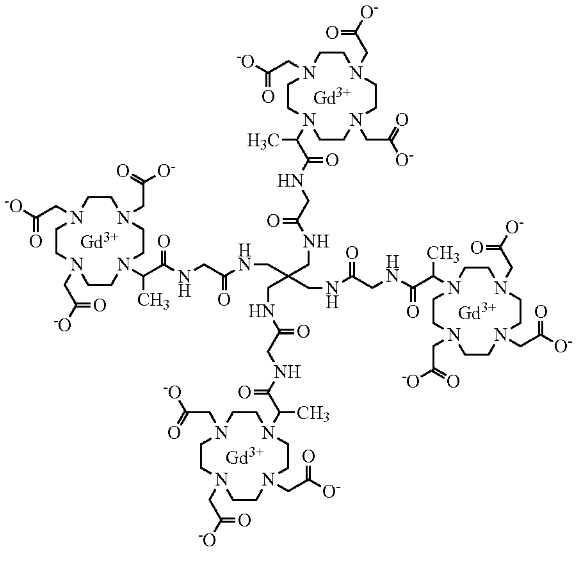

225 mg (1.65 mmol, 1 eq.) 2,2-Bis(aminomethyl)propane-1,3-diamine (see W. Hayes et al., *Tetrahedron* 59 (2003), 7983-7996) were dissolved in 240 mL DMSO. After addition of 1.71 g (13.2 mmol, 8 eq.) N,N-diisopropylethylamine and 14.9 g (19.85 mmol, 12 eq.) gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl] triacetate (see WO 2001/051095 A2), the resulting reaction mixture was stirred and heated for 8 hours at 50° C. The cooled solution was concentrated under reduced pressure to a final volume of 40-50 mL. The concentrate was poured under stirring in 600 mL ethyl acetate, the formed precipitate was filtered off and was dried in vacuo. The solid was dissolved in water, the resulting solution was ultrafiltered with water using a 1 kDa membrane and the final retentate was lyophilized. The crude product was purified by RP-chromatography yielding 3.42 g (80%, 1.33 mmol) of the title compound.

UPLC (ACN-HCOOH): Rt.=0.42 min.

MS ($ES^+$): m/z (z=2)=1290.4 $(M+H)^{2+}$, m/z (z=3)=860.7 $(M+H)^{3+}$.

Example 3 comprises a mixture of stereoisomers, which exhibit the following absolute configurations: all-R, all-S, RRRS, SSSR, RRSS.

Example 3-1

Tetragadolinium {4,10-bis(carboxylatomethyl)-7-[(2R,16R)-3,6,12,15-tetraoxo-16-[4,7,10-tris(carboxylatomethyl)-1,4,7,10-tetraazacyclododecan-1-yl]-9,9-bis({[({(2R)-2-[4,7,10-tris(carboxylatomethyl)-1,4,7,10-tetraazacyclododecan-1-yl]propanoyl}amino)-acetyl]amino}methyl)-4,7,11,14-tetraazaheptadecan-2-yl]-1,4,7,10-tetraazacyclo-dodecan-1-yl}acetate

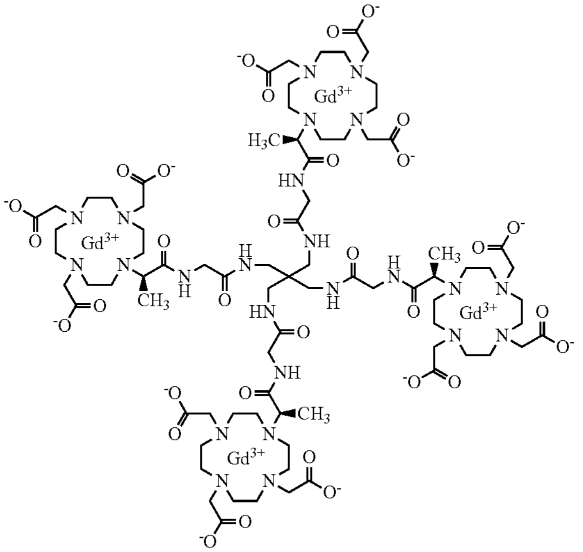

Example 3-1a

Tert-butyl {10,10-bis[({[(tert-butoxycarbonyl)amino]acetyl}amino)methyl]-2,2-dimethyl-4,7,13-trioxo-3-oxa-5,8,12-triazatetradecan-14-yl}carbamate

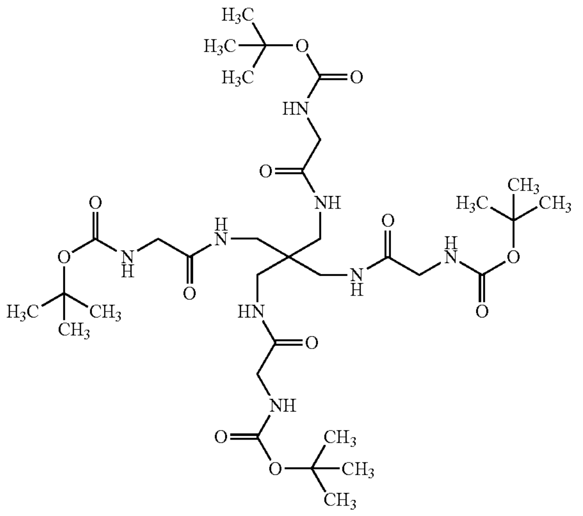 [SMILES: CC(C)(C)OC(=O)NCC(=O)NCC(CNC(=O)CNC(=O)OC(C)(C)C)(CNC(=O)CNC(=O)OC(C)(C)C)CNC(=O)CNC(=O)OC(C)(C)C]

A mixture of 2,2-bis(aminomethyl)propane-1,3-diamine tetrahydrochloride (851 mg, 3.06 mmol, 1 eq.; see W. Hayes et al., *Tetrahedron* 59 (2003), 7983-7996) in dichloromethane (50 mL) was treated with N,N-diisopropylethylamine (6.00 eq., 3.20 mL, 18.4 mmol) and 2,5-dioxopyrrolidin-1-yl N-(tert-butoxycarbonyl)glycinate (CAS No. [3392-07-2]; 6.00 eq., 5.00 g, 18.4 mmol) and stirred at room temperature for 2.5 days. The reaction mixture was diluted with water, the formed precipitate filtered off and washed with water and dichloromethane. The precipitated material was subjected to silica gel chromatography (dichloromethane/methanol) to give the title compound (800 mg, 34%).

$^1$H-NMR (400 MHz, DMSO-$d_6$): δ=1.36 (s, br, 36H), 2.74-2.76 (m, 8H), 3.48-3.50 (m, 8H), 6.96 (s, br, 0.4H*), 7.40-7.42 (m, 3.6H*), 7.91-8.00 (m, 4H) ppm.

LC-MS (ES$^+$): m/z=761.4 $(M+H)^+$; Rt.=1.16 min.

Example 3-1 b

2-Amino-N-(3-[(aminoacetyl)amino]-2,2-bis{[(aminoacetyl)amino]methyl}propyl)acetamide tetrahydrochloride

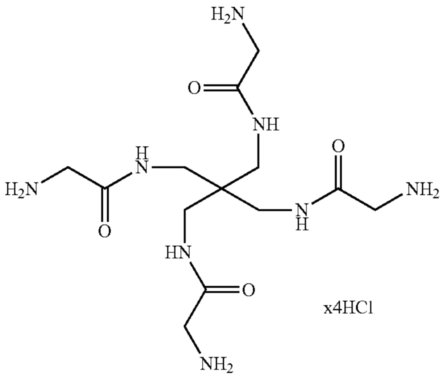 [SMILES: NCC(=O)NCC(CNC(=O)CN)(CNC(=O)CN)CNC(=O)CN]

x4HCl

A suspension of tert-butyl {10,10-bis[({[(tert-butoxycarbonyl)amino]acetyl}amino)methyl]-2,2-dimethyl-4,7,13-trioxo-3-oxa-5,8,12-triazatetradecan-14-yl}carbamate (1.00 eq., 800 mg, 1.05 mmol) from example 11a in CPME (10 mL) was cooled to 0° C. and treated dropwise with HCl in CPME (10 eq., 3.5 mL of a 3 M solution, 10.5 mmol). The reaction mixture was stirred at 0° C. for 1 h and at rt overnight upon which dioxane (4 mL) and another amount of HCl in CPME (30 eq., 11 mL of a 3 M solution, 32 mmol) were added and stirring at rt continued for 2 days. The resulting suspension was concentrated in vacuo to give the title compound (575 mg, quant.) which was not further purified.

$^1$H-NMR (400 MHz, DMSO-$d_6$): δ=3.17-3.18 (m, 8H), 3.59-3.61 (m, 8H), 8.21 (s, br, 12H), 8.55 (t, 4H) ppm.

LC-MS (ES$^+$): m/z=361.2 $(M-3HCl-Cl^-)^+$; Rt.=0.10 min.

Example 3-1c

Benzyl(2S)-2-{[(trifluoromethyl)sulfonyl]oxy}propanoate

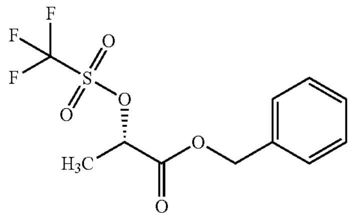 [SMILES: C[C@H](OS(=O)(=O)C(F)(F)F)C(=O)OCc1ccccc1]

Prepared according to H. C. J. Ottenheim et al., *Tetrahedron* 44 (1988), 5583-5595: A solution of (S)-(−)-lactic acid benzyl ester (CAS No. [56777-24-3]; 1.00 eq., 5.00 g, 27.7 mmol) in dry dichloromethane (95 mL) was cooled to 0° C. and treated with trifluoromethanesulfonic anhydride (CAS No. [358-23-6]; 1.1 eq., 5.2 mL, 8.6 g, 31 mmol). After stirring for 5 min, 2,6-dimethylpyridine (1.15 eq., 3.72 mL, 3.42 g) was added and stirring continued for another 5 min. The obtained reaction mixture was directly used in the next step.

Example 3-1d

Benzyl(2R)-2-[4,7,10-tris(2-tert-butoxy-2-oxoethyl)-1,4,7,10-tetraazacyclododecan-1-yl]propanoate

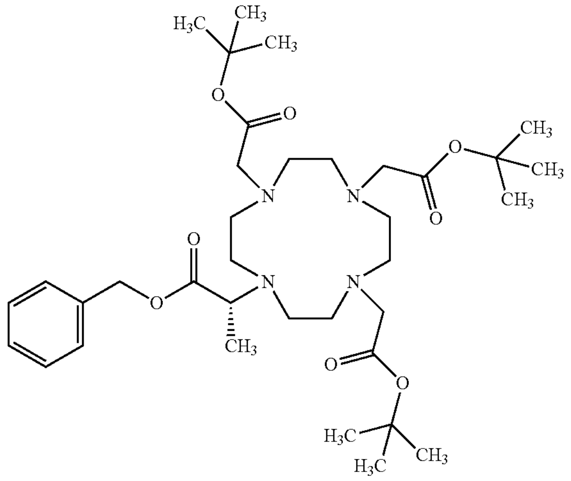 [SMILES: C[C@H](C(=O)OCc1ccccc1)N1CCN(CC(=O)OC(C)(C)C)CCN(CC(=O)OC(C)(C)C)CCN(CC(=O)OC(C)(C)C)CC1]

A solution of tri-tert-butyl 2,2',2''-(1,4,7,10-tetraazacyclododecane-1,4,7-triyl)triacetate (CAS No. [122555-91-3]; 1.00 eq., 9.52 g, 18.5 mmol) in dry dichloromethane (75 mL) was cooled to 0° C. and treated with the reaction mixture of benzyl (2S)-2-{[(trifluoromethyl)sulfonyl]oxy}propanoate in dichloromethane prepared in example 3-1c; and N,N-diisopropylethylamine (3.0 eq., 9.7 mL, 55 mmol). The resulting solution was stirred at rt for 6 days upon which it was diluted with ethyl acetate and washed with saturated aqueous sodium bicarbonate. The organic layer was dried over sodium sulfate and concentrated under reduced pressure. The obtained material was purified by amino phase silica gel chromatography (KP-NH®, hexane/ethyl acetate to dichloromethane/methanol) to give the title compound (1.92 g, 14%).

$^1$H-NMR (400 MHz, DMSO-$d_6$): δ=1.20 (d, 3H), 1.37-1.45 (m, 27H), 1.98-2.01 (m, 3H), 2.08-2.24 (m, 5H), 2.57-2.84 (m, 7H), 2.94-3.11 (m, 4H), 3.38-3.48 (m, 3H), 3.75 (q, 1H), 5.07-5.17 (m, 2H), 7.32-7.40 (m, 5H) ppm.

LC-MS (ES$^+$): m/z=677.5 (M+H)$^+$, m/z (z=2)=339.2 (M+H)$^{2+}$; Rt.=1.06 min.

Example 3-1e (2R)-2-[4,7,10-Tris(2-tert-butoxy-2-oxoethyl)-1,4,7,10-tetraazacyclododecan-1-yl]-propanoic acid

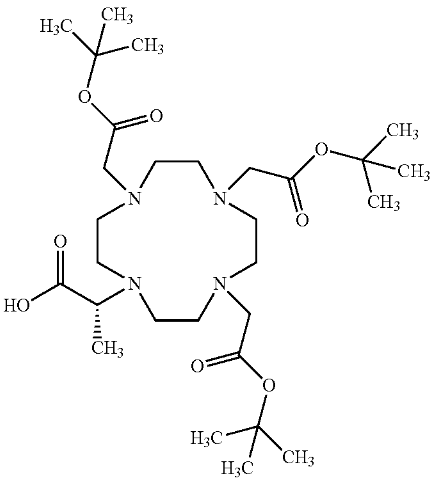 [SMILES: C[C@H](C(=O)O)N1CCN(CC(=O)OC(C)(C)C)CCN(CC(=O)OC(C)(C)C)CCN(CC(=O)OC(C)(C)C)CC1]

A solution of benzyl (2R)-2-[4,7,10-tris(2-tert-butoxy-2-oxoethyl)-1,4,7,10-tetraazacyclododecan-1-yl]propanoate (example 3-1d; 1.92 g, 2.84 mmol) in methanol (17.5 mL) was treated with Pd/C (10 wt %; 0.050 eq., 151 mg, 0.14 mmol) and stirred under a hydrogen atmosphere at room temperature for 20 hours. The reaction mixture was filtrated over Celite®, washed with methanol, and the filtrate concentrated in vacuo to give the title compound (1.51 g, 88%) which was not further purified.

$^1$H-NMR (400 MHz, DMSO-$d_6$): δ=1.11 (s, br, 3H), 1.42-1.43 (m, 27H), 1.97-2.13 (m, 5H), 2.56-2.82 (m, 7H), 2.97-3.07 (m, 4H), 3.34-3.53 (m, 7H), 12.8 (s, br, 1H) ppm.

UPLC (ACN-$NH_3$): Rt.=1.31 min.

MS (ES$^+$): m/z=587 (M+H)$^+$.

LC-MS (ES$^+$): m/z=587 (M+H)$^+$, m/z (z=2)=294.2 (M+H)$^{2+}$; Rt.=0.79 min.

Example 3-1f

Tert-butyl {4,10-bis(2-tert-butoxy-2-oxoethyl)-7-[(2R,16R)-3,6,12,15-tetraoxo-16-[4,7,10-tris(2-tert-butoxy-2-oxoethyl)-1,4,7,10-tetraazacyclododecan-1-yl]-9,9-bis({[({(2R)-2-[4,7,10-tris(2-tert-butoxy-2-oxoethyl)-1,4,7,10-tetraazacyclododecan-1-yl]propanoyl}-amino)acetyl]amino}methyl)-4,7,11,14-tetraazaheptadecan-2-yl]-1,4,7,10-tetraazacyclododecan-1-yl}acetate

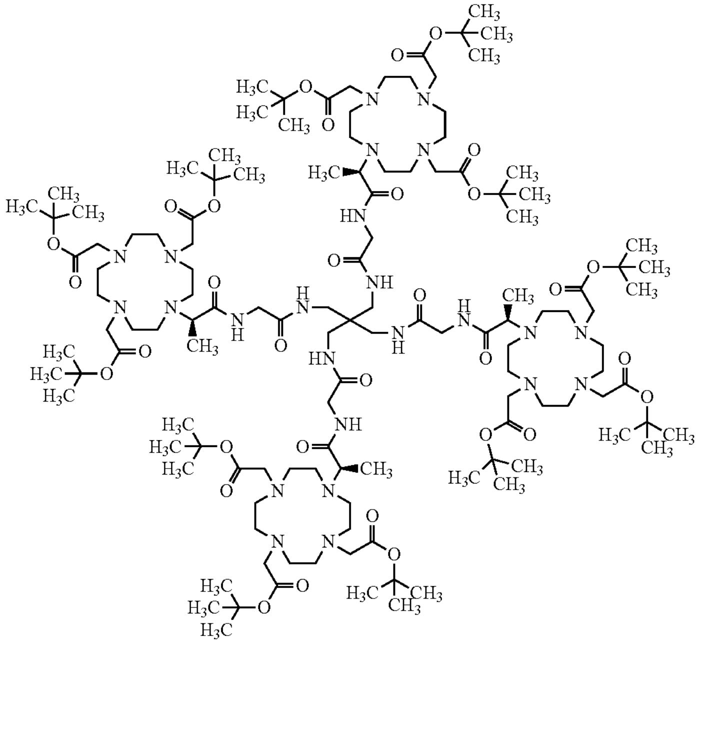 [SMILES: C[C@H](C(=O)NCC(=O)NCC(CNC(=O)CNC(=O)[C@@H](C)N1CCN(CC(=O)OC(C)(C)C)CCN(CC(=O)OC(C)(C)C)CCN(CC(=O)OC(C)(C)C)CC1)(CNC(=O)CNC(=O)[C@@H](C)N1CCN(CC(=O)OC(C)(C)C)CCN(CC(=O)OC(C)(C)C)CCN(CC(=O)OC(C)(C)C)CC1)CNC(=O)CNC(=O)[C@@H](C)N1CCN(CC(=O)OC(C)(C)C)CCN(CC(=O)OC(C)(C)C)CCN(CC(=O)OC(C)(C)C)CC1)N1CCN(CC(=O)OC(C)(C)C)CCN(CC(=O)OC(C)(C)C)CCN(CC(=O)OC(C)(C)C)CC1]

A mixture of (2R)-2-[4,7,10-tris(2-tert-butoxy-2-oxoethyl)-1,4,7,10-tetraazacyclo dodecan-1-yl]propanoic acid (example 3-1e; 12.0 eq., 1.50 g, 2.56 mmol) in N,N-dimethylacetamide (15 mL) was treated with HATU (14.4 eq., 1.17 g, 3.07 mmol) and N,N-diisopropylethylamine (14.4 eq., 534 μL, 3.07 mmol) and stirred at rt for 20 minutes. A suspension of 2-amino-N-(3-[(aminoacetyl)amino]-2,2-bis{[(aminoacetyl)amino]methyl}propyl)acetamide tetrahydrochloride (example 3-1b; 1.00 eq., 108 mg, 213 μmol) in N,N-dimethylacetamide (6 mL) was added and the resulting mixture stirred at 50° C. overnight. The reaction mixture was concentrated under reduced pressure and the obtained residue subjected to amino phase silica gel chromatography (KP-NH©, ethyl acetate to ethyl acetate/methanol) to give the title compound (260 mg, 42%).

$^1$H-NMR (400 MHz, DMSO-$d_6$): δ=1.03 (s, br, 5H), 1.28 (s, br, 7H), 1.36-1.43 (m, 108H), 1.87-2.24 (m, 23H), 2.42 (s, br, 4H), 2.53-2.84 (m, 41H), 2.97-3.18 (m, 17H), 3.28 (s, br, 5H), 3.39-3.46 (m, 6H), 3.58 (s, br, 7H), 3.76 (s, br, 2H), 4.01 (s, br, 3H), 7.81 (s, br, 5H), 8.33 (s, br, 2H), 9.27 (s, br, 1H) ppm.

UPLC (ACN-$NH_3$): Rt.=1.23 min.

MS ($ES^+$): m/z (z=4)=660 $(M+H)^{4+}$.

LC-MS ($ES^+$): m/z (z=2)=1318 $(M+H)^{2+}$, m/z (z=3)=879 $(M+H)^{3+}$, m/z (z=4)=660 $(M+H)^{4+}$; Rt.=0.94 min.

Example 3-1g

{4,10-Bis(carboxymethyl)-7-[(2R,16R)-3,6,12,15-tetraoxo-16-[4,7,10-tris(carboxymethyl)-1,4,7,10-tetraazacyclododecan-1-yl]-9,9-bis({[({(2R)-2-[4,7,10-tris(carboxymethyl)-1,4,7,10-tetraazacyclododecan-1-yl]propanoyl}amino)acetyl]amino}methyl)-4,7,11,14-tetraazaheptadecan-2-yl]-1,4,7,10-tetraazacyclododecan-1-yl}acetic acid

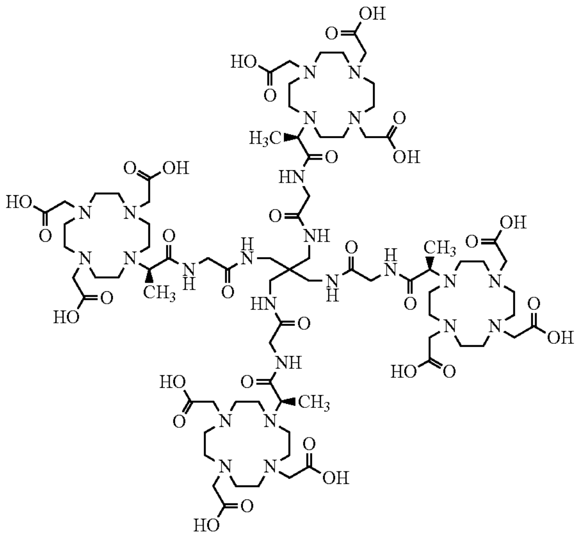 [SMILES: C[C@H](C(=O)NCC(=O)NCC(CNC(=O)CNC(=O)[C@@H](C)N1CCN(CC(=O)O)CCN(CC(=O)O)CCN(CC(=O)O)CC1)(CNC(=O)CNC(=O)[C@@H](C)N1CCN(CC(=O)O)CCN(CC(=O)O)CCN(CC(=O)O)CC1)CNC(=O)CNC(=O)[C@@H](C)N1CCN(CC(=O)O)CCN(CC(=O)O)CCN(CC(=O)O)CC1)N1CCN(CC(=O)O)CCN(CC(=O)O)CCN(CC(=O)O)CC1]

Tert-butyl {4,10-bis(2-tert-butoxy-2-oxoethyl)-7-[(2R,16R)-3,6,12,15-tetraoxo-16-[4,7,10-tris(2-tert-butoxy-2-oxoethyl)-1,4,7,10-tetraazacyclododecan-1-yl]-9,9-bis({[({(2R)-2-[4,7,10-tris(2-tert-butoxy-2-oxoethyl)-1,4,7,10-tetraazacyclododecan-1-yl]propanoyl}amino) acetyl]amino}methyl)-4,7,11,14-tetraazaheptadecan-2-yl]-1,4,7,10-tetraazacyclododecan-1-yl}acetate (example 3-1f; 260 mg, 0.099 mmol) was treated with TFA (25 mL) under stirring at room temperature overnight. The reaction mixture was concentrated under reduced pressure, the obtained residue taken up with water (20 mL) and lyophilized. The crude product was used without further characterization in the next chemical step.

Example 3-1

Tetragadolinium {4,10-bis(carboxylatomethyl)-7-[(2R,16R)-3,6,12,15-tetraoxo-16-[4,7,10-tris(carboxylatomethyl)-1,4,7,10-tetraazacyclododecan-1-yl]-9,9-bis({[({(2R)-2-[4,7,10-tris(carboxylatomethyl)-1,4,7,10-tetraazacyclododecan-1-yl]propanoyl}amino)-acetyl]amino}methyl)-4,7,11,14-tetraazaheptadecan-2-yl]-1,4,7,10-tetraazacyclo-dodecan-1-yl}acetate The crude material {4,10-bis(carboxymethyl)-7-[(2R,16R)-3,6,12,15-tetraoxo-16-[4,7,10-tris(carboxymethyl)-1,4,7,10-tetraazacyclododecan-1-yl]-9,9-bis({[({(2R)-2-[4,7,10-tris(carboxymethyl)-1,4,7,10-tetraazacyclododecan-1-yl]propanoyl}amino)acetyl]amino}methyl)-4,7,11,14-tetraazaheptadecan-2-yl]-1,4,7,10-tetraazacyclododecan-1-yl}acetic acid from example 3-1g was dissolved in water (20 mL). Tris(acetato-kappaO)gadolinium tetrahydrate (298 mg, 0.734 mmol) was added and the reaction mixture stirred at 70° C. for 2 h. The pH value of the resulting solution was adjusted to 4.5 by addition of aqueous sodium hydroxide solution (2 N) and stirring at 70° C. continued for 2 days. The resulting solution was ultrafiltered with water (7×100 mL) using a 1 kDa membrane and the final retentate was lyophilized yielding the title compound (70 mg, 27% over two steps).

UPLC (ACN-HCOOH): Rt.=0.39 min.

MS ($ES^+$): m/z (z=2)=1290.1 $(M+H)^{2+}$, m/z (z=3)=860.3 $(M+H)^{3+}$.

LC-MS ($ES^+$): m/z (z=2)=1290.3 $(M+H)^{2+}$, m/z (z=3)=860.9 $(M+H)^{3+}$, m/z (z=4)=645.6 $(M+H)^{4+}$; Rt.=0.25 min.

Example 3-2

Tetragadolinium {4,10-bis(carboxylatomethyl)-7-[(2S,16S)-3,6,12,15-tetraoxo-16-[4,7,10-tris(carboxylatomethyl)-1,4,7,10-tetraazacyclododecan-1-yl]-9,9-bis({[({(2S)-2-[4,7,10-tris(carboxylatomethyl)-1,4,7,10-tetraazacyclododecan-1-yl]propanoyl}amino)acetyl]-amino}methyl)-4,7,11,14-tetraazaheptadecan-2-yl]-1,4,7,10-tetraazacyclododecan-1-yl}-acetate

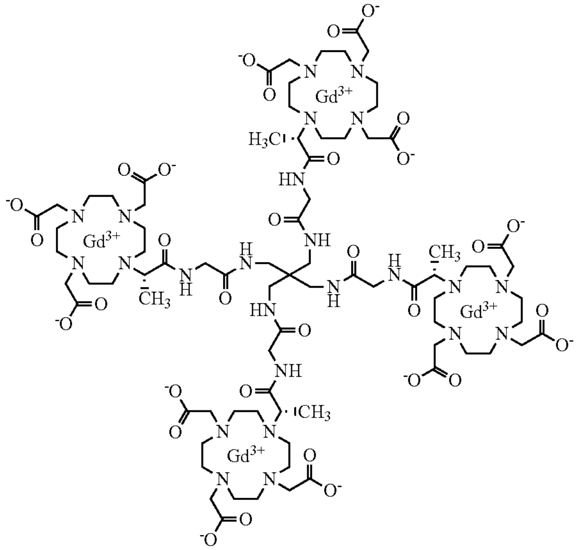

Example 3-2a

Benzyl(2R)-2-{[(trifluoromethyl)sulfonyl]oxy}propanoate

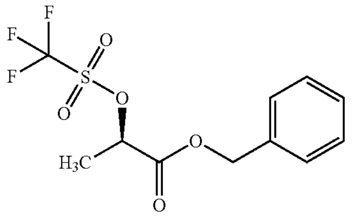 [SMILES: C[C@@H](OS(=O)(=O)C(F)(F)F)C(=O)OCc1ccccc1]

Prepared in analogy to the corresponding S-isomer (example 3-1c) from (R)-(+)-lactic acid benzyl ester (CAS No. [74094-05-6]; 8.00 g, 44.4 mmol) in dichloromethane. The obtained reaction mixture was directly used in the next step.

Example 3-2b

Benzyl(2S)-2-[4,7,10-tris(2-tert-butoxy-2-oxoethyl)-1,4,7,10-tetraazacyclododecan-1-yl]propanoate

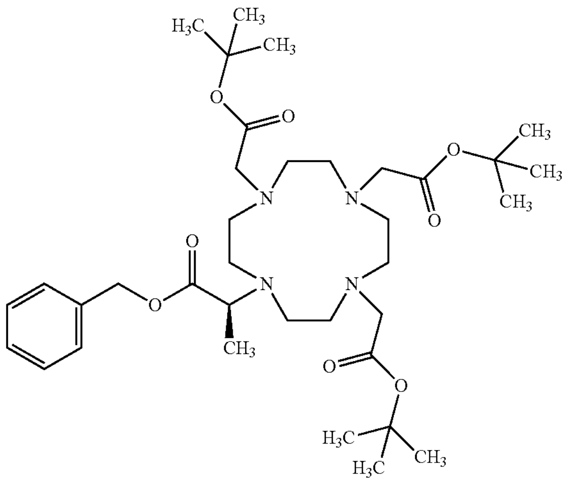 [SMILES: C[C@@H](C(=O)OCc1ccccc1)N1CCN(CC(=O)OC(C)(C)C)CCN(CC(=O)OC(C)(C)C)CCN(CC(=O)OC(C)(C)C)CC1]

Prepared in analogy to the corresponding R-isomer (example 3-1d) from tri-tert-butyl 2,2',2"-(1,4,7,10-tetraazacyclododecane-1,4,7-triyl)triacetate (CAS No. [122555-91-3]; 1.00 eq., 15.2 g, 29.6 mmol) and the reaction mixture of benzyl (2R)-2-{[(trifluoromethyl) sulfonyl]oxy}propanoate in dichloromethane prepared in example 3-2a.

LC-MS ($ES^+$): m/z=677.4 $(M+H)^+$, m/z (z=2)=339.2 $(M+H)^{2+}$; Rt.=0.94 min.

Example 3-2c (2S)-2-[4,7,10-Tris(2-tert-butoxy-2-oxoethyl)-1,4,7,10-tetraazacyclododecan-1-yl]-propanoic acid

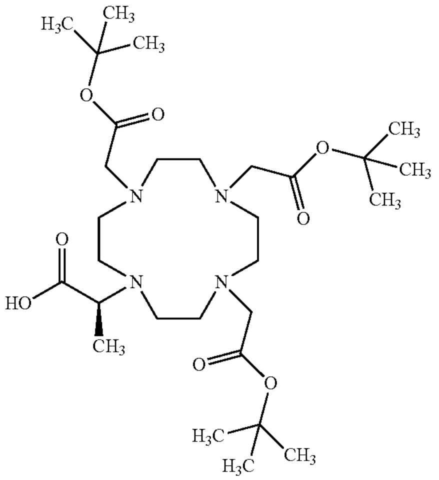 [SMILES: C[C@@H](C(=O)O)N1CCN(CC(=O)OC(C)(C)C)CCN(CC(=O)OC(C)(C)C)CCN(CC(=O)OC(C)(C)C)CC1]

Prepared in analogy to the corresponding R-isomer (example 3-1e) from benzyl (2S)-2-[4,7,10-tris(2-tert-butoxy-2-oxoethyl)-1,4,7,10-tetraazacyclododecan-1-yl]propanoate (example 3-2b).

UPLC ($ACN-NH_3$): Rt.=1.31 min.

MS ($ES^+$): m/z=587 $(M+H)^+$.

LC-MS ($ES^+$): m/z=587.4 $(M+H)^+$, m/z (z=2)=294.2 $(M+H)^{2+}$; Rt.=0.82 min.

Example 3-2d

Tert-butyl {4,10-bis(2-tert-butoxy-2-oxoethyl)-7-[(2S,16S)-3,6,12,15-tetraoxo-16-[4,7,10-tris(2-tert-butoxy-2-oxoethyl)-1,4,7,10-tetraazacyclododecan-1-yl]-9,9-bis({[({(2S)-2-[4,7,10-tris(2-tert-butoxy-2-oxoethyl)-1,4,7,10-tetraazacyclododecan-1-yl]propanoyl}-amino)acetyl]amino}methyl)-4,7,11,14-tetraazaheptadecan-2-yl]-1,4,7,10-tetraazacyclododecan-1-yl}acetate

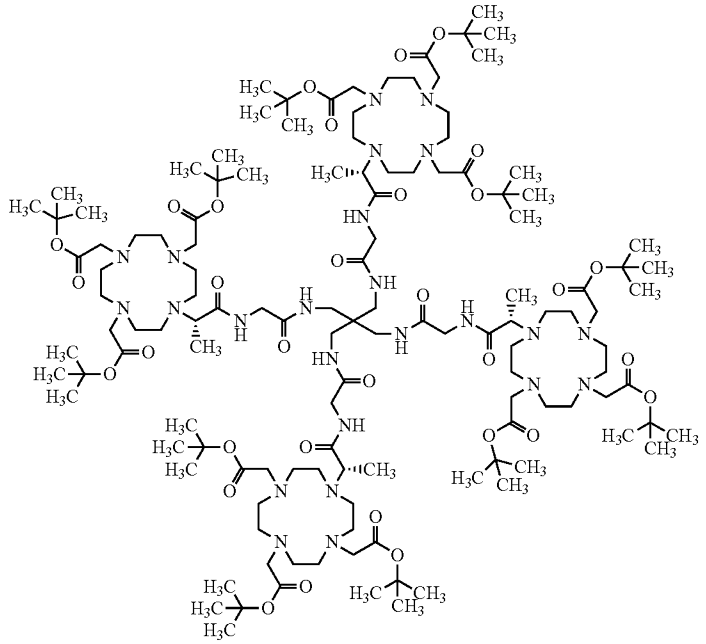 [SMILES: C[C@@H](C(=O)NCC(=O)NCC(CNC(=O)CNC(=O)[C@H](C)N1CCN(CC(=O)OC(C)(C)C)CCN(CC(=O)OC(C)(C)C)CCN(CC(=O)OC(C)(C)C)CC1)(CNC(=O)CNC(=O)[C@H](C)N1CCN(CC(=O)OC(C)(C)C)CCN(CC(=O)OC(C)(C)C)CCN(CC(=O)OC(C)(C)C)CC1)CNC(=O)CNC(=O)[C@H](C)N1CCN(CC(=O)OC(C)(C)C)CCN(CC(=O)OC(C)(C)C)CCN(CC(=O)OC(C)(C)C)CC1)N1CCN(CC(=O)OC(C)(C)C)CCN(CC(=O)OC(C)(C)C)CCN(CC(=O)OC(C)(C)C)CC1]

Prepared in analogy to the corresponding R-isomer (example 3-1f) from (2S)-2-[4,7,10-tris(2-tert-butoxy-2-oxoethyl)-1,4,7,10-tetraazacyclododecan-1-yl]propanoic acid (example 3-2c) and 2-amino-N-(3-[(aminoacetyl)amino]-2,2-bis{[(aminoacetyl)amino]methyl}propyl) acetamide tetrahydrochloride (example 3-1 b).

LC-MS ($ES^+$): m/z (z=2)=1318 $(M+H)^{2+}$, m/z (z=3)=879 $(M+H)^{3+}$, m/z (z=4)=660 $(M+H)^{4+}$; Rt.=0.95 min.

Example 3-2e

{4,10-Bis(carboxymethyl)-7-[(2S,16S)-3,6,12,15-tetraoxo-16-[4,7,10-tris(carboxymethyl)-1,4,7,10-tetraazacyclododecan-1-yl]-9,9-bis({[({(2S)-2-[4,7,10-tris(carboxymethyl)-1,4,7,10-tetraazacyclododecan-1-yl]propanoyl}amino)acetyl]amino}methyl)-4,7,11,14-tetraazaheptadecan-2-yl]-1,4,7,10-tetraazacyclododecan-1-yl}acetic acid

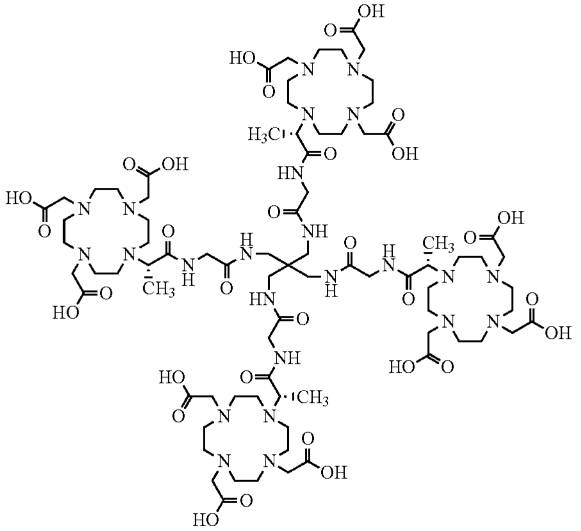 [SMILES: C[C@@H](C(=O)NCC(=O)NCC(CNC(=O)CNC(=O)[C@H](C)N1CCN(CC(=O)O)CCN(CC(=O)O)CCN(CC(=O)O)CC1)(CNC(=O)CNC(=O)[C@H](C)N1CCN(CC(=O)O)CCN(CC(=O)O)CCN(CC(=O)O)CC1)CNC(=O)CNC(=O)[C@H](C)N1CCN(CC(=O)O)CCN(CC(=O)O)CCN(CC(=O)O)CC1)N1CCN(CC(=O)O)CCN(CC(=O)O)CCN(CC(=O)O)CC1]

Prepared in analogy to the corresponding R-isomer (example 3-1g) from tert-butyl {4,10-bis(2-tert-butoxy-2-oxoethyl)-7-[(2S,16S)-3,6,12,15-tetraoxo-16-[4,7,10-tris(2-tert-butoxy-2-oxoethyl)-1,4,7,10-tetraazacyclododecan-1-yl]-9,9-bis({[({(2S)-2-[4,7,10-tris(2-tert-butoxy-2-oxoethyl)-1,4,7,10-tetraazacyclododecan-1-yl]propanoyl}amino)acetyl]amino}methyl)-4,7,11,14-tetraazaheptadecan-2-yl]-1,4,7,10-tetraazacyclododecan-1-yl}acetate (example 3-2d). The crude product was used without further characterization in the next chemical step.

Example 3-2

Tetragadolinium {4,10-bis(carboxylatomethyl)-7-[(2S,16S)-3,6,12,15-tetraoxo-16-[4,7,10-tris(carboxylatomethyl)-1,4,7,10-tetraazacyclododecan-1-yl]-9,9-bis({[({(2S)-2-[4,7,10-tris(carboxylatomethyl)-1,4,7,10-tetraazacyclododecan-1-yl]propanoyl}amino)acetyl]-amino}methyl)-4,7,11,14-tetraazaheptadecan-2-yl]-1,4,7,10-tetraazacyclododecan-1-yl}-acetate Prepared in analogy to the corresponding R-isomer (example 3-1) from {4,10-bis(carboxymethyl)-7-[(2S,16S)-3,6,12,15-tetraoxo-16-[4,7,10-tris(carboxymethyl)-1,4,7,10-tetraazacyclododecan-1-yl]-9,9-bis({[({(2S)-2-[4,7,10-tris(carboxymethyl)-1,4,7,10-tetraaza-cyclododecan-1-yl]propanoyl}amino)acetyl]amino}methyl)-4,7,11,14-tetraazaheptadecan-2-yl]-1,4,7,10-tetraazacyclododecan-1-yl}acetic acid (example 3-2e) and tris(acetato-kappaO) gadolinium tetrahydrate at pH 4.5. The resulting reaction solution was ultrafiltered with water (8×100 mL) using a 1 kDa membrane and the final retentate lyophilized and purified by preparative HPLC.

UPLC (ACN-HCOOH): Rt.=0.41 min.

MS (ES$^+$): m/z (z=2)=1290 $(M+H)^{2+}$, m/z (z=3)=861 $(M+H)^{3+}$.

LC-MS (ES$^+$): m/z (z=2)=1290 $(M+H)^{2+}$, m/z (z=3)=860 $(M+H)^{3+}$, m/z (z=4)=645.6 $(M+H)^{4+}$; Rt.=0.23 min.

Example 4

Pentagadolinium[4-(1-{[2-(bis{2-[({1,4-bis[({2-[4,7,10-tris(carboxylatomethyl)-1,4,7,10-tetraazacyclododecan-1-yl]propanoyl}amino)acetyl]-1,4-diazepan-6-yl}carbonyl)-amino]ethyl}amino)-2-oxoethyl]amino}-1-oxopropan-2-yl)-7,10-bis(carboxylatomethyl)-1,4,7,10-tetraazacyclododecan-1-yl]acetate

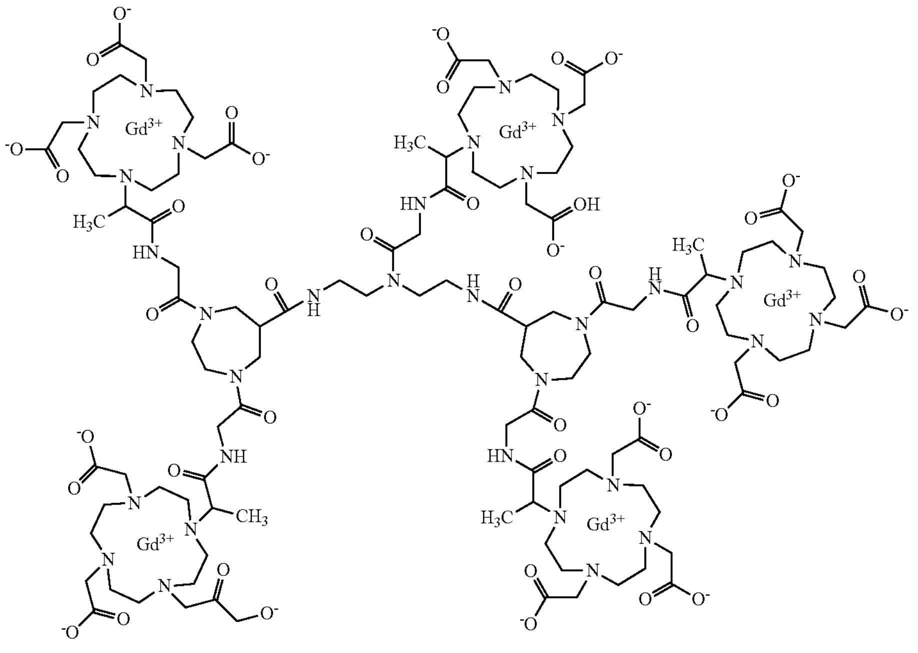

Example 4a 6-(Methoxycarbonyl)-1,4-diazepanediium dichloride

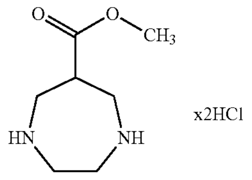

6.00 g (17.7 mmol) Methyl 1,4-dibenzyl-1,4-diazepane-6-carboxylate [see U.S. Pat. No. 5,866,562] were dissolved in 30 mL methanol. After adding of 6 mL aqueous hydrochloric acid (37%), 6 mL water and 600 mg palladium on charcoal (10%), the reaction mixture was hydrogenated (1 atm) for 17 hours at 40° C. The catalyst was filtered off and the solution was evaporated under reduced pressure yielding 4.1 g (17.7 mmol, 100%) of the title compound.

$^1$H-NMR (400 MHz, $D_2O$): δ=3.62-3.84 (m, 9H), 3.87 (s, 3H) ppm.

UPLC (ACN-HCOOH): Rt.=0.20 min.

MS (ES$^+$): m/z=159.1 $(M+H)^+$, free base.

Example 4b 1,4-Di-tert-butyl 6-methyl 1,4-diazepane-1,4,6-tricarboxylate

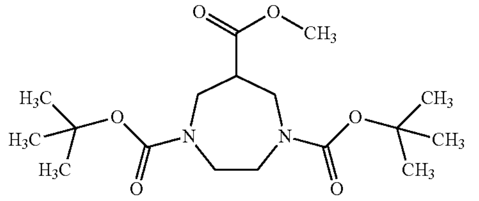 [SMILES: COC(=O)C1CN(C(=O)OC(C)(C)C)CCN(C(=O)OC(C)(C)C)C1]

4.00 g (17.3 mmol, 1 eq.) 6-(Methoxycarbonyl)-1,4-diazepanediium dichloride (example 4a) were dissolved in 80 mL DMF. After addition of 7.71 g (76.2 mmol, 4.4 eq.) trimethyl amine and 8.31 g (38.1 mmol, 2.2 eq.) di-tert-butyl dicarbonate, the resulting reaction mixture was stirred overnight at room temperature. The suspension was filtered, the filtrate evaporated under reduced pressure and diluted with ethyl acetate. The resulting solution was washed with aqueous citric acid (pH=3-4), half saturated aqueous sodium bicarbonate, was dried over sodium sulfate, and evaporated under reduced pressure yielding 4.92 g (13.7 mmol, 79%) of the title compound.

$^1$H-NMR (300 MHz, DMSO-$d_6$): δ=1.36 (s, 18H), 2.69-3.27 (m, 4H), 3.35-4.00 (m, 5H), 3.62 (s, 3H) ppm.

UPLC (ACN-HCOOH): Rt.=1.32 min.

MS (ES$^+$): m/z=359.2 $(M+H)^+$.

Example 4c 1,4-Bis(tert-butoxycarbonyl)-1,4-diazepane-6-carboxylic acid

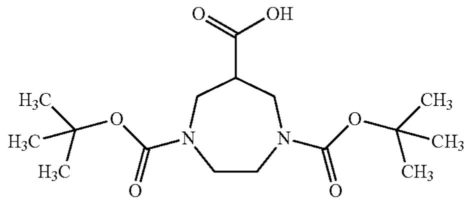 [SMILES: CC(C)(C)OC(=O)N1CCN(C(=O)OC(C)(C)C)CC(C(=O)O)C1]

4.86 g (13.66 mmol) 1,4-Di-tert-butyl 6-methyl 1,4-diazepane-1,4,6-tricarboxylate (example 4b) were dissolved in 82 mL THF. After adding of 27 mL aqueous sodium hydroxide (2 M), the resulting reaction mixture was stirred for 20 hours at room temperature, was diluted with water, and was acidified (pH=3-4) by addition of citric acid. The crude product was extracted with dichloromethane, the organic layer was washed with brine, dried over sodium sulfate, and was evaporated to dryness yielding 4.67 g (12.4 mmol, 91%) of the title compound.

$^1$H-NMR (400 MHz, DMSO-$d_6$): δ=1.38 (s, 18H), 2.58-2.86 (m, 1H), 2.94-4.00 (m, 8H), 12.50 (s, br, 1H) ppm.

UPLC (ACN-HCOOH): Rt.=1.12 min.

MS (ES$^+$): m/z=345.2 $(M+H)^+$.

Example 4d

Di-tert-butyl 6-{[(2,5-dioxopyrrolidin-1-yl)oxy]carbonyl}-1,4-diazepane-1,4-dicarboxylate

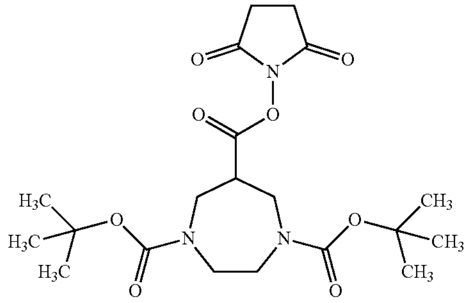 [SMILES: CC(C)(C)OC(=O)N1CCN(C(=O)OC(C)(C)C)CC(C(=O)ON2C(=O)CCC2=O)C1]

1.76 g (5.11 mmol, 1 eq.) 1,4-Bis(tert-butoxycarbonyl)-1,4-diazepane-6-carboxylic acid (example 4c) and 0.65 g (5.62 mmol, 1.1 eq.) 1-hydroxypyrrolidine-2,5-dione were dissolved in 50 mL THF. A solution of 1.16 g (5.62 mmol, 1.1 eq.) N,N-dicyclohexylcarbodiimide in 30 mL THF was added and the resulting reaction mixture was refluxed for 5 hours. The suspension was cooled to 0° C. and the precipitated urea was filtered off. The final solution of the activated ester was directly used for the next chemical step.

UPLC (ACN-HCOOH): Rt.=1.24 min.

MS ($ES^+$): m/z=442.3 $(M+H)^+$.

Example 4e

Tetra-tert-butyl 6,6'-[iminobis(ethane-2,1-diylcarbamoyl)]bis(1,4-diazepane-1,4-dicarboxylate)

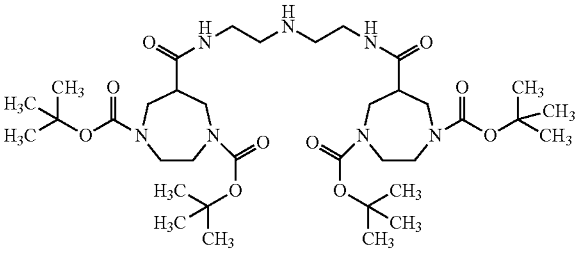 [SMILES: CC(C)(C)OC(=O)N1CCN(C(=O)OC(C)(C)C)CC(C(=O)NCCNCCNC(=O)C2CN(C(=O)OC(C)(C)C)CCN(C(=O)OC(C)(C)C)C2)C1]

To the solution of the activated ester (5.11 mmol, 2.2 eq.) di-tert-butyl 6-{[(2,5-dioxo-pyrrolidin-1-yl)oxy]carbonyl}-1,4-diazepane-1,4-dicarboxylate from example 4d were added 517 mg (5.11 mmol, 2.2 eq.) triethylamine and 240 mg (2.32 mmol, 1 eq.) N-(2-aminoethyl)ethane-1,2-diamine. The resulting reaction mixture was stirred for 20 hours at room temperature and was diluted with dichloromethane. The solution was washed with aqueous sodium hydroxide (0.1 M), then with water, and was dried over sodium sulfate. The crude product was isolated by evaporation and was purified by silica gel chromatography yielding 1.20 g (1.59 mmol, 68%) of the title compound.

$^1H$-NMR (400 MHz, DMSO-$d_6$): δ=1.37 (s, 36H), 2.51-2.70 (m, 7H), 2.85-3.28 (m, 12H), 3.45-4.10 (m, 8H), 7.69-8.27 (m, 2H) ppm.

UPLC (ACN-HCOOH): Rt.=1.20 min.

MS ($ES^+$): m/z=756.7 $(M+H)^+$.

Example 4f

N,N-(Iminodiethane-2,1-diyl)bis(1,4-diazepane-6-carboxamide) pentahydrochloride

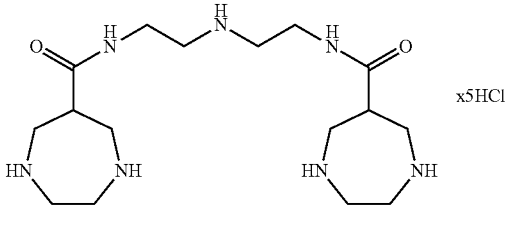 [SMILES: O=C(NCCNCCNC(=O)C1CNCCNC1)C1CNCCNC1]

385 mg (0.51 mmol) Tetra-tert-butyl 6,6'-[iminobis(ethane-2,1-diylcarbamoyl)]bis(1,4-diazepane-1,4-dicarboxylate) (example 4e) were dissolved in 5.7 mL methanol and 1.7 mL aqueous hydrochloric acid (37%). The reaction mixture was heated under stirring for 2 hours at 50° C. For isolation the suspension was evaporated to dryness yielding 277 mg (0.51 mmol, 100%) of the title compound.

$^1H$-NMR (400 MHz, $D_2O$): 6=3.18 (t, 4H), 3.32-3.40 (m, 2H), 3.51 (t, 4H), 3.57-3.69 (m, 16H) ppm.

UPLC (ACN-HCOOH): Rt.=0.24 min.

MS ($ES^+$): m/z=356.3 $(M+H)^+$, free base.

Example 4

Pentagadolinium[4-(1-{[2-(bis{2-[({1,4-bis[({2-[4,7,10-tris(carboxylatomethyl)-1,4,7,10-tetraazacyclododecan-1-yl]propanoyl}amino)acetyl]-1,4-diazepan-6-yl}carbonyl)-amino]ethyl}amino)-2-oxoethyl]amino}-1-oxopropan-2-yl)-7,10-bis(carboxylatomethyl)-1,4,7,10-tetraazacyclododecan-1-yl]acetate 150 mg (279 μmol, 1 eq.) N,N'-(Iminodiethane-2,1-diyl)bis(1,4-diazepane-6-carboxamide) pentahydrochloride (example 4f) were dissolved in 60 mL DMSO. After addition of 451 mg (3.49 mmol, 12.5 eq.), N,N-diisopropylethylamine and 3.67 g (4.88 mmol, 17.5 eq.) gadolinium 2,2',2''-[10-(1-{[2-(4-nitrophenoxy)-2-oxoethyl]amino}-1-oxopropan-2-yl)-1,4,7,10-tetraazacyclododecane-1,4,7-triyl]triacetate (see WO 2001051095 A2), the resulting reaction mixture was stirred and heated for 8 hours at 50° C. The cooled solution was concentrated under reduced pressure to a final volume of 15-20 mL. The concentrate was poured under stirring in 400 mL ethyl acetate, the formed precipitate was filtered off and was dried in vacuo. The solid was dissolved in water, the resulting solution was ultrafiltered with water using a 1 kDa membrane and the final retentate was lyophilized. The crude product was purified by RP-chromatography yielding 672 mg (197 μmol, 70%) of the title compound.

UPLC (ACN-HCOOH): Rt.=0.43 min.

MS ($ES^-$): m/z (z=2)=1706.3 $(M-2H)^{2-}$ m; ($ES^+$): m/z (z=4)=854.5 $(M+4H)^{4+}$.

Example 5

Hexagadolinium 2,2',2'',2''', 2'''', 2''''',2'''''',2''''''', 2'''''''',2''''''''',2'''''''''',2''''''''''',2'''''''''''', 2''''''''''''',2'''''''''''''', 2''''''''''''''', 2'''''''''''''''',2'''''''''''''''''-{ethane-1,2-diylcarbamoyl-1,4-diazepane-6,1,4-triyltris[(2-oxoethane-2,1-diyl)imino(I-oxopropane-1,2-diyl)-1,4,7,10-tetraazacyclododecane-10,1,4,7-tetrayl]}octadecaacetate N-(2-aminoethyl)ethane-1,2-diamine and of 540 mg (4.18 mmol, 3.6 eq.) N,N-diisopropylethylamine in 8 mL DMF, the resulting reaction mixture was heated under stirring for 3 hours at 70° C. After cooling and diluting with dichloromethane, the solution was washed with aqueous sodium hydroxide (0.1 M), with aqueous citric acid (1%), with water and was dried over sodium sulfate. The crude product was isolated by evaporation under reduced pressure and was purified by silica gel chromatography yielding 660 mg (0.61 mmol, 52%) of the title compound.

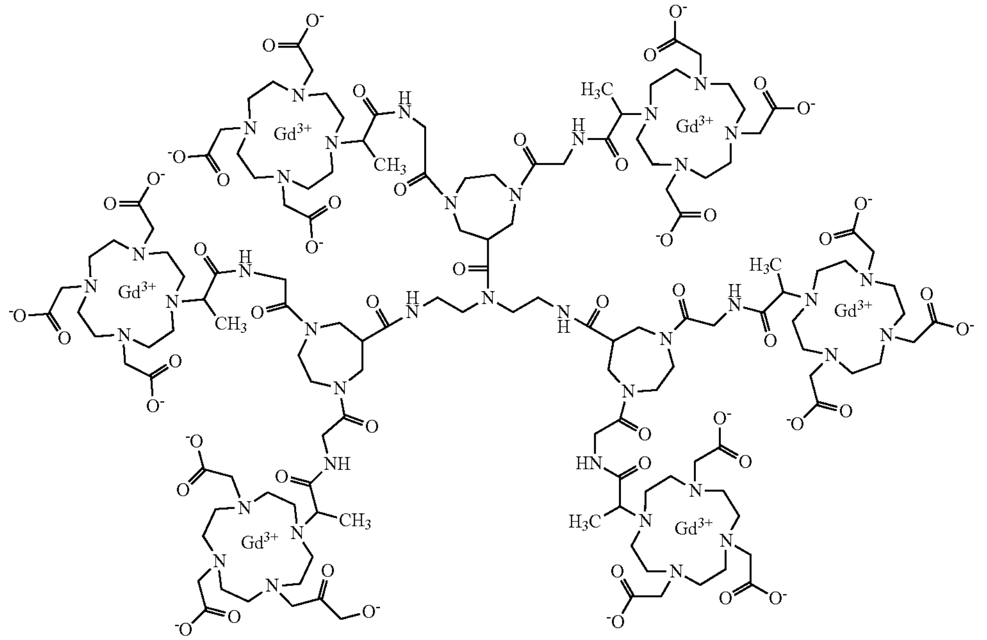

Example 5a

Hexa-tert-butyl 6,6',6''-(ethane-1,2-diylcarbamoyl)tris(1,4-diazepane-1,4-dicarboxylate)

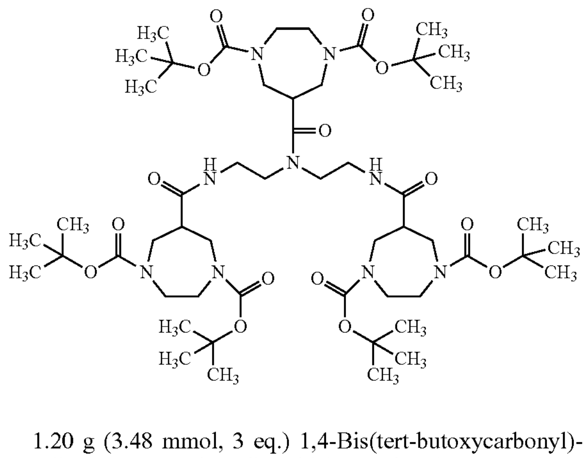

1.20 g (3.48 mmol, 3 eq.) 1,4-Bis(tert-butoxycarbonyl)-1,4-diazepane-6-carboxylic acid (example 4c), 540 mg (4.18 mmol, 3.6 eq.) diisopropylethylamine and 1.59 g (4.18 mmol, 3.6 eq.) HATU were dissolved in 30 mL DMF and stirred for 2 hours at room temperature. After drop wise addition of a solution of 120 mg (1.16 mmol, 1 eq.), $^1$H-NMR (400 MHz, DMSO-$d_6$): δ=1.38 (s, 54H), 2.55-4.06 (m, 35H), 7.90-8.52 (m, 2H) ppm.

UPLC (ACN-HCOOH): Rt.=1.64 min.

MS (ES$^+$): m/z=1082.7 $(M+H)^+$.

Example 5b

N,N-Bis{2-[(1,4-diazepan-6-ylcarbonyl)amino]ethyl}-1,4-diazepane-6-carboxamide hexahydrochloride

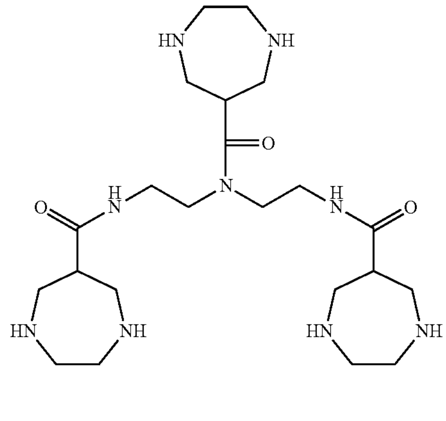

x6HCl 654 mg (0.60 mmol) Hexa-tert-butyl 6,6',6''-(ethane-1,2-diylcarbamoyl)tris(1,4-diazepane-1,4-dicarboxylate) (example 5a) were dissolved in 6.8 mL methanol and 3 mL aqueous hydrochloric acid (37%). The reaction mixture was heated under stirring for 2.5 hours at 50° C. For isolation, the suspension was evaporated to dryness yielding 441 mg (0.63 mmol, 105%) of the title compound.

$^1$H-NMR (400 MHz, DMSO-$d_6$): δ=3.20-3.71 (m, 35H), 8.50-8.80 ppm (m, 2H), 9.76 (s, br, 12H).

UPLC (ACN-HCOOH): Rt.=0.19 min.

MS (ES$^+$): m/z=482.3 $(M+H)^+$, free base.

Example 5

Hexagadolinium 2,2',2'',2''', 2'''', 2''''', 2'''''',2''''''', 2'''''''',2''''''''', 2'''''''''', 2''''''''''', 2'''''''''''',2''''''''''''', 2'''''''''''''', 2''''''''''''''',2''''''''''''''''-{ethane-1,2-diylcarbamoyl-1,4-diazepane-6,1,4-triyltris[(2-oxoethane-2,1-diyl)imino(I-oxopropane-1,2-diyl)-1,4,7,10-tetraazacyclododecane-10,1,4,7-tetrayl]}octadecaacetate 150 mg (214 μmol, 1 eq.) N,N-Bis{2-[(1,4-diazepan-6-ylcarbonyl)amino]ethyl}-1,4-diazepane-6-carboxamide hexahydrochloride (example 5b) were dissolved in 60 mL DMSO. After adding of 0.42 g (3.21 mmol, 15 eq.), N,N-diisopropylethylamine and 3.38 g (4.50 mmol, 21 eq.)

gadolinium 2,2',2''-[10-(1-{[2-(4-nitrophenoxy)-2-oxoethyl]amino}-1-oxopropan-2-yl)-1,4,7,10-tetraazacyclododecane-1,4,7-triyl]triacetate (see WO 2001/051095 A2), the resulting reaction mixture was stirred and heated for 8 hours at 50° C. The cooled solution was concentrated under reduced pressure to a final volume of 15-20 mL. The concentrate was poured under stirring in 400 mL ethyl acetate, the formed precipitate was filtered off and was dried in vacuo. The solid was dissolved in water, the resulting solution was ultrafiltered with water using a 1 kDa membrane and the final retentate was lyophilized. The crude product was purified by RP-chromatography yielding 595 mg (143 μmol, 67%) of the title compound.

UPLC (ACN-HCOOH): Rt.=0.41 min.

MS (ES$^+$): m/z (z=3)=1384.6 $(M+H)^{3+}$, m/z (z=4) =1039.5 $(M+H)^{4+}$, m/z (z=5)=831.6 $(M+H)^{5+}$.

Example 6

Hexagadolinium 2,2',2'',2''', 2'''', 2''''',2'''''', 2''''''', 2'''''''', 2''''''''',2'''''''''',2''''''''''', 2'''''''''''', 2''''''''''''', 2'''''''''''''',2''''''''''''''',2'''''''''''''''',2'''''''''''''''''-(1,4,7-triazonane-1,4,7-triyltris{carbonyl-1,4-diazepane-6,1,4-triylbis[(2-oxoethane-2,1-diyl)imino(I-oxopropane-1,2-diyl)-1,4,7,10-tetraazacyclododecane-10,1,4,7-tetrayl]})octadecaacetate

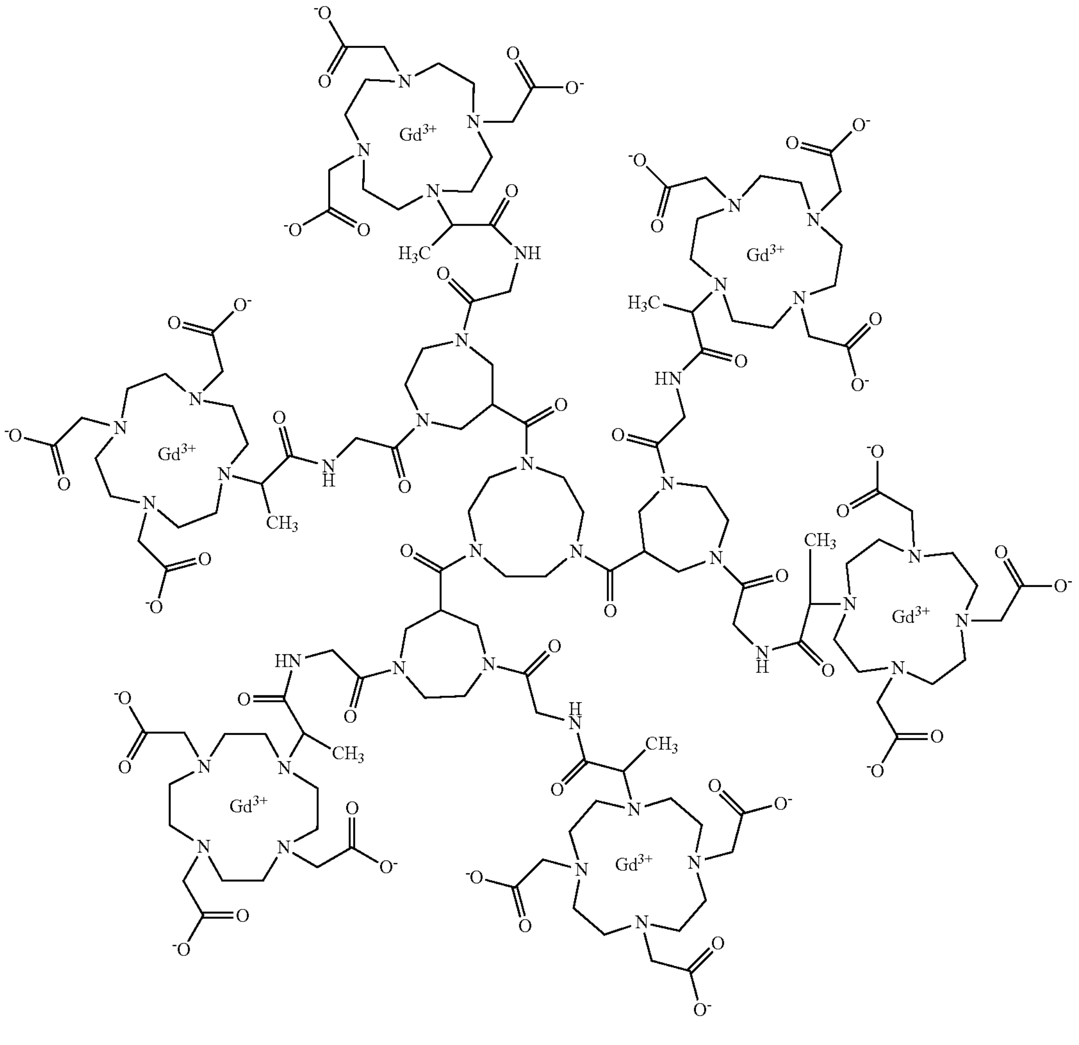

Example 6a

Hexa-tert-butyl 6,6',6"-(1,4,7-triazonane-1,4,7-triyltricarbonyl)tris(1,4-diazepane-1,4-dicarboxylate)

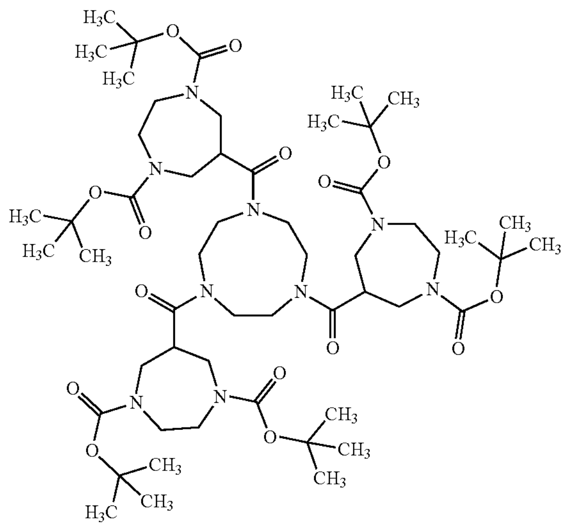 [SMILES: CC(C)(C)OC(=O)N1CCN(C(=O)OC(C)(C)C)CC(C(=O)N2CCN(C(=O)C3CN(C(=O)OC(C)(C)C)CCN(C(=O)OC(C)(C)C)C3)CCN(C(=O)C3CN(C(=O)OC(C)(C)C)CCN(C(=O)OC(C)(C)C)C3)CC2)C1]

800 mg (2.32 mmol, 3 eq.) 1,4-Bis(tert-butoxycarbonyl)-1,4-diazepane-6-carboxylic acid (example 4c), 360 mg (2.79 mmol, 3.6 eq.) diisopropylethylamine and 1.06 g (2.79 mmol, 3.6 eq.) HATU were dissolved in 20 mL DMF and stirred for 2 hours at room temperature. After dropwise adding of a solution of 100 mg (774 μmol, 1 eq.) 1,4,7-triazonane trihydrochloride and of 360 mg (2.79 mmol, 3.6 eq.) N,N-diisopropylethylamine in 5 mL DMF, the resulting reaction mixture was heated under stirring for 3 hours at 70° C. After cooling and diluting with dichloromethane, the solution was washed with aqueous sodium hydroxide (0.1 M), with aqueous citric acid (1%), with water and was dried over sodium sulfate. The crude product was isolated by evaporation under reduced pressure and was purified by silica gel chromatography yielding 545 mg (492 μmol, 63%) of the title compound.

$^1$H-NMR (400 MHz, $CDCl_3$): δ=1.47 (s, 54H), 2.85-4.45 (m, 39H) ppm.

UPLC (ACN-HCOOH): Rt.=1.73 min.

MS ($ES^+$): m/z=1108.8 $(M+H)^+$.

Example 6b

1,4,7-Triazonane-1,4,7-triyltris(1,4-diazepan-6-ylmethanone) hexahydrochloride

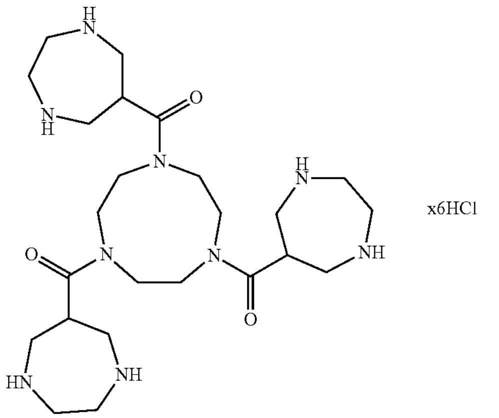 [SMILES: O=C(C1CNCCNC1)N1CCN(C(=O)C2CNCCNC2)CCN(C(=O)C2CNCCNC2)CC1]

380 mg (343 μmol) Hexa-tert-butyl 6,6',6"-(1,4,7-triazonane-1,4,7-triyltricarbonyl)tris(1,4-diazepane-1,4-dicarboxylate) (example 6a) were dissolved in 3.90 mL methanol and 1.72 mL aqueous hydrochloric acid (37%). The reaction mixture was heated under stirring for 2.5 hours at 50° C. For isolation the suspension was evaporated to dryness yielding 257 mg (354 μmol, 103%) of the title compound.

UPLC (ACN-HCOOH): Rt.=0.19 min.

MS ($ES^+$): m/z=508.4 $(M+H)^+$, free base.

Example 6

Hexagadolinium 2,2',2'',2''', 2'''', 2''''',2'''''',2''''''', 2'''''''',2''''''''',2'''''''''',2''''''''''',2'''''''''''', 2''''''''''''',2'''''''''''''', 2''''''''''''''',2'''''''''''''''',2'''''''''''''''''-(1,4,7-triazonane-1,4,7-triyltris{carbonyl-1,4-diazepane-6,1,4-triylbis[(2-oxoethane-2,1-diyl)imino(I-oxopropane-1,2-diyl)-1,4,7,10-tetraazacyclododecane-10,1,4,7-tetrayl]}) octadecaacetate 175 mg (241 μmol, 1 eq.) 1,4,7-Triazonane-1,4,7-triyltris(1,4-diazepan-6-ylmethanone) hexahydrochloride (example 6b) were dissolved in 60 mL DMSO. After adding of 467 mg (3.61 mmol, 15 eq.) N,N-diisopropylethylamine and 3.80 g (5.06 mmol, 21 eq.) gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl]triacetate (see WO 2001051095 A2), the resulting reaction mixture was stirred and heated for 8 hours at 50° C. The cooled solution was concentrated under reduced pressure to a final volume of 15-20 mL. The concentrate was poured under stirring in 400 mL ethyl acetate, the formed precipitate was filtered off and was dried in vacuo. The solid was dissolved in water, the resulting solution was ultrafiltered with water using a 1 kDa membrane and the final retentate was lyophilized. The crude product was purified by RP-chromatography yielding 590 mg (141 μmol, 58%) of the title compound.

UPLC (ACN-HCOOH): Rt.=0.43 min.

MS ($ES^+$): m/z (z=3)=1393.1 $(M+3H)^{3+}$, m/z (z=4) =1045.5 $(M+4H)^{4+}$, m/z (z=5)=837.0 $[(M+5H)^{5+}$.

Example 7

Tetragadolinium 2,2',2",2"', 2"", 2""',2""",2"""', 2"""",2""""',2""""",2"""""'-{1,4,7,10-tetra- azacyclododecane-1,4,7,10-tetrayltetrakis[(2-oxoethane-2, 1-diyl)imino(I-oxopropane-1,2-diyl)-1,4,7,10-tetraazacyclododecane-10,1,4,7-tetrayl] }dodecaacetate

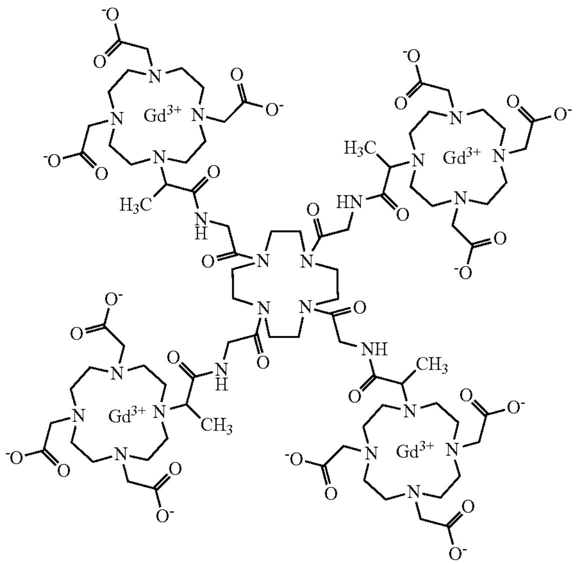

35 mg (203 μmol, 1 eq.) 1,4,7,10-Tetraazacyclododecane were dissolved in 60 mL DMSO. After adding of 2.14 g (2.84 mmol, 14 eq.) gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl]triacetate (see WO 2001051095 A2), the resulting reaction mixture was stirred and heated for 8 hours at 50° C. The cooled solution was concentrated under reduced pressure to a final volume of 15-20 mL. The concentrate was poured under stirring in 400 mL ethyl acetate, the formed precipitate was filtered off and was dried in vacuo. The solid was dissolved in water, the resulting solution was ultrafiltered with water using a 1 kDa membrane and the final retentate was lyophilized. The crude product was purified by RP-chromatography yielding 28 mg (10.6 μmol, 5%) of the title compound.

UPLC (ACN-HCOOH): Rt.=0.41 min.

MS ($ES^+$): m/z (z=2)=1311.7 $(M+2H)^{2+}$, m/z (z=3)=873.1 $(M+3H)^{3+}$.

Example 8

Hexagadolinium 2,2',2",2"', 2"", 2""', 2""",2"""', 2"""",2""""',2""""",2"""""',2"""""", 2""""""',2""""""", 2"""""""',2"""""""",2""""""""'-{3,7,10-triazatricyclo [3.3.3.$0^{1,5}$]un- decane-3,7,10-triyltris[carbonyl(3,6, 11,14-tetraoxo-4,7,10,13-tetraazahexadecane-8,2,15-triyl)di-1,4,7,10-tetraazacyclododecane-10,1,4,7-tetrayl]}octadecaacetate

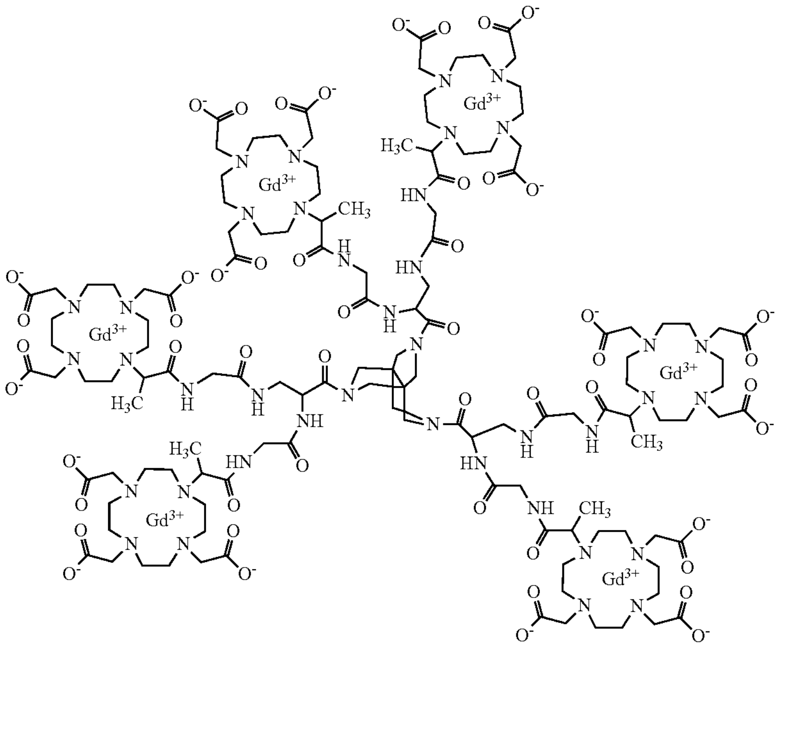

Example 8a

Tetrahydro-1H,4H-3a,6a-(methanoiminomethano)pyrrolo[3,4-c]pyrrole

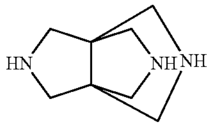 [SMILES: C1NCC23CNCC12CNC3]

4.0 g (6.5 mmol) 2,5,8-Tris((4-methylphenyl)sulfonyl)tetrahydro-1H,4H-3a,6a-(methanoiminomethano)pyrrolo[3,4-c]pyrrole (prepared via the procedures outlined in *J. Org. Chem.* 1996, 61, 8897-8903) was refluxed in 44 mL aqueous hydrobromic acid (47%) and 24 mL acetic acid for 18 hours. The solvent was removed in vacuo, the residue dissolved in water, and the aqueous phase was washed two times with dichloromethane. The aqueous phase was lyophilized and taken up in a small amount of water and passed through an anionic exchange column (DOWEX 1×8) by elution with water. The basic fraction was collected and concentrated to yield 0.89 g of tetrahydro-1H,4H-3a,6a-(methanoiminomethano)pyrrolo[3,4-c]pyrrole as free base.

$^1$H-NMR (400 MHz, $D_2O$): 6=2.74 (s, 12H) ppm.

Example 8b

Tert-butyl-{1-[5,8-bis{2,3-bis[(tert-butoxycarbonyl)amino]propanoyl}dihydro-1H,4H-3a,6a-(methanoiminomethano)pyrrolo[3,4-c]pyrrol-2(3H)-yl]-3-[(tert-butoxycarbonyl)amino]-1-oxopropan-2-yl}carbamate

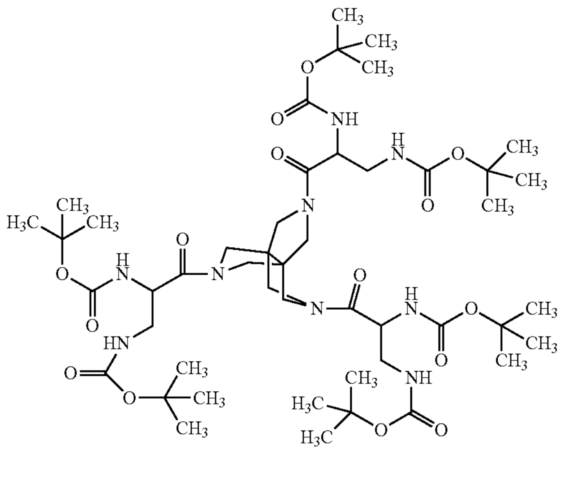 [SMILES: CC(C)(C)OC(=O)NCC(NC(=O)OC(C)(C)C)C(=O)N1CC23CN(C(=O)C(CNC(=O)OC(C)(C)C)NC(=O)OC(C)(C)C)CC2(C1)CN(C(=O)C(CNC(=O)OC(C)(C)C)NC(=O)OC(C)(C)C)C3]

A solution prepared from 431.5 mg (0.89 mmol, CAS [201472-68-6]) N-(tert-butoxycarbonyl)-3-[(tert-butoxycarbonyl)amino]alanine N,N-dicyclohexylammonium salt, 0.44 mL (2.54 mmol) N,N-diisopropylethylamine and 386 mg (1.0 mmol) HATU in 4.3 mL DMF was added to 38.9 mg (254 μmol) of tetrahydro-1H,4H-3a,6a-(methanoiminomethano)pyrrolo[3,4-c]pyrrole in 2 mL DMF. After stirring the combined mixture for 20 min at room temperature, the solvent was removed in vacuo and the residue purified by chromatography on amino phase silica gel (ethyl acetate in hexane, 0 to 100%) followed by preparative HPLC (C18-Chromatorex 10 μm, acetonitrile in water+0.1% formic acid, 65% to 100%) to yield 68.6 mg of tert-butyl-{1-[5,8-bis{2,3-bis[(tert-butoxycarbonyl)amino]propanoyl}dihydro-1H,4H-3a,6a-(methanoiminomethano)pyrrolo[3,4-c]pyrrol-2(3H)-yl]-3-[(tert-butoxycarbonyl)amino]-1-oxopropan-2-yl}carbamate.

$^1$H-NMR (300 MHz, $CDCl_3$): δ=1.43 s, br, 54H), 3.34-3.97 (m, 18H), 4.48 (s, br, 3H), 5.01-5.67 (m, 6H) ppm.

UPLC (ACN-HCOOH): Rt.=1.48 min.

MS ($ES^+$): m/z=1012.6 $(M+H)^+$.

Example 8c 3,3',3''-[1H,4H-3a,6a-(methanoiminomethano)pyrrolo[3,4-c]pyrrole-2,5,8(3H,6H)-triyl]-tris(3-oxopropane-1,2-diaminium) hexachloride

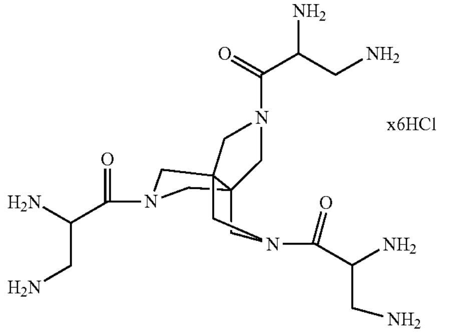 [SMILES: NCC(N)C(=O)N1CC23CN(C(=O)C(N)CN)CC2(C1)CN(C(=O)C(N)CN)C3]

65 mg (60 μmol) Tert-butyl-{1-[5,8-bis{2,3-bis[(tert-butoxycarbonyl)amino]propanoyl}dihydro-1H,4H-3a,6a-(methanoiminomethano)pyrrolo[3,4-c]pyrrol-2(3H)-yl]-3-[(tert-butoxy-carbonyl)amino]-1-oxopropan-2-yl}carbamate (example 8b) were dissolved in 2.0 mL DMF and 0.48 mL hydrochloric acid in dioxane (4 M, 0.19 mmol) were added. The reaction mixture was heated under microwave radiation for 10 min at 80° C. while stirring. The solvent was removed in vacuo, the residue taken up in a small amount of water and lyophilized to yield 38.9 mg of 3,3',3''-[1H,4H-3a,6a-(methanoiminomethano)pyrrolo[3,4-c]pyrrole-2,5,8(3H,6H)-triyl]tris(3-oxopropane-1,2-diaminium) hexachloride.

$^1$H-NMR (600 MHz, $D_2O$): δ=3.40-3.50 (m, 3H), 3.52-3.56 (m, 3H), 3.79-4.19 (m, 12H), 4.51-4.54 (m, 3H) ppm.

UPLC (ACN-HCOOH): Rt.=0.20 min.

MS ($ES^+$): m/z=412.3($[M+H]^+$, free base.

Example 8

Hexagadolinium 2,2',2'',2''', 2'''', 2''''',2'''''',2''''''', 2'''''''',2''''''''',2'''''''''',2''''''''''',2'''''''''''', 2''''''''''''',2'''''''''''''', 2''''''''''''''',2'''''''''''''''',2'''''''''''''''''-{3,7,10-triazatricyclo[3.3.3.0$^{1,5}$]un- decane-3,7,10-triyltris[carbonyl(3,6,11,14-tetraoxo-4,7,10,13-tetraazahexadecane-8,2,15-triyl)di-1,4,7,10-tetraazacyclododecane-10,1,4,7-tetrayl]}octadecaacetate 30 mg (48 μmol) 3,3',3''-[1H,4H-3a,6a-(Methanoiminomethano)pyrrolo[3,4-c]pyrrole-2,5,8 (3H,6H)-triyl]tris(3-oxopropane-1,2-diaminium) hexachloride (example 8c) were dissolved in a mixture of 1.8 mL DMSO, 1.8 mL DMF, and 116 μL pyridine. At 60° C. 281 mg (0.38 mmol, WO 2001051095 A2) of gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl]triacetate were added followed by 44 μL trimethylamine and the resulting reaction mixture was stirred for 15 hours at 60° C. and at room temperature for two days. Another amount of gadolinium 2,2',2"-[10-(1-{[2-(4-nitrophenoxy)-2-oxoethyl]amino}-1-oxopropan-2-yl)-1,4,7,10-tetraazacyclo dodecane-1,4,7-triyl]triacetate (56 mg, 75 μmol) and trimethylamine (5.4 μL) was added at 60° C. and stirring at 60° C. was continued for 15 hours. The solvent was removed in vacuo, the residue taken up in 200 mL of water, and the resulting solution was ultrafiltered using a 1 kDa membrane. After diluting the retentate two times with additional 200 mL of deionized water and continuing the ultrafiltration, the final retentate was lyophilized. The residue was dissolved in a mixture of 1.6 mL DMSO, 1.6 mL DMF, and 105 μL pyridine and addition of 261 mg (0.35 mmol) gadolinium 2,2',2"-[10-(1-{[2-(4-nitrophenoxy)-2-oxoethyl]amino}-1-oxopropan-2-yl)-1,4,7,10-tetraazacyclododecane-1,4,7-triyl]triacetate and 48 μL triethylamine at 60° C. was repeated a third time. After stirring for 18 hours at 60° C. the ultrafiltration procedure using a 1 kDa membrane was repeated and the retentate after three 200 mL filtrations was lyophilized. The crude product was purified by preparative HPLC (XBridge C18, 5 μm, acetonitrile in water+0.1% formic acid, 0% to 7%) to yield 51 mg of the title compound.

UPLC (ACN-HCOOH long run): Rt.=2.95 min.

MS ($ES^+$): m/z (z=3)=1360.4 $(M+3H)^{3+}$, m/z (z=4)=1021.3 $(M+4H)^{4+}$, m/z (z=5)=817.5 $(M+5H)^{5+}$.

Example 9

Tetragadolinium 2,2',2",2"', 2"", 2""',2"""', 2""""', 2"""""',2""""""',2"""""""',2""""""""-(3,7,9-triazabicyclo[3.3.1]nonane-3,7-diylbis{carbonyl-1,4-diazepane-6,1,4-triylbis[(2-oxoethane-2,1-diyl)-1,4,7,10-tetraazacyclododecane-10,1,4,7-tetrayl]}) dodecaacetate

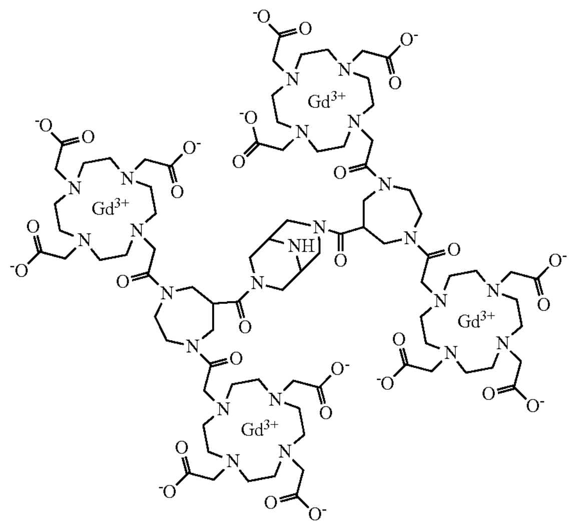

Example 9a

3,7,9-Triazabicyclo[3.3.1]nonane

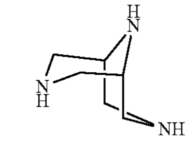

220 mg (0.49 mmol) 3,9-Dibenzyl-7-(phenylsulfonyl)-3,7,9-triazabicyclo[3.3.1]nonane (prepared via the procedures outlined in *Tetrahedron Lett.,* 2005, 46, 5577-5580) was refluxed in 3.4 mL aqueous hydrobromic acid (47%) and 1.8 mL acetic acid for 17 hours. The solvent was removed in vacuo, the residue dissolved in water and the aqueous phase was washed two times with dichloromethane. The aqueous phase was lyophilized and taken up in a small amount of water and passed through an anionic exchange column (DOWEX 1×8) by elution with water. The basic fraction was collected and concentrated to yield 29.6 mg of 3,7,9-triazabicyclo[3.3.1]nonane as the free base.

$^1$H-NMR (400 MHz, $D_2O$): δ=2.88 (t, 2H), 3.15 (d, 8H) ppm.

Example 9b

6-(Methoxycarbonyl)-1,4-diazepanediium dichloride

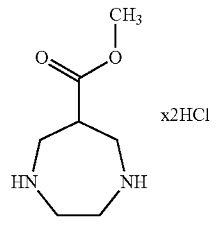

To 8.3 g (24.5 mmol) methyl 1,4-dibenzyl-1,4-diazepane-6-carboxylate (prepared in analogy to U.S. Pat. No. 5,866,562, p. 9) in 42 mL methanol were added 8.3 mL concentrated hydrochloric acid, 2 mL of water and 830 mg palladium on charcoal (10%). The suspension was stirred under a hydrogen atmosphere for 5 hours at 40° C. and 17 hours at room temperature. The mixture was filtrated through a path of Celite® and the filtrate concentrated in vacuo upon which toluene was added two times and removed in vacuo. The residue was dissolved in water and lyophilized to yield 5.65 g of 6-(methoxycarbonyl)-1,4-diazepanediium dichloride.

$^1$H-NMR (400 MHz, $D_2O$): δ=3.49-3.68 (m, 9H), 3.70-3.73 (m, 4H), 3.75 (s, 3H) ppm.

Example 9c

Methyl 1,4-bis{[4,7,10-tris(2-tert-butoxy-2-oxoethyl)-1,4,7,10-tetraazacyclododecan-1-yl]acetyl}-1,4-diazepane-6-carboxylate

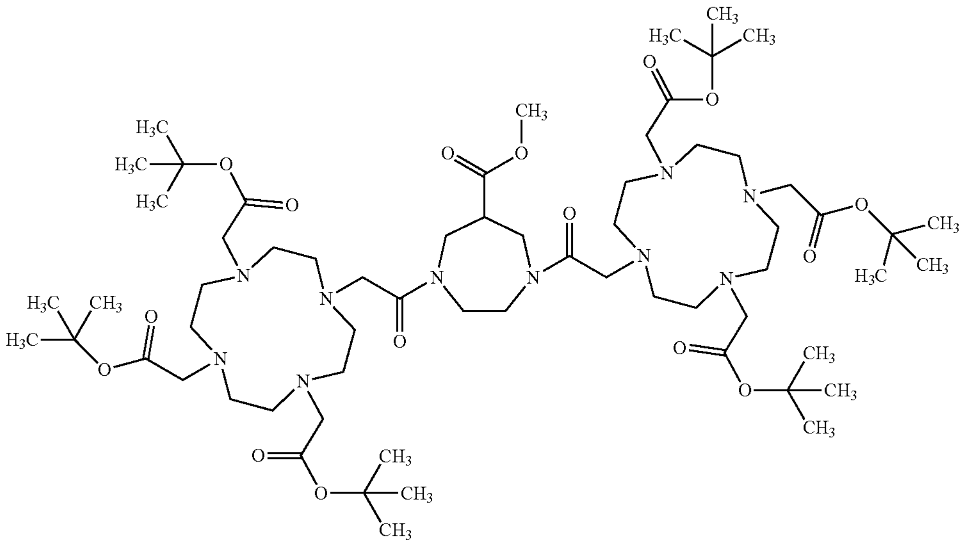 [SMILES: COC(=O)C1CN(C(=O)CN2CCN(CC(=O)OC(C)(C)C)CCN(CC(=O)OC(C)(C)C)CCN(CC(=O)OC(C)(C)C)CC2)CCN(C(=O)CN2CCN(CC(=O)OC(C)(C)C)CCN(CC(=O)OC(C)(C)C)CCN(CC(=O)OC(C)(C)C)CC2)C1]

To 200 mg (0.78 mmol) of 6-(methoxycarbonyl)-1,4-diazepanediium dichloride in 10 mL dichloromethane were added 10 mL (6.2 mmol) N,N-diisopropylethylamine and the mixture stirred for 5 min at room temperature. 1.04 g (1.56 mmol) tri-tert-butyl 2,2',2"-(10-{2-[(2,5-dioxopyrrolidin-1-yl)oxy]-2-oxoethyl}-1,4,7,10-tetraazacyclododecane-1,4,7-triyl)triacetate (prepared in analogy to Cong Li et al., J. Am. Chem. Soc. 2006, 128, p. 15072-15073; S3-5 and Galibert et al., Bioorg. Med. Chem. Letters 2010 (20), 5422-5425) was added and the mixture was stirred for 18 hours at room temperature. The solvent was removed under reduced pressure and the residue was purified by chromatography on amino phase silica gel (ethyl acetate in hexane, 20 to 100%, then ethanol in ethyl acetate 0 to 100%) to yield 210 mg of the title compound.

UPLC (ACN-HCOOH): Rt.=0.94 min.

MS ($ES^+$): m/z=1267.6 $(M+1H)^+$

Example 9d

Dodeca-tert-butyl 2,2',2",2''', 2'''', 2''''',2'''''',2''''''', 2'''''''',2''''''''',2'''''''''',2'''''''''''-(3,7,9-triazabicyclo[3.3.1]nonane-3,7-diylbis{carbonyl-1,4-diazepane-6,1,4-triylbis[(2-oxoethane-2,1-diyl)-1,4,7,10-tetraazacyclododecane-10,1,4,7-tetrayl]})dodecaacetate

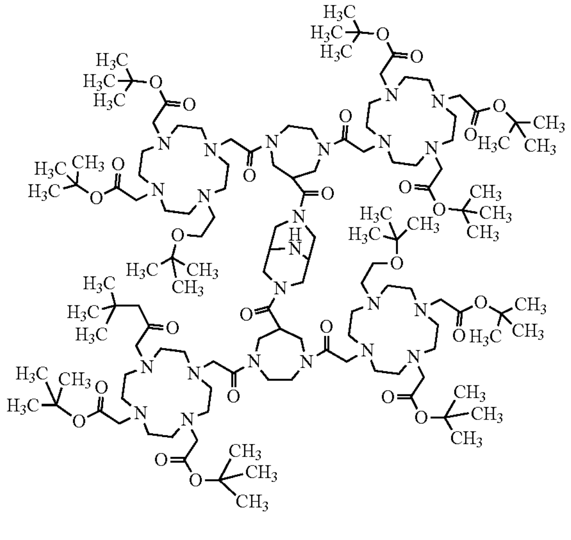 [SMILES: CC(C)(C)CC(=O)CN1CCN(CC(=O)OC(C)(C)C)CCN(CC(=O)OC(C)(C)C)CCN(CC(=O)N2CCN(C(=O)CN3CCN(CCOC(C)(C)C)CCN(CC(=O)OC(C)(C)C)CCN(CC(=O)OC(C)(C)C)CC3)CC(C(=O)N3CC4CN(C(=O)C5CN(C(=O)CN6CCN(CCOC(C)(C)C)CCN(CC(=O)OC(C)(C)C)CCN(CC(=O)OC(C)(C)C)CC6)CCN(C(=O)CN6CCN(CC(=O)OC(C)(C)C)CCN(CC(=O)OC(C)(C)C)CCN(CC(=O)OC(C)(C)C)CC6)C5)CC(C3)N4)C2)CC1]

305 mg (0.24 mmol) Methyl 1,4-bis{[4,7,10-tris(2-tert-butoxy-2-oxoethyl)-1,4,7,10-tetraazacyclododecan-1-yl]acetyl}-1,4-diazepane-6-carboxylate (example 9c) were dissolved in 3.9 mL THF and a solution of 6.6 mg lithium hydroxide in 0.87 mL water was added. After stirring for 15 min, the solvent was removed under reduced pressure and the crude lithium 1,4-bis{[4,7,10-tris(2-tert-butoxy-2-oxoethyl)-1,4,7,10-tetraazacyclododecan-1-yl]acetyl}-1,4-diazepane-6-carboxylate (300 mg) was dissolved in 2.0 mL dichloromethane. 120 μL (0.71 mmol) N,N-Diisopropylethylamine, 112 mg (0.30 mmol) HATU and 40 mg (0.30 mmol) 3H-[1,2,3]triazolo[4,5-b]pyridin-3-ol were added and after stirring for 15 min a solution of 15 mg (0.12 mmol) of 3,7,9-triazabicyclo[3.3.1]nonane in 1 mL dichloromethane was added and the mixture was stirred for 3 days. To additional 170 mg of raw lithium 1,4-bis{[4,7,10-tris(2-tert-butoxy-2-oxoethyl)-1,4,7,10-tetraazacyclododecan-1-yl]acetyl}-1,4-diazepane-6-carboxylate in 1 mL dichloromethane were added 67 mg (0.18 mmol) HATU, 24 mg (0.18 mmol) 3H-[1,2,3]triazolo[4,5-b]pyridin-3-ol over 15 min and 50 μL N,N-diisopropylethylamine. After stirring for 15 minutes the freshly prepared HATU solution was added to the reaction mixture. After one day the solvent was removed under reduced pressure upon which toluene was added six times and removed in vacuo. The residue was purified by chromatography on amino phase silica gel (ethyl acetate in hexane, 0 to 100%, then ethanol in ethyl acetate 0 to 40%) to yield 181 mg of the title compound.

UPLC (ACN-HCOOH): Rt.=0.78-0.84 mi.

MS (ES$^-$): m/z (z=2)=1298.7 $(M-2H)^{2-}$

Example 9

Tetragadolinium 2,2',2'',2''', 2'''', 2''''',2'''''',2''''''', 2'''''''',2''''''''',2'''''''''',2''''''''''',2''''''''''''-(3,7,9-triazabicyclo[3.3.1]nonane-3,7-diylbis{carbonyl-1,4-diazepane-6,1,4-triylbis[(2-oxoethane-2,1-diyl)-1,4,7,10-tetraazacyclododecane-10,1,4,7-tetrayl]}) dodecaacetate 390 mg (mmol) Dodeca-tert-butyl 2,2',2'',2''', 2'''', 2''''', 2'''''',2''''''',2'''''''',2''''''''',2'''''''''',2'''''''''''-(3,7,9-triazabicyclo[3.3.1]nonane-3,7-diylbis{carbonyl-1,4-diazepane-6,1,4-triylbis[(2-oxo-ethane-2,1-diyl)-1,4,7,10-tetraazacyclododecane-10,1,4,7-tetrayl]})dodecaacetate (example 9d) were dissolved in 10.8 mL water and the solution was adjusted to pH 2.5 by addition of aqueous hydrochloric acid (2M). 440 mg (1.25 mmol) Gadolinium (III)oxide were added and the mixture was stirred at 80° C. for 17 hours, while the pH of the suspension changed to pH 5. The mixture was diluted with water, sonicated and filtrated. The filtrate was ultrafiltered using a 1 kDa membrane. After diluting the retentate two times with additional 100 mL of deionized water and continuing the ultrafiltration the final retentate was lyophilized. The crude product was purified by preparative HPLC (C18 YMC-ODS AQ, 10 μm, acetonitrile in water+0.1% formic acid, 1% to 10%) to yield 14.5 mg of the title compound.

UPLC (ACN-HCOOH): Rt.=0.34 min.

MS (ES$^+$): m/z (z=2)=1272.9 $(M+2H)^{2+}$

Example 10

Tetragadolinium {4,10-bis(carboxylatomethyl)-7-[2-oxo-2-({3-({[4,7,10-tris(carboxylato-methyl)-1,4,7,10-tetraazacyclododecan-1-yl]acetyl}amino)-2,2-bis[({[4,7,10-tris-(carboxylatomethyl)-1,4,7,10-tetraazacyclododecan-1-yl]acetyl}amino)methyl]propyl}-amino)ethyl]-1,4,7,10-tetraazacyclododecan-1-yl}acetate

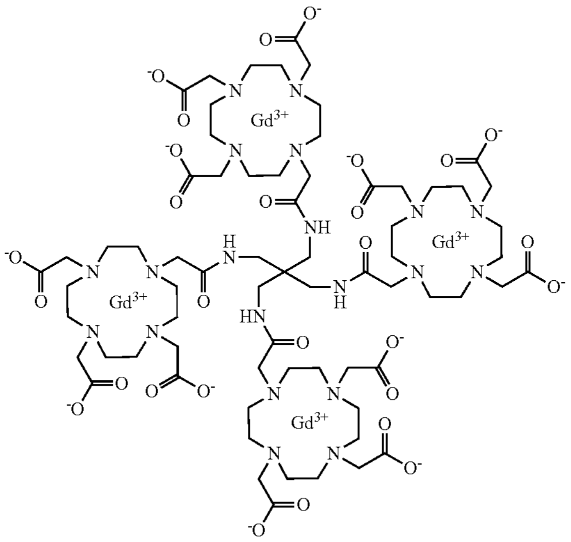

Example 10a

Tert-butyl {4,10-bis(2-tert-butoxy-2-oxoethyl)-7-[2-oxo-2-({3-({[4,7,10-tris(2-tert-butoxy-2-oxoethyl)-1,4,7,10-tetraazacyclododecan-1-yl]acetyl}amino)-2,2-bis[({[4,7,10-tris(2-tert-butoxy-2-oxoethyl)-1,4,7,10-tetraazacyclododecan-1-yl]acetyl}amino)methyl]-propyl}amino)ethyl]-1,4,7,10-tetraazacyclododecan-1-yl}acetate

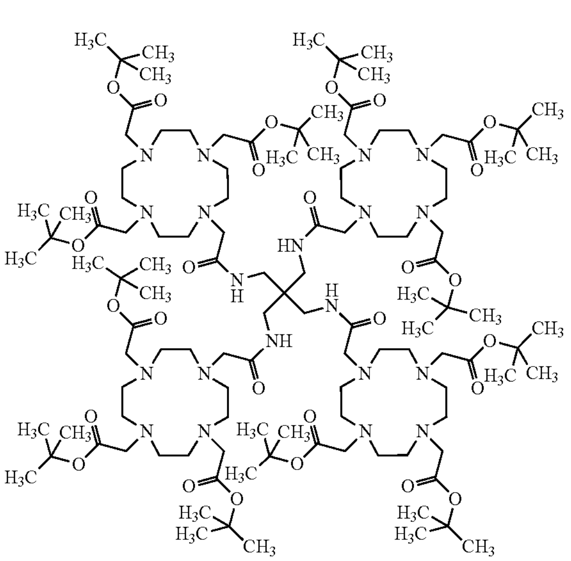 [SMILES: CC(C)(C)OC(=O)CN1CCN(CC(=O)NCC(CNC(=O)CN2CCN(CC(=O)OC(C)(C)C)CCN(CC(=O)OC(C)(C)C)CCN(CC(=O)OC(C)(C)C)CC2)(CNC(=O)CN2CCN(CC(=O)OC(C)(C)C)CCN(CC(=O)OC(C)(C)C)CCN(CC(=O)OC(C)(C)C)CC2)CNC(=O)CN2CCN(CC(=O)OC(C)(C)C)CCN(CC(=O)OC(C)(C)C)CCN(CC(=O)OC(C)(C)C)CC2)CCN(CC(=O)OC(C)(C)C)CCN(CC(=O)OC(C)(C)C)CC1]

6.6 mg (49.8 μmol, 1 eq.) 2,2-Bis(aminomethyl)propane-1,3-diamine (see W. Hayes et al., *Tetrahedron* 59 (2003), 7983-7996) were dissolved in 7 mL DMSO. After adding of 77 mg (0.6 mmol, 12 eq.), N,N-diisopropylethylamine and 400 mg (0.6 mmol, 12 eq.) tri-tert-butyl 2,2',2"-(10-{2-[(2,5-dioxopyrrolidin-1-yl)oxy]-2-oxoethyl}-1,4,7,10-tetraazacyclo dodecane-1,4,7-triyl)triacetate (see M. Galibert et al., *Bioorg. Med. Chem. Letters* 2010 (20), 5422-5425 and *J. Am. Chem. Soc.* 2006, 128, p. 15072-15073; S3-5) the resulting reaction mixture was stirred and heated over night at 50° C. The cooled solution was concentrated under reduced pressure. The crude product was used without further characterization for the next chemical step.

Example 10b

{4,10-bis(carboxymethyl)-7-[2-oxo-2-({3-({[4,7,10-tris(carboxymethyl)-1,4,7,10-tetraaza-cyclododecan-1-yl]acetyl}amino)-2,2-bis[({[4,7,10-tris(carboxymethyl)-1,4,7,10-tetra-azacyclododecan-1-yl]acetyl}amino)methyl]propyl}amino)ethyl]-1,4,7,10-tetraazacyclo-dodecan-1-yl}acetic acid

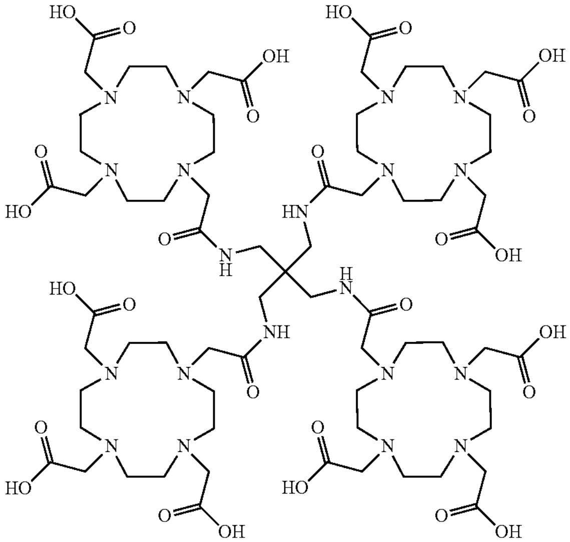 [SMILES: O=C(O)CN1CCN(CC(=O)O)CCN(CC(=O)NCC(CNC(=O)CN2CCN(CC(=O)O)CCN(CC(=O)O)CCN(CC(=O)O)CC2)(CNC(=O)CN2CCN(CC(=O)O)CCN(CC(=O)O)CCN(CC(=O)O)CC2)CNC(=O)CN2CCN(CC(=O)O)CCN(CC(=O)O)CCN(CC(=O)O)CC2)CCN(CC(=O)O)CC1]

The crude tert-butyl {4,10-bis(2-tert-butoxy-2-oxoethyl)-7-[2-oxo-2-({3-({[4,7,10-tris(2-tert-butoxy-2-oxoethyl)-1,4,7,10-tetraazacyclododecan-1-yl]acetyl}amino)-2,2-bis[({[4,7,10-tris(2-tert-butoxy-2-oxoethyl)-1,4,7,10-tetraazacyclododecan-1-yl]acetyl}amino)methyl]propyl}amino)ethyl]-1,4,7,10-tetraazacyclododecan-1-yl}acetate from example 10a was dissolved in 40 mL TFA. The resulting solution was stirred overnight at room temperature and was concentrated under reduced pressure. The crude product was used without further characterization for the next chemical step.

Example 10

Tetragadolinium {4,10-bis(carboxylatomethyl)-7-[2-oxo-2-({3-({[4,7,10-tris(carboxylato-methyl)-1,4,7,10-tetraazacyclododecan-1-yl]acetyl}amino)-2,2-bis[({[4,7,10-tris-(carboxylatomethyl)-1,4,7,10-tetraazacyclododecan-1-yl]acetyl}amino)methyl]propyl}-amino)ethyl]-1,4,7,10-tetraazacyclododecan-1-yl}acetate The crude {4,10-bis(carboxymethyl)-7-[2-oxo-2-({3-({[4,7,10-tris(carboxymethyl)-1,4,7,10-tetraazacyclododecan-1-yl]acetyl}amino)-2,2-bis[({[4,7,10-tris(carboxymethyl)-1,4,7,10-tetraazacyclododecan-1-yl]acetyl}amino)methyl]propyl}amino)ethyl]-1,4,7,10-tetraazacyclododecan-1-yl}acetic acid from example 10b was dissolved in 10 mL water. After addition of 326 mg of tris(acetato-kappaO) gadolinium tetrahydrate the pH value of the resulting solution was adjusted to 3.5-4.5 by addition of aqueous sodium hydroxide solution. The reaction mixture was heated under stirring overnight at 70° C. The resulting solution was ultrafiltered with water using a 1 kDa membrane and the final retentate was lyophilized. The crude product was purified by RP-chromatography yielding 65 mg (28 μmol, 46%) of the title compound.

UPLC (ACN-HCOOH): Rt.=0.40 min.

MS ($ES^+$): m/z (z=2)=1149.7 $(M+2H)^{2+}$, m/z (z=3)=766.0 $(M+3H)^{3+}$.

Example 11

Tetragadolinium [4,10-bis(carboxylatomethyl)-7-{2,5,11,14-tetraoxo-15-[4,7,10-tris-(carboxylatom-ethyl)-1,4,7,10-tetraazacyclododecan-1-yl]-8,8-bis({[({[4,7,10-tris-(carboxylatomethyl)-1,4,7,10-tetraazacyclododecan-1-yl]acetyl}amino)acetyl]amino}-methyl)-3,6,10,13-tetraazapentadec-1-yl}-1,4,7,10-tetraazacyclododecan-1-yl]acetate

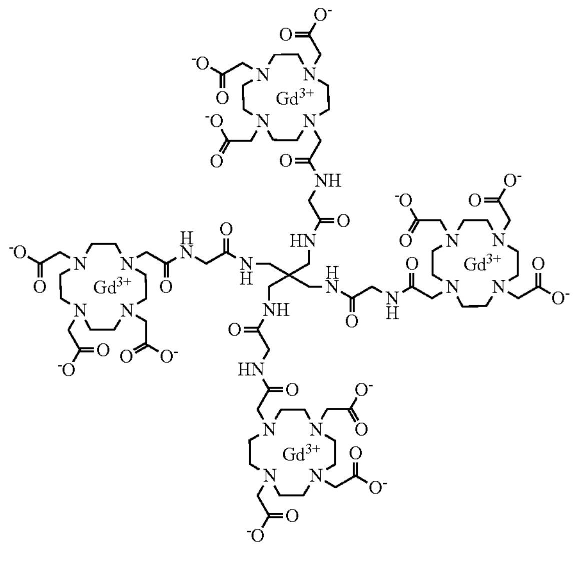

Example 11a

Tert-butyl[4,10-bis(2-tert-butoxy-2-oxoethyl)-7-{2,5,11,14-tetraoxo-15-[4,7,10-tris(2-tert-butoxy-2-oxoethyl)-1,4,7,10-tetraazacyclododecan-1-yl]-8,8-bis({[({[4,7,10-tris(2-tert-butoxy-2-oxoethyl)-1,4,7,10-tetraazacyclododecan-1-yl]acetyl}amino)acetyl]amino}-methyl)-3,6,10,13-tetraazapentadec-1-yl}-1,4,7,10-tetraazacyclododecan-1-yl]acetate

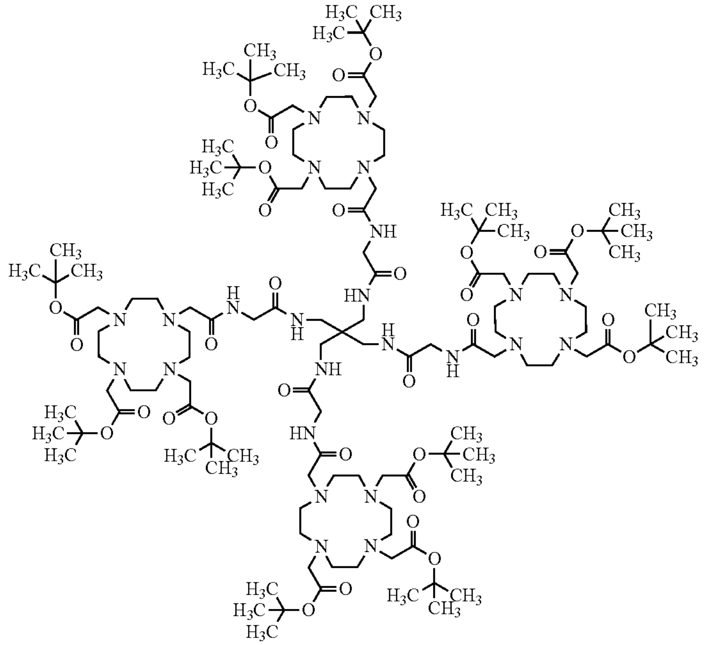 [SMILES: CC(C)(C)OC(=O)CN1CCN(CC(=O)NCC(=O)NCC(CNC(=O)CNC(=O)CN2CCN(CC(=O)OC(C)(C)C)CCN(CC(=O)OC(C)(C)C)CCN(CC(=O)OC(C)(C)C)CC2)(CNC(=O)CNC(=O)CN2CCN(CC(=O)OC(C)(C)C)CCN(CC(=O)OC(C)(C)C)CCN(CC(=O)OC(C)(C)C)CC2)CNC(=O)CNC(=O)CN2CCN(CC(=O)OC(C)(C)C)CCN(CC(=O)OC(C)(C)C)CCN(CC(=O)OC(C)(C)C)CC2)CCN(CC(=O)OC(C)(C)C)CCN(CC(=O)OC(C)(C)C)CC1]

2.99 g (4.75 mmol, 12 eq.) N-{[4,7,10-tris(2-tert-butoxy-2-oxoethyl)-1,4,7,10-tetraazacyclododecan-1-yl]acetyl}glycine (see M. Suchy et al., *Org. Biomol. Chem.* 2010, 8, 2560-2566) and 732 mg (5.70 mmol, 14.4 eq.) ethyldiisopropylamine were dissolved in 40 mL N,N-dimethylformamide. After addition of 2.17 g 1-[bis(dimethylamino)methylene]-1H-1,2,3-triazolo[4,5-b]pyridinium 3-oxide hexafluorophosphate (HATU; 5.70 mmol, 14.4 eq.) the reaction mixture was stirred for 15 minutes at room temperature. 100.1 mg (396 μmol, 1 eq.) 2,2-bis(ammoniomethyl)propane-1,3-diaminium tetrachloride (see W. Hayes et al., *Tetrahedron* 59 (2003), 7983-7996) and 982.7 mg (7.60 mmol, 19.2 eq.) ethyldiisopropylamine were added and the resulting reaction mixture was stirred over night at 50° C. The cooled solution was concentrated under reduced pressure. The crude product was used without further characterization for the next chemical step.

Example 11b

[4,10-bis(carboxymethyl)-7-{2,5,11,14-tetraoxo-15-[4,7,10-tris(carboxymethyl)-1,4,7,10-tetraazacyclododecan-1-yl]-8,8-bis({[({[4,7,10-tris(carboxymethyl)-1,4,7,10-tetraaza-cyclododecan-1-yl]acetyl}amino)acetyl]amino}methyl)-3,6,10,13-tetraazapentadec-1-yl}-1,4,7,10-tetraazacyclododecan-1-yl]acetic acid

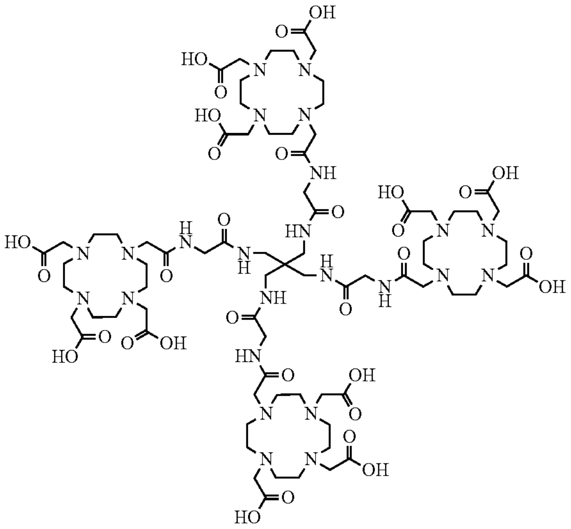 [SMILES: O=C(O)CN1CCN(CC(=O)O)CCN(CC(=O)NCC(=O)NCC(CNC(=O)CNC(=O)CN2CCN(CC(=O)O)CCN(CC(=O)O)CCN(CC(=O)O)CC2)(CNC(=O)CNC(=O)CN2CCN(CC(=O)O)CCN(CC(=O)O)CCN(CC(=O)O)CC2)CNC(=O)CNC(=O)CN2CCN(CC(=O)O)CCN(CC(=O)O)CCN(CC(=O)O)CC2)CCN(CC(=O)O)CC1]

The crude tert-butyl[4,10-bis(2-tert-butoxy-2-oxoethyl)-7-{2,5,11,14-tetraoxo-15-[4,7,10-tris(2-tert-butoxy-2-oxoethyl)-1,4,7,10-tetraazacyclododecan-1-yl]-8,8-bis({[({[4,7,10-tris(2-tert-butoxy-2-oxoethyl)-1,4,7,10-tetraazacyclododecan-1-yl]acetyl}amino)acetyl]amino}-methyl)-3,6,10,13-tetraazapentadec-1-yl}-1,4,7,10-tetraazacyclododecan-1-yl]acetate from example 11a was dissolved in 125 mL TFA. The resulting solution was stirred for 2 hours at 70° C., then overnight at room temperature, and was concentrated under reduced pressure. The oily product was dissolved in 200 mL water, was isolated by lyophilisation, and was used without further characterization for the next chemical step.

Example 11

Tetragadolinium [4,10-bis(carboxylatomethyl)-7-{2,5,11,14-tetraoxo-15-[4,7,10-tris-(carboxylatomethyl)-1,4,7,10-tetraazacyclododecan-1-yl]-8,8-bis({[({[4,7,10-tris-(carboxylatomethyl)-1,4,7,10-tetraazacyclododecan-1-yl]acetyl}amino)acetyl]amino}-methyl)-3,6,10,13-tetraazapentadec-1-yl}-1,4,7,10-tetraazacyclododecan-1-yl]acetate The crude [4,10-bis(carboxymethyl)-7-{2,5,11,14-tetraoxo-15-[4,7,10-tris(carboxy methyl)-1,4,7,10-tetraazacyclododecan-1-yl]-8,8-bis({[({[4,7,10-tris(carboxymethyl)-1,4,7,10-tetraazacyclododecan-1-yl]acetyl}amino)acetyl]amino}methyl)-3,6,10,13-tetraazapentadec-1-yl}-1,4,7,10-tetraazacyclododecan-1-yl]acetic acid from example 11b was dissolved in 100 mL water. After addition of 2.89 g of tris(acetato-kappaO)gadolinium tetrahydrate the pH value of the resulting solution was adjusted to 3.0-3.5 by addition of aqueous sodium hydroxide solution. The reaction mixture was heated under stirring for 24 hours at 70° C. The resulting solution was ultrafiltered with water using a 1 kDa membrane and the final retentate was lyophilized. The crude product was purified by RP-chromatography yielding 296 mg (120 μmol, 30%) of the title compound.

UPLC (ACN-HCOOH): Rt.=0.41 min.

MS ($ES^+$): m/z (z=2)=1262.8 $(M+2H)^{2+}$, m/z (z=3)=841.5 $(M+3H)^{3+}$.

Reference Compound 1

Gadovist® (gadobutrol, Bayer AG, Leverkusen, Germany)

Reference Compound 2

Magnevist® (gadopentetate dimeglumine, Bayer AG, Leverkusen, Germany)

Reference Compound 3

Primovist® (gadoxetate disodium, Bayer AG, Leverkusen, Germany)

Reference Compound 4

Gadomer-17 was synthesized as described in EP0836485B1, Example 1 k.

In Vitro and In Vivo Characterization of Example Compounds

Examples were tested in selected assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from assays represent average values or median values calculated utilizing data sets obtained from testing of one or more synthetic batch.

Example A

Relaxivity Measurements at 1.4 T

Relaxivity measurements at 1.41 T were performed using a MiniSpec mq60 spectrometer (Bruker Analytik, Karlsruhe, Germany) operating at a resonance frequency of 60 MHz and a temperature of 37° C. The $T_1$ relaxation times were determined using the standard inversion recovery (IR) method with a fixed relaxation delay of at least $5\times T_1$. The variable inversion time (TI) was calculated automatically by the standard software of the MiniSpec mq60 (8 steps). The $T_2$ measurements were done by using a Carr-Purcell-Meiboom-Gill (CPMG) pulse sequence, applying a relaxation delay of at least $5\times T_1$.

Each relaxivity measurement was performed using three different Gd concentrations (3 concentrations between 0.05 and 2 mM). The $T_1$ and $T_2$ relaxation times of the example compounds 1-10 were measured in different media for example in water, fetal bovine serum (FBS, Sigma, F7524) and human plasma.

Human plasma preparation: For each experiment fresh blood was taken from a volunteer using 10 mL citrate-tubes (Sarstedt S-Monovette 02.1067.001, 10 mL, Citrate). The 10 mL citrate-tubes were carefully inverted 10 times to mix blood and anticoagulant and centrifuged for 15 minutes at 1811 g at room temperature (Eppendorf, Centrifuge 5810R).

The relaxivities $r_i$ (where i=1, 2) were calculated on the basis of the measured relaxation rates $R_i$ in water and plasma:

$$R_i = R_{i(0)} + r_1\,[C_{Gd}],$$

where $R_{i(0)}$ represent the relaxation rate of the respective solvent and $C_{Gd}$ the concentration of the compound normalized to the Gadolinium. The Gadolinium concentrations of the investigated solutions were verified by Inductively Coupled Plasma Mass Spectroscopy (ICP-MS Agilent 7500a, Waldbronn, Germany). The determined relaxivity values are summarized in Table 1.

TABLE 1

Relaxivities of investigated compounds in water, fetal bovine serum (FBS) and human plasma at 1.41 T and relaxivities of Reference compounds 1-4 (RC1-RC4) at 1.5 T in water and bovine plasma. All values were measured at 37° C., are normalized to Gd and given in L $mmol^{-1}$ $s^{-1}$.

| Example No | $r_1$ water* | $r_2$ water* | $r_1$ FBS* | $r_2$ FBS* | $r_1$ human plasma* | $r_2$ human plasma* |
|---|---|---|---|---|---|---|
| 1 | 11.1 | 12.9 | 13.2 | 16.3 | 13.0 | 19.5 |
| 2 | 12.1 | 14.2 | 13.4 | 16.4 | 13.9 | 17.6 |
| 3 | 10.1 | 11.7 | 11.5 | 13.7 | 11.8 | 14.7 |
| 3-1 | 9.5 | 11.1 | n.d. | n.d. | 10.4 | 13.1 |
| 3-2 | 9.4 | 10.8 | n.d. | n.d. | 11.4 | 14.2 |
| 4 | 11.5 | 13.5 | 13.3 | 16.0 | 13.2 | 16.5 |
| 5 | 13.0 | 15.2 | 14.6 | 18.1 | 14.3 | 17.7 |
| 6 | 13.4 | 15.7 | 14.2 | 17.5 | 14.6 | 18.6 |
| 7 | 10.8 | 12.6 | 11.7 | 14.4 | 12.1 | 14.9 |
| 8 | 12.5 | 14.5 | 14.5 | 17.9 | 14.6 | 18.1 |
| 9 | 7.4 | 8.5 | 8.8 | 10.4 | n.d. | n.d. |
| 10 | 7.3 | 8.3 | 9.2 | 10.7 | 9.7 | 11.3 |
| RC1^ | 3.3 | 3.9 | 5.2 | 6.1 | n.d. | n.d. |
| RC2^ | 3.3 | 3.9 | 4.1 | 4.6 | n.d. | n.d. |
| RC3^ | 4.7 | 5.1 | 6.9 | 8.7 | n.d. | n.d. |
| RC4^ | 17.3 | 22 | 16 | 19 | n.d. | n.d. |

*values are depicted in L $mmol^{-1}$ $s^{-1}$

^Relaxivities from reference compounds from Rohrer et. al. (Invest. Radiol. 2005; 40, 11: 715-724), bovine plasma (Kreaber GmbH, Pharmaceutical Raw Material, Ellerbek, Germany)

Relaxivity measurements at 3.0 T were performed with a whole body 3.0 T MRI Scanner (Philips Intera, Philips Healthcare, Hamburg, Germany) using a knee-coil (SENSE-Knee-8, Philips Healthcare, Hamburg, Germany). The sample tubes (CryoTube™ Vials, Thermo Scientific 10.8 mL, Roskilde, Denmark) were positioned in 3 rows of 4 and 5 tubes in a plastic holder in a box filled with water. The temperature was adjusted to 37° C. For the MRI sequence, the shortest possible echo-time (TE) with 7.46 milliseconds was used. The inversion times were chosen to optimize the sequence to measure $T_1$ values corresponding to the estimated $T_1$ range of all relaxation times of contrast media containing solutions. The following inversion times (TIs) were applied: 50, 100, 150, 200, 300, 500, 700, 1000, 1400, 2100, 3200, and 4500 milliseconds. The sequence was run with a constant relaxation delay of 3.4 seconds after the registration of the last echo (variable TR in the range from 3450 to 7900 milliseconds). For details of the fit procedure, see Rohrer et. al. (*Invest. Radiol.* 2005; 40(11): 715-724). The experimental matrix of the phantom measurement was 320×320.

The relaxivities were evaluated using three different concentrations of each compound (3 concentrations between 0.05 and 2 mM).

The $T_1$ relaxation times of the Example compounds 1-6 were measured in water and human plasma. Human plasma preparation: For each experiment fresh blood was taken from a volunteer using 10 mL citrate-tubes (Sarstedt S-Monovette 02.1067.001, 10 mL, Citrate). The 10 mL citrate-tubes were carefully inverted 10 times to mix blood and anticoagulant and centrifuged for 15 minutes at 1811 g at room temperature (Eppendorf, Centrifuge 5810R).

The relaxivities $r_i$ (where i=1, 2) were calculated on the basis of the measured relaxation rates $R_i$ in water and plasma:

$$R_i = R_{i(0)} + r_i\,[C_{Gd}],$$

where $R_{i(0)}$ represent the relaxation rate of the respective solvent and $C_{Gd}$ the concentration of the compound normalized to the Gadolinium (Table 2).

TABLE 2

Relaxivities (normalized to Gd) in water and human plasma at 3.0 T and 37° C. [L $mmol^{-1}$ $s^{-1}$]

| Example No | $r_1$ water* | $r_1$ human plasma* |
|---|---|---|
| 1 | 9.5 ± 0.2 | 10.8 ± 0.1 |
| 2 | 9.2 ± 0.3 | 11.4 ± 0.1 |
| 3 | 9.2 ± 0.3 | 10.2 ± 0.2 |
| 3-1 | 8.9 ± 0.2 | 10.1 ± 0.1 |
| 3-2 | 9.0 ± 0.4 | 11.4 ± 0.2 |
| 4 | 10.1 ± 0.2 | 11.8 ± 0.3 |
| 5 | 10.8 ± 0.3 | 12.4 ± 0.2 |

TABLE 2-continued

| Relaxivities (normalized to Gd) in water and human plasma at 3.0 T and 37° C. [L $mmol^{-1}$ $s^{-1}$] | | |
|---|---|---|
| Example No | $r_1$ water* | $r_1$ human plasma* |
| 6 | 11.3 ± 0.4 | 12.8 ± 0.3 |
| RC1^ | 3.2 ± 0.3 | 5.0 ± 0.3 |
| RC2^ | 3.1 ± 0.3 | 3.7 ± 0.2 |
| RC3^ | 4.3 ± 0.3 | 6.2 ± 0.3 |
| RC4^ | 13.0 ± 0.7 | 13 ± 1 |

*Average ± standard deviation, values are depicted in L $mmol^{-1}$ $s^{-1}$

Example B

Pharmacokinetic Parameters

Pharmacokinetic parameters of the compound of Example 3 were determined in male rats (Han-Wistar, 220-230 g, n=3). The compound was administered as a sterile aqueous solution (52.5 mmol Gd/L) as a bolus in the tail vein of the animals. The dose was 0.1 mmol Gd/kg. Blood was sampled 1, 3, 5, 10, 15, 30, 60, 90, 120, 240, 360, 480 and 1440 min post injection and the Gd concentration was determined by Inductively Coupled Plasma Mass Spectroscopy (ICP-MS Agilent 7500a, Waldbronn, Germany). The blood level was converted to plasma concentrations by division by 0.625 (plasma fraction of rat blood, assuming strictly extracellular distribution). As a control, 3 animals were treated in the same way with Gadovist®, a low molecular weight contrast agent. The time courses of the blood plasma levels are shown in FIG. 1.

The fit of the obtained data to a three compartment model (Phoenix—WinNonlin) yielded the pharmacokinetic parameters which are shown in Table 3.

TABLE 3

| Time courses of blood plasma levels | | | | | | |
|---|---|---|---|---|---|---|
| | | | Gadovist ® | | Example 3 | |
| Parameter | | unit | mean | SD | mean | SD |
| t½ α | Half-life, compartment V1 | [min] | 1.6 | 0.4 | 1.7 | 0.3 |
| t½ β | Half-life, compartment V2 | [min] | 20.5 | 1.9 | 18.2 | 3.4 |
| t½ γ | Half-life, compartment V3 | [min] | 232 | 126 | 133 | 22.0 |
| MRT | Mean residence time | [min] | 30.1 | 3.8 | 24.1 | 4.4 |
| AUC∞ | Area under the curve (to infinity) | [μmol/l*min] | 11500 | 1180 | 9040 | 1220 |
| $V_c$ (V1) | Volume, central compartment V1 | [l/kg] | 0.14 | 0.01 | 0.11 | 0.01 |
| V2 | Volume, compartment V2 | [l/kg] | 0.12 | 0.01 | 0.15 | 0.01 |
| V1 + V2 | Volume, compartments V1 + V2 | [l/kg] | 0.25 | 0.02 | 0.26 | 0.01 |
| $V_{d,ss}$ | Volume of distribution at steady state | [l/kg] | 0.28 | 0.02 | 0.28 | 0.01 |
| $Cl_{tot}$ | Total Clearance | [ml/min*kg] | 9.30 | 0.9 | 11.8 | 1.7 |

Example C

Excretion and Residual Organ Gadolinium Concentration after 5 Days

The excretion and organ distribution of Example 3 were determined in male rats (Han-Wistar, 100-110 g, n=3). The compound was administered as a sterile aqueous solution (54 mmol Gd/L) as a bolus in the tail vein of the animals. The dose was 0.1 mmol Gd/kg. Urine was collected in the following time periods 0-1 h, 1-3 h, 3-6 h, 6-24 h, 1-2 d and 2-5 d post injection and feces 0-1 d, 1-2 d and 2-5 d post injection. As a control, 3 animals were treated in the same way with Gadovist®, a low molecular weight contrast agent. On day 7 the animals were sacrificed, and the following organs were excised: blood, liver, kidney, spleen, heart, lung, brain, mesenteric lymph nodes, muscle, skin, stomach, gut, bone and bone marrow. The remaining carcass was freeze dried and ground to a fine powder. The Gd concentration in the organs and the carcass was determined by ICP-MS (IOP-MS Agilent 7500a, Waldbronn, Germany). The results of the organ distribution of Example 3 and Reference compound 1 (Gadovist®) are summarized in Table 4. The Example 3 is excreted quickly via the kidneys. After 3 h 95.8%±3.4% of the injected dose was found in urine and 96.9%±3.7% after 5 days. About 1.4%±0.6% was excreted via the feces. Less than 0.5% of the administered dose was present in the body 7 days after the injection. The individual organs contained less than 0.03% of the injected dose, except the kidney which is the excretion organ.

TABLE 4

| Excretion and organ distribution of Gadovist ® and Example 3 in rats | | |
|---|---|---|
| | Gadovist ® [% Dose] | Example 3 [% Dose] |
| Time period post injection | Urine | Urine |
| 0-1 h | 91.28 ± 2.69% | 90.36 ± 4.4% |
| 1-3 h | 7.38 ± 1.50% | 5.43 ± 1.04% |
| 3-6 h | 0.22 ± 0.08% | 0.46 ± 0.38% |
| 6-24 h | 0.28 ± 0.03% | 0.17 ± 0.02% |
| 1-2 d | 0.20 ± 0.02% | 0.14 ± 0.01% |
| 2-5 d | 0.64 ± 0.18% | 0.34 ± 0.03% |
| Time period post injection | Feces | Feces |
| 0-1 d | 1.47 ± 1.38% | 1.13 ± 0.62% |
| 1-2 d | 0.13 ± 0.08% | 0.10 ± 0.02% |
| 2-5 d | 0.13 ± 0.02% | 0.13 ± 0.01% |
| Time point post injection | Σ organs and carcass | Σ organs and carcass |
| 7 d | 0.50 ± 0.07% | 0.49 ± 0.01% |
| Total recovery | 101.9 ± 0.4% | 98.8 ± 3.1% |

Example D

Chemical Stability

Examples 1, 2, 3 and 6 were separately dissolved in 10 mM Tris-HCl buffer, pH 7.4 at a final concentration of 5 mmol Gd/L. An aliquot was removed, and the rest of the clear and colorless solution was autoclaved at 121° C. for 20 min. After autoclaving, the solution was still clear and colorless. The aliquot removed before and after autoclaving was analyzed by HPLC-ICP-MS to determine the integrity of the compound.

HPLC: Column: Hypercarb 2.5 mm×15 cm. Solvent A: 0.1% formic acid in water. Solvent B: acetonitrile. Gradient from 100% A to 5% A+95% B in 10 min. Flow 1 ml/min. Detection by ICP-MS, tuned to $^{158}$Gd. The chromatograms, displaying the intensity of the detected Gd, were visually compared. No changes in the chromatograms before and after autoclaving were detected. The compounds were stable during the autoclaving procedure.

Example E

Gadolinium Release after the Addition of Zinc and Phosphate

Figure 2:
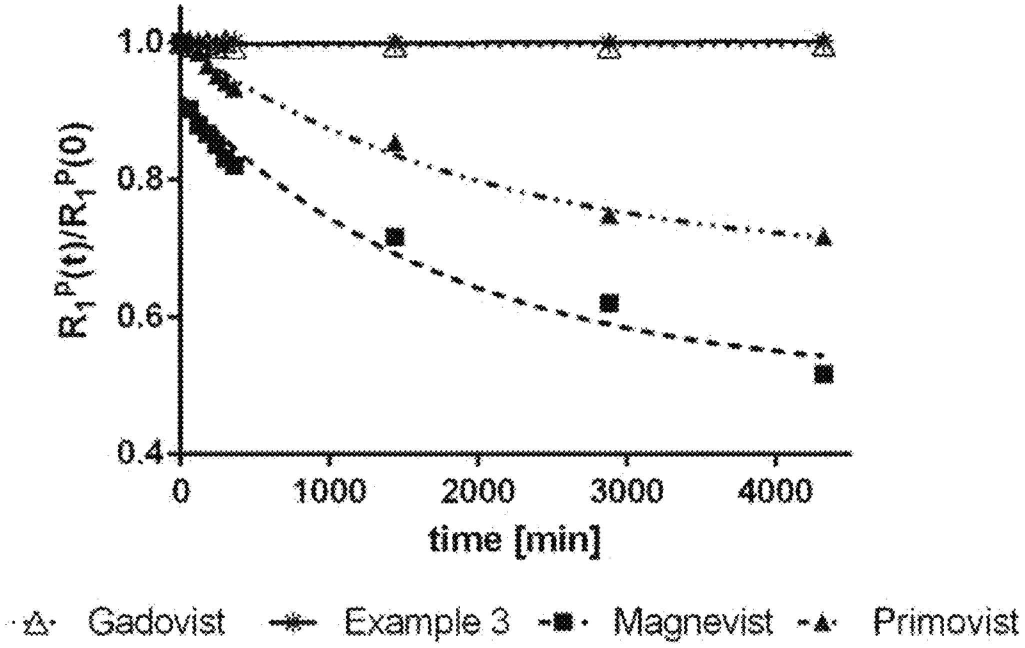
FIG. 2: shows the evolution of the relative water proton paramagnetic longitudinal relaxation rate $R_1^P(t)/R_1^P(0)$ versus time of Example 3, Reference compound 1 (Gadovist®), Reference compound 2 (Magnevist®) and Reference compound 3 (Primovist®). The stability of Example 3 is comparable to the high stability macrocyclic Reference compound 1 (Gadovist®).

The proton relaxometric protocol for the transmetallation assessment for the stability determination of MRI contrast media is described in Laurent S., et al. (*Invest. Radiol.* 2001; 36(2): 115-122). The technique is based on measurement of the evolution of the water proton paramagnetic longitudinal relaxation rate in phosphate buffer (pH 7.00, 26 mmol/L, $KH_2PO_4$ Merck, Hessen, Germany) containing 2.5 mmol/L gadolinium complex and 2.5 mmol/L $ZnCl_2$ Sigma-Aldrich, Munich, Germany). One hundred microliters of a 250 mmol/L solution of $ZnCl_2$ were added to 10 mL of a buffered solution of paramagnetic complex (Reference compounds 1-4 and Example 3). The mixture was vigorously stirred, and 300 μL were taken out for the relaxometric study at 0 min, 60 min, 120 min, 3 h, 4 h, 5 h, 24 h, 48 h and 72 h. The measurements were performed on a MiniSpec mq60 spectrometer (Bruker Analytik, Karlsruhe, Germany) at 60 MHz and 37° C. The results of Example 3 in comparison to Reference compound 1 (Gadovist®), Reference compound 2 (Magnevist®) and Reference compound 3 (Primovist®) are shown in FIG. 2. If Gadolinium transmetallation is triggered by the $Zn^{2+}$ ions in a phosphate-buffered solution, then free released $Gd^{3+}$ would react with the free $PO_4^{3-}$ ions to form $GdPO_4$. Due to the low solubility of $GdPO_4$, a part of the Gadolinium precipitates as solid and has no further influence on the longitudinal relaxation rate of water. A decrease of the proton relaxation rate would be observed for Gadolinium chelates with a low stability [see linear contrast media in FIG. 2: Reference compounds 2 (Magnevist®) and 3 (Primovist®)]. The stability of Example 3 is comparable to the high stability of Reference compound 1 (Gadovist®).

Example F

Gd-Complex Stabilities in Human Plasma at 37° C., 15 d

Examples 3 and 10 were separately dissolved in human plasma at 1 mmol Gd/L. As a reference for released $Gd^{3+}$, 0.1 mmol/L Gadolinium chloride ($GdCl_3$) was dissolved in human plasma. The plasma samples were incubated for 15 days at 37° C. under 5% $CO_2$ atmosphere to maintain the pH at 7.4. Aliquots were taken at the start and end of the incubation. The amount of $Gd^{3+}$ released from the complexes was determined by HPLC-ICP-MS. Column: Chelating Sepharose (HiTrap, 1 mL). Solvent A: 10 mM BisTris-HCl pH 6.0. Solvent B: 15 mM $HNO_3$. Gradient: 3 min at 100% A, from 3 to 10 min at 100% B. Flow 1 mL/min. Detection by ICP-MS, tuned to $^{158}$Gd. The chromatograms, displaying the intensity of the detected Gd, were evaluated by peak area analysis. The size of the peak of $Gd^{3+}$, eluting after the change from solvent A to B, was recorded. For both compounds the increase of this peak and thus the release of $Gd^{3+}$ were below the limit of quantification (<0.1% of the injected total amount of Gadolinium). Both Gd-complexes are stable under physiological conditions.

Example G

Water Solubility

The water solubility of the compounds was determined at room temperature (20° C.) in 0.5 mL buffer solution (10 mM Tris-HCl) in the microcentrifuge tubes (Eppendorf, 2.0 mL safe-lock caps). The solid compound was added stepwise to the buffer solution. The suspension was mixed using a shaker (Heidolph Reax 2000) and treated 5 min in an ultrasound bath (Bandelin, Sonorex Super RK255H) The suspension was stored at room temperature (20° C.) over night and final Gadolinium concentration was determined by inductively coupled plasma mass spectrometry (ICP-MS). The results are summarized in Table 5.

TABLE 5

| Solubilities of compounds in water at 20° C. | |
|---|---|
| Example No | Solubility [mmol Gd/L] |
| 1 | >1200 |
| 2 | >1200 |
| 3 | >1400 |
| 4 | >1200 |
| 5 | >1100 |
| 6 | >1100 |
| 7 | >1400 |
| 8 | >1000 |
| 9 | >800 |
| 10 | >800 |

Example H

Contrast-Enhanced Magnetic Resonance Angiography (CE-MRA)

The potential of a significant dose reduction was shown by an intraindividual comparison of 100 μmol Gadolinium per kilogram body weight [100 μmol Gd/kg bw], which is comparable to the human standard dose, and a low dose protocol using 30 μmol Gadolinium per kilogram body weight. Reference compound 1 (Gadovist®), as an approved representative of the Gadolinium-based MRI contrast agents, was used in both dose protocols (100 μmol Gd/kg bw and 30 μmol Gd/kg bw) and compared to Example 3 (30 μmol Gd/kg bw).

The contrast-enhanced magnetic resonance angiography study was performed at a clinical 1.5 T Scanner (Magnetom Avanto, Siemens Healthcare, Erlangen, Germany). For optimal signal exploitation, a standard spine coil was used for the data acquisition. The study was done using male New Zealand white rabbits (weight 2.5-2.9 kg, n=6, Charles River Kisslegg). All animals were initially anesthetized using a body weight-adjusted intramuscular injection of a mixture (1+2) of xylazine hydrochloride (20 mg/mL, Rompun 2%, Bayer Vital GmbH, Leverkusen, Germany) and ketamine hydrochloride (100 mg/mL, Ketavet, Pfizer, Pharmacia GmbH, Berlin, Germany) using 1 mL/kg body weight. The continuous anesthesia of the intubated animals (endotracheal tube, Rueschelit Super Safety Clear, cuff 3.0 mm, Willy Ruesch A G, Kernen, Germany) was achieved by the intravenous injection of 0.9 mg propofol per kilogram per hour (10 mg/mL, Propofol-Lipuro 1%, B. Braun Melsungen AG, Melsungen, Germany). The continuous intravenous injection was performed using a MR infusion system (Continuum MR Infusion System, Medrad Europe B. V., A E Beek, Germany). The tracheal respiration (SV 900C, Maquet, Rastatt, Germany) was performed with 55% oxygen, forty breaths per minute and a breathing volume of 7 mL per kilogram body weight per minute.

Based on a localizer sequence oriented in coronal, axial, and sagittal directions, the anatomic course of the aorta was acquired. The time to peak was determined using a small intravenous test bolus (0.25 mL/2.5-2.7 kg or 0.3 mL/2.8-2.9 kg bw, Reference compound 1) and a 3D FLASH sequence (test bolus sequence: repetition time: 36.4 millisecond, echo time 1.45 millisecond, flip angle: 30 degree, spatial resolution: 1.0×0.8×17 mm). The angiography 3D FLASH sequence was characterized by a repetition time of 3.24 milliseconds, an echo time of 1.17 milliseconds, a flip angle of 25 degree and a slice thickness of 0.94 mm. The field of view of 141×300 mm was combined with a matrix of 150×320 resulting in a spatial resolution of 0.9×0.9×0.9 mm and a whole acquisition time of 13 seconds per 3D block. The 3D FLASH sequence was performed once before and immediately after injection of the contrast agent. The time interval for the intraindividual comparison between the different contrast agent applications was twenty to thirty minutes (n=3 animals).

Figures 3A, 3B, 3C:
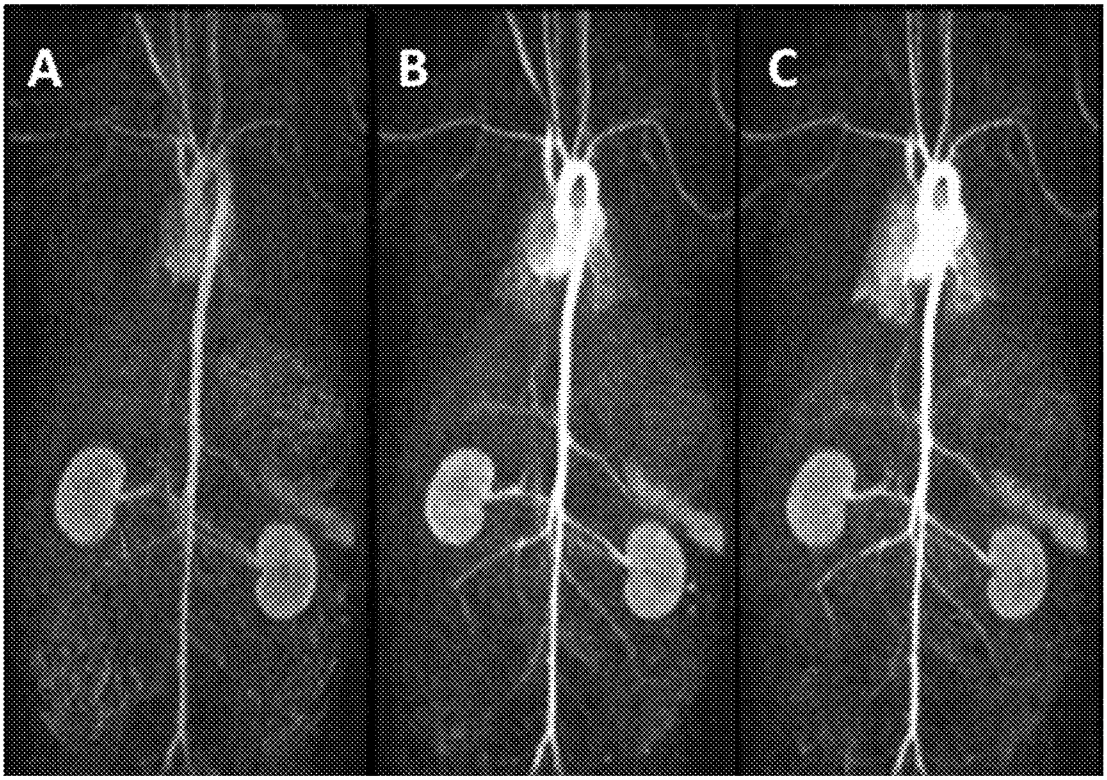
FIGS. 3A to 3C: show the magnetic resonance angiography data in male New Zealand white rabbits.

The resulting magnetic resonance angiographs of the intraindividual comparison in rabbits are depicted in FIGS. 3A-3C: FIG. 3A shows 30 μmol Gd/kg bw Reference compound 1 (Gadovist®); FIG. 3B shows 30 μmol Gd/kg bw Example 3 and FIG. 3C shows 100 μmol Gd/kg bw Reference compound 1. The contrast enhancement of the low dose protocol with Example 3 (FIG. 3B) is comparable to that of the standard dose of Reference compound 1 (FIG. 3C). Furthermore, the image quality of the low dose protocol of Example 3 (FIG. 3B) is significantly better than the low dose protocol of Reference compound 1 (FIG. 3A). The angiography study demonstrates the potential of Example 3 for a significant dose reduction.

Example J

Whole Body Imaging

Classical extracellular Gadolinium-based contrast agents exhibit a rapid extracellular passive distribution in the whole body and are excreted exclusively via the kidney. The fast extracellular distribution in the whole body enables the classical imaging possibilities as for example angiography and the imaging of the central nervous system, extremities, heart, head/face/neck, abdomen and breast. The comparability of the pharmacokinetic and diagnostic behavior of Reference compound 1 (Gadovist®) and other ECCM has been shown and forms the basis for bridging the efficacy to all body parts usually imaged in the diagnostic workup of a variety of diseases (Tombach B., et al., *Eur. Radiol.* 2002; 12(6):1550-1556). The described contrast-enhanced magnetic resonance study compares the pharmacokinetic distribution and the diagnostic performance of Example 3 to Reference compound 1 (Gadovist®), as an approved representative of the Gadolinium-based MRI contrast agents.

To demonstrate that Example 3 has the same mode of action, MRI signal intensity over time and Gd concentrations were determined in various tissues. The study was performed with a clinical whole body MRI equipped with body spine coil, abdomen flex coil, neck coil (1.5 T Magnetom Avanto, Siemens Healthcare, Erlangen, Germany). The study was done using male New Zealand white rabbits (weight 2.3-3.0 kg, n=8, Charles River Kisslegg). All animals were initially anesthetized using a body weight-adjusted intramuscular injection of a mixture (1+2) of xylazine hydrochloride (20 mg/mL, Rompun 2%, Bayer Vital GmbH, Leverkusen, Germany) and ketamine hydrochloride (100 mg/mL, Ketavet, Pfizer, Pharmacia GmbH, Berlin, Germany) using 1 mL/kg body weight. The continuous anesthesia of the intubated animals (endotracheal tube, Rueschelit Super Safe Clear, cuff 3.0 mm, Willy Ruesch A G, Kernen, Germany) was achieved by the intravenous injection of 0.9 mg propofol per kilogram per hour (10 mg/mL, Propofol-Lipuro 1%, B. Braun Melsungen AG, Melsungen, Germany). The continuous intravenous injection was performed using a MR infusion system (Continuum MR Infusion System, Medrad Europe B. V., AE Beek, Germany). The tracheal respiration (SV 900C, Maquet, Rastatt, Germany) was performed with 55% oxygen, forty breaths per minute and a breathing volume of 7 mL per kilogram body weight per minute.

Dynamic MRI measurements up to 22 min post injection with subsequent quantitative signal analysis (Siemens Mean Curve software (SYNGO Task Card, Siemens Healthcare, Erlangen, Germany), were performed for three different regions head and neck (brain, tongue, chops muscle, neck muscle), abdomen (spleen, liver, blood) and pelvis (extremity muscle). For the three different slice groups a 3D T1-weighted Vibe sequence was used (TR=4.74 ms, TE=2.38, flip=10°, 1:29 min). The dynamic measurements of the three slice groups (Head/Neck: 1:29 min, Abdomen: 0:49 min, Pelvis: 1:16 min) were done up to 22 min post injection: 1. Head/Neck: baseline, 1.4, 5.2, 8.9, 12.8, 16.5, 20.4 min, 2. Abdomen: baseline, 0.5, 4.3, 8.1, 11.9, 15.7, 19.5 min and 3. Pelvis: baseline, 2.9, 6.7, 10.5, 14.4, 18.1, 22.0 min. At 30 min post injection the animals were sacrificed and the Gd concentrations were measured using Inductively Coupled Plasma Mass Spectroscopy (ICP-MS Agilent 7500a, Waldbronn, Germany) in the following tissue samples: blood, brain, tongue, liver and extremity muscle. A quantitative image evaluation was performed for the 30 min time point p.i. due to the combination of the quantitative ICP-MS Gadolinium concentrations and the MRI region-of-interest analysis.

Figure 4A:
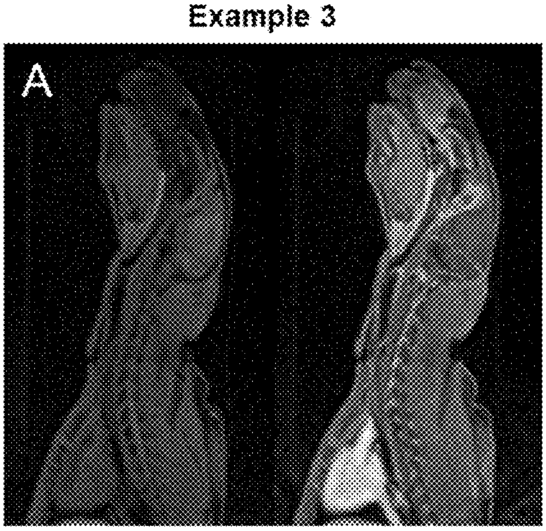
FIGS. 4A and 4B: MR images before and after administration of contrast agent. Representative images of the head and neck region before and 1.4 min after administration of Example 3 (FIG. 4A) and reference compound 1 (FIG. 4B). The strong signal enhancement is visible for example in the heart, the tongue and the neck muscle.
Figure 4B:
Figure 6A:
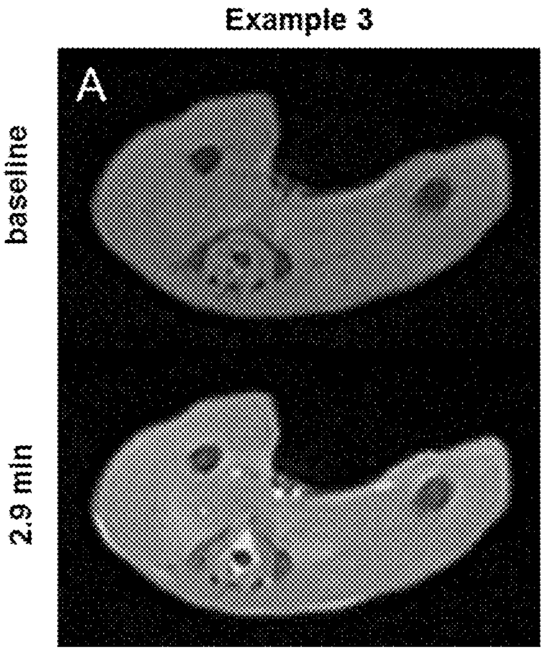
FIGS. 6A and 6B: MR images before and after administration of contrast agent. Representative images of the pelvis region before and 2.9 min after administration of Example 3 (FIG. 6A) and reference compound 1 (FIG. 6B). The strong signal enhancement is visible for example in the vascular system (vessels) and the extremity muscles.
Figure 6B:
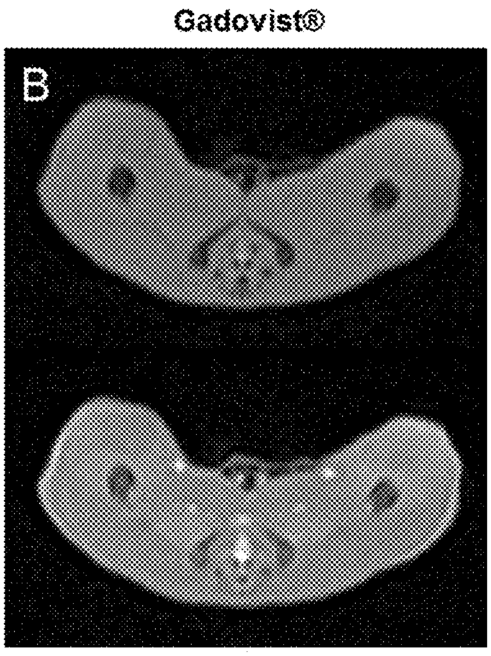

The administration of the contrast agent leads to a signal increase in the vascular system and in the extravascular, extracellular space of the body. The signal enhancement is based on the pharmacokinetic and physicochemical properties of the contrast agents. FIGS. 4A and 4B show representative images of the head and neck region before and 1.4 min after administration of Example 3 (FIG. 4A) and Reference compound 1 (FIG. 4B). FIGS. 5A and 5B show representative abdominal images before and 0.5 min after administration of Example 3 (FIG. 5A) and Reference compound 1 (FIG. 5B). FIGS. 6A and 6B show representative images of the pelvis region before and 0.5 min after administration of Example 3 (FIG. 6A) and Reference compound 1 (FIG. 6B). All images show a clear signal enhancement for example in the heart, tongue, aorta, kidney, liver, spleen, the whole vascular system and muscles.

Figure 7:
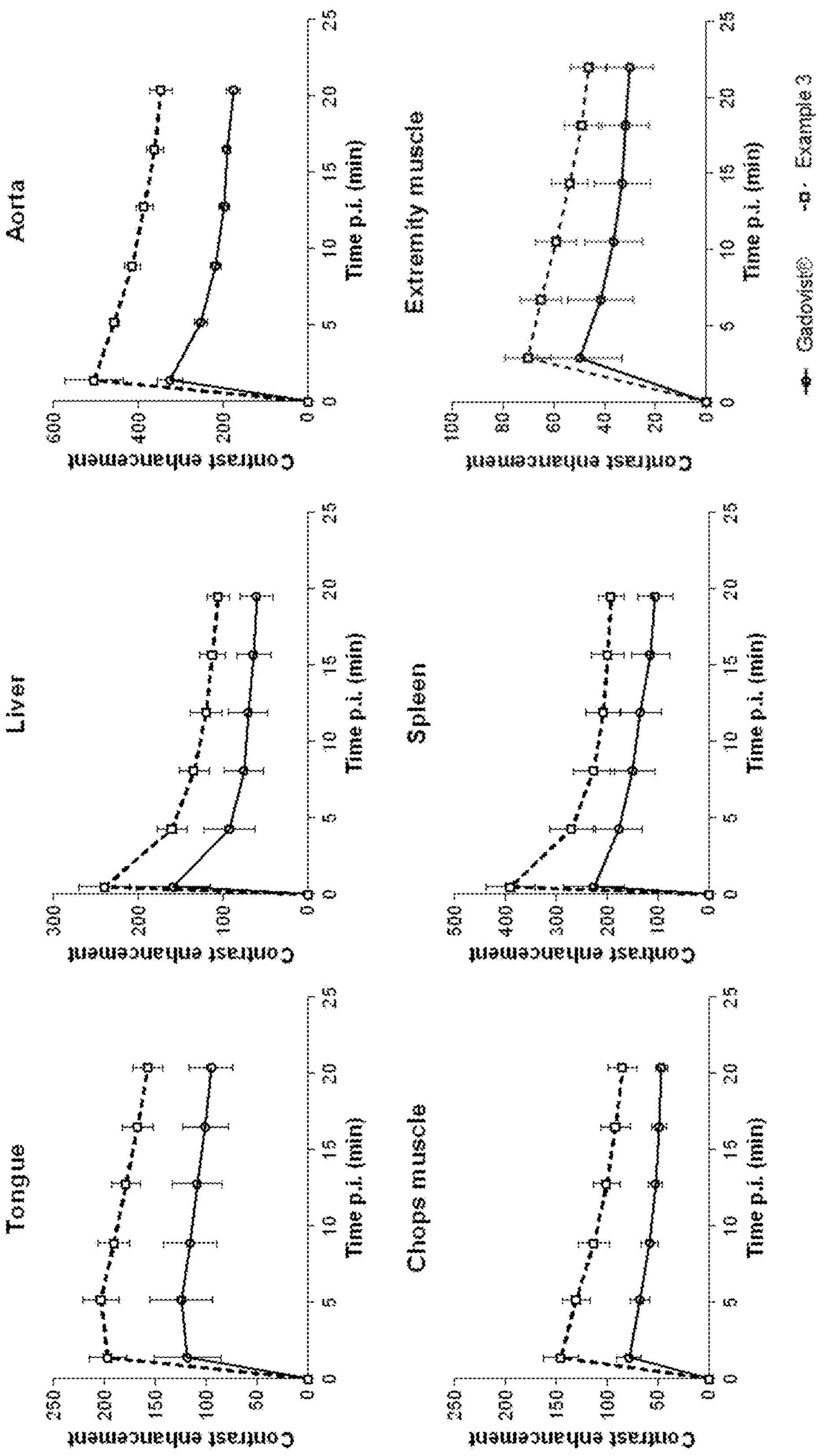
FIG. 7: MRI signal enhancements for different body regions. Signal enhancement over time after administration of Example 3 and Reference compound 1 (Gadovist®) for tongue, chops muscle, liver, spleen, aorta and extremity muscle. No differences in the time course of signal changes were observed between Example 3 and reference compound 1. This demonstrates identical pharmacokinetic properties and indicates the potential of Example 3 for the imaging of different body regions. As expected from the approximately 2-fold higher relaxivity (see example A), the observed contrast enhancements of Example 3 were higher compared to that of reference compound 1 (Gadovist®). The vertical bars represent the standard deviation.

The signal-time curves show the signal change over time after contrast agent administration and represent the contrast agent pharmacokinetics in the respective tissue (FIG. 7). In all investigated tissues a rapid increase of signal intensity was observed after contrast agent injection which was followed by a continuous signal decrease. The degree of these contrast enhancements is tissue specific. However, no differences in the time course of contrast enhancements were observed between Example 3 (dotted line) and Reference compound 1 (solid line). This demonstrates identical pharmacokinetic properties and shows that Example 3 is suitable for different body regions (FIG. 7). The amplitude of contrast enhancement depends on tissue characteristics, especially on tissue perfusion and the physicochemical properties, especially on relaxivity. As expected from the approximately 2-fold higher relaxivity (see Example A) the contrast enhancement using Example 3 is higher compared to that of Reference compound 1.

Figure 8A:
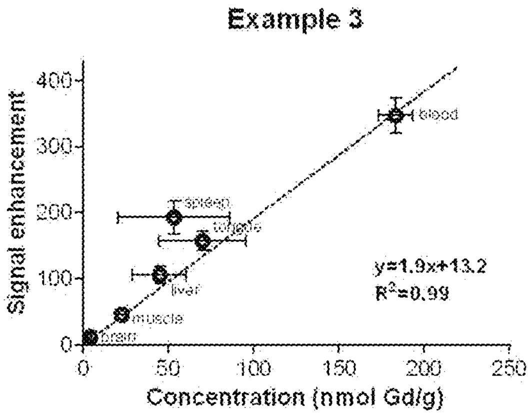
FIGS. 8A and 8B: Correlation of tissue gadolinium concentration and MRI signal enhancement. The gadolinium concentration was measured in tissue samples of the brain, tongue, liver, spleen, blood and extremity muscle (muscle) and respective MRI signal changes determined in-vivo, after administration of Example 3 (FIG. 8A) and reference compound 1 (FIG. 8B). The vertical and horizontal error bars represent the standard deviation. The dotted lines represent the linear regression between gadolinium concentration and MRI signal change.
Figure 8B:
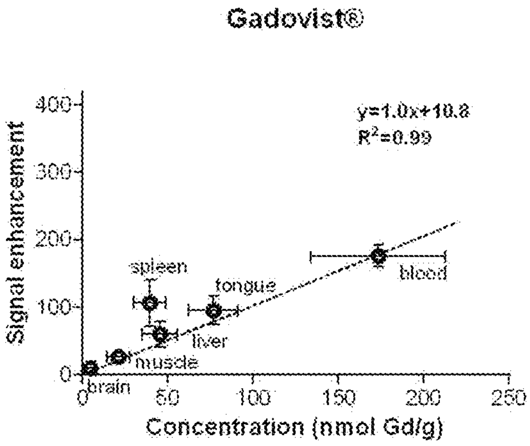

The relation between Gadolinium concentration and MRI signal change were investigated by comparing the amount of Gadolinium in tissue 30 min p.i. with the signal change at the MRI measurement performed at 19.5 min p.i. (abdomen), 20.4 min p.i. (head and neck) and 22.0 min p.i. (pelvis). The respective data for Example 3 and Reference compound 1 are shown in FIGS. 8A and 8B, respectively. A linear correlation between the Gadolinium concentrations in various tissues and the respective MRI signal changes were observed. This demonstrates that the efficacy of Example 3 (FIG. 8A) and Reference compound 1 (FIG. 8B) are independent of the body region or tissue investigated. A slight deviation from this correlation was observed for the spleen, which shows a higher MRI signal enhancement than it would be expected from the Gadolinium tissue concentration. This was observed for both contrast agents and relates to the significantly higher blood volume of the spleen in comparison to other organs and tissues. Consequently, the spleen loses much of its Gadolinium concentration by the exsanguination which in turn results in a mismatch between in-vivo imaging and ex-vivo Gadolinium determination. The correlation between signal change and tissue Gadolinium concentration of all other tissues and organs, which represents the respective relaxivity, depends on the efficacy of the contrast agent used. A larger slope was determined for Example 3 (1.9) (FIG. 8A) than for Reference compound 1 (1.0) (FIG. 8B), which is in good agreement with the known higher relaxivity of Example 3 (FIGS. 8A and 8B; see also relaxivity data described in Example A).

Example K

Dynamic CT Diffusion Phantom Study

As indicated in Example A, the Reference compound 4 has a relaxivity which is in a similar range as the compounds of the present invention. Following intravenous injection, all clinically approved small monomer GBCAs (gadopentetate dimeglumine, gadoterate meglumine, gadoteridol, gadodiamide, gadobutrol and gadoversetamide) distribute in the blood and extravascular/extracellular space by passive distribution (Aime S., et al., *J. Magn. Reson. Imaging* 2009; 30, 1259-1267). Contrast agents with a high protein binding, for example gadofosveset trisodium with a prolonged period in the blood vessels caused by the reversible binding to HSA, or large hydrodynamic sizes as for example Reference compound 4 are hindered to pass the vessel wall. For good imaging results a fast diffusion through the vessel walls is required due to the fast renal excretion of GBCAs.

The described dynamic CT diffusion study compares the ability of Examples 1, 2, 3, 4, 5, 6 and Reference compounds 1 and 4 to pass a semipermeable membrane (20 kDa). A 128-row clinical CT device (SOMATOM Definition, 128; Siemens Healthcare, Forchheim, Germany) was used to monitor the diffusion through a semipermeable membrane at 100 kV and 104 mA. Single measurements were performed at 0 min, 1 min, 2 min, 3 min, 5 min, 10 min, 15 min, 20 min, 30 min, 45 min, 60 min, 2 h, 3 h, 5 h, 7 h, 22 h, 24 h, 30 h, 46 h and 48 h after placing the dialysis cassette (Slide-A-Lyser, 20,000 MWCO, 0.1-0.5 mL Capacity, Thermo Scientific, Roskilde, Denmark) filled with contrast agent in fetal bovine serum solution (FBS, Sigma, F7524). The images were reconstructed with a slice thickness of 2.4 mm and a B30 convolution kernel. The used concentration in the dialysis cassettes of the investigated Examples 1, 2, 3, 4, 5, 6 and Reference compounds 1 and 4 was 20 mmol Gd/L.

Figure 10:
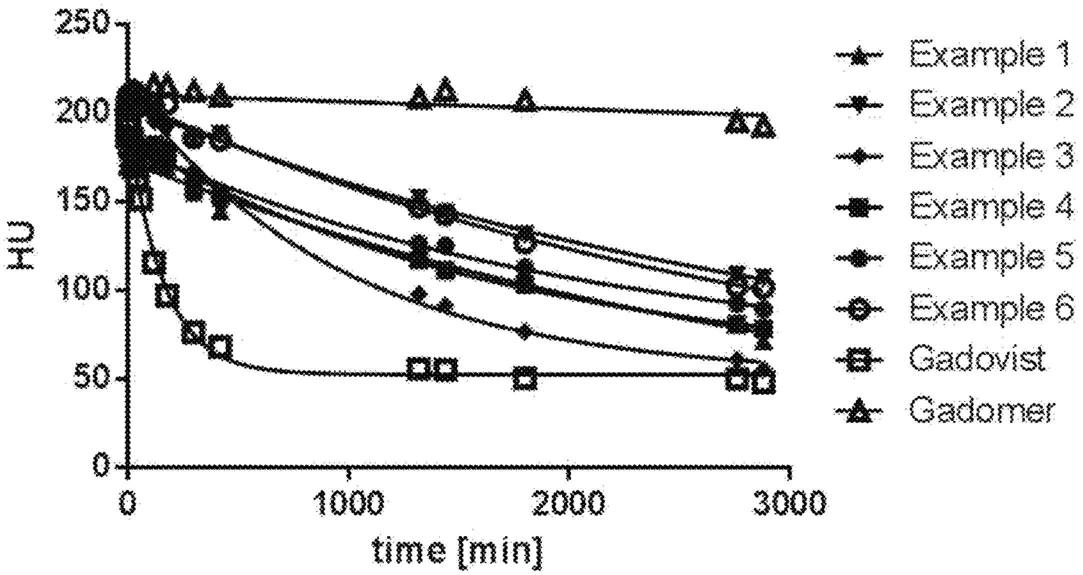
FIG. 10: Signal analysis of dynamic CT diffusion phantom study over time. Signal in Hounsfield units (HU) over time of the dialysis cassette in fetal bovine serum for Example 1-6 and reference compounds 1 and 4 demonstrate that contrary to Reference compound 4 (Gadomer), all of the investigated compounds are able to pass the semipermeable membrane (20 kDa).

The imaging results for all investigated Examples and the Reference compounds 1 and 4 for the time points 0 min and 48 h after placing the cassettes in the FBS solution are depicted in FIGS. 9A and 9B, respectively. For image analysis, regions of interest were manually drawn on 1 centrally located slice for each time point (a representative measurement region is indicated by the arrow in FIG. 9A: Image 1A). The results of the Hounsfield units (HU) of the analyzed regions over time are shown in FIG. 10. The calculated diffusion half-lives of the investigated Examples and Reference compounds are summarized in Table 6.

TABLE 6

Diffusion half-live through a semipermeable membrane (20 kDa)

| Example No | Diffusion half-life (20 kDa) [h] |
|---|---|
| 1 | 39 |
| 2 | 39 |
| 3 | 11 |
| 4 | 21 |
| 5 | 24 |
| 6 | 36 |
| RC 1 | 2 |
| RC 4 | ~90000 |

FIG. 10 and the calculated half-life data show, similar to the Reference compound 1 (Gadovist®) and in contrast to the Reference compound 4, that the Examples 1-6 are able to pass the semipermeable membrane. Furthermore, the data of the investigated compounds show contrary to other high relaxivity agents, which have a high protein binding or very slow tumbling rates (e.g. Reference compound 4), that the compounds of the present invention have hydrodynamic dimensions which can overcome barriers in a timely manner. These findings indicate the ability of the compounds of the invention to overcome barriers as for example endothelial walls in the vascular system, which is a requirement for whole body imaging.

Example L

Evaluation of Potential Side Effects

None of the investigated example compounds showed undesired negative side effects in animals after application. Additionally, the off target activity of the Example 3 was screened in commercial radioligand binding and enzyme assays (LeadProfilingScreen®, Eurofins Panlabs, Taipei, Taiwan) and revealed no critical finding.

Example M

Contrast-Enhanced MRI of Brain Tumors in Rats

The potential of a significant dose reduction was shown by an intraindividual comparison of 0.3 mmol Gadolinium per kilogram body weight (300 μmol Gd/kg bw) and a low dose protocol using 0.1 mmol Gadolinium per kilogram body weight (100 μmol Gd/kg bw). Reference compound 1 (Gadovist®), as an approved representative of the Gadolinium-based MRI contrast agents, was used in both dose protocols (0.3 mmol Gd/kg bw and 0.1 mmol Gd/kg bw) and compared to Example 3 (0.1 mmol Gd/kg bw).

GS9L cell line (European Collection of Cell Cultures, Cancer Res. 1990; 50:138-141; *J. Neurosurg.* 1971; 34:335) were grown in Dulbecco's Modified Eagle Medium (DMEM, GlutaMAX™, Ref: 31966-021, Gibco) supplement with 10% fetal bovine serum (FBS, Sigma F75249) and 1% Penicillin-Streptomycin (10.000 units/mL, Gibco). The study was done using male Fisher rats (F344, weight 170-240 g, n=4, Charles River Kisslegg). Inoculation was performed under ketamine/xylazine anesthesia using a body weight-adjusted intramuscular injection of a mixture (1+2) of xylazine hydrochloride (20 mg/mL, Rompun 2%, Bayer Vital GmbH, Leverkusen, Germany) and ketamine hydrochloride (100 mg/mL, Ketavet, Pfizer, Pharmacia GmbH, Berlin, Germany) using 1 mL/kg body weight. For orthotopically intracerebral implantation anesthetized animals were fixed in a stereotactic apparatus and 1.0E+06 GS9L cells suspended in a volume of 5 μl medium were injected slowly into the brain using a Hamilton syringe.

Figure 11A:
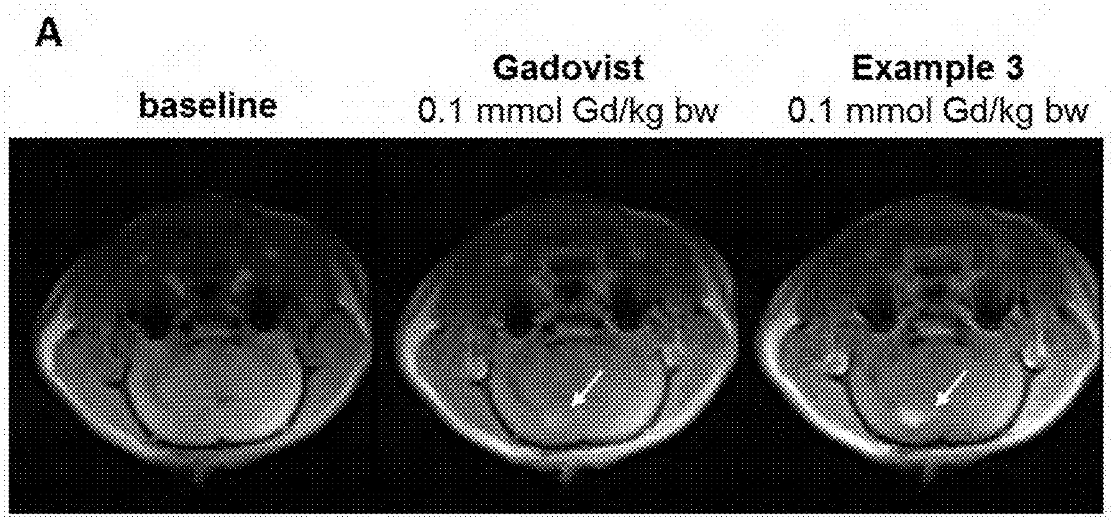
FIGS. 11A and 11B: Contrast-enhanced magnetic resonance images of GS9L brain tumors in rats (marked with white arrows).
Figure 11B:
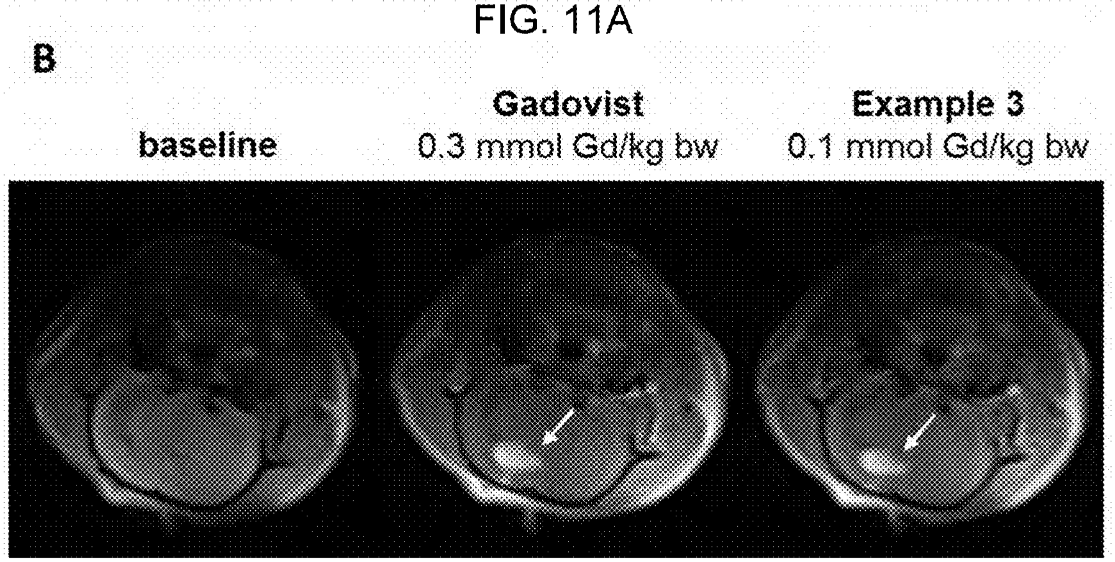

The contrast-enhanced MRI study was performed at a clinical 1.5 T Scanner (Magnetom Avanto, Siemens Healthcare, Erlangen, Germany). A rat head coil (coil and animal holder for rats, RAPID Biomedical GmbH) was used for the data acquisition. The rats were anesthetized using a mixture of isoflurane (2.25%), oxygen gas (ca. 0.5 L/min) and nitrous oxide (flow ca. 1 L/min). MR Imaging was done using a 3D turbo-spin echo sequence (121 mm slices in a 3 D block, field of view: 80 mm (33% oversampling), repetition time: 500 millisecond, echo time 19 millisecond, spatial resolution: 0.3×0.3×1.0 mm). The animals were imaged at two consecutive days. The first day the Reference compound 1 (Gadovist®) and the Example 3 were intraindividually compared at the same dose of 0.1 mmol Gd/kg bw, which is comparable to the human standard dose. The second day the Reference compound 1 (Gadovist®) at 0.3 mmol Gd/kg bw, which is comparable to the triple human dose (clinically approved in certain CNS indications), was compared to the standard dose of Example 3 (0.1 mmol Gd/kg bw). The resulting MR images of the GS9L rat brain tumors are depicted in FIGS. 11A and 11B: FIG. 11A shows an intraindividual comparison of Reference compound 1 (Gadovist®) and Example 3 at the same dose of 0.1 mmol Gd/kg body weight (bw). Example 3 showed at the same dose higher lesion-to-brain contrast and an excellent demarcation of the tumor rim. FIG. 11B shows a comparison of the Reference compound 1 (Gadovist®) at 0.3 mmol Gd/kg bw (triple dose) and Example 3 at 0.1 mmol Gd/kg bw (standard dose). Example 3 showed similar lesion-to-brain contrast at one third of the dose of Reference compound 1.

We claim:

1. A compound having the structure:

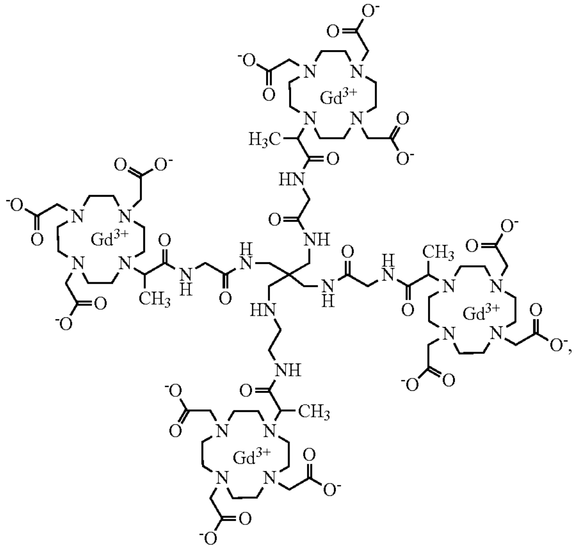

wherein each chiral carbon atom has a stereochemistry that is either R or S, or a tautomer, a hydrate, a solvate, or a salt thereof, or a mixture of same.

2. The compound of claim 1, wherein the structure comprises a stereochemistry selected from the group consisting of:

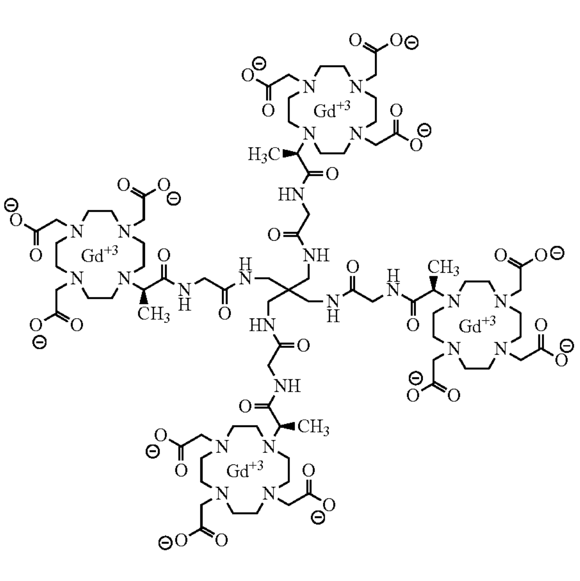

-continued
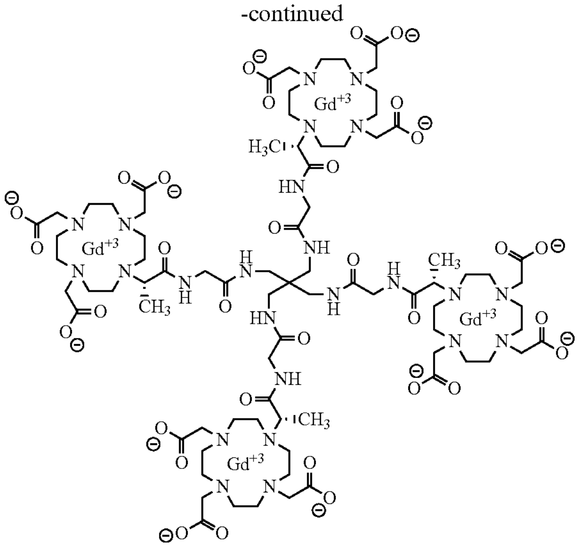
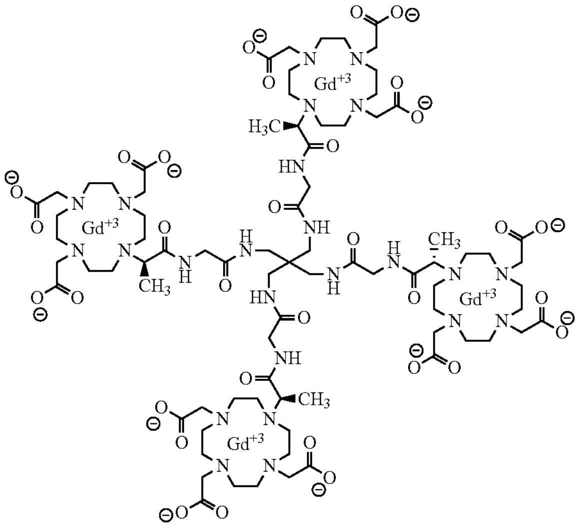
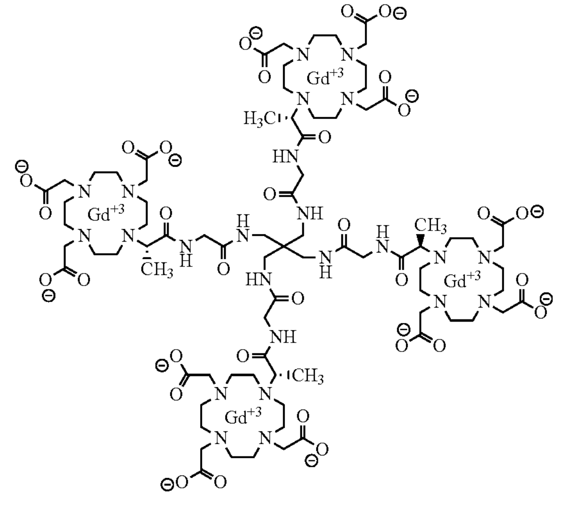
-continued
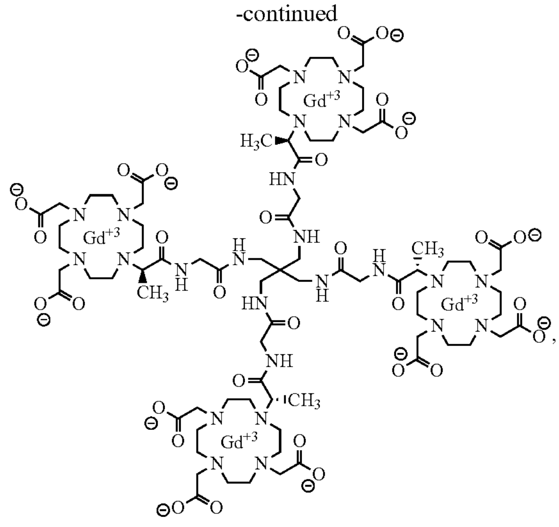
,
and combinations and mixtures of any thereof.
3. The compound of claim 2, wherein the structure of the compound is:
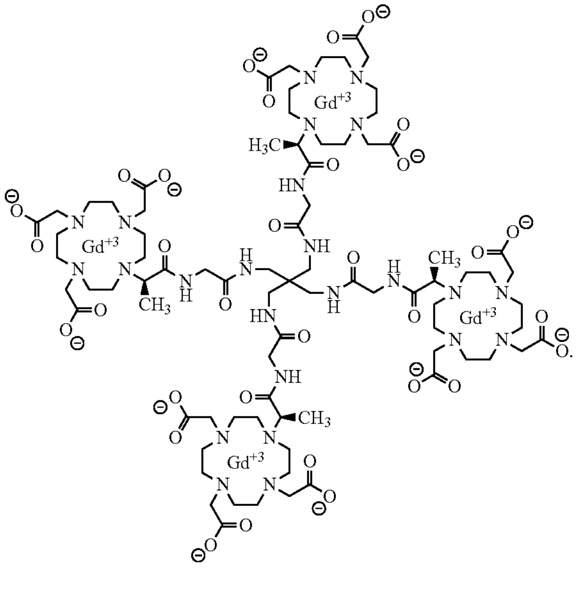
.

4. The compound of claim 2, wherein the structure of the compound is:

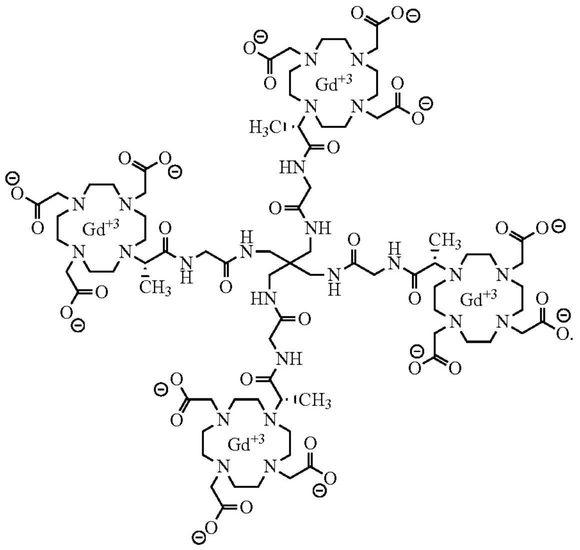

5. The compound of claim 2, wherein the structure of the compound is:

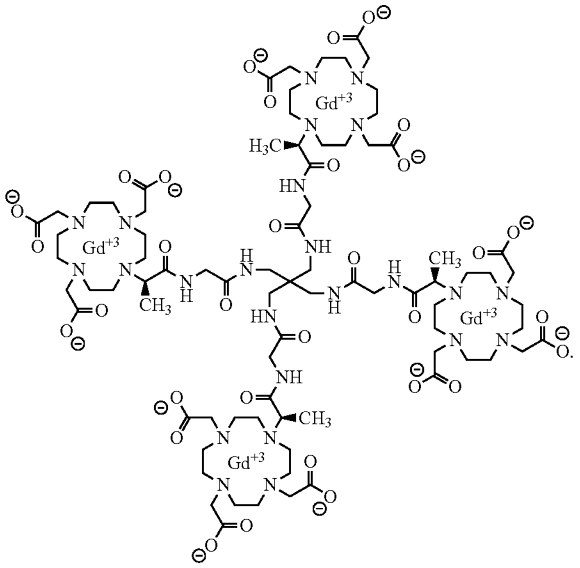

6. The compound of claim 2, wherein the structure of the compound is:

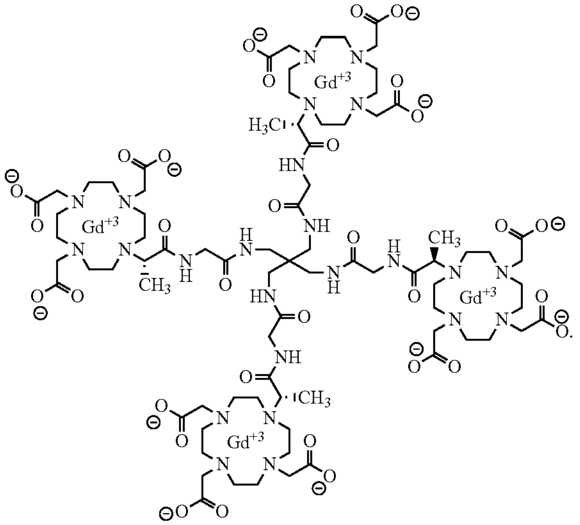

7. The compound of claim 2, wherein the structure of the compound is:

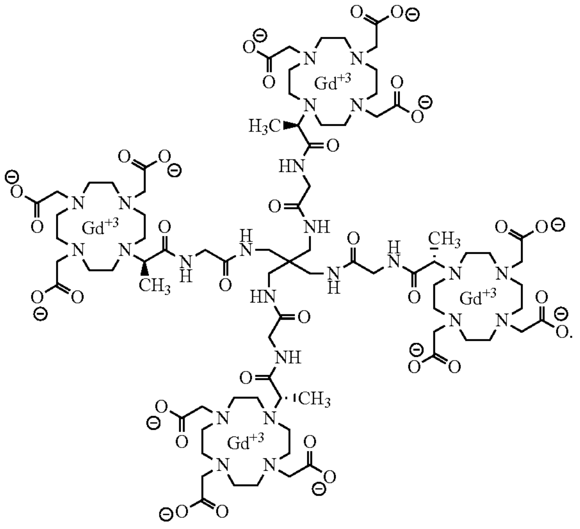

8. A compound selected from the group consisting of:

Tetragadolinium [4,10-bis (carboxylatomethyl)-7-{(2R, 16R)-3,6,12,15-tetraoxo-16-[4,7,10-tris-(carboxylatomethyl)-1,4,7,10-tetraazacyclododecan-1-yl]-9,9-bis({[{{(2R)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, Tetragadolinium [4,10-bis (carboxylatomethyl)-7-{(2S, 16S)-3,6,12,15-tetraoxo-16-[4,7,10-tris-(carboxylatomethyl)-1,4,7,10-tetraazacyclododecan-1-yl]-9,9-bis ({[{{(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, Tetragadolinium [4,10-bis (carboxylatomethyl)-7-{(2R, 16S)-3,6,12,15-tetraox9.0-16-[4,7,10-tris-(carboxylatomethyl)-1,4,7,10-tetraazacyclododecan-1-yl]-9,9-bis({[({(2S)-2-[4,7,10-tris-(carboxylatomethyl)-1,4,7, 10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, Tetragadolinium [4,10-bis (carboxylatomethyl)-7-{(2R, 16R)-3,6,12,15-tetraoxo-16-[4,7,10-tris-(carboxylatomethyl)-1,4,7,10-tetraazacyclododecan-1-yl]-9,9-bis ({[{{(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, and Tetragadolinium [4,10-bis (carboxylatomethyl)-7-{(2S, 16R)-3,6,12,15-tetraoxo-16-[4,7,10-tris-(carboxylatomethyl)-1,4,7,10-tetraazacyclododecan-1-yl]-9,9-bis({[{{(2R)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, or a tautomer, a hydrate, a solvate, or a salt thereof, or a mixture of same.

9. The compound of claim 8, wherein the compound is:

Tetragadolinium [4,10-bis (carboxylatomethyl)-7-{(2R, 16R)-3,6,12,15-tetraoxo-16-[4,7,10-tris-(carboxylatomethyl)-1,4,7,10-tetraazacyclododecan-1-yl]-9,9-bis({[{{(2R)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate.

10. The compound of claim 8, wherein the compound is:

Tetragadolinium [4,10-bis (carboxylatomethyl)-7-{(2S, 16S)-3,6,12,15-tetraoxo-16-[4,7,10-tris-(carboxylatomethyl)-1,4,7,10-tetraazacyclododecan-1-yl]-9,9-bis ({[({(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate.

11. The compound of claim 8, wherein the compound is:

Tetragadolinium [4,10-bis (carboxylatomethyl)-7-{(2R, 16R)-3,6,12,15-tetraoxo-16-[4,7,10-tris-(carboxylatomethyl)-1,4,7,10-tetraazacyclododecan-1-yl]-9,9-bis({[{{(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate.

12. The compound of claim 8, wherein the compound is:

Tetragadolinium [4,10-bis (carboxylatomethyl)-7-{(2R, 16S)-3,6,12,15-tetraoxo-16-[4,7,10-tris-(carboxylatomethyl)-1,4,7,10-tetraazacyclododecan-1-yl]-9,9-bis ({[({(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate.

13. The compound of claim 8, wherein the compound is:

Tetragadolinium [4,10-bis (carboxylatomethyl)-7-{(2S, 16R)-3,6,12,15-tetraoxo-16-[4,7,10-tris-(carboxylatomethyl)-1,4,7,10-tetraazacyclododecan-1-yl]-9,9-bis ({[{{(2R)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate.

14. The compound of claim 8, wherein the compound is a mixture of two or more compounds selected from the group consisting of:

Tetragadolinium [4,10-bis (carboxylatomethyl)-7-{(2R, 16R)-3,6,12,15-tetraoxo-16-[4,7,10-tris-(carboxylatomethyl)-1,4,7,10-tetraazacyclododecan-1-yl]-9,9-bis ({[{{(2R)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, Tetragadolinium [4,10-bis (carboxylatomethyl)-7-{(2S, 16S)-3,6,12,15-tetraoxo-16-[4,7,10-tris-(carboxylatomethyl)-1,4,7,10-tetraazacyclododecan-1-yl]-9,9-bis ({[{{(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, Tetragadolinium [4,10-bis (carboxylatomethyl)-7-{(2R, 16S)-3,6,12,15-tetraox9.0-16-[4,7,10-tris-(carboxylatomethyl)-1,4,7,10-tetraazacyclododecan-1-yl]-9,9-bis({[{{(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, Tetragadolinium [4,10-bis (carboxylatomethyl)-7-{(2R, 16R)-3,6,12,15-tetraoxo-16-[4,7,10-tris-(carboxylatomethyl)-1,4,7,10-tetraazacyclododecan-1-yl]-9,9-bis ({[{{(2S)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate, and Tetragadolinium [4,10-bis (carboxylatomethyl)-7-{(2S, 16R)-3,6,12,15-tetraoxo-16-[4,7,10-tris-(carboxylatomethyl)-1,4,7,10-tetraazacyclododecan-1-yl]-9,9-bis({[({(2R)-2-[4,7,10-tris-(carboxylatomethyl)-1,4,7,10-tetraazacyclododecan-1-yl]propanoyl}amino) acetyl]amino}methyl)-4,7,11,14-tetraazaheptadecan-2-yl}-1,4,7,10-tetraazacyclododecan-1-yl]acetate.

* * * * *